(12) United States Patent
Fujiwara et al.

(10) Patent No.: US 8,324,245 B2
(45) Date of Patent: Dec. 4, 2012

(54) QUINOLINE DERIVATIVE AND QUINAZOLINE DERIVATIVE INHIBITING SELF-PHOSPHORYLATION OF HEPATOCYTUS PROLIFERATOR RECEPTOR, AND MEDICINAL COMPOSITION CONTAINING THE SAME

(75) Inventors: Yasunari Fujiwara, Tokyo-To (JP);
Terufumi Senga, Takasaki (JP);
Tsuyoshi Nishitoba, Tokyo-To (JP);
Tatsushi Osawa, Takasaki (JP); Atsushi Miwa, Takasaki (JP); Kazuhide Nakamura, Takasaki (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 12/987,610

(22) Filed: Jan. 10, 2011

(65) Prior Publication Data

US 2011/0105747 A1 May 5, 2011

Related U.S. Application Data

(60) Continuation of application No. 12/175,361, filed on Jul. 17, 2008, now abandoned, which is a division of application No. 10/480,632, filed as application No. PCT/JP02/06239 on Jun. 21, 2002, now Pat. No. 7,425,564.

(30) Foreign Application Priority Data

Jun. 22, 2001 (JP) .................. 2001-190238

(51) Int. Cl.
*A61K 31/04* (2006.01)
*C07D 215/38* (2006.01)
(52) U.S. Cl. .............. 514/312; 546/153; 546/159
(58) Field of Classification Search .......... 546/153, 546/159; 514/312
See application file for complete search history.

(56) References Cited

U.S. PATENT DOCUMENTS

| 4,376,202 | A |   | 3/1983  | Ura et al.       |         |
|-----------|---|---|---------|------------------|---------|
| 4,425,343 | A |   | 1/1984  | Sakata et al.    |         |
| 4,914,098 | A |   | 4/1990  | Boeger et al.    |         |
| 4,963,550 | A |   | 10/1990 | Boeger et al.    |         |
| 5,624,937 | A |   | 4/1997  | Reel et al.      |         |
| 6,143,764 | A | * | 11/2000 | Kubo et al.      | 514/312 |
| 6,797,823 | B1|   | 9/2004  | Kubo et al.      |         |
| 7,135,466 | B2| * | 11/2006 | Sakai et al.     | 514/217.07 |
| 7,169,789 | B2| * | 1/2007  | Kubo et al.      | 514/266.3 |
| 7,211,587 | B2|   | 5/2007  | Kubo et al       |         |
| 7,253,286 | B2|   | 8/2007  | Funahashi et al. |         |
| 7,612,092 | B2|   | 11/2009 | Funahashi et al. |         |
| 2006/0160832 | A1 |   | 7/2006  | Funahashi et al. |         |
| 2006/0211717 | A1 |   | 9/2006  | Sakai et al.     |         |
| 2007/0027318 | A1 |   | 2/2007  | Kubo et al.      |         |
| 2010/0197911 | A1 |   | 8/2010  | Funahashi et al. |         |

FOREIGN PATENT DOCUMENTS

| EP | 860433      |    | 6/1998 |
| EP | 1 243 582   | A1 | 9/2002 |
| JP | 11-158149   |    | 6/1999 |
| WO | 00/43368    |    | 7/2000 |
| WO | 01/47890    |    | 7/2001 |
| WO | 02/32872    |    | 5/2002 |

OTHER PUBLICATIONS

Extended European Search Report issued in corresponding EP 10 17 9308 dated Dec. 16, 2011.
Opinion under Rule 62(1) EPC issued in corresponding EP 10179308.1.

* cited by examiner

*Primary Examiner* — D M Seaman
(74) *Attorney, Agent, or Firm* — Oblon, Spivak, McClelland, Maier & Neustadt, L.L.P.

(57) ABSTRACT

An objective of the present invention is to provide compounds having potent antitumor activity. The compounds of the present invention are represented by formula (I) or a pharmaceutically acceptable salt or solvate thereof:

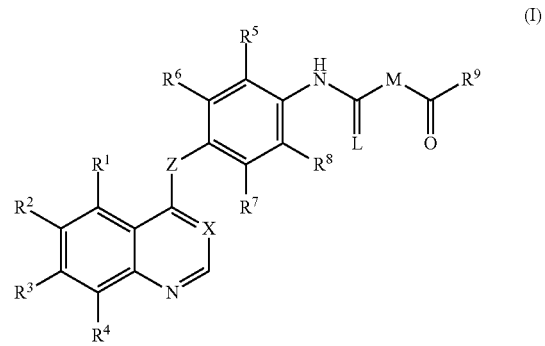

wherein X=CH or N; Z=O or S; L=O or S; M=$CR^{10}R^{11}$, wherein $R^{10}$ and $R^{11}$=H, alkyl, or alkoxy, $NR^{12}$ wherein $R^{12}$=H or alkyl; $R^1$, $R^2$, and $R^3$=H or optionally substituted alkoxy; $R^4$=H; $R^{5-8}$=H, halogen, alkoxy or the like; and $R^9$=alkyl optionally substituted by —$R^{14}$, -T-$R^{15}$, or —$NR^{16}R^{17}$ wherein T=O, S, or NH; $R^{14}$=an optionally substituted carbocyclic or heterocyclic ring; and $R^{15-17}$=alkyl or an optionally substituted carbocyclic or heterocyclic ring, or —$NR^{18}R^{19}$ wherein $R^{18}$ and $R^{19}$=H, optionally substituted alkyl, or an optionally substituted carbocyclic or heterocyclic ring, or optionally substituted carbocyclic or heterocyclic ring.

16 Claims, No Drawings

QUINOLINE DERIVATIVE AND QUINAZOLINE DERIVATIVE INHIBITING SELF-PHOSPHORYLATION OF HEPATOCYTUS PROLIFERATOR RECEPTOR, AND MEDICINAL COMPOSITION CONTAINING THE SAME

BACKGROUND OF THE INVENTION

1. Field of the Invention

The present invention relates to quinoline derivatives and quinazoline derivatives which have antitumor activity. More particularly, the present invention relates to quinoline derivatives and quinazoline derivatives which have inhibitory activity against the autophosphorylation of hepatocyte growth factor receptors and have inhibitory activity against abnormal cell proliferation or cell movement.

2. Background Art

Growth factors such as epithelial growth factors, platelet-derived growth factors, insulin-like growth factors, and hepatocyte growth factors (hereinafter abbreviated to "HGF") play an important role in cell proliferation. Among others, HGF is known to be involved, as a liver regenerating factor and a kidney regenerating factor, in the regeneration of damaged liver and kidney (Oncogenesis, 3, 27 (1992)).

However, the overexpression of HGF and a receptor thereof (hereinafter abbreviated to "met") is reported to be found in various tumors such as brain tumors, lung cancer, gastric cancer, pancreatic cancer, colon cancer, ovarian cancer, renal cancer, and prostate cancer (Oncology Reports, 5, 1013 (1998)). In particular, in gastric cancer, excessive development of met and an increase in HGF level of serum mainly in scirrhous gastric cancers are reported (Int. J. Cancer, 55, 72, (1993)). Further, it is also known that HGF has angiogenesis activity due to the acceleration of the proliferation and migration of vascular endothelial cells (Circulation, 97, 381 (1998), and Clinical Cancer Res., 5, 3695, (1999)) and induces the dispersion and invasion of cells (J Biol Chem, 270, 27780 (1995)). For this reason, HGF-met signals are considered to be involved in the proliferation, invasion, and metastasis of various cancer cells.

NK4, a partial peptide of HGF, is reported as an HGF receptor antagonist. For example, it is reported that NK4 inhibits met phosphorylation of various cancer cells and, further, suppresses cell movement and cell invasion and has tumor growth inhibitory activity in in-vivo cancer xenograft models probably through angiogenesis inhibitory activity (Oncogene, 17, 3045 (1998), Cancer Res., 60, 6737 (2000), British J Cancer, 84, 864 (2001), and Int J Cancer, 85, 563 (2000)).

Since, however, NK4 is a peptide, the use of NK4 as a therapeutic agent requires a design regarding reliable stability in vivo, administration method and the like. On the other hand, there is no report on low toxic orally active small molecule compounds having met autophosphorylation inhibitory activity.

SUMMARY OF THE INVENTION

The present inventors have found that a certain group of quinoline derivatives and quinazoline derivatives have met autophosphorylation inhibitory activity and, at the same time, have antitumor effects.

An object of the present invention is to provide compounds having potent antitumor activity.

According to the present invention, there is provided a compound represented by formula (I) or a pharmaceutically acceptable salt or solvate thereof:

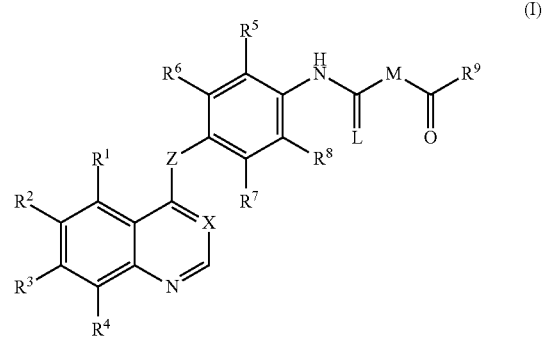

wherein
X represents CH or N;
Z represents O or S;
L represents O or S;
M represents
—C(—$R^{10}$)(—$R^{11}$)— wherein $R^{10}$ and $R^{11}$, which may be the same or different, represent a hydrogen atom, $C_{1-4}$ alkyl, or $C_{1-4}$ alkoxy, or —N(—$R^{12}$)— wherein $R^{12}$ represents a hydrogen atom or $C_{1-4}$ alkyl;
$R^1$, $R^2$, and $R^3$, which may be the same or different, represent
a hydrogen atom,
hydroxyl,
a halogen atom,
nitro,
amino,
$C_{1-6}$ alkyl,
$C_{2-6}$ alkenyl,
$C_{2-6}$ alkynyl, or
$C_{1-6}$ alkoxy,
in which one or two hydrogen atoms on the amino group are optionally substituted by $C_{1-6}$ alkyl which is optionally substituted by hydroxyl or $C_{1-6}$ alkoxy, and
in which the $C_{1-6}$ alkyl, $C_{2-6}$ alkenyl, $C_{2-6}$ alkynyl, and $C_{1-6}$ alkoxy groups are optionally substituted by hydroxyl; a halogen atom; $C_{1-6}$ alkoxy; $C_{1-6}$ alkylcarbonyl; $C_{1-6}$ alkoxy carbonyl; amino on which one or two hydrogen atoms is optionally substituted by $C_{1-6}$ alkyl which is optionally substituted by hydroxyl or $C_{1-6}$ alkoxy; or a saturated or unsaturated three- to eight-membered carbocyclic or heterocyclic group which is optionally substituted by $C_{1-6}$ alkyl which is optionally substituted by hydroxyl or $C_{1-6}$ alkoxy;
$R^4$ represents a hydrogen atom;
$R^5$, $R^6$, $R^7$, and $R^8$, which may be the same or different, represent a hydrogen atom, a halogen atom, $C_{1-4}$ alkyl, or $C_{1-4}$ alkoxy;
$R^9$ represents
$C_{1-6}$ alkyl on which one or more hydrogen atoms are optionally substituted by —$R^{14}$, or —$NR^{16}R^{17}$ wherein T represents —O—, —S—, or —NH—; $R^{19}$ represents a saturated or unsaturated three- to eight-membered carbocyclic or heterocyclic group; $R^{15}$, $R^{16}$, and $R^{17}$, which may be the same or different, represent $C_{1-6}$ alkyl or a saturated or unsaturated three- to eight-membered carbocyclic or heterocyclic group;
the three- to eight-membered carbocyclic or heterocyclic group represented by $R^{14}$, $R^{15}$, $R^{16}$, and $R^{17}$ is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring; when the three- to eight-membered carbocyclic or heterocyclic group is substituted by two $C_{1-6}$ alkyl groups, the two alkyl groups may combine together to form an alkylene chain; and the three- to eight-membered carbocyclic or heterocyclic group may be a bicyclic group condensed with another saturated or unsaturated three- to eight-membered carbocyclic or heterocyclic group, —N(—$R^{18}$)(—$R^{19}$) wherein $R^{18}$ and $R^{19}$, which may be the same or different, represent a hydrogen atom; $C_{1-6}$ alkyl which is optionally substituted by $C_{1-6}$ alkoxy, $C_{1-6}$ alkylthio, or a saturated or unsaturated three- to eight-membered carbocyclic or heterocyclic group in which the three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring and, when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group; or a saturated or unsaturated three- to eight-membered carbocyclic or heterocyclic group which is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring and in which, when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or a saturated or unsaturated three- to eight-membered carbocyclic or heterocyclic group which is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring and in which, when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, provided that, when X represents CH; Z represents O; L represents an oxygen atom; M represents —NH—; $R^1$, $R^4$, $R^5$, $R^6$, $R^7$, and $R^8$ represent a hydrogen atom; and $R^2$ and $R^3$ represent methoxy, $R^9$ does not represent phenyl, ethoxy, or pyridin-2-yl.

The compound according to the present invention can be used for the treatment of malignant tumors.

DETAILED DESCRIPTION OF THE INVENTION

Compound

The terms "alkyl," "alkoxy," "alkenyl," and "alkynyl" as used herein as a group or a part of a group respectively mean straight chain or branched chain alkyl, alkoxy, alkenyl, and alkynyl.

$C_{1-6}$ alkyl is preferably $C_{1-4}$ alkyl.
$C_{1-6}$ alkoxy is preferably $C_{1-4}$ alkoxy.
$C_{2-6}$ alkenyl is preferably $C_{2-4}$ alkenyl.
$C_{2-6}$ alkynyl is preferably $C_{2-4}$ alkynyl.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propynyl, butynyl, pentynyl, and hexynyl.

The expression "alkyl optionally substituted by" as used herein refers to alkyl, on which one or more hydrogen atoms are substituted by one or more substituents which may be the same or different, and unsubstituted alkyl. It will be understood by those skilled in the art that the maximum number of substituents may be determined depending upon the number of substitutable hydrogen atoms on the alkyl group. This applies to a group having a substituent other than the alkyl group.

The term "halogen atom" means a fluorine, chlorine, bromine, or iodine atom.

The saturated or unsaturated three- to eight-membered carbocyclic ring is preferably a four- to seven-membered, more preferably five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

The saturated or unsaturated three- to eight-membered heterocyclic ring contains at least one hetero-atom selected from oxygen, nitrogen, and sulfur atoms. The saturated or unsaturated three- to eight-membered heterocyclic ring preferably contains one or two hetero-atoms with the remaining ring-constituting atoms being carbon atoms. The saturated or unsaturated three- to eight-membered heterocyclic ring is preferably a saturated or unsaturated four- to seven-membered heterocyclic ring, more preferably a saturated or unsaturated five- or six-membered heterocyclic ring. Examples of saturated or unsaturated three- to eight-membered heterocyclic groups include thienyl, pyridyl, 1,2,3-triazolyl, imidazolyl, isoxazolyl, pyrazolyl, piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

The saturated or unsaturated carboxylic and heterocyclic groups may condense with another saturated or heterocyclic group to form a bicyclic group, preferably a saturated or unsaturated nine- to twelve-membered bicyclic carbocyclic or heterocyclic group. Bicyclic groups include naphthyl, quinolyl, 1,2,3,4-tetrahydroquinolyl, 1,4-benzoxanyl, indanyl, indolyl, and 1,2,3,4-tetrahydronaphthyl.

When the carbocyclic or heterocyclic group is substituted by two $C_{1-6}$ alkyl groups, the two alkyl groups may combine together to form an alkylene chain, preferably a $C_{1-3}$ alkylene chain. Carbocyclic or heterocyclic groups having this crosslinked structure include bicyclo[2.2.2]octanyl and norbornanyl.

$R^1$ preferably represents a hydrogen atom.

$R^2$ and $R^3$ preferably represents a group other than a hydrogen atom. More preferably, $R^2$ represents unsaturated $C_{1-6}$ alkoxy, still further preferably methoxy, and $R^3$ represents optionally substituted $C_{1-6}$ alkoxy.

The substituent of substituted $C_{1-6}$ alkoxy, which may be represented by $R^3$, is preferably a halogen atom, hydroxyl, amino optionally mono- or disubstituted by optionally substituted $C_{1-6}$ alkyl, or optionally substituted saturated or unsaturated three- to eight-membered carbocyclic or heterocyclic group, more preferably a saturated or unsaturated five- to seven-membered carbocyclic or heterocyclic group. Such substituents include amino mono- or disubstituted by $C_{1-6}$ alkyl, phenyl, piperazinyl, piperazino, piperidyl, piperidino, morpholinyl, morpholino, homopiperazinyl, homopiperazino, thiomorpholinyl, thiomorpholino, tetrahydropyrrolyl, azepanyl, imidazolyl, diazepanyl, and pyrrolidyl.

Optionally substituted alkoxy represented by $R^3$ preferably represents —O—$(CH_2)_m$—$R^{13}$ wherein m is an integer of 1 to 6, $R^{13}$ is a substituent of the alkoxy group, that is, hydroxyl, a halogen atom, $C_{1-6}$ alkoxy, $C_{1-6}$ alkylcarbonyl, $C_{1-6}$ alkoxy carbonyl, optionally substituted amino, or an optionally substituted saturated or unsaturated three- to eight-membered carbocyclic or heterocyclic group.

Preferably, all of $R^5$, $R^6$, $R^7$, and $R^8$ represent a hydrogen atom, or alternatively any one or two of $R^5$, $R^6$, $R^7$, and $R^8$ represent a group other than a hydrogen atom with all the remaining groups representing a hydrogen atom.

Carbocyclic group represented by $R^9$, $R^{14}$, $R^{15}$, $R^{16}$, $R^{17}$, $R^{18}$, and $R^{19}$ and $R^{109}$, $R^{114}$, $R^{115}$, $R^{116}$, $R^{117}$, $R^{118}$, $R^{119}$, $R^{209}$, $R^{214}$, $R^{215}$, $R^{216}$, $R^{217}$, $R^{218}$, $R^{219}$, $R^{319}$, $R^{419}$, and $R^{520}$, which will be described later, and carbocyclic groups on the alkyl group represented by these groups include phenyl, cyclopropyl, cyclobutyl, cyclopentyl, cyclohexyl, cycloheptyl, naphthyl, indanyl, and 1,2,3,4-tetrahydronaphthyl. Preferred substituents of the carbocyclic group include a fluorine atom, a chlorine atom, methyl, and methoxy. Examples of preferred carbocyclic groups include phenyl and naphthyl.

Heterocyclic groups represented by $R^9$, $R^{14}$, $R^{15}$, $R^{16}$, $R^{17}$, $R^{18}$ and $R^{19}$ and $R^{109}$, $R^{114}$, $R^{115}$, $R^{116}$, $R^{117}$, $R^{118}$, $R^{119}$, $R^{209}$, $R^{214}$, $R^{215}$, $R^{216}$, $R^{217}$, $R^{218}$, $R^{219}$, $R^{319}$, $R^{419}$, and $R^{520}$, which will be described later, and heterocyclic groups on the alkyl group represented by these groups include thienyl, pyridyl, tetrahydropyrrolyl, indolyl, 1,2,3-triazolyl, imidazolyl, isoxazolyl, pyrazolyl, quinolyl, 1,2,3,4-tetrahydroquinolyl, thiomorpholino, and 1,4-benzoxanyl. Preferred substituents of the heterocyclic group include a chlorine atom, a bromine atom, and methyl. Examples of preferred heterocyclic groups include thienyl, pyridyl, isoxazolyl, and quinolyl.

The optionally substituted alkyl group represented by $R^9$ preferably represents —$(CH_2)p$-$R^{14}$, —$(CH_2)p$-T-$R^{15}$, or —$(CH_2)p$-$NR^{16}R^{17}$ wherein p is an integer of 1 to 6 and $R^{14}$, $R^{15}$, $R^{16}$ and $R^{17}$ are as defined above.

In (—$R^{18}$)(—$R^{19}$) represented by $R^9$, preferably, $R^{18}$ represents a hydrogen atom or $C_{1-6}$ alkyl, and $R^{18}$ represents $C_{1-6}$ alkyl which is optionally substituted by an optionally substituted saturated or unsaturated five- or six-membered carbocyclic or heterocyclic group; or an optionally substituted saturated or unsaturated five- or six-membered carbocyclic or heterocyclic group.

Preferred examples of $R^9$ include benzyl, fluorobenzyl, difluorobenzyl, chlorobenzyl, methylbenzyl, methoxybenzyl, anilino, fluoroanilino, difluoroanilino, chloroanilino, methylanilino, methoxyanilino, naphthyl, thienyl-2-yl-methyl, and thienyl-3-yl-methyl.

Both $R^{10}$ and $R^{11}$ preferably represent a hydrogen atom or alkyl, or alternatively any one of $R^{10}$ and $R^{11}$ represents alkoxy with the other group representing a hydrogen atom.

$R^{12}$ preferably represents a hydrogen atom.

Examples of preferred compounds according to the present invention include compounds of formula (I) wherein X represents CH or N, Z represents O, L represents O, and M represents —N(—$R^{12}$)—, compounds of formula (I) wherein X represents CH or N, Z represents O, L represents O, M represents —C(—$R^{10}$)(—$R^{11}$)—, and compounds of formula (I) wherein X represents CH or N, Z represents O, L represents S, and M represents —N(—$R^{12}$)—.

Another examples of preferred compounds according to the present invention include compounds of formula (I) wherein X represents CH or N, Z represents O, L represents O, M represents (—$R^{12}$)—, $R^1$ and $R^4$ represent a hydrogen atom, $R^2$ represents unsubstituted $C_{1-6}$ alkoxy, $R^3$ represents optionally substituted $C_{1-6}$ alkoxy, and all of $R^5$, $R^6$, $R^7$, and $R^8$ represent a hydrogen atom or alternatively any one of $R^5$, $R^6$, $R^7$, and $R^8$ represents a group other than a hydrogen atom with all the remaining groups representing a hydrogen atom, compounds of formula (I) wherein X represents CH or N, Z represents O, L represents O, M represents —C(—$R^{10}$)(—$R^{11}$)—, $R^1$ and $R^4$ represent a hydrogen atom, $R^2$ represents unsubstituted alkoxy, $R^3$ represents optionally substituted $C_{1-6}$ alkoxy, and all of $R^5$, $R^6$, $R^7$, and $R^8$ represent a hydrogen atom or alternatively any one of $R^5$, $R^6$, $R^7$, and $R^8$ represents a group other than a hydrogen atom with all the remaining groups representing a hydrogen atom, and compounds of formula (I) wherein X represents CH or N, Z represents O, L represents S, M represents —N(—$R^{12}$)—, $R^1$ and $R^4$ represent a hydrogen atom, $R^2$ represents unsubstituted $C_{1-6}$ alkoxy, $R^3$ represents optionally substituted $C_{1-6}$ alkoxy, all of $R^5$, $R^6$, $R^7$, and $R^8$ represent a hydrogen atom or alternatively any one of $R^5$, $R^6$, $R^7$, and $R^8$ represents a group other than a hydrogen atom with all the remaining groups representing a hydrogen atom.

Examples of preferred compounds according to the present invention include compounds represented by formula (100):

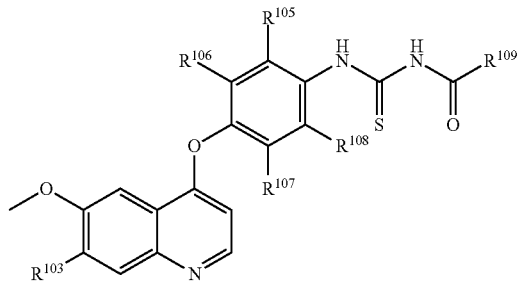

(100)

wherein $R^{103}$ represents hydroxyl or $C_{1-4}$ alkoxy which is optionally substituted by a halogen atom; hydroxyl; amino on which one or two hydrogen atoms are optionally substituted by $C_{1-6}$ alkyl which is optionally substituted by hydroxyl or $C_{1-6}$ alkoxy; or a saturated or unsaturated five- to seven-membered carbocyclic or heterocyclic group which is optionally substituted by $C_{1-6}$ alkyl which is optionally substituted by hydroxyl or $C_{1-6}$ alkoxy, $R^{105}$, $R^{106}$, $R^{107}$, and $R^{108}$, which may be the same or different, represents a hydrogen atom, a halogen atom, $C_{1-4}$ alkyl, or $C_{1-4}$ alkoxy, and $R^{109}$ represents $C_{1-6}$ alkyl on which one or more hydrogen atoms are optionally substituted by —$R^{114}$, -T-$R^{115}$, or —$NR^{116}R^{117}$ in which T represents —O—, —S—, or —NH—; $R^{114}$ represents saturated or unsaturated three- to eight-membered carbocyclic or heterocyclic group; $R^{115}$ represents $C_{1-6}$ alkyl or a saturated or unsaturated three- to eight-membered carbocyclic or heterocyclic group; $R^{116}$ and $R^{117}$, which may be the same or different, represent $C_{1-6}$ alkyl or a saturated or unsaturated three- to eight-membered carbocyclic or heterocyclic group; the three- to eight-membered carbocyclic or heterocyclic group represented by $R^{114}$, $R^{115}$, $R^{116}$, and $R^{117}$ is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring; when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group or a saturated or unsaturated three- to eight-membered carbocyclic or heterocyclic group which is optionally substituted by $C_{1-6}$ alkyl, $C_{1-6}$ alkoxy, a halogen atom, nitro, trifluoromethyl, $C_{1-6}$ alkoxycarbonyl, cyano, cyano $C_{1-6}$ alkyl, $C_{1-6}$ alkylthio, phenoxy, acetyl, or a saturated or unsaturated five- or six-membered heterocyclic ring; when the three- to eight-membered carbocyclic or heterocyclic group is substituted by two $C_{1-6}$ alkyl groups, the two alkyl groups may combine together to form an alkylene chain; and the three- to eight-membered carbocyclic or heterocyclic group may be a bicyclic group condensed with another saturated or unsaturated three- to eight-carbocyclic or heterocyclic group.

Preferably, all of $R^{105}$, $R^{106}$, $R^{107}$ and $R^{108}$ represent a hydrogen atom or alternatively any one of $R^{105}$, $R^{106}$, $R^{107}$ and $R^{108}$ represents a group other than a hydrogen atom with all the remaining groups representing a hydrogen atom.

In formula (100), the optionally substituted alkyl group represented by $R^{109}$ preferably represents $—(CH_2)p-R^{114}$, wherein p is an $—(CH_2)p-T-R^{115}$, or $—(CH_2)p-NR^{116}R^{117}$ integer of 1 to 6 and $R^{114}$, $R^{115}$, $R^{116}$, and $R^{117}$ are as defined above.

In $—N(—R^{118})(—R^{119})$ represented by $R^{109}$, preferably, $R^{118}$ represents a hydrogen atom or $C_{1-6}$ alkyl, and $R^{119}$ represents $C_{1-6}$ alkyl which is optionally substituted by an optionally substituted saturated or unsaturated five- or six-membered carbocyclic or heterocyclic group; or an optionally substituted saturated or unsaturated five- or six-membered carbocyclic or heterocyclic group.

Preferred examples of $R^{109}$ include benzyl, fluorobenzyl, difluorobenzyl, chlorobenzyl, methylbenzyl, methoxybenzyl, naphthyl, and thienyl.

Examples of preferred compounds according to the present invention include compounds of formula (200):

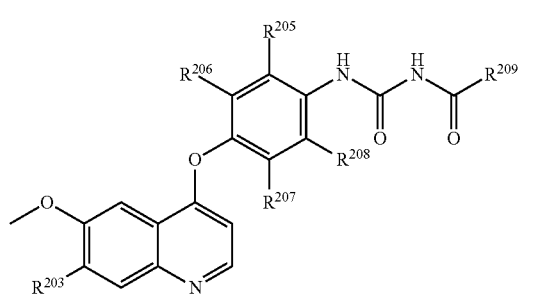

(200)

wherein
$R^{203}$ represents hydroxyl or $C_{1-2}$ alkoxy which is optionally substituted by a halogen atom; hydroxyl; amino on which one or two hydrogen atoms are optionally substituted by $C_{1-6}$ alkyl which is optionally substituted by hydroxyl or $C_{1-6}$ alkoxy; or a saturated or unsaturated five- to seven-membered carbocyclic or heterocyclic group which is optionally substituted by $C_{1-6}$ alkyl which is optionally substituted by hydroxyl or $C_{1-6}$ alkoxy, $R^{205}$, $R^{206}$, $R^{207}$ and $R^{208}$, which may be the same or different, represent a hydrogen atom, a halogen atom, $C_{1-4}$ alkyl, or $C_{1-4}$ alkoxy, and $R^{209}$ represents $C_{1-6}$ alkyl on which one or more hydrogen atoms are optionally substituted by $—R^{214}$, $-T-R^{215}$, or $—NR^{216}R^{217}$ wherein T represents $—O—$, $—S—$, or $—NH—$; $R^{214}$ represents a saturated or unsaturated three- to eight-membered carbocyclic or heterocyclic group; $R^{215}$ represents $C_{1-6}$ alkyl or a saturated or unsaturated three- to eight-membered carbocyclic or heterocyclic group; $R^{216}$ and $R^{217}$, which may be the same or different, represent $C_{1-6}$ alkyl or a saturated or unsaturated three- to eight-membered carbocyclic or heterocyclic group; the three- to eight-membered carbocyclic or heterocyclic group represented by $R^{214}$, $R^{215}$, $R^{216}$, and $R^{217}$ is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring; when the three- to eight-membered carbocyclic or heterocyclic group is substituted by two $C_{1-6}$ alkyl groups, the two alkyl groups may combine together to form an alkylene chain; and the three- to eight-membered carbocyclic or heterocyclic group may be a bicyclic group condensed with another saturated or unsaturated three- to eight-membered carbocyclic or heterocyclic group, or a saturated or unsaturated three- to eight-membered carbocyclic or heterocyclic group which is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring; when the three- to eight-membered carbocyclic or heterocyclic group is substituted by two $C_{1-6}$ alkyl groups, the two alkyl groups may combine together to form an alkylene chain; and the three- to eight-membered carbocyclic or heterocyclic group may be a bicyclic group condensed with another saturated or unsaturated three- to eight-membered carbocyclic or heterocyclic group.

Preferably, all of $R^{205}$, $R^{206}$, $R^{207}$, and $R^{208}$ represent a hydrogen atom, or alternatively any one of $R^{205}$, $R^{206}$, $R^{207}$, and $R^{208}$ represents a group other than a hydrogen atom with all the remaining groups representing a hydrogen atom.

In formula (200), preferably, the optionally substituted alkyl group represented by $R^{209}$ represents $—(CH_2)p-R^{214}$, $—(CH_2)p-T-R^{215}$, or $—(CH_2)p-NR^{216}R^{217}$ wherein p is an integer of 1 to 6, $R^{214}$, $R^{215}$, $R^{216}$, and $R^{217}$ are as defined above.

In $—N(—R^{218})(—R^{219})$ represented by $R^{209}$, preferably, $R^{218}$ represents a hydrogen atom or $C_{1-6}$ alkyl, and $R^{219}$ represents $C_{1-6}$ alkyl which is optionally substituted by an optionally substituted saturated or unsaturated five- or six-membered carbocyclic or heterocyclic group; or an optionally substituted saturated or unsaturated five- or six-membered carbocyclic or heterocyclic group.

Preferred examples of $R^{209}$ include benzyl, fluorobenzyl, difluorobenzyl, chlorobenzyl, methylbenzyl, and methoxybenzyl.

Examples of preferred compounds according to the present invention include compounds represented by formula (300):

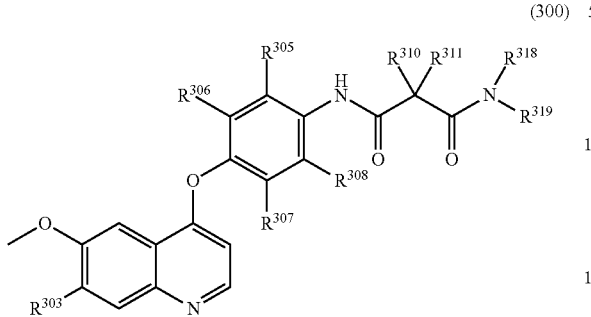

(300)

wherein $R^{303}$ represents hydroxyl or $C_{1-4}$ alkoxy which is optionally substituted by a halogen atom or a saturated or unsaturated six-membered carbocyclic or heterocyclic group which is optionally substituted by $C_{1-6}$ alkyl which is optionally substituted by hydroxyl or $C_{1-6}$ alkoxy, $R^{305}$, $R^{306}$, $R^{307}$, and $R^{308}$, which may be the same or different, represent a hydrogen atom, a halogen atom, $C_{1-4}$ alkyl, or $C_{1-4}$ alkoxy, $R^{310}$ and $R^{311}$ represent a hydrogen atom, $C_{1-4}$ alkyl, or $C_{1-4}$ alkoxy, $R^{318}$ represents a hydrogen atom or $C_{1-4}$ alkyl, $R^{319}$ represents $C_{1-4}$ alkyl which is optionally substituted by a saturated or unsaturated six-membered carbocyclic group which is optionally substituted by $C_{1-6}$ alkyl; $C_{1-6}$ alkoxy; a halogen atom; nitro; trifluoromethyl; $C_{1-6}$ alkoxy carbonyl; cyano; cyano $C_{1-6}$ alkyl; $C_{1-6}$ alkylthio; phenoxy; acetyl; or a saturated or unsaturated five- or six-membered heterocyclic ring and in which, when substituted by two $C_{1-6}$ alkyl groups, the two alkyl groups may combine together to form an alkylene chain, or may be a bicyclic group condensed with another saturated or unsaturated three- to eight-membered carbocyclic or heterocyclic group, or a saturated or unsaturated four- to seven-membered carbocyclic or heterocyclic group which is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring; when the four- to seven-membered carbocyclic or heterocyclic group is substituted by two $C_{1-6}$ alkyl groups, the two alkyl groups may combine together to form an alkylene chain; and the four- to seven-membered carbocyclic or heterocyclic group may be a bicyclic group condensed with another saturated or unsaturated three- to eight-membered carbocyclic or heterocyclic group.

Preferably, all of $R^{305}$, $R^{306}$, $R^{307}$, and $R^{308}$ represent a hydrogen atom, or alternatively any one of $R^{305}$, $R^{306}$ $R^{307}$, and $R^{308}$ represents a group other than a hydrogen atom with all the remaining groups representing a hydrogen atom.

Preferred examples of $R^{319}$ include phenyl, fluorophenyl, difluorophenyl, chlorophenyl, methylphenyl, and methoxyphenyl.

Examples of preferred compounds according to the present invention include compounds represented by formula (400):

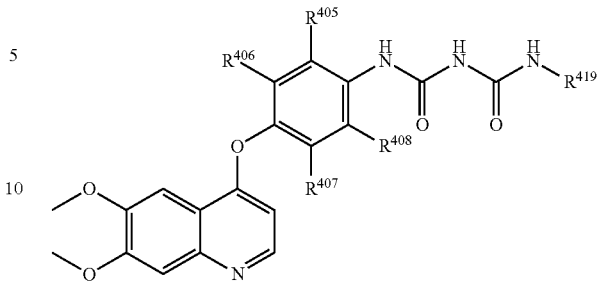

(400)

wherein $R^{405}$, $R^{406}$, $R^{407}$, and $R^{408}$, which may be the same or different, represent a hydrogen atom, a halogen atom, $C_{1-4}$ alkyl, or $C_{1-4}$ alkoxy, $R^{419}$ represents an unsaturated five- or six-membered carbocyclic or heterocyclic group which is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring; when the five- or six-membered carbocyclic or heterocyclic group is substituted by two $C_{1-6}$ alkyl groups, the two alkyl groups may combine together to form an alkylene chain; and the five- or six-membered carbocyclic or heterocyclic group may be a bicyclic group condensed with another saturated or unsaturated three- to eight-membered carbocyclic or heterocyclic group.

Preferably, all of $R^{405}$, $R^{406}$, $R^{407}$ and $R^{408}$ represent a hydrogen atom, or alternatively any one of $R^{405}$, $R^{406}$, $R^{407}$ and $R^{408}$ represents a group other than a hydrogen atom with all the remaining groups representing a hydrogen atom.

Preferred examples of $R^{419}$ include phenyl, fluorophenyl, difluorophenyl, chlorophenyl, methylphenyl, methoxyphenyl, pyridyl, isoxazolyl, and quinolyl.

Examples of preferred compounds according to the present invention include compounds represented by formula (500):

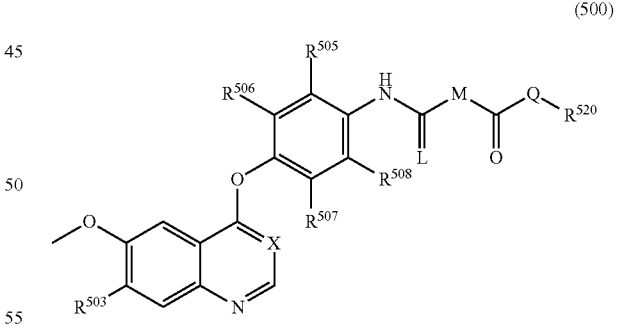

(500)

wherein

X represents CH or N, when L represents O and M represents —N(—$R^{12}$)—, Q represents $CH_2$ or NH, when L represents O and M represents —C(—$R^{10}$)(—$R^{11}$)—, Q represents NH, when L represents S and M represents —N(—$R^{12}$)—, Q represents $CH_2$, $R^{503}$ represents hydroxyl or $C_{1-4}$ alkoxy which is optionally substituted by a halogen atom; hydroxyl; amino on which one or two hydrogen atoms are optionally substituted by $C_{1-6}$ alkyl which is optionally substituted by hydroxyl or $C_{1-6}$ alkoxy; or a saturated or unsaturated five- to seven-membered carbocyclic or heterocyclic group which is optionally substituted by $C_{1-6}$ alkyl which is optionally substituted by hydroxyl or $C_{1-6}$ alkoxy, $R^{505}$, $R^{506}$, $R^{507}$, and $R^{508}$, which may be the same or different, represent a hydrogen atom, a halogen atom, $C_{1-4}$ alkyl, or $C_{1-4}$ alkoxy, and $R^{520}$ represents a saturated or unsaturated five- or six-membered carbocyclic or heterocyclic group which is optionally substituted by $C_{1-6}$ alkyl, $C_{1-6}$ alkoxy, or a halogen atom.

Preferably, all of $R^{505}$, $R^{506}$, $R^{507}$, and $R^{508}$ represent a hydrogen atom, or alternatively any one of $R^{505}$, $R^{506}$, $R^{507}$, and $R^{508}$ represents a group other than a hydrogen atom with all the remaining groups representing a hydrogen atom.

Examples of preferred compounds according to the present invention are as follows. The number attached to the compound represents the number of the corresponding working example described below.

(1)  N-[4-(6,7-dimethoxyquinolin-4-yloxy)-3-fluoro-phenyl]-N1-phenylacetylthiourea;
(2)  N-[4-(6,7-dimethoxyquinolin-4-yloxy)-3-fluoro-phenyl]-N'-[2-(4-fluorophenyl)acetyl]thiourea;
(3)  N-[4-(6,7-dimethoxyquinolin-4-yloxy)-2-fluoro-phenyl]-N'-[2-(4-fluorophenyl)acetyl]urea;
(4)  1-[4-(6,7-dimethoxyquinolin-4-yloxy)phenyl]-3-phenylacetylurea;
(5)  N-[4-(6,7-dimethoxyquinolin-4-yloxy)phenyl]-N'-(4-fluorophenyl)malonamide;
(6)  N-[3-chloro-4-(6,7-dimethoxyquinolin-4-yloxy)-phenyl]-N'-(2,4-difluorophenyl)malonamide;
(7)  1-(2-cyclopentylsulfanylacetyl)-3-[4-(6,7-dimethoxyquinolin-4-yloxy)phenyl]urea;
(8)  1-[3-chloro-4-(6,7-dimethoxyquinolin-4-yloxy)-phenyl]-3-[2-(2,3-dihydro-1H-1-indol-1-yl)acetyl]-urea;
(9)  N-phenyl-({[4-(6,7-dimethoxyquinolin-4-yloxy)-anilino]carbonyl}amino)methanamide;
(10)  N-(4-fluorophenyl)-({[4-(6,7-dimethoxy-quinolin-4-yloxy)anilino]carbonyl}amino)methanamide;
(11)  1-{3-fluoro-4-[6-methoxy-7-(3-morpholin-4-yl-propoxy)quinolin-4-yloxy]phenyl}-3-phenylacetylurea;
(12)  1-(3-fluoro-4-{6-methoxy-7-[4-(4-methyl-piperazin-1-yl)-butoxy]quinolin-4-yloxy}phenyl)-3-phenylacetylurea;
(13)  1-{3-fluoro-4-[6-methoxy-7-(2-piperidin-1-yl-ethoxy)quinolin-4-yloxy]phenyl}-3-phenylacetylurea;
(14)  1-{4-[7-(3-chloro-propoxy)-6-methoxyquinolin-4-yloxy]-3-fluorophenyl}-3-phenylacetylurea;
(15) N-(2,4-difluorophenyl)-N'-[4-(6,7-dimethoxy-quinolin-4-yloxy)phenyl]-2-methylmalonamide;
(16)  1-[4-(6,7-dimethoxyquinolin-4-yloxy)-2-fluoro-phenyl]-3-phenylacetylurea;
(17)  1-[4-(6,7-dimethoxyquinolin-4-yloxy)-3-fluoro-phenyl]-3-phenylacetylurea;
(18)  1-[3-chloro-4-(6,7-dimethoxyquinolin-4-yloxy)-phenyl]-3-phenylacetylurea;
(19)  1-[4-(6,7-dimethoxyquinolin-4-yloxy)-2-fluoro-phenyl]-3-(2-thiophen-3-ylacetyl)urea;
(20)  1-[4-(6,7-dimethoxyquinolin-4-yloxy)-3-fluoro-phenyl]-3-(2-thiophen-3-ylacetyl)urea;
(21)  1-[3-chloro-4-(6,7-dimethoxyquinolin-4-yloxy)-phenyl]-3-(2-thiophen-3-ylacetyl)urea;
(22)  1-[4-(6,7-dimethoxyquinolin-4-yloxy)phenyl]-3-[2-(4-fluorophenyl)acetyl]urea;
(23)  1-[4-(6,7-dimethoxyquinolin-4-yloxy)-3-fluoro-phenyl]-3-[2-(4-fluorophenyl)acetyl]urea;
(24)  1-[3-chloro-4-(6,7-dimethoxyquinolin-4-yloxy)phenyl]-3-[2-(4-fluorophenyl)acetyl]urea;
(25)  1-[4-(6,7-dimethoxyquinolin-4-yloxy)phenyl]-3-[2-(2-fluorophenyl)acetyl]urea;
(26)  1-[4-(6,7-dimethoxyquinolin-4-yloxy)-2-fluoro-phenyl]-3-[2-(2-fluorophenyl)acetyl]urea;
(27)  1-[4-(6,7-dimethoxyquinolin-4-yloxy)-3-fluoro-phenyl]-3-[2-(2-fluorophenyl)acetyl]urea;
(28)  1-[3-chloro-4-(6,7-dimethoxyquinolin-4-yloxy)-phenyl]-3-[2-(2-fluorophenyl)acetyl]urea;
(29)  1-[4-(6,7-dimethoxyquinolin-4-yloxy)phenyl]-3-(2-thiophen-2-ylacetyl)urea;
(30)  1-[4-(6,7-dimethoxyquinolin-4-yloxy)-2-fluoro-phenyl]-3-(2-thiophen-2-ylacetyl)urea;
(31)  1-[4-(6,7-dimethoxyquinolin-4-yloxy)-3-fluoro-phenyl]-3-(2-thiophen-2-ylacetyl)urea;
(32)  1-[3-chloro-4-(6,7-dimethoxyquinolin-4-yloxy)-phenyl]-3-(2-thiophen-2-ylacetyl)urea;
(33)  1-[2-(2,4-difluorophenyl)acetyl]-3-[4-(6,7-dimethoxyquinolin-4-yloxy)-2-fluorophenyl]urea;
(34)  1-[2-(2,4-difluorophenyl)acetyl]-3-[4-(6,7-dimethoxyquinolin-4-yloxy)-3-fluorophenyl]urea;
(35)  1-[2-(3,4-difluorophenyl)acetyl]-3-[4-(6,7-dimethoxyquinolin-4-yloxy)-3-fluorophenyl]urea;
(36)  1-[4-(6,7-dimethoxyquinolin-4-yloxy)-2-fluoro-phenyl]-3-[2-(3-fluorophenyl)acetyl]urea;
(37)  1-[4-(6,7-dimethoxyquinolin-4-yloxy)-3-fluoro-phenyl]-3-[2-(3-fluorophenyl)acetyl]urea;
(38) 1-[4-(6,7-dimethoxyquinolin-4-yloxy)-2-methoxyphenyl]-3-[2-(4-fluorophenyl)acetyl]urea;
(39)  1-[2-(3,4-difluorophenyl)acetyl]-3-[4-(6,7-dimethoxyquinolin-4-yloxy)phenyl]urea;
(40)  1-[4-(7-benzyloxy-6-methoxyquinolin-4-yloxy)-2-fluorophenyl]-3-[2-(4-fluorophenyl)acetyl]urea;
(41)  1-{3-fluoro-4-[6-methoxy-7-(4-morpholin-4-yl-butoxy)quinolin-4-yloxy]phenyl}-3-[2-(4-fluorophenyl)-acetyl]urea;
(42) 1-{3-fluoro-4-[6-methoxy-7-(4-piperidine-1-yl-butoxy)quinolin-4-yloxy]phenyl}-3-[2-(4-fluorophenyl)-acetyl]urea;
(43)  1-(3-fluoro-4-{6-methoxy-7-[4-(4-methyl-piperazin-1-yl)-butoxy]quinolin-4-yloxy}phenyl)-3-[2-(4-fluorophenyl)acetyl]urea;
(44)  1-{2-fluoro-4-[6-methoxy-7-(4-morpholin-4-yl-butoxy)quinolin-4-yloxy]phenyl}-3-[2-(4-fluorophenyl)-acetyl]urea;
(45) 1-{2-fluoro-4-[6-methoxy-7-(4-piperidine-1-yl-butoxy)quinolin-4-yloxy]phenyl}-3-[2-(4-fluorophenyl)-acetyl]urea;
(46)  1-{3-fluoro-4-[6-methoxy-7-(3-morpholin-4-yl-propoxy)quinolin-4-yloxy]phenyl}-3-[2-(4-fluorophenyl)-acetyl]urea;
(47)  1-{3-fluoro-4-[6-methoxy-7-(3-piperidin-1-yl-propoxy)quinolin-4-yloxy]phenyl}-3-[2-(4-fluorophenyl)-acetyl]urea;
(48)  1-{3-fluoro-4-[6-methoxy-7-(2-piperidin-1-yl-ethoxy)quinolin-4-yloxy]phenyl}-3-[2-(4-fluorophenyl)-acetyl]urea;
(49)  1-(3-fluoro-4-{6-methoxy-7-[2-(4-methyl-piperazin-1-yl)-ethoxy]quinolin-4-yloxy}phenyl)-3-[2-(4-fluorophenyl)acetyl]urea;
(50)  1-{2-fluoro-4-[6-methoxy-7-(3-piperidin-1-yl-propoxy)quinolin-4-yloxy]phenyl}-3-[2-(4-fluorophenyl)-acetyl]urea;
(51) 1-(2-fluoro-4-{6-methoxy-7-[3-(4-methyl-piperazin-1-yl)-propoxy]quinolin-4-yloxy}phenyl)-3-[2-(4-fluorophenyl)acetyl]urea;

(52) 1-{3-fluoro-4-[6-methoxy-7-(3-piperidin-1-yl-propoxy)quinolin-4-yloxy]phenyl}-3-phenylacetylurea;
(53) 1-(3-fluoro-4-{6-methoxy-7-[3-(4-methyl-piperazin-1-yl)-propoxy]quinolin-4-yloxy}phenyl)-3-phenylacetylurea;
(54) 1-{3-fluoro-4-[6-methoxy-7-(2-morpholin-4-ylethoxy)quinolin-4-yloxy]phenyl}-3-phenylacetylurea;
(55) 1-{3-fluoro-4-[6-methoxy-7-(2-morpholin-4-ylethoxy)quinolin-4-yloxy]phenyl}-3-[2-(4-fluorophenyl)-acetyl]urea;
(56) 1-[4-(6,7-dimethoxyquinolin-4-yloxy)phenyl]-3-(naphthalene-1-carbonyl)thiourea;
(57) 1-[4-(6,7-dimethoxyquinolin-4-yloxy)-2-fluoro-phenyl]-3-(naphthalene-1-carbonyl)thiourea;
(58) 1-[4-(6,7-dimethoxyquinolin-4-yloxy)-2-fluorophenyl]-3-phenylacetylthiourea;
(59) 1-[2-(2-chlorophenyl)acetyl]-3-[4-(6,7-dimethoxyquinolin-4-yloxy)phenyl]thiourea;
(60) 1-[4-(6,7-dimethoxyquinolin-4-yloxy)phenyl]-3-phenylacetylthiourea;
(61) 1-(2-cyclohexylacetyl)-3-[4-(6,7-dimethoxy-quinolin-4-yloxy)phenyl]thiourea;
(62) 1-[4-(6,7-dimethoxyquinolin-4-yloxy)phenyl]-3-(3-ethoxypropionyl)thiourea;
(63) 1-[3-chloro-4-(6,7-dimethoxyquinolin-4-yloxy)-phenyl]-3-phenylacetylthiourea;
(64) 1-[4-(6,7-dimethoxyquinolin-4-yloxy)-3-fluoro-phenyl]-3-(3-o-tolylpropionyl)thiourea;
(65) 1-[2-chloro-4-(6,7-dimethoxyquinolin-4-yloxy)-phenyl]-3-phenylacetylthiourea;
(66) 1-[4-(6,7-dimethoxyquinolin-4-yloxy)phenyl]-3-(2-thiophen-2-ylacetyl)thiourea;
(67) 1-[4-(6,7-dimethoxyquinolin-4-yloxy)-3-methyl-phenyl]-3-phenylacetylthiourea;
(68) 1-[4-(6,7-dimethoxyquinolin-4-yloxy)-3-methoxyphenyl]-3-phenylacetylthiourea;
(69) 1-[4-(6,7-dimethoxyquinolin-4-yloxy)-2-methoxyphenyl]-3-phenylacetylthiourea;
(70) 1-[3,5-dichloro-4-(6,7-dimethoxyquinolin-4-yloxy)phenyl]-3-phenylacetylthiourea;
(71) 1-[4-(6,7-dimethoxyquinolin-4-yloxy)phenyl]-3-[2-(4-fluorophenyl)acetyl]thiourea;
(72) 1-[4-(6,7-dimethoxyquinolin-4-yloxy)-2-fluoro-phenyl]-3-[2-(4-fluorophenyl)acetyl]thiourea;
(73) 1-[3-chloro-4-(6,7-dimethoxyquinolin-4-yloxy)-phenyl]-3-[2-(4-fluorophenyl)acetyl]thiourea;
(74) 1-[4-(6,7-dimethoxyquinolin-4-yloxy)-2-fluoro-phenyl]-3-[2-(3-fluorophenyl)acetyl]thiourea;
(75) 1-[4-(6,7-dimethoxyquinolin-4-yloxy)-3-fluoro-phenyl]-3-[2-(3-fluorophenyl)acetyl]thiourea;
(76) 1-[3-chloro-4-(6,7-dimethoxyquinolin-4-yloxy)-phenyl]-3-[2-(3-fluorophenyl)acetyl]thiourea;
(77) 1-[4-(6,7-dimethoxyquinolin-4-yloxy)phenyl]-3-(2-m-tolylacetyl)thiourea;
(78) 1-[3-chloro-4-(6,7-dimethoxyquinolin-4-yloxy)-phenyl]-3-(2-m-tolylacetyl)thiourea;
(79) 1-[4-(6,7-dimethoxyquinolin-4-yloxy)phenyl]-3-(2-o-tolylacetyl)thiourea;
(80) 1-[4-(6,7-dimethoxyquinolin-4-yloxy)-2-fluoro-phenyl]-3-[2-(2-fluorophenyl)acetyl]thiourea;
(81) 1-[4-(6,7-dimethoxyquinolin-4-yloxy)-3-fluoro-phenyl]-3-[2-(2-fluorophenyl)acetyl]thiourea;
(82) 1-[3-chloro-4-(6,7-dimethoxyquinolin-4-yloxy)-phenyl]-3-(2-p-tolylacetyl)thiourea;
(83) 1-[4-(6,7-dimethoxyquinolin-4-yloxy)-3-fluoro-phenyl]-3-[2-(2-methoxyphenyl)acetyl]thiourea;
(84) 1-[4-(6,7-dimethoxyquinolin-4-yloxy)-3-fluorophenyl]-3-(2-o-tolylacetyl)thiourea;
(85) 1-[4-(6,7-dimethoxyquinolin-4-yloxy)-3-fluoro-phenyl]-3-(2-thiophen-3-ylacetyl)thiourea;
(86) 1-[4-(6,7-dimethoxyquinolin-4-yloxy)-2-methoxyphenyl]-3-(2-thiophen-3-ylacetyl)thiourea;
(87) 1-[2-(2-chlorophenyl)acetyl]-3-[4-(6,7-dimethoxyquinolin-4-yloxy)-3-fluorophenyl]thiourea;
(88) 1-(2-bicyclo[2.2.1]hepto-7-ylacetyl)-3-[4-(6,7-dimethoxyquinolin-4-yloxy)phenyl]thiourea;
(89) 1-(2-bicyclo[2.2.1]hepto-7-ylacetyl)-3-[4-(6,7-dimethoxyquinolin-4-yloxy)phenyl]thiourea;
(90) 1-(2-bicyclo[2.2.1]hepto-7-ylacetyl)-3-[4-(6,7-dimethoxyquinolin-4-yloxy)-3-fluorophenyl]thiourea;
(91) 1-(2-bicyclo[2.2.1]hepto-7-ylacetyl)-3-[3-chloro-4-(6,7-dimethoxyquinolin-4-yloxy)phenyl]thiourea;
(92) 1-[4-(6,7-dimethoxyquinolin-4-yloxy)-2-fluoro-phenyl]-3-(2-p-tolylacetyl)thiourea;
(93) 1-[2-(2,4-difluorophenyl)acetyl]-3-[4-(6,7-dimethoxyquinolin-4-yloxy)-2-fluorophenyl]thiourea;
(94) 1-[2-(2,4-difluorophenyl)acetyl]-3-[4-(6,7-dimethoxyquinolin-4-yloxy)-3-fluorophenyl]thiourea;
(95) 1-[2-(2,6-difluorophenyl)acetyl]-3-[4-(6,7-dimethoxyquinolin-4-yloxy)-3-fluorophenyl]thiourea;
(96) 1-[2-(2,5-difluorophenyl)acetyl]-3-[4-(6,7-dimethoxyquinolin-4-yloxy)-2-fluorophenyl]thiourea;
(97) 1-[2-(2,6-dichlorophenyl)acetyl]-3-[4-(6,7-dimethoxyquinolin-4-yloxy)-3-fluorophenyl]thiourea;
(98) N-(2,4-difluorophenyl)-N'-[4-(6,7-dimethoxy-quinolin-4-yloxy)-2-fluorophenyl]malonamide;
(99) N-(2,4-difluorophenyl)-N'-[4-(6,7-dimethoxy-quinolin-4-yloxy)-3-fluorophenyl]malonamide;
(100) N-[4-(6,7-dimethoxyquinolin-4-yloxy)phenyl]-N'-phenylmalonamide;
(101) N-cycloheptyl-N'-[4-(6,7-dimethoxyquinolin-4-yloxy)phenyl]malonamide;
(102) N-(2,4-difluorophenyl)-N'-[4-(6,7-dimethoxy-quinolin-4-yloxy)phenyl]malonamide;
(103) N-(2,4-difluorophenyl)-N'-[4-(6,7-dimethoxy-quinolin-4-yloxy)phenyl]-2-methoxymalonamide;
(104) N-(2,4-difluorophenyl)-N'-[4-(6,7-dimethoxy-quinolin-4-yloxy)phenyl]-2,2-dimethylmalonamide;
(105) N-(4-methyl-2-pyridyl)-({[4-(6,7-dimethoxy-quinolin-4-yloxy)anilino]carbonyl}amino)methanamide;
(106) 1-[3-fluoro-4-(7-hydroxy-6-methoxyquinolin-4-yloxy)phenyl]-3-phenylacetylurea;
(107) 1-(2-chloro-benzoyl)-3-[4-(6,7-dimethoxy-quinolin-4-yloxy)-2-fluorophenyl]urea;
(108) 1-[4-(6,7-dimethoxyquinolin-4-yloxy)-2-fluorophenyl]-3-(2-methyl-benzoyl)urea;
(109) 1-[3-chloro-4-(6,7-dimethoxyquinolin-4-yloxy)phenyl]-3-pentanoylurea;
(110) 1-[3-chloro-4-(6,7-dimethoxyquinolin-4-yloxy)phenyl]-3-(2-diethylaminoacetyl)urea;
(111) 1-[3-chloro-4-(6,7-dimethoxyquinolin-4-yloxy)phenyl]-3-(2-pyrrolidin-1-ylacetyl)urea;
(112) 1-[3-chloro-4-(6,7-dimethoxyquinolin-4-yloxy)phenyl]-3-[2-(isopropylmethylamino)acetyl]urea;
(113) 1-(2-cyclohexylsulfanylacetyl)-3-[4-(6,7-dimethoxyquinolin-4-yloxy)phenyl]urea;
(114) 1-(2-cyclohexylsulfanylacetyl)-3-[4-(6,7-dimethoxyquinolin-4-yloxy)-2-fluorophenyl]urea;
(115) 1-(2-cyclohexylsulfanylacetyl)-3-[4-(6,7-dimethoxyquinolin-4-yloxy)-3-fluorophenyl]urea;
(116) 1-[3-chloro-4-(6,7-dimethoxyquinolin-4-yloxy)phenyl]-3-(2-cyclopentylsulfanylacetyl)urea;

(117) 1-[4-(6,7-dimethoxyquinolin-4-yloxy)phenyl]-3-(2-o-tolylaminoacetyl)urea;
(118) 1-[4-(6,7-dimethoxyquinolin-4-yloxy)phenyl]-3-(2-thiophen-3-ylacetyl)urea;
(119) 1-[4-(6,7-dimethoxyquinolin-4-yloxy)-2-fluorophenyl]-3-[2-(6-methyl-3,4-dihydro-2H-quinolin-1-yl)acetyl]urea;
(120) 1-[2-(4-benzyl-piperidin-1-yl)acetyl]-3-[4-(6,7-dimethoxyquinolin-4-yloxy)-3-fluorophenyl]urea;
(121) 1-[2-(2,3-dihydro-1H-1-indol-1-yl)acetyl]-3-[4-(6,7-dimethoxyquinolin-4-yloxy)-2-fluorophenyl]urea;
(122) 1-[2-(2,3-dihydro-1H-1-indol-1-yl)acetyl]-3-[4-(6,7-dimethoxyquinolin-4-yloxy)-3-fluorophenyl]urea;
(123) 1-[3-chloro-4-(6,7-dimethoxyquinolin-4-yloxy)phenyl]-3-(2-[1,2,3]triazol-1-ylacetyl)urea;
(124) 1-[4-(6,7-dimethoxyquinolin-4-yloxy)-2-fluorophenyl]-3-(2-p-tolylacetyl)urea;
(125) 1-(2-bicyclo[2.2.1]hepto-7-ylacetyl)-3-[4-(6,7-dimethoxyquinolin-4-yloxy)phenyl]urea;
(126) 1-(2-bicyclo[2.2.1]hepto-7-ylacetyl)-3-[4-(6,7-dimethoxyquinolin-4-yloxy)-2-fluorophenyl]urea;
(127) 1-(2-bicyclo[2.2.1]hepto-7-ylacetyl)-3-[4-(6,7-dimethoxyquinolin-4-yloxy)-3-fluorophenyl]urea;
(128) 1-(2-bicyclo[2.2.1]hepto-7-ylacetyl)-3-[3-chloro-4-(6,7-dimethoxyquinolin-4-yloxy)phenyl]urea;
(129) 1-[4-(6,7-dimethoxyquinolin-4-yloxy)phenyl]-3-(2-phenylsulfanylacetyl)urea;
(130) 1-[3-chloro-4-(6,7-dimethoxyquinolin-4-yloxy)phenyl]-3-[2-(1-methyl-1H-imidazol-2-ylsulfanyl)-acetyl]urea;
(131) 1-[3-chloro-4-(6,7-dimethoxyquinolin-4-yloxy)phenyl]-3-(2-thiomorpholin-4-ylacetyl)urea;
(132) 1-[3-chloro-4-(6,7-dimethoxyquinolin-4-yloxy)phenyl]-3-(2-thiomorpholin-4-ylacetyl)urea;
(133) 1-[2-(2,5-difluorophenyl)acetyl]-3-[4-(6,7-dimethoxyquinolin-4-yloxy)-3-fluorophenyl]urea;
(134) 1-[2-(2,6-difluorophenyl)acetyl]-3-[4-(6,7-dimethoxyquinolin-4-yloxy)-2-fluorophenyl]urea;
(135) 1-[2-(2,6-difluorophenyl)acetyl]-3-[4-(6,7-dimethoxyquinolin-4-yloxy)-3-fluorophenyl]urea;
(136) 1-[4-(6,7-dimethoxyquinolin-4-yloxy)-2-fluorophenyl]-3-[2-(2-trifluoromethylphenyl)acetyl]urea;
(137) 1-[4-(6,7-dimethoxyquinolin-4-yloxy)-3-fluorophenyl]-3-[2-(2-trifluoromethylphenyl)acetyl]urea;
(138) 1-[2-(2,3-difluorophenyl)acetyl]-3-[4-(6,7-dimethoxyquinolin-4-yloxy)-2-fluorophenyl]urea;
(139) 1-[2-(2,3-difluorophenyl)acetyl]-3-[4-(6,7-dimethoxyquinolin-4-yloxy)-3-fluorophenyl]urea;
(140) 1-[2-(3,4-difluorophenyl)acetyl]-3-[4-(6,7-dimethoxyquinolin-4-yloxy)-2-fluorophenyl]urea;
(141) 1-[2-(3,5-difluorophenyl)acetyl]-3-[4-(6,7-dimethoxyquinolin-4-yloxy)-2-fluorophenyl]urea;
(142) 1-[2-(3,5-difluorophenyl)acetyl]-3-[4-(6,7-dimethoxyquinolin-4-yloxy)-3-fluorophenyl]urea;
(143) 1-cyclopentanecarbonyl-3-[4-(6,7-dimethoxy-quinolin-4-yloxy)-2-fluorophenyl]thiourea;
(144) 1-[4-(6,7-dimethoxyquinolin-4-yloxy)-3-fluorophenyl]-3-(3-methoxybenzoyl)thiourea;
(145) 1-[4-(6,7-dimethoxyquinolin-4-yloxy)phenyl]-3-(3-trifluoromethyl-benzoyl)thiourea;
(146) 1-(2-bromobenzoyl)-3-[4-(6,7-dimethoxy-quinolin-4-yloxy)-3-fluorophenyl]thiourea;
(147) 1-[4-(6,7-dimethoxyquinolin-4-yloxy)-3-fluorophenyl]-3-(3-methylsulfanylpropionyl)thiourea;
(148) 1-(4-chloro-butyryl)-3-[4-(6,7-dimethoxy-quinolin-4-yloxy)-3-fluorophenyl]thiourea;
(149) 1-[3-chloro-4-(6,7-dimethoxyquinolin-4-yloxy)phenyl]-3-(2-o-tolylacetyl)thiourea;
(150) 1-[4-(6,7-dimethoxyquinolin-4-yloxy)phenyl]-3-(2-phenylcyclopropanecarbonyl)thiourea;
(151) 1-[4-(6,7-dimethoxyquinolin-4-yloxy)phenyl]-3-[2-(2-fluorophenyl)acetyl]thiourea;
(152) 1-[3-chloro-4-(6,7-dimethoxyquinolin-4-yloxy)phenyl]-3-[2-(2-fluorophenyl)acetyl]thiourea;
(153) 1-[4-(6,7-dimethoxyquinolin-4-yloxy)phenyl]-3-[2-(2-methoxyphenyl)acetyl]thiourea;
(154) 1-[4-(6,7-dimethoxyquinolin-4-yloxy)phenyl]-3-[2-(2-methoxyphenyl)acetyl]thiourea;
(155) 1-[4-(6,7-dimethoxyquinolin-4-yloxy)phenyl]-3-[2-(2-nitrophenyl)acetyl]thiourea;
(156) 1-[3-chloro-4-(6,7-dimethoxyquinolin-4-yloxy)phenyl]-3-[2-(2-nitrophenyl)acetyl]thiourea;
(157) 1-[3-chloro-4-(6,7-dimethoxyquinolin-4-yloxy)phenyl]-3-(2-phenoxyacetyl)thiourea;
(158) 1-[4-(6,7-dimethoxyquinolin-4-yloxy)phenyl]-3-(2-phenylpropionyl)thiourea;
(159) 1-[3-chloro-4-(6,7-dimethoxyquinolin-4-yloxy)phenyl]-3-(3-ethoxypropionyl)thiourea;
(160) 1-[4-(6,7-dimethoxyquinolin-4-yloxy)phenyl]-3-(5-methylthiophen-2-carbonyl)thiourea;
(161) 1-(3-cyclopentylpropionyl)-3-[4-(6,7-dimethoxyquinolin-4-yloxy)phenyl]thiourea;
(162) 1-[4-(6,7-dimethoxyquinolin-4-yloxy)-2-methylphenyl]-3-phenylacetylthiourea;
(163) 1-[4-(6,7-dimethoxyquinolin-4-yloxy)-2,5-dimethylphenyl]-3-phenylacetylthiourea;
(164) 1-[4-(6,7-dimethoxyquinolin-4-yloxy)phenyl]-3-[2-(3-fluorophenyl)acetyl]thiourea;
(165) 1-[4-(6,7-dimethoxyquinolin-4-yloxy)-3-fluorophenyl]-3-(3-ethoxypropionyl)thiourea;
(166) 1-(2-cyclohexylacetyl)-3-[4-(6,7-dimethoxy-quinolin-4-yloxy)-2-fluorophenyl]thiourea;
(167) 1-(2-butoxyacetyl)-3-[4-(6,7-dimethoxy-quinolin-4-yloxy)-3-fluorophenyl]thiourea;
(168) 1-[4-(6,7-dimethoxyquinolin-4-yloxy)phenyl]-3-(2-p-tolylacetyl)thiourea;
(169) 1-[4-(6,7-dimethoxyquinolin-4-yloxy)-2-fluorophenyl]-3-[2-(2-methoxyphenyl)acetyl]thiourea;
(170) 1-[4-(6,7-dimethoxyquinolin-4-yloxy)-2-fluorophenyl]-3-(2-o-tolylacetyl)thiourea;
(171) 1-[2-(3-chlorophenyl)acetyl]-3-[4-(6,7-dimethoxyquinolin-4-yloxy)phenyl]thiourea;
(172) 1-[2-(3-chlorophenyl)acetyl]-3-[4-(6,7-dimethoxyquinolin-4-yloxy)-2-fluorophenyl]thiourea;
(173) 1-[2-(3-chlorophenyl)acetyl]-3-[4-(6,7-dimethoxyquinolin-4-yloxy)-3-fluorophenyl]thiourea;
(174) 1-[3-chloro-4-(6,7-dimethoxyquinolin-4-yloxy)phenyl]-3-[2-(3-chlorophenyl)acetyl]thiourea;
(175) 1-[4-(6,7-dimethoxyquinolin-4-yloxy)-2-fluorophenyl]-3-(2-m-tolylacetyl)thiourea;
(176) 1-[4-(6,7-dimethoxyquinolin-4-yloxy)-3-fluorophenyl]-3-(2-m-tolylacetyl)thiourea;
(177) 1-[4-(6,7-dimethoxyquinolin-4-yloxy)phenyl]-3-(5-methyl-hexanoyl)thiourea;
(178) 1-[4-(6,7-dimethoxyquinolin-4-yloxy)-2-fluorophenyl]-3-(5-methyl-hexanoyl)thiourea;
(179) 1-[4-(6,7-dimethoxyquinolin-4-yloxy)-3-fluorophenyl]-3-(5-methyl-hexanoyl)thiourea;
(180) 1-[3-chloro-4-(6,7-dimethoxyquinolin-4-yloxy)phenyl]-3-(3-methoxy-propionyl)thiourea;
(181) 1-[4-(6,7-dimethoxyquinolin-4-yloxy)-3-fluorophenyl]-3-[2-(3-methoxyphenyl)acetyl]thiourea;

(182) 1-[2-(2-chlorophenyl)acetyl]-3-[4-(6,7-dimethoxyquinolin-4-yloxy)-2-fluorophenyl]thiourea;
(183) 1-[3-chloro-4-(6,7-dimethoxyquinolin-4-yloxy)phenyl]-3-[2-(2-chlorophenyl)acetyl]thiourea;
(184) 1-[4-(6,7-dimethoxyquinolin-4-yloxy)phenyl]-3-[2-(3-methoxyphenyl)acetyl]thiourea;
(185) 1-[4-(6,7-dimethoxyquinolin-4-yloxy)-2-fluorophenyl]-3-[2-(3-methoxyphenyl)acetyl]thiourea;
(186) 1-[3-chloro-4-(6,7-dimethoxyquinolin-4-yloxy)phenyl]-3-[2-(3-methoxyphenyl)acetyl]thiourea;
(187) 1-[2-(4-chlorophenyl)acetyl]-3-[4-(6,7-dimethoxyquinolin-4-yloxy)phenyl]thiourea;
(188) 1-[2-(4-chlorophenyl)acetyl]-3-[4-(6,7-dimethoxyquinolin-4-yloxy)-2-fluorophenyl]thiourea;
(189) 1-[3-chloro-4-(6,7-dimethoxyquinolin-4-yloxy)phenyl]-3-[2-(4-chlorophenyl)acetyl]thiourea;
(190) 1-[4-(6,7-dimethoxyquinolin-4-yloxy)-3-fluorophenyl]-3-(2-p-tolylacetyl)thiourea;
(191) 1-[4-(6,7-dimethoxyquinolin-4-yloxy)-2-fluorophenyl]-3-[2-(4-methyl-cyclohexyl)acetyl]thiourea;
(192) 1-[4-(6,7-dimethoxyquinolin-4-yloxy)-3-fluorophenyl]-3-[2-(4-methyl-cyclohexyl)acetyl]thiourea;
(193) 1-(2-butoxyacetyl)-3-[3-chloro-4-(6,7-dimethoxyquinolin-4-yloxy)phenyl]thiourea;
(194) 1-[2-(2,3-difluorophenyl)acetyl]-3-[4-(6,7-dimethoxyquinolin-4-yloxy)-2-fluorophenyl]thiourea;
(195) 1-[2-(2,5-difluorophenyl)acetyl]-3-[4-(6,7-dimethoxyquinolin-4-yloxy)-3-fluorophenyl]thiourea;
(196) 1-[2-(3,5-difluorophenyl)acetyl]-3-[4-(6,7-dimethoxyquinolin-4-yloxy)-2-fluorophenyl]thiourea;
(197) 1-[2-(3,5-difluorophenyl)acetyl]-3-[4-(6,7-dimethoxyquinolin-4-yloxy)-3-fluorophenyl]thiourea;
(198) 1-[2-(3,4-difluorophenyl)acetyl]-3-[4-(6,7-dimethoxyquinolin-4-yloxy)-2-fluorophenyl]thiourea;
(199) 1-[2-(3,4-difluorophenyl)acetyl]-3-[4-(6,7-dimethoxyquinolin-4-yloxy)-3-fluorophenyl]thiourea;
(200) 1-[4-(6,7-dimethoxyquinolin-4-yloxy)-2-fluorophenyl]-3-[2-(2-trifluoromethylphenyl)acetyl]-thiourea;
(201) 1-[4-(6,7-dimethoxyquinolin-4-yloxy)-3-fluorophenyl]-3-[2-(2-trifluoromethylphenyl)acetyl]-thiourea;
(202) 1-[4-(6,7-dimethoxyquinolin-4-yloxy)-2-fluorophenyl]-3-[2-(3-trifluoromethylphenyl)acetyl]-thiourea;
(203) 1-[4-(6,7-dimethoxyquinolin-4-yloxy)-3-fluorophenyl]-3-[2-(3-trifluoromethylphenyl)acetyl]-thiourea;
(204) 1-[4-(6,7-dimethoxyquinolin-4-yloxy)phenyl]-3-[2-(2,3,6-trifluorophenyl)acetyl]thiourea;
(205) 1-[4-(6,7-dimethoxyquinolin-4-yloxy)-2-fluorophenyl]-3-[2-(2,3,6-trifluorophenyl)acetyl]-thiourea;
(206) 1-[4-(6,7-dimethoxyquinolin-4-yloxy)-3-fluorophenyl]-3-[2-(2,3,6-trifluorophenyl)acetyl]-thiourea;
(207) 1-[3-chloro-4-(6,7-dimethoxyquinolin-4-yloxy)phenyl]-3-[2-(2,3,6-trifluorophenyl)acetyl]-thiourea;
(208) 1-[2-(2,6-dichlorophenyl)acetyl]-3-[4-(6,7-dimethoxyquinolin-4-yloxy)-2-fluorophenyl]thiourea;
(209) N-butyl-N'-[4-(6,7-dimethoxyquinolin-4-yloxy)phenyl]malonamide;
(210) N-(3-chlorophenyl)-N'-[4-(6,7-dimethoxy-quinolin-4-yloxy)phenyl]malonamide;
(211) N-[4-(6,7-dimethoxyquinolin-4-yloxy)phenyl]-N'-(2-methoxyphenyl)malonamide;
(212) N-cyclobutyl-N'-[4-(6,7-dimethoxyquinolin-4-yloxy)phenyl]malonamide;
(213) methyl 3-{2-[4-(6,7-dimethoxyquinolin-4-yloxy)phenylcarbamoyl]acetylamino}benzoate;
(214) N-[4-(6,7-dimethoxyquinolin-4-yloxy)phenyl]-N'-(1-phenylethyl)malonamide;
(215) N-benzyl-N'-[4-(6,7-dimethoxyquinolin-4-yloxy)phenyl]malonamide;
(216) N-[4-(6,7-dimethoxyquinolin-4-yloxy)phenyl]-N'-methyl-N'-phenylmalonamide;
(217) N-cyclohexyl-N'-[4-(6,7-dimethoxyquinolin-4-yloxy)phenyl]malonamide;
(218) N-cyclohexylmethyl-N'-[4-(6,7-dimethoxy-quinolin-4-yloxy)phenyl]malonamide;
(219) N-(4-chlorophenyl)-N'-[4-(6,7-dimethoxy-quinolin-4-yloxy)phenyl]malonamide;
(220) N-[4-(6,7-dimethoxyquinolin-4-yloxy)phenyl]-N'-(3-hydroxyphenyl)malonamide;
(221) N-[4-(6,7-dimethoxyquinolin-4-yloxy)phenyl]-N'-(3,3-dimethyl-butyl)malonamide;
(222) N-[2-chloro-4-(6,7-dimethoxyquinolin-4-yloxy)phenyl]-N'-(2,4-difluorophenyl)malonamide;
(223) N-(2,4-difluorophenyl)-N'-[4-(6,7-dimethoxy-quinolin-4-yloxy)-2-methylphenyl]malonamide;
(224) N-(2,4-difluorophenyl)-N'-[4-(6,7-dimethoxy-quinolin-4-yloxy)-2,5-dimethylphenyl]malonamide;
(225) N-[4-(6,7-dimethoxyquinolin-4-yloxy)phenyl]-2-methyl-N'-phenylmalonamide;
(226) N-cyclohexyl-N'-[4-(6,7-dimethoxyquinolin-4-yloxy)phenyl]-2-methylmalonamide;
(227) N-[4-(6,7-dimethoxyquinolin-4-yloxy)phenyl]-N'-pyridin-3-ylmalonamide;
(228) N-[4-(6,7-dimethoxyquinolin-4-yloxy)phenyl]-2,2-dimethyl-N'-phenylmalonamide;
(229) N-(2,4-difluorophenyl)-({[4-(6,7-dimethoxy-quinolin-4-yloxy)anilino]carbonyl}amino)methanamide;
(230) N-(3-bromo-5-methyl-2-pyridyl)-({[4-(6,7-dimethoxyquinolin-4-yloxy)anilino]carbonyl}amino)-methanamide;
(231) N-(5-chloro-2-pyridyl)-({[4-(6,7-dimethoxy-quinolin-4-yloxy)anilino]carbonyl}amino)methanamide;
(232) N-(5-methyl-3-isoxazolyl)-({[4-(6,7-dimethoxyquinolin-4-yloxy)anilino]carbonyl}amino)-methanamide;
(233) N-(3-methyl-2-pyridyl)-({[4-(6,7-dimethoxy-quinolin-4-yloxy)anilino]carbonyl}amino)methanamide;
(234) N-(6-methyl-2-pyridyl)-({[4-(6,7-dimethoxy-quinolin-4-yloxy)anilino]carbonyl}amino)methanamide;
(235) N-(5-methyl-2-pyridyl)-({[4-(6,7-dimethoxy-quinolin-4-yloxy)anilino]carbonyl}amino)methanamide;
(236) N-(2-pyridyl)-({[4-(6,7-dimethoxyquinolin-4-yloxy)anilino]carbonyl}amino)methanamide;
(237) N-(1-methyl-1H-5-pyrazolyl)-({[4-(6,7-dimethoxyquinolin-4-yloxy)anilino]carbonyl}amino)-methanamide;
(238) N-(2,3-dihydro-1,4-benzodioxin-6-yl)-({[4-(6,7-dimethoxyquinolin-4-yloxy)anilino]carbonyl}amino)-methanamide;
(239) N-(3-cyanophenyl)-({[4-(6,7-dimethoxy-quinolin-4-yloxy)anilino]carbonyl}amino)-methanamide;
(240) N-[2-(trifluoromethyl)phenyl]-({[4-(6,7-dimethoxyquinolin-4-yloxy)anilino]carbonyl}amino)methanamide;
(241) N-[4-(cyanomethyl)phenyl]-({[4-(6,7-dimethoxyquinolin-4-yloxy)anilino]carbonyl}amino)-methanamide;
(242) N-(4-chloro-2-methylphenyl)-({[4-(6,7-dimethoxyquinolin-4-yloxy)anilino]carbonyl}amino)-methanamide;
(243) N-(2,3-dihydro-1H-5-indenyl)-({[4-(6,7-dimethoxyquinolin-4-yloxy)anilino]carbonyl}amino)-methanamide;

(244) N-(3-methoxyphenyl)-({[4-(6,7-dimethoxy-quinolin-4-yloxy)anilino]carbonyl}amino)methanamide;
(245) methyl 2-({({[4-(6,7-dimethoxyquinolin-4-yloxy)anilino]carbonyl}amino)carbonyl}amino)benzoate;
(246) N-(2-benzylphenyl)-({[4-(6,7-dimethoxy-quinolin-4-yloxy)anilino]carbonyl}amino)methanamide;
(247) N-(2-bromophenyl)-({[4-(6,7-dimethoxy-quinolin-4-yloxy)anilino]carbonyl}amino)methanamide;
(248) N-(2-chlorophenyl)-({[4-(6,7-dimethoxy-quinolin-4-yloxy)anilino]carbonyl}amino)methanamide;
(249) N-(4-chlorophenyl)-({[4-(6,7-dimethoxy-quinolin-4-yloxy)anilino]carbonyl}amino)methanamide;
(250) N-(2-chloro-4-fluorophenyl)-({[4-(6,7-dimethoxyquinolin-4-yloxy)anilino]carbonyl}amino)-methanamide;
(251) N-(3-fluorophenyl)-({[4-(6,7-dimethoxy-quinolin-4-yloxy)anilino]carbonyl}amino)methanamide;
(252) N-(2-fluorophenyl)-({[4-(6,7-dimethoxy-quinolin-4-yloxy)anilino]carbonyl}amino)methanamide;
(253) N-[2-(methylsulfanyl)phenyl]-({[4-(6,7-dimethoxyquinolin-4-yloxy)anilino]carbonyl}amino)-methanamide;
(254) N-(4-nitrophenyl)-({[4-(6,7-dimethoxy-quinolin-4-yloxy)anilino]carbonyl}amino)methanamide;
(255) N-(2-phenoxyphenyl)-({[4-(6,7-dimethoxy-quinolin-4-yloxy)anilino]carbonyl}amino)methanamide;
(256) N-(3-methylphenyl)-({[4-(6,7-dimethoxy-quinolin-4-yloxy)anilino]carbonyl}amino)methanamide;
(257) N-(4-methylphenyl)-({[4-(6,7-dimethoxy-quinolin-4-yloxy)anilino]carbonyl}amino)methanamide;
(258) N-(2,6-dimethylphenyl)-({[4-(6,7-dimethoxy-quinolin-4-yloxy)anilino]carbonyl}amino)methanamide;
(259) N-[2-(1H-1-pyrrolyl)phenyl]-({[4-(6,7-dimethoxyquinolin-4-yloxy)anilino]carbonyl}amino)-methanamide;
(260) N-(8-quinolyl)-({[4-(6,7-dimethoxyquinolin-4-yloxy)anilino]carbonyl}amino)methanamide;
(261) N-(3-acetylphenyl)-({[4-(6,7-dimethoxy-quinolin-4-yloxy)anilino]carbonyl}amino)-methanamide;
(262) N-(5-quinolyl)-({[4-(6,7-dimethoxyquinolin-4-yloxy)anilino]carbonyl}amino)methanamide;
(263) N-(2,6-dichlorophenyl)-({[4-(6,7-dimethoxy-quinolin-4-yloxy)anilino]carbonyl}amino)methanamide;
(264) N-(3,4-difluorophenyl)-({[4-(6,7-dimethoxy-quinolin-4-yloxy)anilino]carbonyl}amino)methanamide;
(265) N-(2,6-difluorophenyl)-({[4-(6,7-dimethoxy-quinolin-4-yloxy)anilino]carbonyl}amino)methanamide;
(266) N-(2-methoxyphenyl)-({[4-(6,7-dimethoxy-quinolin-4-yloxy)anilino]carbonyl}amino)methanamide;
(267) N-[2-(2-hydroxyethyl)phenyl]-({[4-(6,7-dimethoxyquinolin-4-yloxy)anilino]carbonyl}amino)-methanamide;
(268) N-{3-fluoro-4-[6-methoxy-7-(3-morpholin-4-yl-propoxy)quinolin-4-yloxy]phenyl}-N'-phenylacetyl-thiourea;
(269) N-{3-fluoro-4-[6-methoxy-7-(3-morpholin-4-yl-propoxy)quinolin-4-yloxy]phenyl}-N'-(4-fluorophenyl)-malonamide;
(270) 1-(3-fluoro-4-{6-methoxy-7-[2-(4-methyl-piperazin-1-yl)-ethoxy]-quinolin-4-yloxy}-phenyl)-3-phenylacetyl-thiourea;
(271) 1-(3-fluoro-4-{6-methoxy-7-[2-(4-methyl-piperazin-1-yl)-ethoxy]-quinolin-4-yloxy}-phenyl)-3-[2-(4-fluoro-phenyl)-acetyl]-thiourea;
(272) 1-{4-[7-(2-diethylamino-ethoxy)-6-methoxy-quinolin-4-yloxy]-3-fluoro-phenyl}-3-phenylacetylthio-urea;
(273) 1-(3-fluoro-4-{6-methoxy-7-[2-(4-methyl-[1,4]diazepan-1-yl)-ethoxy]-quinolin-4-yloxy}-phenyl)-3-phenylacetyl-thiourea;
(275) 1-{4-[7-(2-diethylamino-ethoxy)-6-methoxy-quinolin-4-yloxy]-3-fluoro-phenyl}-3-[2-(4-fluoro-phenyl)-acetyl]-thiourea;
(276) 1-{3-fluoro-4-[6-methoxy-7-(2-morpholin-4-yl-ethoxy)-quinolin-4-yloxy]-phenyl}-3-phenylacetyl-thiourea;
(277) 1-{3-fluoro-4-[6-methoxy-7-(2-morpholin-4-yl-ethoxy)-quinolin-4-yloxy]-phenyl}-3-[2-(4-fluoro-phenyl)-acetyl]-thiourea;
(278) 1-{3-fluoro-4-[6-methoxy-7-(2-morpholin-4-yl-ethoxy)-quinolin-4-yloxy]-phenyl}-3-[2-(2-fluoro-phenyl)-acetyl]-thiourea;
(279) 1-{3-fluoro-4-[6-methoxy-7-(2-morpholin-4-yl-ethoxy)-quinolin-4-yloxy]-phenyl}-3-[2-(3-fluoro-phenyl)-acetyl]-thiourea;
(282) 1-(3-fluoro-4-{7-[2-(4-hydroxymethyl-piperidin-1-yl)-ethoxy]-6-methoxy-quinolin-4-yloxy}-phenyl)-3-[2-(4-fluoro-phenyl)-acetyl]-thiourea;
(283) 1-(3-fluoro-4-{7-[2-(4-hydroxymethyl-piperidin-1-yl)-ethoxy]-6-methoxy-quinolin-4-yloxy}-phenyl)-3-phenylacetylurea;
(284) 1-(3-fluoro-4-{7-[2-(4-hydroxymethyl-piperidin-1-yl)-ethoxy]-6-methoxy-quinolin-4-yloxy}-phenyl)-3-phenylacetyl-thiourea;
(285) 1-[2-(2-chloro-phenyl)-acetyl]-3-{3-fluoro-4-[6-methoxy-7-(3-morpholin-4-yl-propoxy)-quinolin-4-yloxy]-phenyl}-thiourea;
(286) 1-{2-fluoro-4-[(6-methoxy-7-(3-morpholin-4-yl-propoxy)-quinolin-4-yloxy]-phenyl}-3-[2-(4-fluoro-phenyl)-acetyl]-urea;
(287) 1-{2-fluoro-4-[6-methoxy-7-(3-morpholin-4-yl-propoxy)-quinolin-4-yloxy]-phenyl}-3-phenyl-acetyl-urea;
(288) 1-{3-fluoro-4-[6-methoxy-7-(3-morpholin-4-yl-propoxy)-quinolin-4-yloxy]-phenyl}-3-[2-(2-fluoro-phenyl)-acetyl]-thiourea;
(289) 1-{3-fluoro-4-[6-methoxy-7-(3-morpholin-4-yl-propoxy)-quinolin-4-yloxy]-phenyl}-3-[2-(3-fluoro-phenyl)-acetyl]-thiourea;
(291) 1-{4-[7-(3-diethylamino-propoxy)-6-methoxy-quinolin-4-yloxy]-3-fluoro-phenyl}-3-phenylacetyl-urea;
(292) 1-{3-fluoro-4-[6-methoxy-7-(3-pyrrolidin-1-yl-propoxy)-quinolin-4-yloxy]-phenyl}-3-phenylacetyl-urea;
(293) 1-{4-[7-(3-diethylamino-propoxy)-6-methoxy-quinolin-4-yloxy]-3-fluoro-phenyl}-3-[2-(2-fluoro-phenyl)-acetyl]-urea;
(294) 1-{3-fluoro-4-[6-methoxy-7-(3-pyrrolidin-1-yl-propoxy)-quinolin-4-yloxy]-phenyl}-3-[2-(2-fluoro-phenyl)-acetyl]-urea;
(295) 1-{3-fluoro-4-[6-methoxy-7-(3-piperidin-1-yl-propoxy)-quinolin-4-yloxy]-phenyl}-3-[2-(2-fluoro-phenyl)-acetyl]-urea;
(296) 1-(3-fluoro-4-{6-methoxy-7-[3-(4-methyl-piperazin-1-yl)-propoxy]-quinolin-4-yloxy}-phenyl)-3-[2-(2-fluoro-phenyl)-acetyl]-urea;
(297) 1-(3-fluoro-4-{6-methoxy-7-[3-(4-methyl-piperazin-1-yl)-propoxy]-quinolin-4-yloxy}-phenyl)-3-(2-m-toluoyl-acetyl)-thiourea;
(298) 1-{3-chloro-4-[6-methoxy-7-(3-morpholin-4-yl-propoxy)-quinolin-4-yloxy]-phenyl}-3-[2-(2-fluoro-phenyl)-acetyl]-thiourea;
(299) 1-{3-chloro-4-[6-methoxy-7-(3-morpholin-4-yl-propoxy)-quinolin-4-yloxy]-phenyl}-3-[2-(3-fluoro-phenyl)-acetyl]-thiourea;

(300) 1-{3-chloro-4-[6-methoxy-7-(3-morpholin-4-yl-propoxy)-quinolin-4-yloxy]-phenyl}-3-phenylacetyl-thiourea;
(301) 1-{3-chloro-4-[6-methoxy-7-(3-morpholin-4-yl-propoxy)-quinolin-4-yloxy]-phenyl}-3-(2-o-toluoyl-acetyl)-thiourea;
(302) 1-{3-fluoro-4-[6-methoxy-7-(3-morpholin-4-yl-propoxy)-quinolin-4-yloxy]-phenyl}-3-(2-o-toluoyl-acetyl)-thiourea;
(303) 1-{3-fluoro-4-[6-methoxy-7-(3-morpholin-4-yl-propoxy)-quinolin-4-yloxy]-phenyl}-3-(2-m-toluoyl-acetyl)-thiourea;
(304) 1-{3-fluoro-4-[6-methoxy-7-(3-morpholin-4-yl-propoxy)-quinolin-4-yloxy]-phenyl}-3-(2-p-toluoyl-acetyl)-thiourea;
(305) 1-{3-fluoro-4-[7-(3-imidazol-1-yl-propoxy)-6-methoxy-quinolin-4-yloxy]-phenyl}-3-phenylacetyl-urea;
(306) 1-{3-fluoro-4-[7-(3-imidazol-1-yl-propoxy)-6-methoxy-quinolin-4-yloxy]-phenyl}-3-[2-(2-fluoro-phenyl)-acetyl]-urea;
(307) 1-{3-fluoro-4-[(7-(3-imidazol-1-yl-propoxy)-6-methoxy-quinolin-4-yloxy]-phenyl}-3-phenylacetyl-thiourea;
(308) 1-(3-fluoro-4-{7-[3-(4-hydroxymethyl-piperidin-1-yl)-propoxy]-6-methoxy-quinolin-4-yloxy}-phenyl)-3-phenylacetyl-urea;
(309) (4-hydroxymethyl-phenyl)-3-phenylacetyl-thiourea;
(310) 1-(3-fluoro-4-{7-[3-(4-hydroxymethyl-piperidin-1-yl)-propoxy]-6-methoxy-quinolin-4-yloxy}-phenyl)-3-[2-(4-fluoro-phenyl)-acetyl]-thiourea;
(311) 1-(2-fluoro-4-{7-[3-(4-hydroxymethyl-piperidin-1-yl)-propoxy]-6-methoxy-quinolin-4-yloxy}-phenyl)-3-phenylacetyl-urea;
(312) 1-{3-fluoro-4-[7-(2-hydroxy-3-morpholin-4-yl-propoxy)-6-methoxy-quinolin-4-yloxy]-phenyl}-3-phenylacetyl-thiourea;
(313) 1-{3-fluoro-4-[7-(2-hydroxy-3-morpholin-4-yl-propoxy)-6-methoxy-quinolin-4-yloxy]-phenyl}-3-[2-(4-fluoro-phenyl)-acetyl]-thiourea;
(314) 1-[2-(2-chloro-phenyl)-acetyl]-3-{3-fluoro-4-[7-(2-hydroxy-3-morpholin-4-yl-propoxy)-6-methoxy-quinolin-4-yloxy]-phenyl}-thiourea;
(315) 1-{(3-fluoro-4-[7-(2-hydroxy-3-morpholin-4-yl-propoxy)-6-methoxy-quinolin-4-yloxy]-phenyl}-3-[2-(2-fluoro-phenyl)-acetyl]-thiourea;
(316) 1-[2-(2-chloro-phenyl)-acetyl]-3-{3-fluoro-4-[7-(2-hydroxy-3-piperidin-1-yl-propoxy)-6-methoxy-quinolin-4-yloxy]-phenyl}-thiourea;
(317) 1-[2-(2-chloro-phenyl)-acetyl]-3-{(3-fluoro-4-[7-(2-hydroxy-3-pyrrolidin-1-yl-propoxy)-6-methoxy-quinolin-4-yloxy]-phenyl}-thiourea;
(318) 1-{3-fluoro-4-[7-(2-hydroxy-3-piperidin-1-yl-propoxy)-6-methoxy-quinolin-4-yloxy]-phenyl}-3-[2-(2-fluoro-phenyl)-acetyl]-thiourea;
(319) 1-{3-fluoro-4-[7-(2-hydroxy-3-pyrrolidin-1-yl-propoxy)-6-methoxy-quinolin-4-yloxy]-phenyl}-3-[2-(2-fluoro-phenyl)-acetyl]-thiourea;
(320) 1-[2-(3-chloro-phenyl)-acetyl]-3-{3-fluoro-4-[7-(2-hydroxy-3-morpholin-4-yl-propoxy)-6-methoxy-quinolin-4-yloxy]-phenyl}-thiourea;
(321) 1-[2-(3-chloro-phenyl)-acetyl]-3-{3-fluoro-4-[7-(2-hydroxy-3-piperidin-1-yl-propoxy)-6-methoxy-quinolin-4-yloxy]-phenyl}-thiourea;
(322) 1-[2-(3-chloro-phenyl)-acetyl]-3-{3-fluoro-4-[7-(2-hydroxy-3-pyrrolidin-1-yl-propoxy)-6-methoxy-quinolin-4-yloxy]-phenyl}-thiourea;
(323) 1-{3-fluoro-4-[7-(2-hydroxy-3-morpholin-4-yl-propoxy)-6-methoxy-quinolin-4-yloxy]-phenyl}-3-[2-(3-fluoro-phenyl)-acetyl]-thiourea;
(324) 1-{3-fluoro-4-[7-(2-hydroxy-3-piperidin-1-yl-propoxy)-6-methoxy-quinolin-4-yloxy]-phenyl}-3-[2-(3-fluoro-phenyl)-acetyl]-thiourea;
(325) 1-{3-fluoro-4-[7-(2-hydroxy-3-pyrrolidin-1-yl-propoxy)-6-methoxy-quinolin-4-yloxy]-phenyl}-3-[2-(3-fluoro-phenyl)-acetyl]-thiourea;
(326) 1-[2-(4-chloro-phenyl)-acetyl]-3-{3-fluoro-4-[7-(2-hydroxy-3-morpholin-4-yl-propoxy)-6-methoxy-quinolin-4-yloxy]-phenyl}-thiourea;
(327) 1-[2-(4-chloro-phenyl)-acetyl]-3-{3-fluoro-4-[7-(2-hydroxy-3-piperidin-1-yl-propoxy)-6-methoxy-quinolin-4-yloxy]-phenyl}-thiourea;
(328) 1-[2-(4-chloro-phenyl)-acetyl]-3-{3-fluoro-4-[7-(2-hydroxy-3-pyrrolidin-1-yl-propoxy)-6-methoxy-quinolin-4-yloxy]-phenyl}-thiourea;
(329) 1-{3-fluoro-4-[7-(2-hydroxy-3-piperidin-1-yl-propoxy)-6-methoxy-quinolin-4-yloxy]-phenyl}-3-[2-(4-fluoro-phenyl)-acetyl]-thiourea;
(330) 1-{3-fluoro-4-[7-(2-hydroxy-3-pyrrolidin-1-yl-propoxy)-6-methoxy-quinolin-4-yloxy]-phenyl}-3-[2-(4-fluoro-phenyl)-acetyl]-thiourea;
(331) 1-{3-fluoro-4-[7-(2-hydroxy-3-piperidin-1-yl-propoxy)-6-methoxy-quinolin-4-yloxy]-phenyl}-3-(2-phenylacetyl)-thiourea;
(332) 1-{3-fluoro-4-[7-(2-hydroxy-3-pyrrolidin-1-yl-propoxy)-6-methoxy-quinolin-4-yloxy]-phenyl}-3-(2-phenylacetyl)-thiourea;
(333) 1-{3-fluoro-4-[7-(2-hydroxy-3-morpholin-1-yl-propoxy)-6-methoxy-quinolin-4-yloxy]-phenyl}-3-(2-O—toluoyl-acetyl)-thiourea;
(334) 1-{3-fluoro-4-[7-(2-hydroxy-3-morpholin-1-yl-propoxy)-6-methoxy-quinolin-4-yloxy]-phenyl}-3-(2-m-toluoyl-acetyl)-thiourea;
(335) 1-{3-fluoro-4-[7-(2-hydroxy-3-morpholin-1-yl-propoxy)-6-methoxy-quinolin-4-yloxy]-phenyl}-3-(2-p-toluoyl-acetyl)-thiourea;
(336) 1-{3-fluoro-4-[7-(2-hydroxy-3-morpholin-1-yl-propoxy)-6-methoxy-quinolin-4-yloxy]-phenyl}-3-[2-(4-fluoro-phenyl)-acetyl]-urea; and
(337) 1-{3-fluoro-4-[7-(2-hydroxy-3-morpholin-1-yl-propoxy)-6-methoxy-quinolin-4-yloxy]-phenyl}-3-(2-phenylacetyl)-urea.

Examples of particularly preferred compounds according to the present invention include compounds 1 to 6, 9 to 13, 16 to 39, 42, 43, 49, 52 to 54, 56 to 102, 105, 106, 266 to 269, 285, 286, 288, 312, 313, 333, and 334.

Examples of most preferred compounds according to the present invention include compounds 1, 2, 3, 11, and 268.

The compounds according to the present invention may form pharmaceutically acceptable salts thereof. Preferred examples of such salts include: alkali metal or alkaline earth metal salts such as sodium salts, potassium salts or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

The compounds according to the present invention may form solvates. Such solvates include, for example, hydrates, alcoholates, for example, methanolates and ethanolates, and etherates, for example, diethyl etherate.

Production of Compounds

Compounds according to the present invention may be produced, for example, according to schemes 1 to 9. Starting compounds necessary for the synthesis of the compounds according to the present invention are commercially available or alternatively can be easily produced by conventional methods. In the schemes, $R^1$, $R^2$, $R^3$, $R^4$, $R^5$, $R^6$, $R^7$, $R^8$, $R^9$, $R^{10}$, $R^{11}$, $R^{18}$, $R^{19}$, and X are as defined above; PG represents a protective group; $R^{3'}O$ represents optionally substituted alkoxy; Hal represents a halogen atom; $R^{51}$ and $R^{52}$, which may be the same or different, represent optionally substituted $C_{1-6}$ alkyl, or alternatively $R^{51}$ and $R^{52}$ may combine to form a saturated or unsaturated three- to eight-membered heterocylic ring together with a nitrogen atom attached thereto; and n is an integer of 1 to 6.

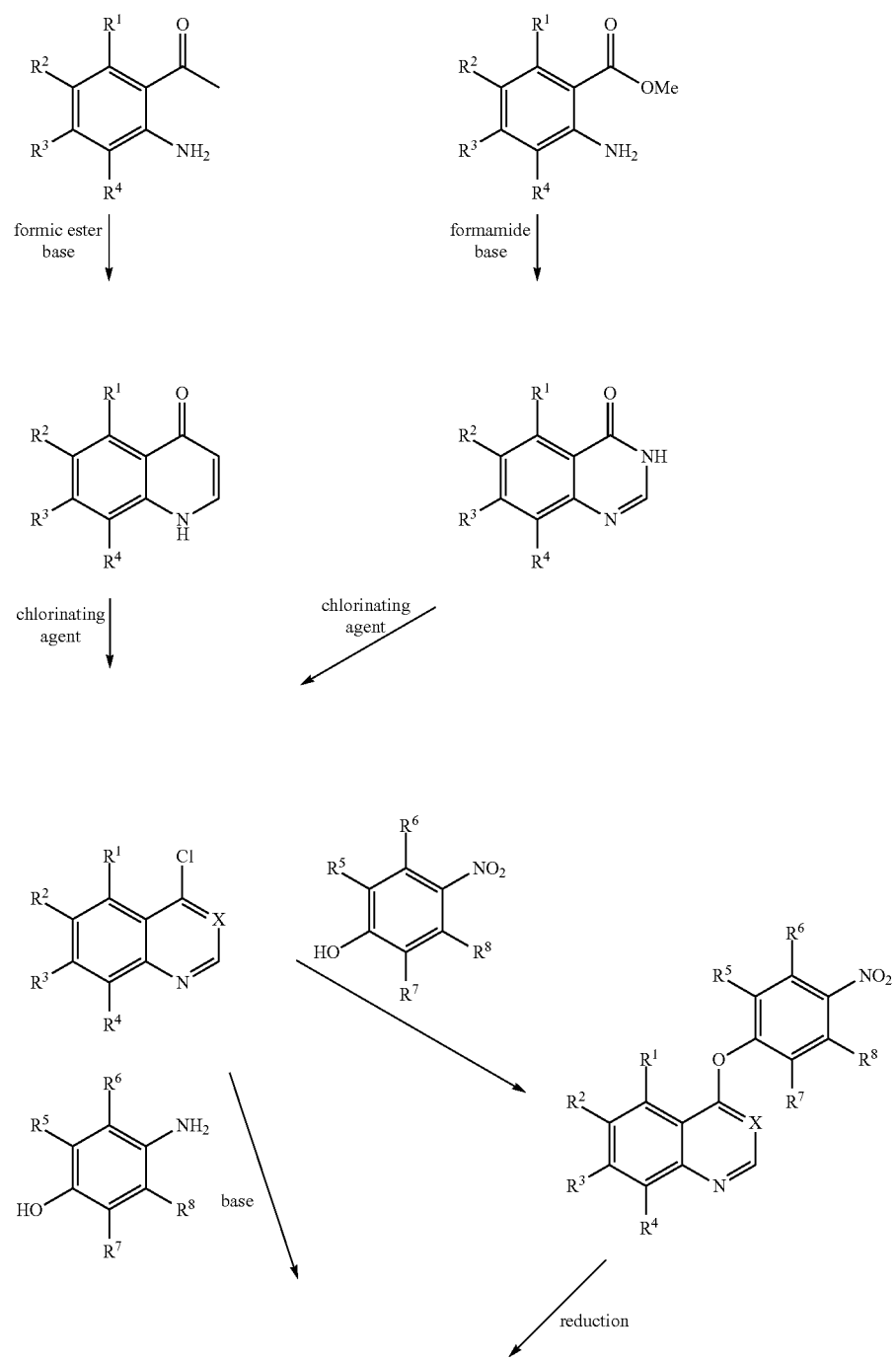

Scheme 1: Production of 4-(aminophenoxy)quinoline derivatives and corresponding quinazoline derivatives -continued

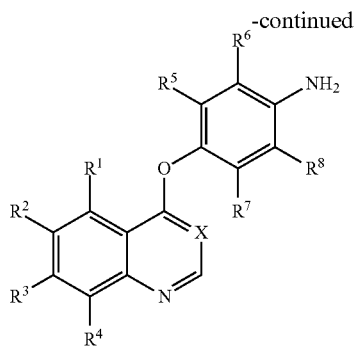

For example, a 4-chloroquinoline derivative can be synthesized by a conventional method as described, for example, in Org. Synth. Col. Vol. 3, 272 (1955), Acta Chim. Hung., 112, 241 (1983), or WO 98/47873. Scheme 1 shows an example of the synthesis of the 4-chloroquinoline derivative. A quinolone derivative is produced by reacting a 2-aminoacetophenone derivative with a formic ester, for example, ethyl formate, in a suitable solvent, for example, tetrahydrofuran, in the presence of a base, for example, sodium methoxide. The 4-chloroquinoline derivative is produced by reacting the quinolone derivative in the presence of a chlorinating agent, for example, phosphorus oxychloride.

For example, a 4-chloroquinazoline derivative may be produced as follows. A quinazolone derivative is produced by reacting a 2-aminobenzoic acid derivative with formamide in a suitable solvent, for example, a mixed solvent composed of N,N-dimethylformamide and methanol, in the presence of a base, for example, sodium methoxide. The 4-chloroquinazoline derivative is produced by reacting the quinazolone derivative in the presence of a chlorinating agent, for example, phosphorus oxychloride.

Next, a 4-(aminophenoxy)quinoline derivative or a corresponding quinazoline derivative is produced by reacting a nitrophenol derivative with the 4-chloroquinoline derivative or corresponding quinazoline derivative in a suitable solvent, for example, chlorobenzene, to synthesize a 4-(nitrophenoxy)quinoline derivative or a corresponding quinazoline derivative and then reacting the 4-(nitrophenoxy)quinoline derivative or corresponding quinazoline derivative in a suitable solvent, for example, N,N-dimethyl formamide, in the presence of a catalyst, for example, palladium hydroxide-carbon, palladium-carbon, under a hydrogen atmosphere. The nitro group can also be reduced with zinc, iron or the like.

Alternatively, the 4-(aminophenoxy)quinoline derivative or corresponding quinazoline derivative may be produced by reacting an aminophenol derivative with the 4-chloroquinoline derivative or corresponding quinazoline derivative in a suitable solvent, for example, dimethyl sulfoxide, in the presence of a base, for example, sodium hydride. Alternatively, the 4-(aminophenoxy)quinazoline derivative may also be produced by dissolving an aminophenol derivative in an aqueous sodium hydroxide solution and subjecting the solution to a two-phase reaction with a solution of the 4-chloroquinazoline derivative in a suitable organic solvent, for example, ethyl methyl ketone, in the presence of a phase transfer catalyst, for example, tetra-n-butylammonium chloride, or in the absence of the catalyst.

Scheme 2: Production of compounds of formula (I)

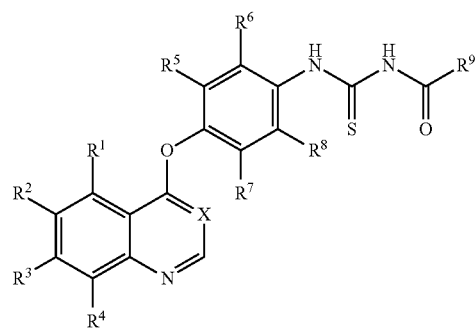

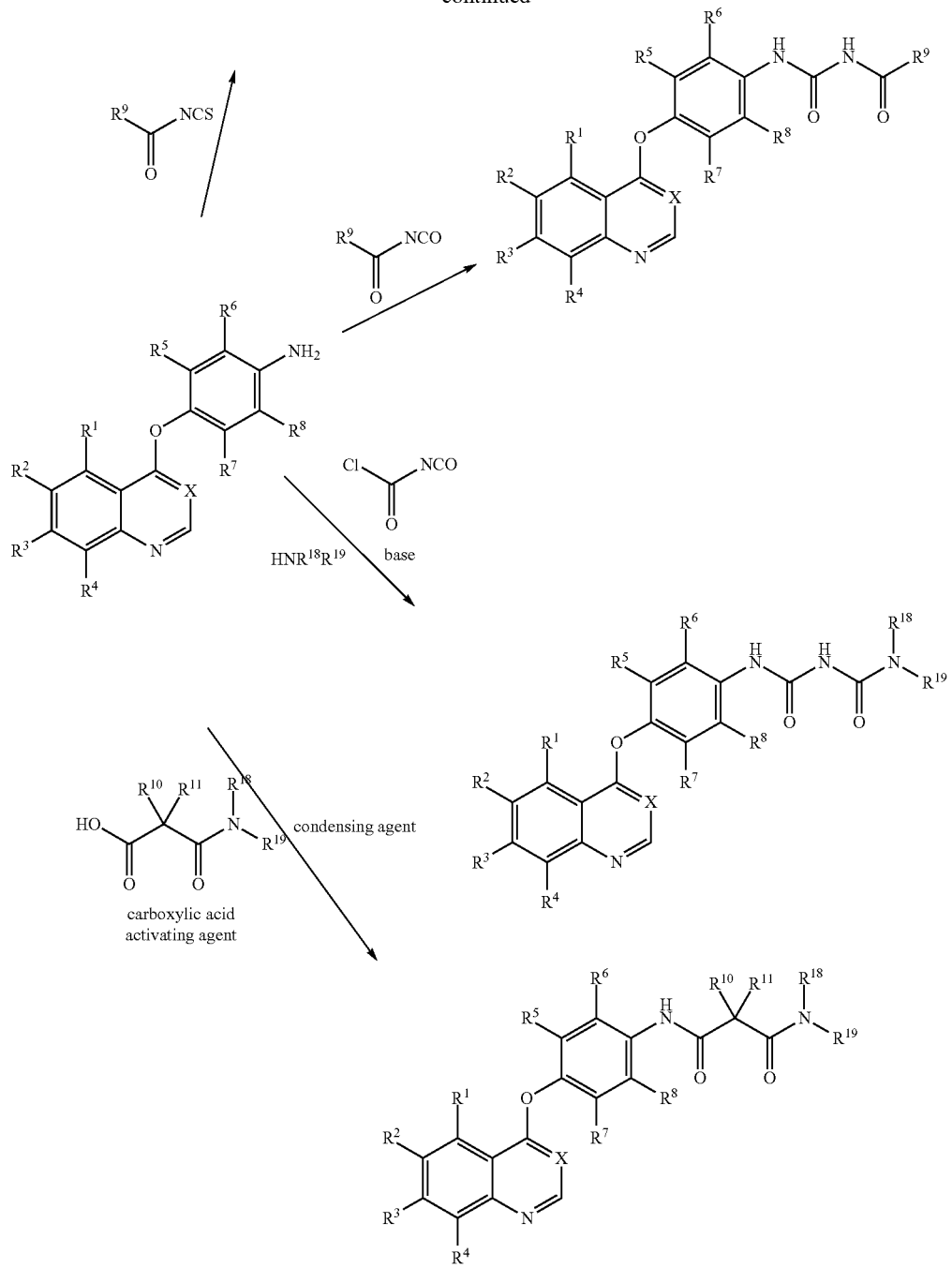

A carbonylthiourea derivative is produced by reacting a 4-(aminophenoxy)quinoline derivative or a quinazoline derivative with a carbonyl thioisocyanate derivative in a suitable solvent, for example, a mixed solvent composed of toluene and ethanol. The carbonyl thioisocyanate derivative is commercially available or can be easily produced by a conventional method. For example, the carbonyl thioisocyanate derivative is produced by reacting an acid chloride derivative with potassium thiocyanate in a suitable solvent, for example, acetonitrile.

A carbonylurea derivative is produced by reacting a 4-(aminophenoxy)quinoline derivative or a quinazoline derivative with a carbonyl isocyanate derivative in a suitable solvent, for example, N,N-dimethylformamide. The carbonyl isocyanate derivative is commercially available or can be easily produced by a conventional method. For example, as described in J. Org. Chem., 30, 4306 (1965), the carbonyl isocyanate derivative is produced by reacting an amide derivative with oxalyl chloride in a suitable solvent, for example, 1,2-dichloroethane.

An aminocarbonylurea derivative is produced by reacting a 4-(aminophenoxy)quinoline derivative or a quinazoline derivative with N-(chlorocarbonyl) isocyanate in a suitable solvent, for example, dichloromethane, in the presence of a base, for example, diisopropylamine and then reacting the product with an amine derivative.

An amide derivative is produced by reacting a 4-(aminophenoxy)quinoline derivative or a quinazoline derivative with a carboxylic acid derivative or a metal salt thereof in a suitable solvent, for example, in chloroform, in the presence of a condensing agent, for example, 1-ethyl-3-(3-dimethylaminopropyl)carbodiimide hydrochloride and a carboxylic acid activating agent, for example, 1-hydroxybenzotriazole monohydrate.

Scheme 3: Production of 4-(aminophenoxy)quinoline derivative in which 7-position of quinoline ring has been modified with specific group

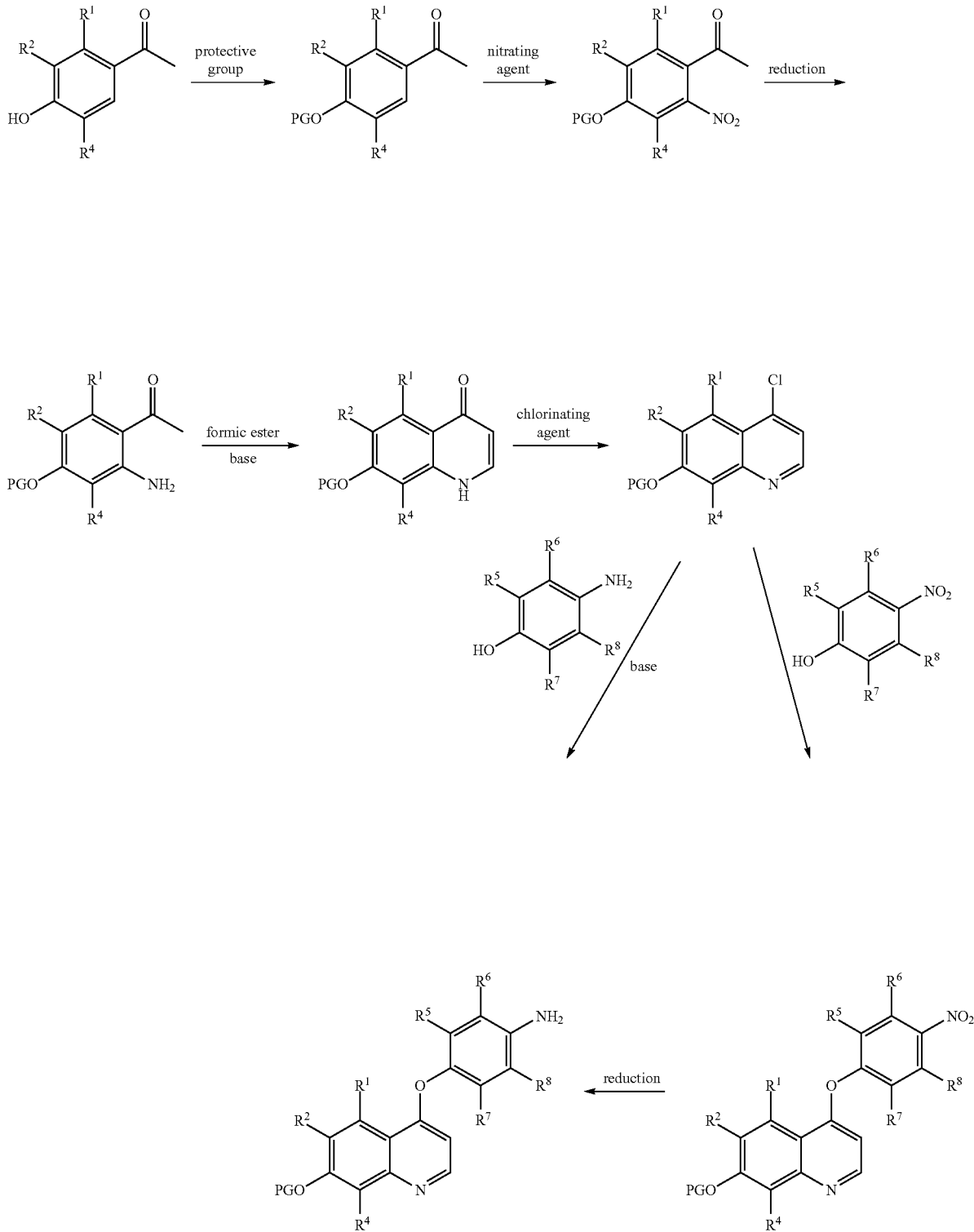

For example, a derivative having a specific substituent at the 7-position of the quinoline ring can be produced according to scheme 3. A nitro group can be introduced by protecting a commercially available 4'-hydroxyacetophenone derivative with a suitable substituent, for example, benzyl, and then reacting the protected 4'-hydroxyacetophenone derivative with a nitrating agent, for example, fuming nitric acid-acetic acid. The later steps are carried out as shown in scheme 1. Specifically, the nitro group is reduced to an amino group which is then reacted with a formic ester in the presence of a base to give a quinolone ring. Next, the quinolone ring is reacted with a chlorinating agent to give a 4-chloroquinoline derivative. In the chlorination reaction, when phosphorus oxychloride is used as the chlorinating agent, the yield can be improved by adding a base, for example, N,N-diisopropylethylamine. Next, a 4-(aminophenoxy)quinoline derivative is produced by reacting the nitrophenol derivative with a 4-chloroquinoline derivative to synthesize a 4-(nitrophenoxy)quinoline derivative which is then reacted in a suitable solvent in a hydrogen atmosphere in the presence of a catalyst. The nitro group can also be reduced with zinc, iron or the like. Alternatively, the 4-(aminophenoxy)quinoline derivative may be produced by reacting an aminophenol derivative with a 4-chloroquinoline derivative in the presence of a base.

Scheme 4: Production of 4-(aminophenoxy)quinazoline derivative in which 7-position of quinazoline ring has been modified with specific group

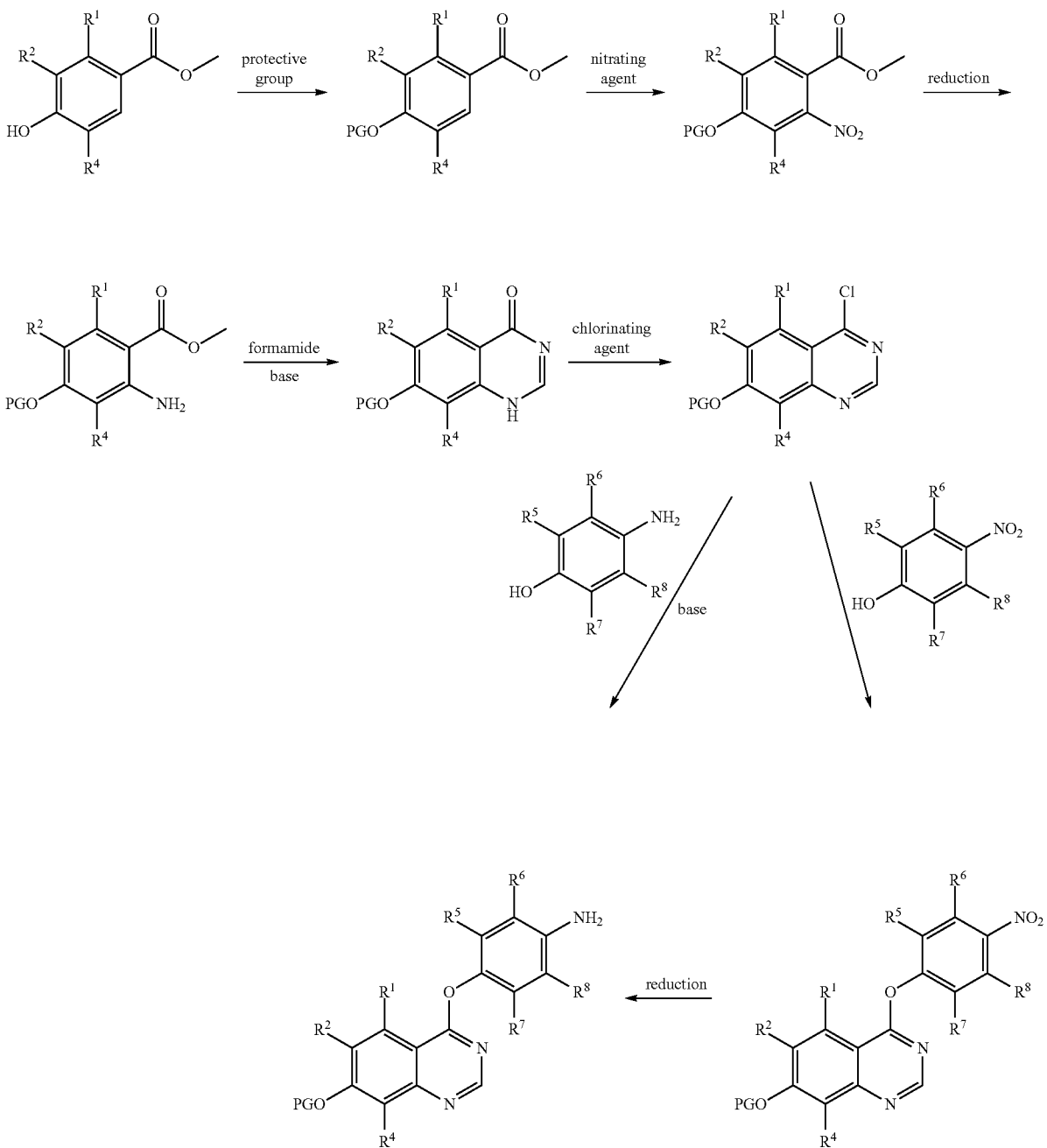

For example, a derivative having a specific substituent at the 7-position of the quinazoline ring can be produced according to scheme 4. A nitro group can be introduced by protecting a hydroxyl group in a commercially available 4'-hydroxybenzoic acid ester derivative with a suitable substituent, for example, benzyl, and then reacting the product with a nitrating agent, for example, fuming nitric acid-acetic acid. Later steps are carried out as shown in scheme 1. Specifically, a quinazolone ring is formed by reducing the nitro group to an amino group and then reacting the product with formamide in the presence of a base. Next, a 4-chloroquinazoline derivative can be produced by reacting the product with a chlorinating agent. In the chlorination reaction, when phosphorus oxychloride is used as a chlorinating agent, the addition of a base, for example, N,N-diisopropylethylamine can improve the yield. Next, a 4-(aminophenoxy)quinazoline derivative is produced by reacting the nitrophenol derivative with a 4-chloroquinazoline derivative to synthesize a 4-(nitrophenoxy)quinazoline derivative which is then reacted in a suitable solvent in a hydrogen atmosphere in the presence of a catalyst. The nitro group can also be reduced with zinc, iron or the like. The 4-(aminophenoxy)quinazoline derivative may also be produced by reacting an aminophenol derivative with a 4-chloroquinazoline derivative in the presence of a base. Alternatively, the 4-(aminophenoxy)quinazoline derivative may be produced by dissolving an aminophenol derivative in an aqueous sodium hydroxide solution and subjecting the solution to a two-phase reaction with a solution of the 4-chloroquinazoline derivative in an organic solvent in the presence of a phase transfer catalyst or in the absence of the catalyst.

Scheme 5: Production of carbonylthiourea derivatives in which 7-position of quinoline ring or quinazoline ring has been modified with specific group (compounds of formula (I) where in L = ——S—— and M = ——NR$^{12}$——)

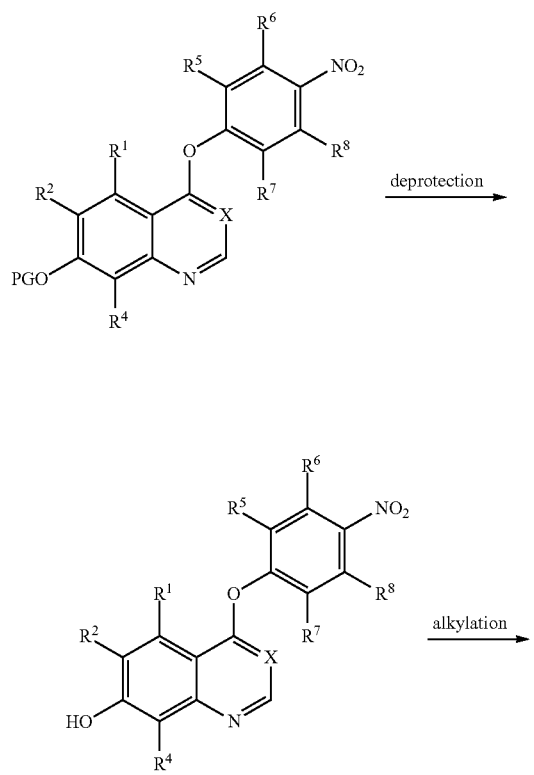

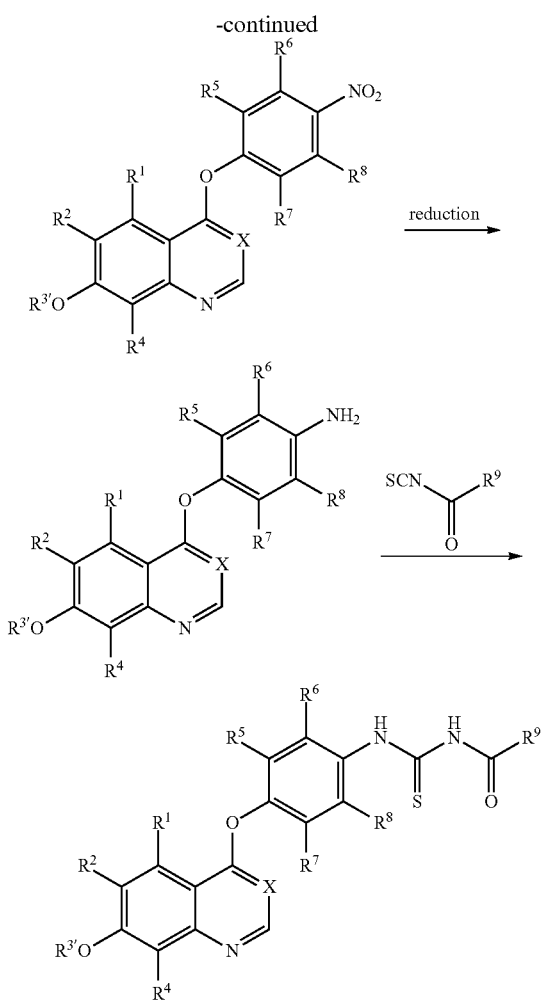

For example, a carbonylthiourea derivative having a specific substituent at the 7-position of the quinoline or quinazoline ring can be produced according to scheme 5. Specifically, a 7-hydroxyquinoline derivative or a corresponding 7-hydroxyquinazoline derivative is produced by removing the protective group of the hydroxyl group in the 4-(nitrophenoxy)quinoline derivative or quinazoline derivative produced in scheme 3 or 4 under suitable conditions. For example, when the protective group is benzyl, for example, the deprotection reaction is carried out in N,N-dimethylformamide in a hydrogen atmosphere in the presence of palladium hydroxide-carbon or palladium-carbon. Next, a 4-((aminophenoxy)quinoline derivative or a corresponding quinazoline derivative is produced by alkylating the 7-hydroxyquinoline derivative or corresponding 7-hydroxyquinazoline derivative under suitable conditions, for example, by reacting the 7-hydroxyquinoline derivative or corresponding 7-hydroxyquinazoline derivative with an alkyl halide in a suitable solvent in the presence of a base and then reacting the alkylation product in a suitable solvent, for example, N,N-dimethylformamide, in a hydrogen atmosphere in the presence of a catalyst, for example, palladium hydroxide-carbon or palladium-carbon. The nitro group can also be reduced with zinc, iron or the like. Later steps are carried out as shown in scheme 2. Specifically, a carbonylthiourea derivative is produced by reacting the 4-(aminophenoxy)quinoline derivative or the quinazoline derivative with a carbonylthio isocyanate derivative in a suitable solvent.

Scheme 6: Production of carbonylurea derivatives in which 7-position of quinoline ring or quinazoline ring has been modified with specific group (compounds of formula (I) where in L = —O— and M = —NR$^{12}$—)

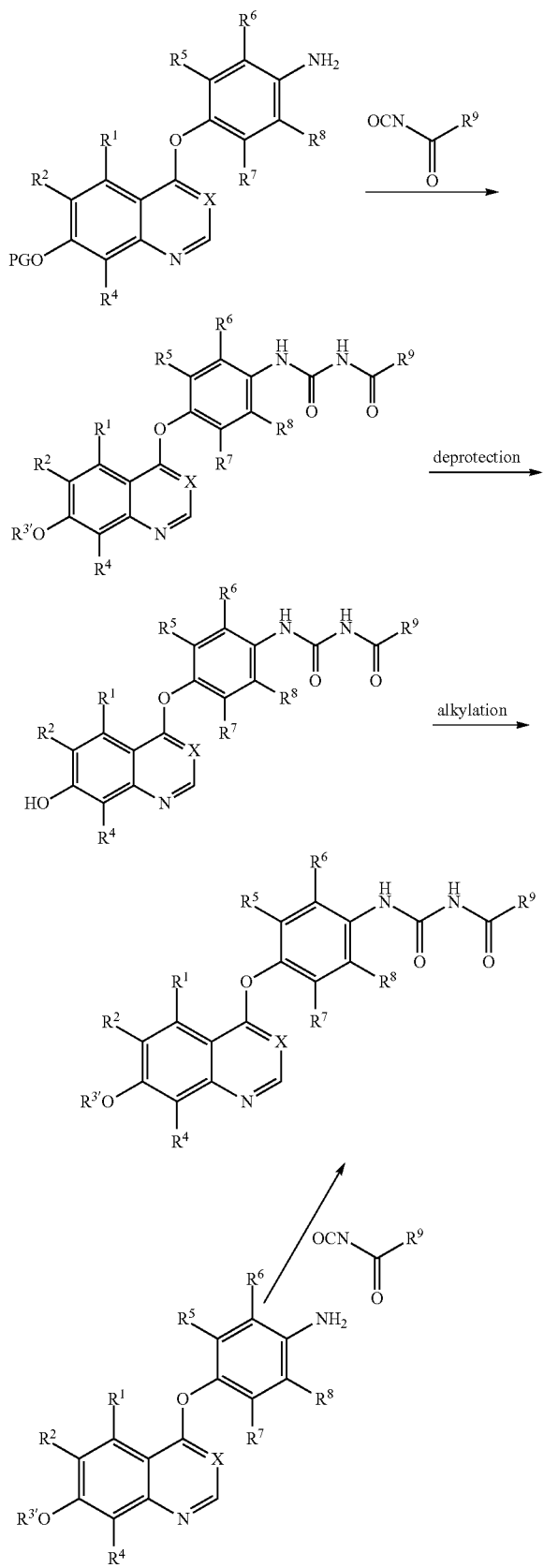

For example, a carbonylurea derivative having a specific substituent at the 7-position of the quinoline or quinazoline ring can be produced according to scheme 6. Specifically, the 4-(aminophenoxy)quinoline derivative or corresponding quinazoline derivative, of which the 7-position has been alkylated in scheme 5, is reacted as shown in scheme 2. More specifically, a carbonylurea derivative is produced by reacting the 4-(aminophenoxy)quinoline derivative or quinazoline derivative with a carbonyl isocyanate derivative in a suitable solvent. The carbonylurea derivative having a specific substituent at the 7-position of the quinoline or quinazoline ring can also be synthesized by other methods. At the outset, the 4-(aminophenoxy)quinoline derivative or quinazoline derivative produced in scheme 3 or 4 is reacted as shown in scheme 2. Specifically, a carbonylurea derivative is produced by reacting the 4-(aminophenoxy)quinoline derivative or the quinazoline derivative with a carbonyl isocyanate derivative in a suitable solvent. A 7-hydroxyquinoline derivative or a corresponding 7-hydroxyquinazoline derivative is produced by removing the protective group of the hydroxyl group in the carbonylurea derivative under suitable conditions. For example, when the protective group is benzyl, for example, the deprotection reaction is carried out in a hydrogen atmosphere in N,N-dimethylformamide in the presence of palladium hydroxide-carbon or palladium-carbon. Next, a carbonylurea derivative having a specific substituent at the 7-position of the quinoline or quinazoline ring is produced by alkylating the 7-hydroxyquinoline derivative or corresponding 7-hydroxyquinazoline derivative under suitable conditions, for example, by reacting the 7-hydroxyquinoline derivative or corresponding 7-hydroxyquinazoline derivative with an alkyl halide in a suitable solvent in the presence of a base.

Scheme 7: Production of aminocarbonylurea derivatives in which 7-position of quinoline ring or quinazoline ring has been modified with specific group (compounds of formula (I) where in L = —O—, M = —NR$^{12}$—, and R$^9$ = —NR$^{18}$R$^{19}$

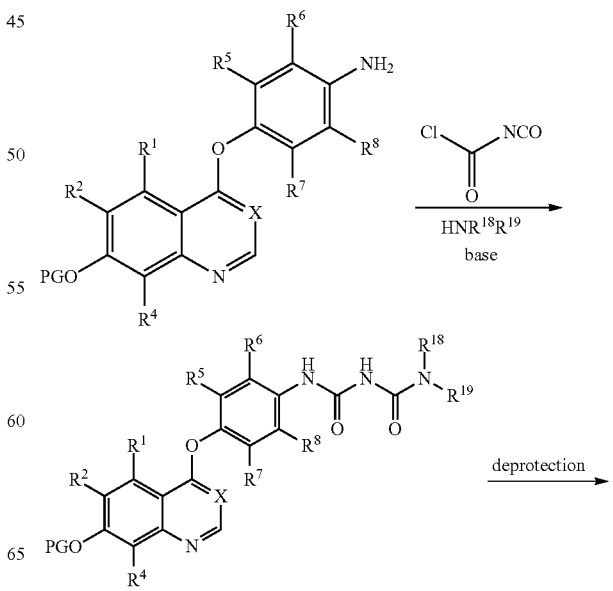

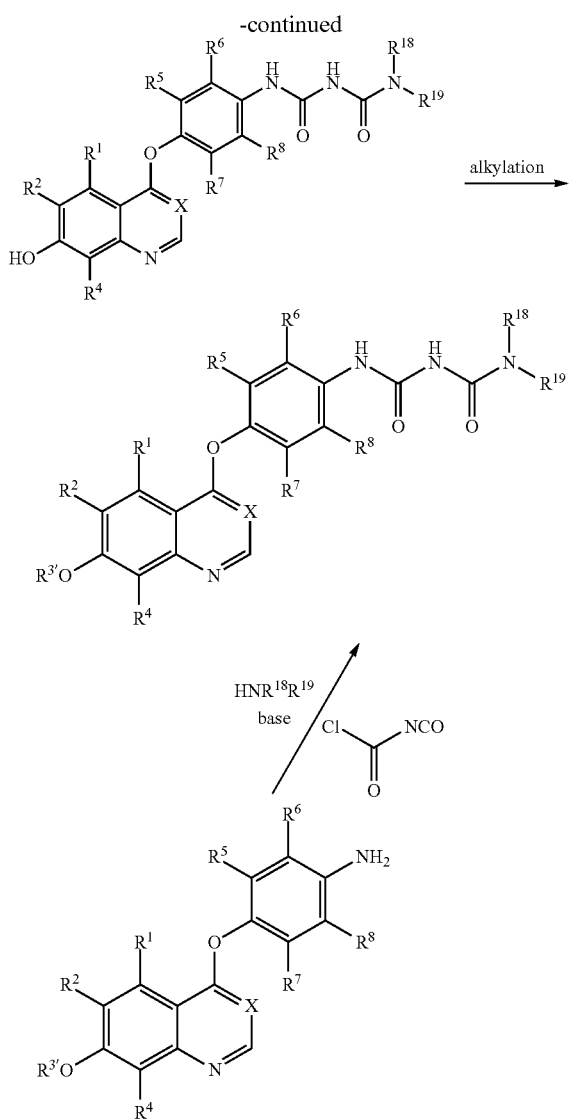

For example, an aminocarbonylurea derivative having a specific substituent at the 7-position of the quinoline or quinazoline ring can be produced according to scheme 7. Specifically, the 4-(aminophenoxy)quinoline derivative or corresponding quinazoline derivative, of which the 7-position has been alkylated, prepared in scheme 5 is reacted as shown in scheme 2. That is, an aminocarbonylurea derivative is produced by reacting the 4-(aminophenoxy)quinoline derivative or the quinazoline derivative with N-(chlorocarbonyl)isocyanate in a suitable solvent in the presence of a base and then reacting the product with an amine derivative. The aminocarbonylurea derivative having a specific substituent at the 7-position of the quinoline or quinazoline ring can also be synthesized by other methods. At the outset, the 4-(aminophenoxy)quinoline derivative or quinazoline derivative produced in scheme 3 or 4 is reacted as shown in scheme 2. Specifically, an aminocarbonylurea derivative is produced by reacting the 4-(aminophenoxy)quinoline derivative or the quinazoline derivative with N-(chlorocarbonyl)isocyanate in a suitable solvent in the presence of a base and then reacting the product with an amine derivative. A 7-hydroxyquinoline derivative or a corresponding 7-hydroxyquinazoline derivative is produced by removing the protective group of the hydroxyl group in the aminocarbonylurea derivative under suitable conditions. For example, when the protective group is benzyl, the deprotection reaction is carried out, for example, in N,N-dimethylformamide, in a hydrogen atmosphere in the presence of palladium hydroxide-carbon or palladium-carbon. Next, an aminocarbonylurea derivative having a specific substituent at the 7-position of the quinoline or quinazoline ring is produced by alkylating the 7-hydroxyquinoline derivative or corresponding 7-hydroxyquinazoline derivative under suitable conditions, for example, with an alkyl halide in a suitable solvent in the presence of a base.

Scheme 8: Production of amide derivatives in which 7-position of quinoline ring or quinazoline ring has been modified with specific group (compounds of formula (I) where in L = —O—, M = —$CR^{10}R^{11}$—, and $R^9$ = —$NR^{18}R^{19}$

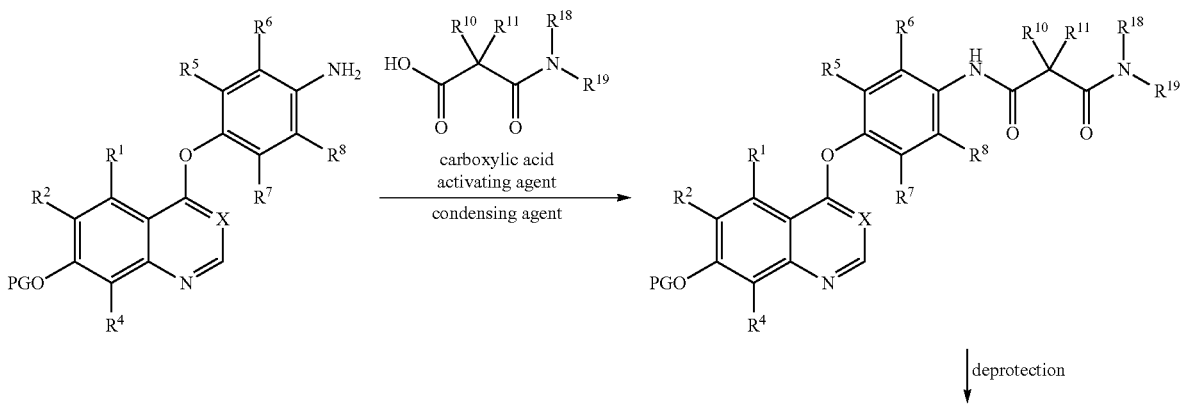

-continued

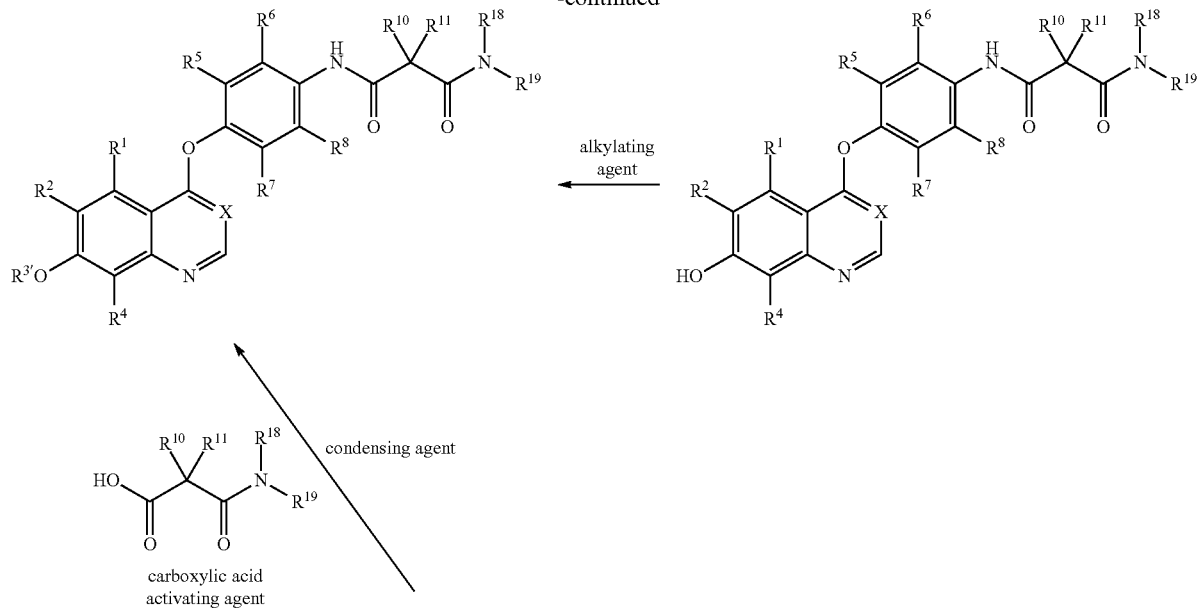

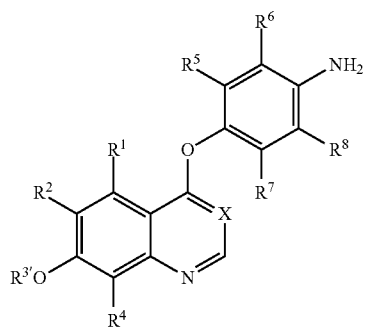

For example, an amide derivative having a specific substituent at the 7-position of the quinoline or quinazoline ring can be produced according to scheme 8. Specifically, the 4-(aminophenoxy)quinoline derivative or corresponding quinazoline derivative, of which the 7-position has been alkylated, prepared in scheme 5 is reacted as shown in scheme 2. That is, an amide derivative is produced by reacting the 4-(aminophenoxy)quinoline derivative or the quinazoline derivative with a carboxylic acid derivative or a metal salt thereof in a suitable solvent in the presence of a condensing agent and a carboxylic acid activating agent. The amide derivative having a specific substituent at the 7-position of the quinoline or quinazoline ring can also be synthesized by other methods. At the outset, the 4-(aminophenoxy)quinoline derivative or the quinazoline derivative produced in scheme 3 or 4 is reacted as shown in scheme 2. That is, an amide derivative is produced by reacting the 4-(aminophenoxy)quinoline derivative or the quinazoline derivative with a carboxylic acid derivative or a metal salt thereof in a suitable solvent in the presence of a condensing agent and a carboxylic acid activating agent. A 7-hydroxyquinoline derivative or a corresponding 7-hydroxyquinazoline derivative is produced by removing the protective group of the hydroxyl group in the amide derivative under suitable conditions. For example, when the protective group is benzyl, the deprotection reaction is carried out, for example, in N,N-dimethylformamide, in a hydrogen atmosphere in the presence of palladium hydroxide-carbon or palladium-carbon. Next, an amide derivative having a specific substituent at the 7-position of the quinoline or quinazoline ring is produced by alkylating the 7-hydroxyquinoline derivative or corresponding 7-hydroxyquinazoline derivative under suitable conditions, for example, by reacting the 7-hydroxyquinoline derivative or corresponding 7-hydroxyquinazoline derivative with an alkyl halide in a suitable solvent in the presence of a base.

Scheme 9: Production of carbonylurea derivatives and carbonylthiourea derivatives having specific substituent at 7-position of quinoline or quinazoline ring
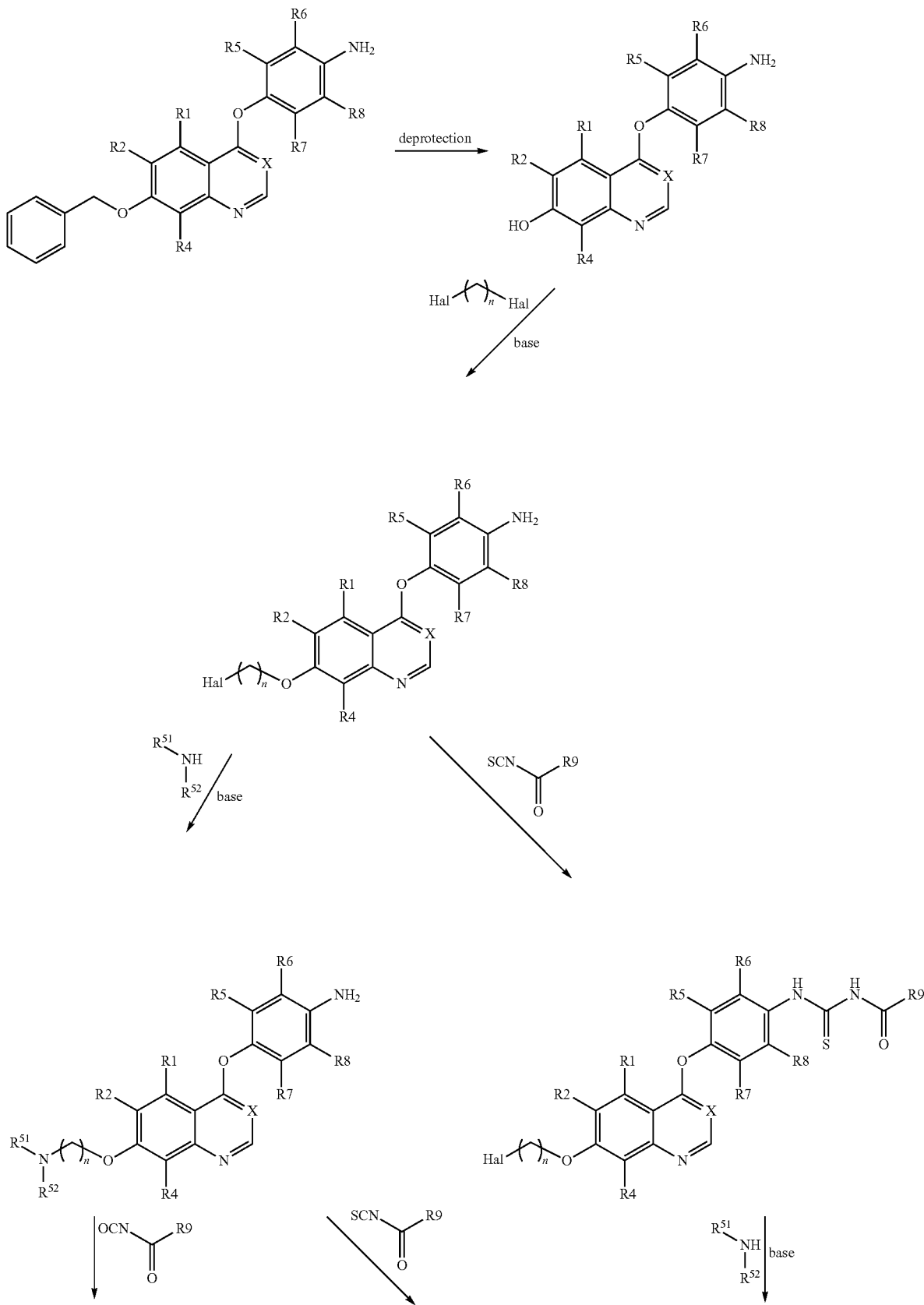

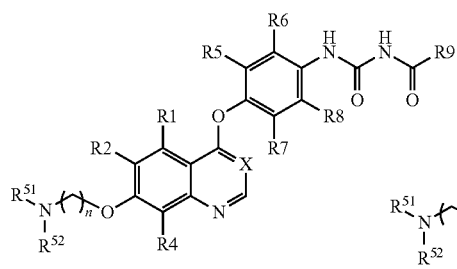 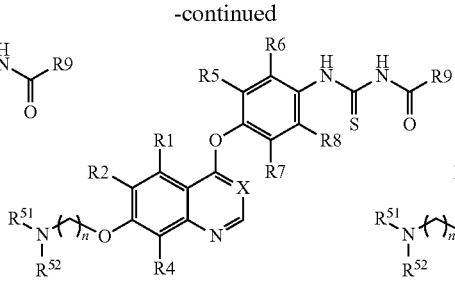 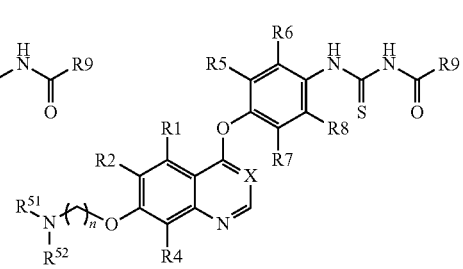

For example, a carbonylurea derivative and carbonylthiourea derivative having a specific substituent at the 7-position of the quinoline or quinazoline ring can be produced according to scheme 9. Specifically, a carbonylurea derivative or a carbonylthiourea derivative can be produced by deprotecting the 4-aminophenoxyquinoline derivative or corresponding quinazoline derivative, of which the 7-position has been protected by benzyl, under acidic conditions to give a phenol compound, then reacting the phenol compound with an alkyl halide in a suitable solvent in the presence of a base to give a corresponding ether compound, and then reacting the product with a suitable amine in a suitable solvent in the presence of a base to give a corresponding 7-amino-substituted (4-aminophenoxy)quinoline derivative and then reacting this derivative with a carbonyl isocyanate derivative or a carbonylisothiocyanate derivative. Alternatively, a corresponding carbonylthiourea derivative having a specific substituent at the 7-position can be produced by reacting the ether compound, provided after the reaction with the alkyl halide, with a carbonylisothiocyanate derivative to give a carbonylthiourea derivative and then reacting the carbonylthiourea derivative with a suitable amine in a suitable solvent in the presence of a base.

Use of Compounds/Pharmaceutical Composition

The compounds according to the present invention have tumor growth inhibitory activity in vivo (see Pharmacological Test Examples 3, 4, and 5).

Further, the compounds according to the present invention inhibit in vitro the met autophosphorylation caused by the stimulation of human epidermal cancer cells A431 with HGF and the met autophosphorylation which constantly occurs in gastric cancer cells MKN45 non-dependently upon HGF (see Pharmacological Test Examples 1 and 2).

Upon HGF stimulation or in a HGF-non-dependent manner for certain cancer cells, met accelerates proliferation and motility in various cell species through the autophosphorylation of intracellular region with tyrosine kinase (J. Biochem., 119, 591, (1996), Jpn. J. Cancer Res., 88, 564, (1997), and Int. J. Cancer, 78, 750, (1998)). In particular, in a plurality of cancers, for example, the increasing of HGF concentration in the blood, excessive development of met, and the development of met mutants which have acquired HGF non-dependency are reported. met signals are considered to be involved in the proliferation and invasion of various cancer cells and metastasis (Int. J. Cancer, 55, 72, (1993), Oncology Reports, 5, 1013 (1998), Proc. Natl. Acad. Sci. USA, 88, 4892, (1991), and Cancer, 88, 1801, (2000)). Further, it is also reported that HGF accelerates through met the proliferation and migration activity of vascular endothelial cells and accelerates angiogenesis (Circulation, 97, 381 (1998) and Clinical Cancer Res., 5, 3695, (1999)), and, consequently, it is estimated that HGF is also related to angiogenesis in cancers.

Accordingly, the compounds according to the present invention can inhibit the growth, invasion, metastasis, and angiogenesis of cancer cells and thus can be used in the treatment of malignant tumors.

According to the present invention, there is provided a pharmaceutical composition comprising the compound according to the present invention. The pharmaceutical composition according to the present invention can be used in the treatment of malignant tumors such as brain tumors, gastric cancer, colon cancer, pancreatic cancer, lung cancer, renal cancer, ovarian cancer, and prostate cancer.

Further, according to the present invention, there is provided a method for treating a malignant tumor, comprising the step of administering a therapeutically effective amount of the compound according to the present invention together with a pharmaceutically acceptable carrier to a mammal including a human.

Furthermore, according to the present invention, there is provided use of the compound according to the present invention, for the manufacture of a medicament for use in the treatment of a malignant tumor.

The compounds according to the present invention can be administered to human and non-human animals orally or parenterally by administration routes, for example, intravenous administration, intramuscular administration, subcutaneous administration, rectal administration, or percutaneous administration. Therefore, the pharmaceutical composition comprising as an active ingredient the compound according to the present invention is formulated into suitable dosage forms according to the administration routes. Specifically, oral preparations include tablets, capsules, powders, granules, and syrups, and parental preparations include injections, suppositories, tapes, and ointments.

These various preparations may be prepared by conventional methods, for example, with commonly used excipients, disintegrants, binders, lubricants, colorants, and diluents.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

In preparing the injections, if necessary, for example, buffers, pH adjustors, stabilizers, tonicity agents, and preservatives may be added.

The content of the compound according to the present invention in the pharmaceutical composition according to the present invention may vary depending upon the dosage form. In general, however, the content is 0.5 to 50% by weight, preferably 1 to 20% by weight, based on the whole composition.

The dose may be appropriately determined in consideration of, for example, the age, weight, sex, difference in diseases, and severity of condition of individual patients, preferably in the range of 1 to 100 mg/kg. This dose is administered at a time daily or divided doses of several times daily.

The compound according to the present invention may be administered in combination with other medicament, for example, a carcinostatic agent. In this case, the compound according to the present invention may be administered simultaneously with or after or before the administration of other medicament. The type, administration intervals and the like of the carcinostatic agent may be determined depending upon the type of cancer and the condition of patients.

EXAMPLES

The present invention is further illustrated by Examples that are not intended as a limitation of the invention.

Starting compounds necessary for synthesis were produced as described in WO 97/17329, WO 98/47873, WO 00/43366, and Japanese Patent Laid-Open Publication No. 328782/1997. Starting compounds not described in these publications were produced as described in Production Examples below.

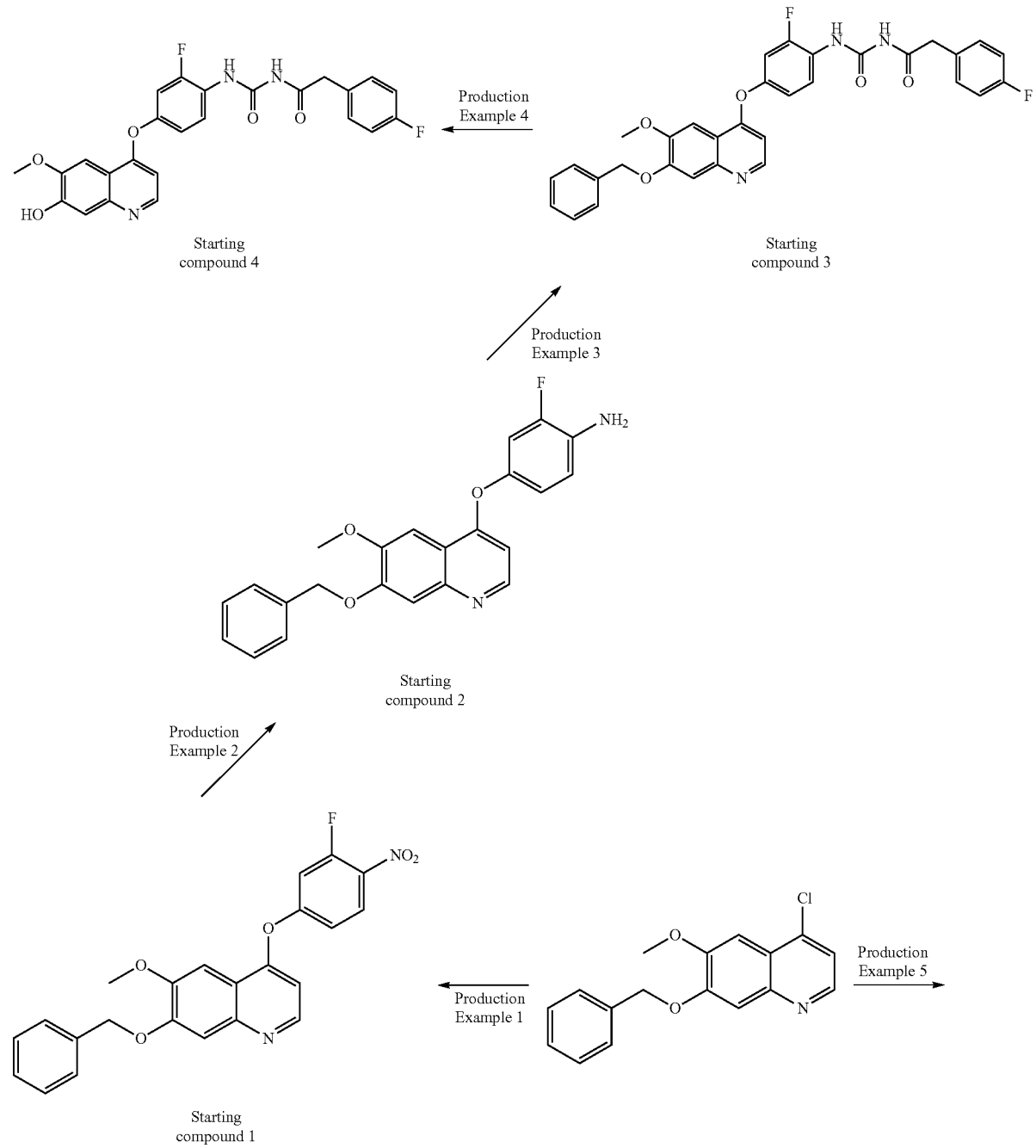

Scheme 10: Production of starting compounds 1 to 10

-continued
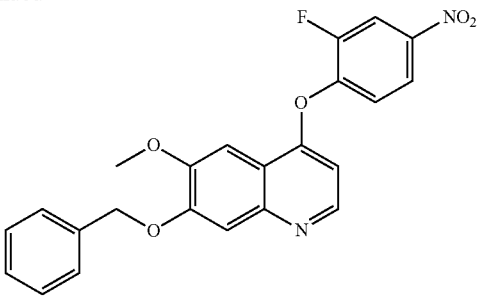
Starting compound 5
Production Example 6
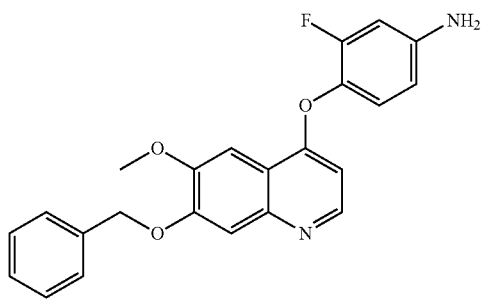
Starting compound 6
Production Example 7
Production Example 9
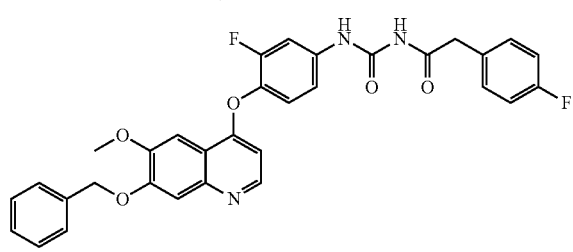
Starting compound 7
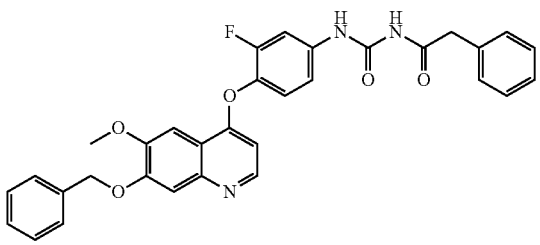
Starting compound 9
Production Example 8
Production Example 10
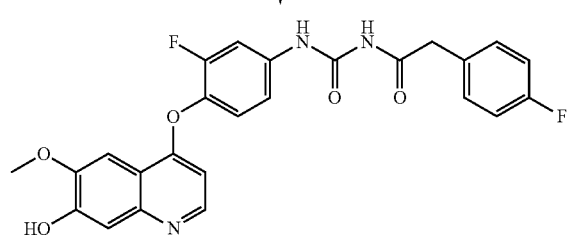
Starting compound 8
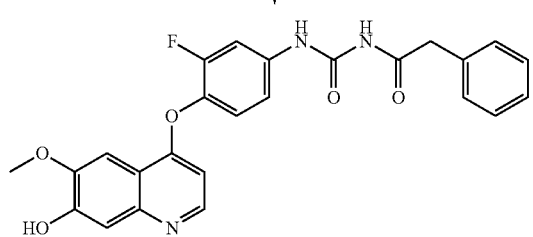
Starting compound 10

Scheme 11: Production of starting compounds 11 and 12

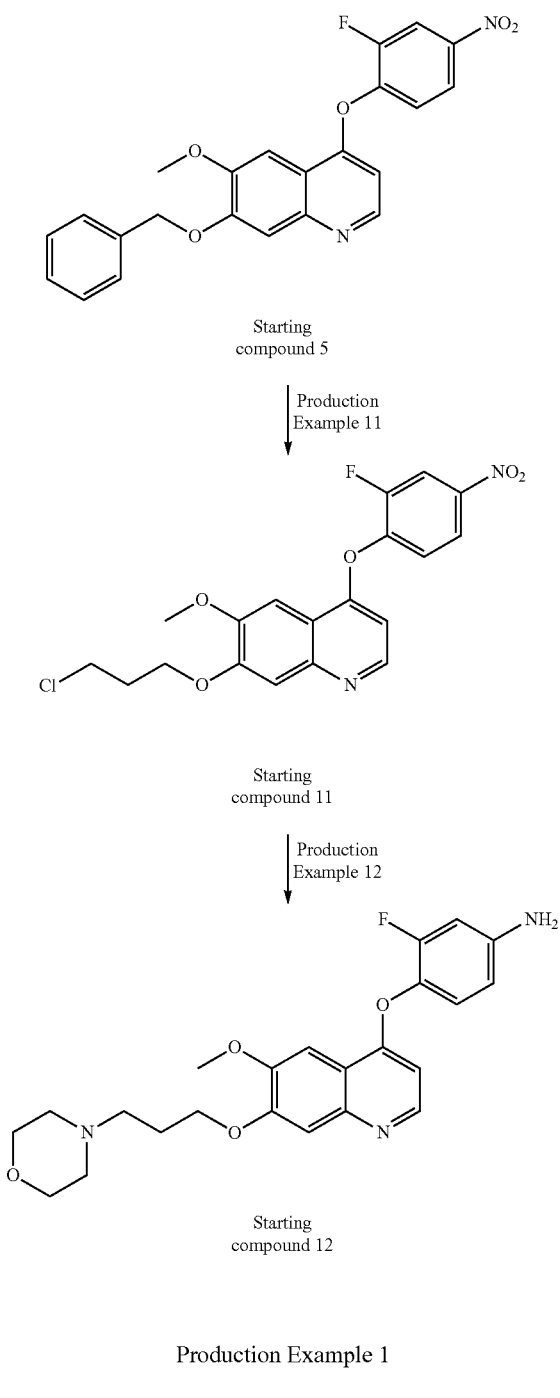

Starting compound 5

Production Example 11

Starting compound 11

Production Example 12

Starting compound 12

Production Example 1

Starting Compound 1

7-(Benzyloxy)-4-chloro-6-methoxyquinoline (29 g), 3-fluoro-4-nitrophenol (20 g), N,N-diisopropylethylamine (33 ml), and chlorobenzene (14 ml) were added, and the mixture was stirred with heating at 140° C. for 15 hr. After the completion of the reaction, a 2 N aqueous sodium hydroxide solution (30 ml) was added thereto, and the mixture was stirred at room temperature for 3 hr. Water was added to the reaction solution, and the mixture was extracted with chloroform. The chloroform layer was dried over anhydrous sodium sulfate. The solvent was removed by evaporation under the reduced pressure to give the target compound (40 g, yield 50%).

$^1$H-NMR (CDCl$_3$, 400 MHz): δ 8.58 (d, J=5.1 Hz, 1H), 8.48-8.44 (m, 1H), 8.21-8.19 (m, 1H), 7.64-7.35 (m, 8H), 6.79 (d, J=5.1 Hz, 1H), 5.33 (s, 2H), 3.94 (s, 3H)

Mass spectrometric value (m/z): 421 [M+H]$^+$

Production Example 2

Starting Compound 2

7-(Benzyloxy)-4-(3-fluoro-4-nitrophenoxy)-6-methoxyquinoline (35 g), zinc (74 g), and ammonium chloride (14 g) were added to ethanol/water (20/1, 525 ml), and the mixture was stirred with heating at 120° C. for 18 hr. After the completion of the reaction, the reaction solution was filtered through Celite. The filtrate was concentrated, and the concentrate was washed with water to give the target compound (32 g, yield 94%).

$^1$H-NMR (CDCl$_3$, 400 MHz): δ 8.58 (d, J=5.1 Hz, 1H), 8.48-8.44 (m, 1H), 8.24 (m, 2H), 7.64-7.38 (m, 9H), 6.75 (d, J=5.1 Hz, 1H), 5.31 (s, 2H), 3.94 (s, 3H)

Mass spectrometric value (m/z): 391 [M+H]$^+$

Production Example 3

Starting Compound 3

4-Fluorophenylacetamide (78 mg, see Example 3 for the production process thereof) was dissolved in 1,2-dichloroethane (20 ml) to prepare a solution. Oxalyl chloride (56 µl) was then added to the solution, and the mixture was heated under reflux at 110° C. for 15.5 hr. After the completion of the reaction, the reaction solution was concentrated under the reduced pressure to give a crude. Dimethylformamide (10 ml) and 4-{[7-(benzyloxy)-6-methoxy-4-quinolyl]oxy}-2-fluoroaniline (50 mg) were added to the crude, and the mixture was stirred at room temperature for 5 hr. After the completion of the reaction, the reaction solution was concentrated under the reduced pressure to give a crude which was then purified by chromatography on silica gel using chloroform/methanol for development to give the target compound (49 mg, yield 67%).

$^1$H-NMR (DMSO-d$_6$, 400 MHz): δ 11.16 (br, 1H), 10.75 (br, 1H), 8.49 (d, J=4.9 Hz, 1H), 8.24-8.19 (m, 1H), 7.53-7.35 (m, 10H), 7.19-7.11 (m, 3H), 6.56 (d, J=5.4 Hz, 1H), 5.31 (s, 2H), 3.94 (s, 3H), 3.75 (s, 2H)

Mass spectrometric value (m/z): 570 [M+H]$^+$

Production Example 4

Starting Compound 4

N-(4-{[7-(Benzyloxy)-6-methoxy-4-quinolyl]oxy}-2-fluorophenyl)-N'-[2-(4-fluorophenyl)acetyl]urea (1.6 g) and palladium hydroxide-carbon (1.3 g) were added to dimethylformamide (14 ml), and the mixture was stirred in a hydrogen atmosphere at room temperature for 10 hr. After the completion of the reaction, the reaction solution was filtered through Celite, and the filtrate was concentrated to give the target compound (1.3 g, yield 98%).

¹H-NMR (CDCl₃, 400 MHz): δ 8.39 (m, 2H), 8.21-8.18 (m, 1H), 7.45 (m, 1H), 7.33-7.23 (m, 8H), 7.01 (m, 1H), 6.42 (m, 1H), 6.18 (m, 2H), 3.92 (s, 3H)
Mass spectrometric value (m/z): 480 [M+H]⁺

Production Example 5

Starting Compound 5

7-(Benzyloxy)-4-chloro-6-methoxyquinoline (81 g), 2-fluoro-4-nitrophenol (51 g), N,N-diisopropylethylamine (94 ml), and chlorobenzene (40 ml) were added, and the mixture was stirred with heating at 140° C. for 18 hr. After the completion of the reaction, a 2 N aqueous sodium hydroxide solution (40 ml) was added thereto, and the mixture was stirred at room temperature for 3 hr. Water was added to the reaction solution, and the mixture was extracted with chloroform. The chloroform layer was dried over anhydrous sodium sulfate. The solvent was removed by evaporation under the reduced pressure to give the target compound (100 g, yield 92%).
¹H-NMR (CDCl₃, 400 MHz): δ 8.45 (d, J=5.4 Hz, 1H), 7.53-7.34 (m, 7H), 7.07-7.03 (m, 1H), 6.89-6.82 (m, 2H), 6.43 (d, J=5.4 Hz, 1H), 5.29 (s, 2H), 3.94 (s, 3H)
Mass spectrometric value (m/z): 421 [M+H]⁺

Production Example 6

Starting Compound 6

7-(Benzyloxy)-4-(2-fluoro-4-nitrophenoxy)-6-methoxyquinoline (36 g), zinc (74 g), and ammonium chloride (14 g) were added to ethanol/water (20/1, 525 ml), and the mixture was stirred with heating at 120° C. for 19 hr. After the completion of the reaction, the reaction solution was filtered through Celite. The filtrate was concentrated, and the concentrate was washed with water to give the target compound (35 g, yield 96%).
¹H-NMR (CDCl₃, 400 MHz): δ 8.57 (d, J=5.1 Hz, 1H), 8.44-8.37 (m, 1H), 8.22 (m, 2H), 7.65-7.38 (m, 9H), 6.78 (d, J=5.1 Hz, 1H), 5.33 (s, 2H), 3.96 (s, 3H)
Mass spectrometric value (m/z): 391 [M+H]⁺

Production Example 7

Starting Compound 7

4-Fluorophenylacetamide (86 mg, see Example 3 for the production process thereof) was dissolved in 1,2-dichloroethane (200 ml) at 80° C. to prepare a solution. Oxalyl chloride (150 μl) was added to the solution, and the mixture was stirred at 80° C. for 10 hr. After the completion of the reaction, the reaction solution was concentrated under the reduced pressure to give a crude. Dimethylformamide (2 ml) and 4-{[7-(benzyloxy)-6-methoxy-4-quinolyl]oxy}-3-fluoroaniline (170 mg) were added to the crude, and the mixture was stirred at room temperature for 3 hr. After the completion of the reaction, the reaction solution was concentrated under the reduced pressure to give 248 mg of the target compound.
¹H-NMR (CDCl₃, 400 MHz): δ 8.46 (d, J=5.1 Hz, 1H), 7.50-6.85 (m, 16H), 6.44 (d, J=5.2 Hz, 1H), 5.31 (s, 2H), 3.93 (s, 3H), 3.74 (s, 2H)
Mass spectrometric value (m/z): 570 [M+H]⁺

Production Example 8

Starting Compound 8

N-(4-{[7-(Benzyloxy)-6-methoxy-4-quinolyl]oxy}-3-fluorophenyl)-N'-[2-(4-fluorophenyl)acetyl]urea (1.5 g) and palladium hydroxide-carbon (1.1 g) were added to dimethylformamide (20 ml), and the mixture was stirred in a hydrogen atmosphere at room temperature for 10 hr. After the completion of the reaction, the reaction solution was filtered through Celite. The filtrate was concentrated to give the target compound (1.1 g, yield 88%).
¹H-NMR (CDCl₃, 400 MHz): δ 8.51 (d, J=5.2 Hz, 1H), 7.89-7.70 (m, 1H), 7.51-7.07 (m, 11H), 6.31 (d, J=5.1 Hz, 1H), 3.94 (s, 3H), 3.74 (s, 2H)
Mass spectrometric value (m/z): 480 [M+H]⁺

Production Example 9

Starting Compound 9

2-Phenylacetamide (76 mg) was dissolved in 1,2-dichloroethane (200 ml) at 80° C. to prepare a solution. Oxalyl chloride (150 μl) was added to the solution, and the mixture was stirred at 80° C. for 10 hr. After the completion of the reaction, the reaction solution was concentrated under the reduced pressure to give a crude. Dimethylformamide (2 ml) and 4-{[7-(benzyloxy)-6-methoxy-4-quinolyl]oxy}-3-fluoroaniline (170 mg) were added to the crude which was then stirred at room temperature for 3 hr. After the completion of the reaction, the reaction solution was concentrated under the reduced pressure to give 228 mg of the target compound.
¹H-NMR (CDCl₃, 400 MHz): δ 8.43 (d, J=5.3 Hz, 1H), 7.55-7.19 (m, 17H), 6.42 (d, J=5.4 Hz, 1H), 5.31 (s, 2H), 3.95 (s, 3H), 3.75 (s, 2H)
Mass spectrometric value (m/z): 552 [M+H]⁺

Production Example 10

Starting Compound 10

N-(4-{[7-(Benzyloxy)-6-methoxy-4-quinolyl]oxy}-3-fluorophenyl)-N'-(2-phenylacetyl)urea (1.2 g) and palladium hydroxide-carbon (1.0 g) were added to dimethylformamide (20 ml), and the mixture was stirred in a hydrogen atmosphere at room temperature for 10 hr. After the completion of the reaction, the reaction solution was filtered through Celite. The filtrate was concentrated to give the target compound (0.85 g, yield 85%).
¹H-NMR (CDCl₃, 400 MHz): δ 8.43 (d, J=5.1 Hz, 1H), 7.82-7.79 (m, 1H), 7.49-7.08 (m, 12H), 6.36 (d, J=5.1 Hz, 1H), 3.95 (s, 3H), 3.75 (s, 2H)
Mass spectrometric value (m/z): 462 [M+H]⁺

Production Example 11

Starting Compound 11

3-Fluoro-4-[(7-benzyloxy-6-methoxy-4-quinolyl)oxy]-nitrobenzene (2.5 g), together with trifluoroacetic acid (15 ml) and methanesulfonic acid (0.7 ml), was heated under reflux for one hr. The solvent was removed by evaporation, and the residue was then neutralized with a 10% aqueous sodium hydroxide solution. The precipitated crystal was collected by suction filtration to give a crude crystal (1.95 g). The crude crystal was dissolved in dimethylformamide (50 ml) without purification. Potassium carbonate (4.3 g) and 1-bromo-3-chloropropane (4.9 g) were added to the solution, and the mixture was stirred at room temperature for 16 hr. The reaction solution was extracted with ethyl acetate, followed by washing with saturated brine. The extract was then dried over anhydrous sodium sulfate. The solvent was removed by evaporation under the reduced pressure to give a crude which was then washed with an ethyl acetate/hexane (1/1) mixed solution to give the target compound (1.76 g, yield 73%).

$^1$H-NMR (CDCl$_3$, 400 MHz): δ 2.35-2.41 (m, 2H), 3.80 (t, J=6.3 Hz, 2H), 3.99 (s, 3H), 4.34 (t, J=6.3 Hz, 2H), 6.53 (d, J=5.1 Hz, 1H), 7.27-7.34 (m, 1H), 7.42 (s, 1H), 7.46 (s, 1H), 8.10-8.18 (m, 2H), 8.56 (d, J=5.1 Hz, 1H)

Production Example 12

Starting Compound 12

3-Fluoro-4-{[7-(3-chloropropyl)-6-methoxy-4-quinolyl]oxy}nitrobenzene (500 mg) was dissolved in dimethylformamide (20 ml) to prepare a solution. Potassium carbonate (890 mg), sodium iodide (290 mg), and morpholine (645 mg) were added to the solution, and the mixture was stirred at 70° C. for 18 hr. The mixture was extracted with ethyl acetate, followed by washing with saturated brine. The extract was dried over anhydrous sodium sulfate. The solvent was removed by evaporation under the reduced pressure to give a crude. The crude was dissolved in methanol (30 ml) without purification. Ammonium chloride (207 mg) and zinc (1.26 g) were added to the solution, and the mixture was heated under reflux for 5 hr. Zinc was removed by filtration. Chloroform was added to the filtrate, the mixture was washed with a saturated sodium hydrogencarbonate solution, and the solvent was then removed by evaporation under the reduced pressure to give a crude. The crude was purified by column chromatography on silica gel using chloroform/methanol for development to give the target compound (440 mg, yield 80%).

$^1$H-NMR (CDCl$_3$, 400 MHz): δ 2.02-2.11 (m, 2H), 2.35-2.47 (m, 4H), 2.50 (t, J=6.3 Hz, 2H), 3.61-3.69 (m, 4H), 3.75 (s, 2H), 3.96 (s, 3H), 4.20 (t, J=6.6 Hz, 2H), 6.33 (d, J=5.4 Hz, 1H), 6.41-6.51 (m, 2H), 6.96 (t, J=8.5 Hz, 1H), 7.35 (s, 1H), 7.51 (s, 1H), 8.39 (d, J=5.4 Hz, 1H)

Example 1

Phenylacetyl chloride [starting compound B] (1.89 ml) and potassium thiocyanate (2.09 g) were dissolved in acetonitrile (15 ml) to prepare a solution, and the solution was then stirred at 80° C. for one hr. Water was added to the reaction solution, the mixture was extracted with chloroform, and chloroform was then removed by evaporation under the reduced pressure to give a crude. The crude was dissolved in toluene/ethanol (1/1). 4-[(6,7-Dimethoxy-4-quinolyl)oxy]-3-fluoroaniline [starting compound A] (3.03 g) was added to the solution, and the mixture was stirred at room temperature overnight. The reaction solvent was removed by evaporation under the reduced pressure. The residue was purified by chromatography on silica gel using chloroform/acetone for development to give the title compound (0.69 g, yield 14.5%.

$^1$H-NMR (CDCl$_3$, 400 MHz): δ 3.76 (s, 2H), 4.05 (s, 3H), 4.06 (s, 3H), 6.46 (d, J=4.4 Hz, 1H), 7.23-7.34 (m, 3H), 7.38-7.48 (m, 5H), 7.56 (s, 1H), 7.93 (m, 1H), 8.48 (br, 1H), 8.51 (d, J=5.4 Hz, 1H), 12.47 (br, 1H)

Mass spectrometric value (m/z): 492 [M+H]$^+$

Example 2

Thionyl chloride (348 μl) was added to 4-fluorophenylacetic acid [starting compound B] (123 mg), and the mixture was stirred with heating at 50° C. for one hr. After the completion of the reaction, the reaction solution was concentrated under the reduced pressure to give a crude. The crude was dissolved in acetonitrile (20 ml). Potassium thiocyanate (155 mg) was added to the solution, and the mixture was stirred with heating at 50° C. for 40 min. Thereafter, 4-[(6,7-dimethoxy-4-quinolyl)oxy]-3-fluoroaniline [starting compound A] (50 mg) was added thereto, and the mixture was then further stirred with heating for 60 min. After the completion of the reaction, the reaction solution was concentrated under the reduced pressure to give a crude. An aqueous saturated sodium hydrogencarbonate solution was added to the crude, and the mixture was extracted with ethyl acetate. The ethyl acetate layer was dried over anhydrous sodium sulfate and was concentrated under the reduced pressure. The concentrate was purified by chromatography on silica gel using chloroform/acetone for development to give the title compound (61 mg, yield 75%).

$^1$H-NMR (CDCl$_3$, 400 MHz): δ 3.87 (s, 2H), 4.05 (s, 3H), 4.06 (s, 3H), 6.45 (d, J=5.1 Hz, 1H), 7.12 (m, 2H), 7.23-7.32 (m, 3H), 7.40 (m, 1H), 7.44 (s, 1H), 7.56 (s, 1H), 7.93 (m, 1H), 8.51 (d, J=5.1 Hz, 1H), 8.70 (br, 1H), 12.45 (br, 1H)

Mass spectrometric value (m/z): 510 [M+H]$^+$

Example 3

4-Fluorophenylacetic acid [starting compound B] (15 g) was dissolved in thionyl chloride (15 ml) to prepare a solution which was then heated at 60° C. for one hr. Excess thionyl chloride was removed by evaporation under the reduced pressure to give 4-fluorophenylacetyl chloride. The acid chloride was dissolved in acetone (200 ml). Ammonium acetate (112 g) was added to the solution, and the mixture was stirred at room temperature for 17 hr. An aqueous saturated sodium hydrogencarbonate solution (150 ml) was added thereto, and the mixture was stirred at room temperature for one hr. The reaction solution was then extracted with chloroform, and the solvent in the extract was removed by evaporation to give a crude crystal. The resultant crude crystal was washed with a hexane/ethyl acetate (2/1) mixed solution to give 4-fluorophenylacetamide (10.5 g, yield 70%).

$^1$H-NMR (CDCl$_3$, 400 MHz): δ 3.53 (s, 2H), 5.25-5.70 (m, 2H), 7.00-7.05 (m, 2H), 7.20-7.26 (m, 2H)

4-Fluorophenylacetamide (2.05 g) was dissolved in 1,2-dichloroethane (250 ml) to prepare a solution. Oxalyl chloride (1.63 ml) was then added to the solution, and the mixture was heated for 15.5 hr under reflux. The solvent was removed by evaporation under the reduced pressure to give a crude. The crude was then dissolved in dimethylformamide (50 ml) to prepare a solution which was then added at room temperature to a previously prepared solution of 4-[(6,7-dimethoxy-4-quinolyl)oxy]-2-fluoroaniline [starting compound A] (2.10 g) in dimethylformamide (30 ml). The mixture was stirred at that temperature for 5 hr. The solvent was removed by evaporation under the reduced pressure to give a crude. The crude was purified by column chromatography on silica gel using chloroform/methanol for development. The solvent was removed by evaporation under the reduced pressure to give a crude compound which was then washed with methanol to give the title compound (2.27 g, yield 69%).

$^1$H-NMR (CDCl$_3$, 400 MHz): δ 3.74 (s, 2H), 4.04 (s, 3H), 4.05 (s, 3H), 6.52 (d, J=5.4 Hz, 1H), 6.99 (m, 2H), 7.10 (m, 2H), 7.30 (m, 2H), 7.45 (s, 1H), 7.49 (s, 1H), 8.17-8.24 (m, 2H), 8.52 (d, J=5.4 Hz, 1H), 10.73 (br, 1H)

Mass spectrometric value (m/z): 494 [M+H]$^+$

Example 4

2-Phenylacetamide [starting compound B] (91 mg) was dissolved in 1,2-dichloroethane (250 ml) to prepare a solution. Oxalyl chloride (73 μl) was added to the solution, and the mixture was heated under reflux at 110° C. for 15.5 hr. After the completion of the reaction, the reaction solution was concentrated under the reduced pressure to give a crude. Dimethylformamide (10 ml) and 4-[(6,7-dimethoxy-4-quinolyl)oxy]aniline [starting compound A] (50 mg) were added to the crude, and the mixture was stirred at room temperature for 5 hr. After the completion of the reaction, the reaction solution was concentrated under the reduced pressure to give a crude. The crude was purified by chromatography on silica gel using chloroform/methanol for development to give the title compound (44 mg, yield 57%).

$^1$H-NMR (DMSO-$d_6$, 400 MHz): δ 10.96 (s, 1H), 10.52 (s, 1H), 8.45 (d, J=5.1 Hz, 1H), 8.30 (s, 1H), 7.64 (d, J=9.0 Hz, 2H), 7.49 (s, 1H), 7.43-6.84 (m, 7H), 6.44 (d, J=5.4 Hz, 1H), 3.95 (s, 3H), 3.86 (s, 3H), 3.72 (s, 2H)

Mass spectrometric value (m/z): 458 [M+H]$^+$

Example 5

4-[(6,7-Dimethoxy-4-quinolyl)oxy]aniline [starting compound A] (5.00 g) was dissolved in chloroform (100 ml) to prepare a solution. Potassium carbonate (4.66 g) was added to the solution, and the mixture was stirred at 0° C. Methylmalonyl chloride [starting compound B] (2.18 ml) was added to the reaction solution, and the mixture was stirred at room temperature for 60 min. Water was added to the reaction solution, and the mixture was extracted with chloroform. The chloroform layer was washed with saturated brine and was dried over anhydrous sodium sulfate. The dried chloroform layer was then concentrated under the reduced pressure to give a crude. The crude was then dissolved in ethanol/water (10/1, 165 ml). Lithium hydroxide monohydrate (1.42 g) was added to the solution, and the mixture was stirred at room temperature for 4 hr. The reaction solution was concentrated under the reduced pressure. Water was then added to the concentrate, and the solution was made weakly acidic by the addition of hydrochloric acid. The solution was allowed to stand overnight at 0° C., followed by filtration to give 6.45 g of a crystal (hereinafter referred to simply as "carboxylic acid"). The carboxylic acid (30 mg), 1-ethyl-3-(3-dimethylaminopropyl)-carbodiimide hydrochloride (30 mg), 1-hydroxybenzotriazole monohydrate (24 mg), and 4-fluoroaniline [starting compound C] (10 mg) were dissolved in chloroform (3 ml) to prepare a solution which was then stirred at 60° C. overnight. The reaction solution was developed on diatomaceous earth impregnated with an aqueous saturated sodium hydrogencarbonate solution, followed by extraction with chloroform. The solvent in the extract was removed by evaporation to give a crude. The crude was purified by HPLC using chloroform/methanol for development to give the title compound (0.7 mg, yield 1.9%).

$^1$H-NMR (CDCl$_3$/CD$_3$OD, 400 MHz): δ 3.49 (s, 2H), 4.05 (s, 3H), 4.06 (s, 3H), 6.46 (d, J=5.1 Hz, 1H), 7.01-7.08 (m, 2H), 7.15-7.19 (m, 2H), 7.41 (s, 1H), 7.52-7.56 (m, 3H), 7.66-7.70 (m, 2H), 8.46 (d, J=5.4 Hz, 1H)

Mass spectrometric value (m/z): 476 [M+H]$^+$

Example 6

2,4-Difluoroaniline [starting compound C] (3.0 g) was dissolved in chloroform (50 ml) to prepare a solution. Potassium carbonate (6.24 g) was added to the solution, and the mixture was stirred. Ethylmalonyl chloride [starting compound B] (4 ml) was added to the reaction solution, and the mixture was stirred at room temperature for 10 min. Water was added to the reaction solution, and the mixture was extracted with chloroform. The chloroform layer was washed with saturated brine and was dried over anhydrous sodium sulfate. The dried chloroform layer was concentrated under the reduced pressure to give 5.12 g of a crude. In ethanol/water (10/1, 33 ml) was dissolved 2.85 g out of 5.12 g of the crude. Lithium hydroxide monohydrate (0.99 g) was added to the solution, and the mixture was stirred at room temperature for 4 hr. The reaction solution was concentrated under the reduced pressure to give 3.76 g of a crude (hereinafter referred to simply as "carboxylic acid"). Chloroform (3 ml) was added to 3-chloro-4-[(6,7-dimethoxy-4-quinolyl)oxy]aniline [starting compound A] (32 mg), carboxylic acid (31 mg), 1-ethyl-3-(3-dimethylaminopropyl)carbodiimide hydrochloride (28 mg), and 1-hydroxybenzotriazole monohydrate (22 mg), and the mixture was stirred at 60° C. overnight. The reaction solution was developed on diatomaceous earth impregnated with an aqueous saturated sodium hydrogencarbonate solution, followed by extraction with chloroform. The solvent in the extract was removed by evaporation to give a crude. The crude was purified by HPLC using chloroform/methanol for development to give the title compound (0.1 mg, yield 2.0%).

$^1$H-NMR (CDCl$_3$, 400 MHz): δ 3.59 (s, 2H), 4.05 (s, 3H), 4.07 (s, 3H), 6.33 (d, J=5.1 Hz, 1H), 6.90-7.33 (m, 4H), 7.45 (s, 1H), 7.52 (s, 1H), 7.58 (s, 1H), 7.90-7.93 (m, 1H), 8.48 (d, J=5.4 Hz, 1H)

Mass spectrometric value (m/z): 528 [M+H]$^+$

Example 7

4-[(6,7-Dimethoxy-4-quinolyl)oxy]aniline [starting compound A] (100 mg) was dissolved in chloroform (3 ml) to prepare a solution. Chloroacetyl isocyanate [starting compound B] (40 mg) was added to the solution, and the mixture was stirred at room temperature for 10 hr. The reaction solution was purified by chromatography on silica gel to give N-(2-chloroacetyl)-N'-{4-[(6,7-dimethoxy-4-quinolyl)oxy]phenyl}urea (116 mg, yield 83%). Next, N-(2-chloroacetyl)-N'-{4-[(6,7-dimethoxy-4-quinolyl)oxy]phenyl}urea (50 mg) and potassium carbonate (26 mg) were added to chloroform, and cyclopentanethiol [starting compound C] (38 μl) was added to the mixture with stirring. The mixture was stirred at room temperature for 3 hr, and the reaction solution was filtered through Celite. The filtrate was then concentrated under the reduced pressure to give a crude. The crude was purified by chromatography on silica gel using chloroform/methanol for development to give the title compound (35 mg, yield 60%).

$^1$H-NMR (DMSO-$d_6$, 400 MHz): δ 10.84 (br, 1H), 10.49 (br, 1H), 8.48 (d, J=5.1 Hz, 1H), 7.69-7.67 (m, 4H), 7.51 (s, 1H), 7.39 (s, 1H), 7.26-7.24 (d, J=9.0 Hz, 1H), 3.93 (s, 6H), 3.41 (s, 2H), 2.08-1.97 (m, 2H), 1.67-1.42 (m, 7H)

Mass spectrometric value (m/z): 482 [M+H]$^+$

Example 8

3-Chloro-4-[(6,7-dimethoxy-4-quinolyl)oxy]aniline [starting compound A] (100 mg) was dissolved in chloroform (3 ml) to prepare a solution. Chloroacetyl isocyanate [starting compound B] (42 mg) was added to the solution, and the mixture was stirred at room temperature for 10 hr. The reaction solution was purified by chromatography on silica gel to give N-(2-chloroacetyl)-N'-{3-chloro-4-[(6,7-dimethoxy-4-quinolyl)oxy]phenyl}urea (115 mg, yield 85%). Next, N-(2-chloroacetyl)-N'-{3-chloro-4-[(6,7-dimethoxy-4-quinolyl)oxy]phenyl}urea (50 mg) and potassium carbonate (28 mg) were added to chloroform, and indoline [starting compound C] (36 μl) was added to the mixture with stirring. The mixture was stirred at room temperature for 3 hr, and the reaction solution was filtered through Celite. The filtrate was then concentrated under the reduced pressure. The concentrate was purified by chromatography on silica gel using chloroform/methanol for development to give the title compound (33 mg, yield 56%).

$^1$H-NMR (DMSO-d$_6$, 400 MHz): δ 10.64 (br, 1H), 8.46 (d, J=5.6 Hz, 1H), 7.90 (d, J=2.7 Hz, 1H), 7.63 (s, 1H), 7.54-7.51 (m, 2H), 7.34 (s, 1H), 7.22-7.11 (m, 3H), 6.86-6.83 (m, 1H), 6.48 (d, J=7.8 Hz, 1H), 6.42 (d, J=5.6 Hz, 1H), 4.08 (s, 6H), 3.87 (s, 2H), 3.55-3.51 (m, 2H), 3.13-3.09 (m, 2H)

Mass spectrometric value (m/z): 533 [M+H]$^+$

Example 9

4-[(6,7-Dimethoxy-4-quinolyl)oxy]aniline [starting compound A] (415 mg) was dissolved in 10 ml of a 1% AcOH/DMF solution to prepare a solution. Further, aldehyde linker lanthanum (D-series; 28 μmol/unit) (10 units) was added to the solution. The reaction mixture was slowly shaken for 19 hr. Sodium boron triacetoxyhydride (475 mg) was added thereto, and the mixture was further slowly shaken for 24 hr. Lanthanum was taken out of the reaction solution and was washed with alternate N,N-dimethylformamide and dichloromethane each three times, followed by drying under the reduced pressure to give lanthanum with 4-[(6,7-dimethoxy-4-quinolyl)oxy]aniline supported thereon. This lanthanum (3 units) was added to 1 ml of dichloromethane, and a solution of N-(chlorocarbonyl)isocyanate [starting compound B] (55 μl) in dichloromethane (0.2 ml) was added to the mixture at 0° C. The mixture was slowly shaken overnight at room temperature. Further, a mixed solution composed of aniline [starting compound C] (68 μl), diisopropylamine (0.2 ml), and dichloromethane (0.3 ml) was then added thereto at 0° C. The mixture was shaken at room temperature for 7 hr and was then washed with alternate N,N-dimethylformamide and dichloromethane each five times. Drying under the reduced pressure was carried out, a 50% TFA/dichloromethane solution (1 ml) was added thereto, and the mixture was shaken at room temperature for 50 min to take off the product from lanthanum, followed by purification by thin layer chromatography on silica gel to give 6.8 mg of the title compound.

$^1$H-NMR (CDCl$_3$, 400 MHz): δ 3.98 (s, 6H), 6.40 (d, J=5.4 Hz, 1H), 7.09 (m, 1H), 7.10 (d, J=9 Hz, 2H), 7.27 (t, J=7.8 Hz, 2H), 7.33 (s, 1H), 7.38 (d, J=7.8 Hz, 2H), 7.47 (s, 1H), 7.48 (d, J=8.5 Hz, 2H), 8.37 (d, J=5.4 Hz, 1H)

Mass spectrometric value (m/z): 457 [M−H]$^+$

Example 10

4-[(6,7-Dimethoxy-4-quinolyl)oxy]aniline [starting compound A] (500 mg) was dissolved in 20 ml of dichloromethane to prepare a solution, and N-(chlorocarbonyl)isocyanate [starting compound 13] (145 μl) was slowly added to the solution. The mixture was stirred at room temperature for 2.5 hr. 4-Fluoroaniline [starting compound C] (205 mg) and diisopropylamine (0.35 ml) were then added thereto at 0° C. Further, the temperature of the reaction solution was returned to room temperature before stirring for 2.5 hr. Water was added to the reaction solution, and the mixture was then extracted with chloroform. The chloroform layer was dried over anhydrous sodium sulfate. The dried chloroform layer was concentrated under the reduced pressure, and the concentrate was then purified by chromatography on silica gel to give 380 mg of the title compound.

$^1$H-NMR (CDCl$_3$, 400 MHz): δ 4.03 (s, 3H), 4.04 (s, 3H), 6.42 (d, J=5.4 Hz, 1H), 7.00 (m, 2H), 7.14 (d, J=9 Hz, 2H), 7.33 (br, 2H), 7.40 (s, 1H), 7.45 (br, 2H), 7.53 (s, 1H), 8.48 (d, J=5.4 Hz, 1H)

Mass spectrometric value (m/z): 475 [M−H]$^+$

Example 11

N-{3-Fluoro-4-[(7-hydroxy-6-methoxy-4-quinolyl)-oxy]phenyl}-N'-(2-phenylacetyl)urea [starting compound A] (100 mg), potassium carbonate (150 mg), and 1,3-dibromopropane [starting compound C] (66 μl) were dissolved in dimethylformamide (5 ml) to prepare a solution which was then stirred at room temperature for 5 hr. Thereafter, morpholine [starting compound B] (57 μl) was further added thereto, and the mixture was stirred at room temperature for 3 hr. After the completion of the reaction, the reaction solution was filtered through Celite, and the filtrate was then concentrated under the reduced pressure to give a crude. The crude was purified by thin layer chromatography on silica gel using chloroform/methanol for development to give the title compound (23 mg, yield 18%).

$^1$H-NMR (CDCl$_3$, 400 MHz): δ 2.07 (m, 2H), 2.44 (m, 4H), 2.53 (t, J=7.1 Hz, 2H), 3.66 (m, 4H), 3.69 (s, 2H), 3.96 (s, 3H), 4.20 (t, J=6.6 Hz, 2H), 6.33 (d, J=5.4 Hz, 1H), 7.11-7.45 (m, 8H), 7.49 (s, 1H), 7.61 (m, 1H), 8.01 (br, 1H), 8.41 (d, J=5.4 Hz, 1H), 10.59 (br, 1H)

Mass spectrometric value (m/z): 589 [M+H]$^+$

Example 12

N-{3-Fluoro-4-[(7-hydroxy-6-methoxy-4-quinolyl)-oxy]phenyl}-N'-(2-phenylacetyl)urea [starting compound A] (100 mg), potassium carbonate (150 mg), and 1,4-dibromobutane [starting compound C] (78 μl) were dissolved in dimethylformamide (5 ml) to prepare a solution which was then stirred at room temperature for 5 hr. Thereafter, 1-methylpiperazine [starting compound B] (72 μl) was further added thereto, and the mixture was stirred at room temperature for 3 hr. After the completion of the reaction, the reaction solution was filtered through Celite, and the filtrate was then concentrated under the reduced pressure to give a crude. The crude was purified by thin layer chromatography on silica gel using chloroform/methanol for development to give the title compound (24 mg, yield 18%).

$^1$H-NMR (DMSO-d$_6$, 400 MHz): δ 11.07 (br, 1H), 10.70 (br, 1H), 8.76 (d, J=6.3 Hz, 1H), 7.88 (d, J=11.7 Hz, 1H), 7.70 (s, 1H), 7.55 (s, 1H), 7.53-7.49 (m, 3H), 7.34-7.27 (m, 4H), 6.86 (br, 1H), 4.28-4.26 (m, 2H), 4.01 (s, 4H), 3.74 (s, 3H), 3.65-3.63 (m, 1H), 3.28-3.16 (m, 3H), 2.99-2.49 (m, 3H), 2.31-1.89 (m, 8H)

Mass spectrometric value (m/z): 616 [M+H]$^+$

Example 13

N-{3-Fluoro-4-[(7-hydroxy-6-methoxy-4-quinolyl)-oxy]phenyl}-N'-(2-phenylacetyl)urea [starting compound A] (100 mg), potassium carbonate (150 mg), and 1,2-dibromoethane [starting compound C] (54 μl) were dissolved in dimethylformamide (5 ml) to prepare a solution which was then stirred at room temperature for 5 hr. Thereafter, piperidine [starting compound B] (64 μl) was further added thereto, and the mixture was stirred at room temperature for 3 hr. After the completion of the reaction, the reaction solution was filtered through Celite, and the filtrate was then concentrated under the reduced pressure to give a crude. The crude was purified by thin layer chromatography on silica gel using chloroform/methanol for development to give the title compound (22 mg, yield 18%).

$^1$H-NMR (DMSO-d$_6$, 400 MHz): δ 11.08 (br, 1H), 10.71 (br, 1H), 8.77 (d, J=6.3 Hz, 1H), 7.88 (d, J=13.6 Hz, 1H), 7.73

(s, 1H), 7.59 (s, 1H), 7.53-7.36 (m, 2H), 7.34-7.25 (m, 5H), 6.87 (d, J=6.3 Hz, 1H), 4.59-4.56 (m, 2H), 4.04 (s, 4H), 3.95-3.92 (m, 2H), 3.74 (s, 2H), 2.08 (s, 9H)

Mass spectrometric value (m/z): 573 [M+H]$^+$

Example 14

N-{3-Fluoro-4-[(7-hydroxy-6-methoxy-4-quinolyl)-oxy]phenyl}-N'-(2-phenylacetyl)urea (100 mg), potassium carbonate (145 mg), and 1-bromo-3-chloropropane (53 μl) were dissolved in dimethylformamide (5 ml) to prepare a solution which was then stirred at room temperature for 5 hr. The reaction solution was filtered through Celite, and the filtrate was concentrated under the reduced pressure to give a crude. The crude was purified by thin layer chromatography on silica gel using chloroform/methanol for development to give the title compound (90 mg, yield 78%).

$^1$H-NMR (DMSO-d$_6$, 400 MHz): δ 11.21 (br, 1H), 10.34 (br, 1H), 8.43 (d, J=5.4 Hz, 1H), 7.92 (d, J=10.2 Hz, 1H), 7.83 (d, J=12.2 Hz, 1H), 7.50 (s, 1H), 7.39-7.28 (m, 7H), 6.41 (d, J=5.1 Hz, 1H), 3.94 (s, 3H), 3.63 (s, 2H), 2.67 (m, 3H), 2.43 (s, 1H), 1.93-1.82 (m, 2H)

Mass spectrometric value (m/z): 538 [M+H]$^+$

Example 15

Dimethyl methyl malonate [starting compound B] (1.33 ml) was dissolved in ethanol/water (10/1, 6 ml) to prepare a solution. Lithium hydroxide monohydrate (0.42 g) was added to the solution, and the mixture was stirred at room temperature overnight. The reaction solution was concentrated under the reduced pressure to give 1.41 g of a crude. This crude (0.71 g), 4-[(6,7-dimethoxy-4-quinolyl)oxy]aniline [starting compound A] (1.00 g), 1-ethyl-3-(3-dimethylaminopropyl)carbodiimide hydrochloride (0.97 g), and 1-hydroxybenzotriazole monohydrate (0.78 g) were dissolved in chloroform (30 ml), and the solution was heated under reflux overnight.

An aqueous saturated sodium hydrogencarbonate solution was added to the reaction solution, and the mixture was extracted with chloroform. The chloroform layer was washed with saturated brine. The chloroform layer was dried over anhydrous sodium sulfate, and the dried chloroform layer was concentrated under the reduced pressure to give a crude. The crude was dissolved in ethanol/water (10/1, 50 ml). Lithium hydroxide monohydrate (0.28 g) was added to the solution, and the mixture was stirred at room temperature overnight. The reaction solution was concentrated under the reduced pressure. Water was added to the concentrate, and the solution was made weakly acidic by the addition of hydrochloric acid, followed by extraction with chloroform. The chloroform layer was dried over anhydrous sodium sulfate, and the dried chloroform layer was concentrated under the reduced pressure to give 0.68 g of a crude (hereinafter referred to simply as "carboxylic acid"). This carboxylic acid (96 mg), 2,4-difluoroaniline [starting compound C] (0.037 ml), 1-ethyl-3-(3-dimethylaminopropyl)carbodiimide hydrochloride (70 mg), and 1-hydroxybenzotriazole monohydrate (56 mg) were dissolved in chloroform (4 ml), and the solution was heated under reflux overnight. The reaction solution was developed on diatomaceous earth impregnated with an aqueous saturated sodium hydrogencarbonate solution, followed by extraction with chloroform. The solvent in the extract was removed by evaporation to give a crude. The crude was purified by thin layer chromatography on silica gel using chloroform/methanol for development to give 105 mg of the title compound.

$^1$H-NMR (CDCl$_3$, 400 MHz): δ 1.74 (d, J=7.3 Hz, 3H), 3.47 (q, J=7.3 Hz, 1H), 4.05 (s, 3H), 4.06 (s, 3H), 6.47 (d, J=5.4 Hz, 1H), 6.87-6.95 (m, 2H), 7.18 (d, J=9.0 Hz, 2H), 7.48 (s, 1H), 7.55 (s, 1H), 7.68 (d, J=8.8 Hz, 2H), 8.15-8.23 (m, 1H), 8.45-8.50 (m, 2H), 8.63 (br, 1H)

Mass spectrometric value (m/z): 508 [M+H]$^+$

Example 268

Phenylacetyl chloride (86 μl) and potassium thiocyanate (80 mg) were dissolved in acetonitrile (50 ml) to prepare a solution which was then stirred at 40° C. for 50 min. Acetonitrile was removed by evaporation under the reduced pressure to give a crude. An aqueous saturated sodium hydrogencarbonate solution and ethyl acetate were added to the crude, and the mixture was stirred at room temperature for 20 min. The mixture was extracted with ethyl acetate, followed by washing with saturated brine. The extract was dried over sodium sulfate, and the solvent was then removed by evaporation under the reduced pressure to give a crude which was then dissolved in toluene/ethanol (1/1). 3-Fluoro-4-{[7-(3-morpholinopropoxy)-6-methoxy-4-quinolyl]oxy}aniline (70 mg) was added to the solution, and the mixture was stirred at room temperature for 3 hr. The reaction solvent was removed by evaporation under the reduced pressure, and the residue was purified by thin layer chromatography on silica gel using chloroform/methanol for development to give the title compound (43.6 mg, yield 44.0%).

$^1$H-NMR (CDCl$_3$, 400 MHz): δ 2.13 (m, 2H), 2.49 (m, 4H), 2.58 (t, J=7.2 Hz, 2H), 3.73 (m, 4H), 3.76 (s, 2H), 4.03 (s, 3H), 4.28 (t, J=6.6 Hz, 2H), 6.44 (d, J=5.1 Hz, 1H), 7.22-7.48 (m, 8H), 7.54 (s, 1H), 7.93 (m, 1H), 8.46 (br, 1H), 8.50 (d, J=5.1 Hz, 1H), 12.47 (br, 1H)

Mass spectrometric value (m/z): 605 [M+H]$^+$

Example 269

3-Fluoro-4-{[7-(3-morpholinopropoxy)-6-methoxy-4-quinolyl]oxy}aniline (60 mg) was dissolved in chloroform (15 ml) to prepare a solution. 3-(4-Fluoroanilino)-3-oxopropanoic acid (50 mg), 1-hydroxybenzotriazole monohydrate (43 mg), and 1-ethyl-3-(3-dimethylaminopropyl)carbodiimide hydrochloride (54 mg) were added to the solution, and the mixture was heated under reflux for 3 hr, followed by washing with an aqueous saturated sodium hydrogencarbonate solution. The solvent was then removed by evaporation under the reduced pressure to give a crude. The crude was purified by column chromatography on silica gel using chloroform/methanol for development to give the title compound (41 mg, yield 48%).

$^1$H-NMR (CDCl$_3$, 400 MHz): δ 2.04-2.10 (m, 2H), 2.35-2.46 (m, 4H), 2.51 (t, J=7.1 Hz, 2H), 3.50 (s, 2H), 3.63-3.68 (m, 4H), 3.96 (s, 3H), 4.18 (t, J=6.6 Hz, 2H), 6.32 (d, J=5.3 Hz, 1H), 6.97-7.02 (m, 2H), 7.13-7.24 (m, 2H), 7.36 (s, 1H), 7.43-7.50 (m, 2H), 7.49 (s, 1H), 7.70-7.74 (m, 1H), 8.40 (d, J=5.3 Hz, 1H), 8.55 (s, 1H), 9.35 (s, 1H)

Mass spectrometric value (ESI-MS, m/z): 607 [M+H]$^+$

Compounds of Examples 1 to 15, 268, and 269 had the following respective structures.

Example 1
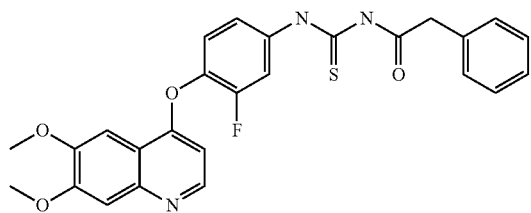
Example 2
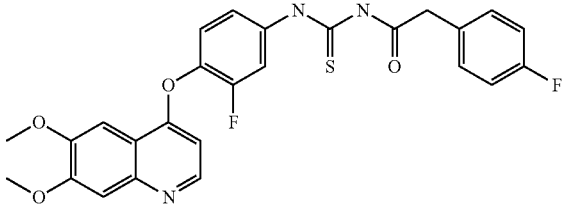
Example 3
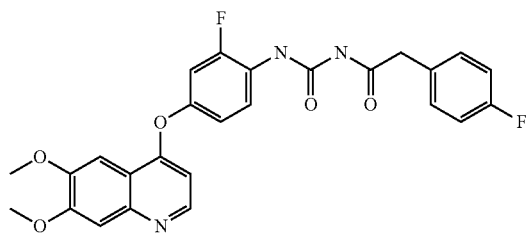
Example 4
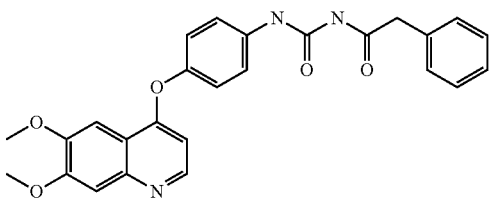
Example 5
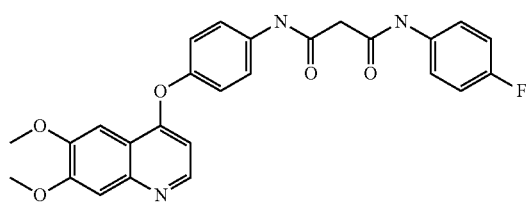
Example 6
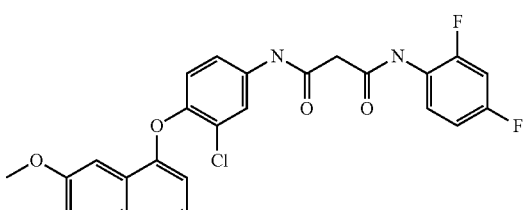
Example 7
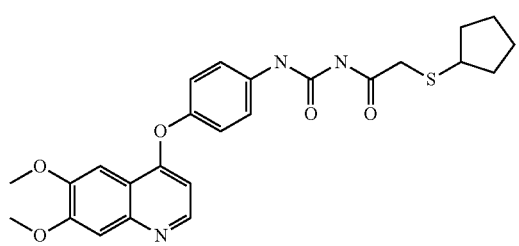
Example 8
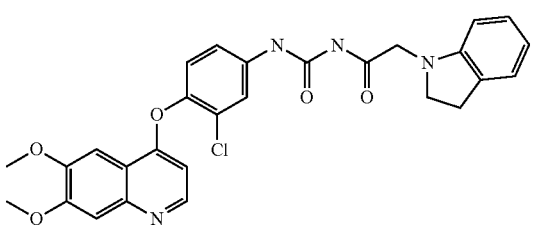
Example 9
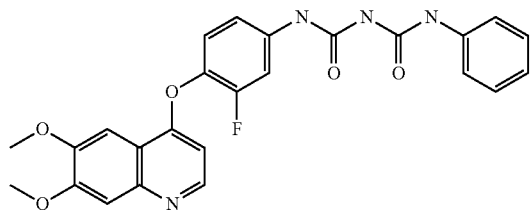
Example 10
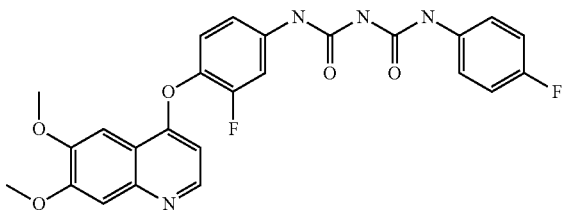
Example 11
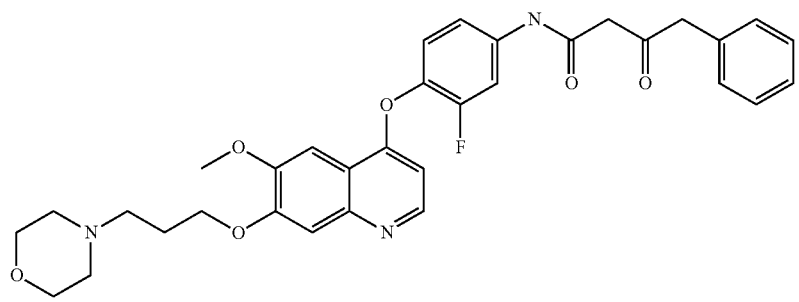

-continued
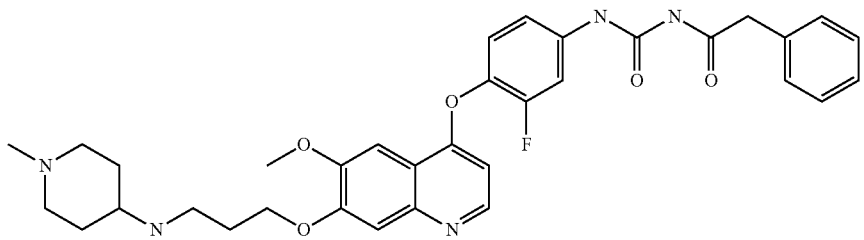
Example 12
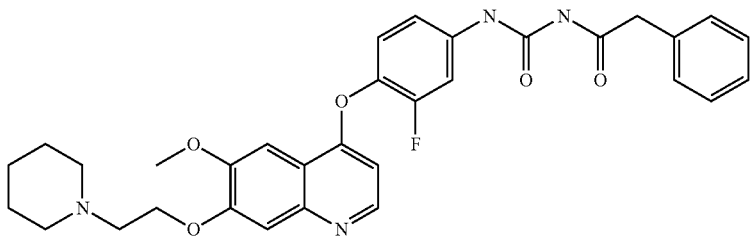
Example 13
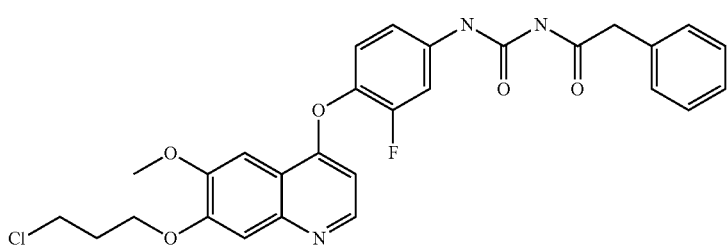
Example 14
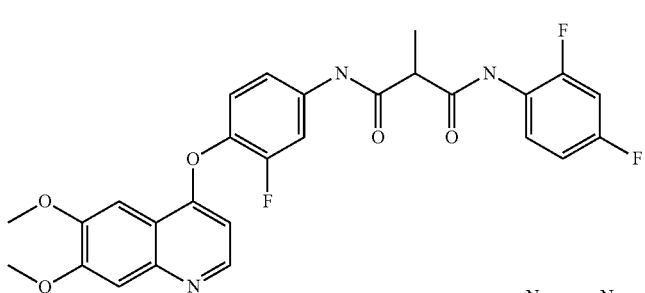
Example 15
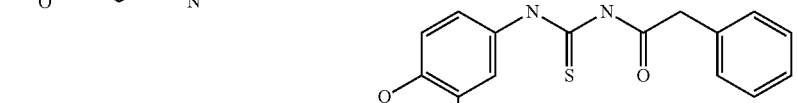
Example 268
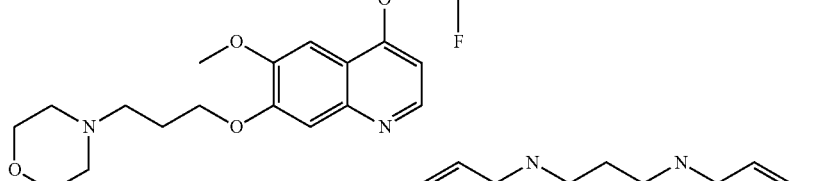
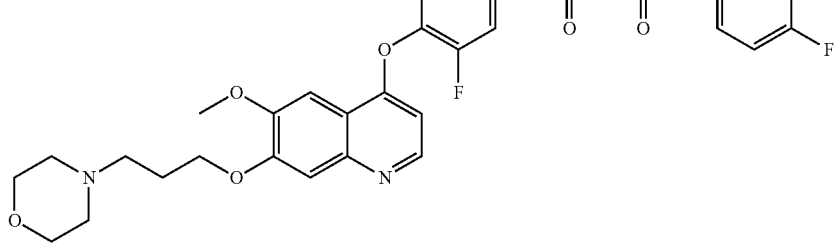
Example 269
Compounds of Examples 16 to 267 were synthesized as described in Examples 1 to 15, 268, and 269. For these compounds, chemical structural formulae, starting compounds, synthesis methods, and data for identifying the compounds are as follows.

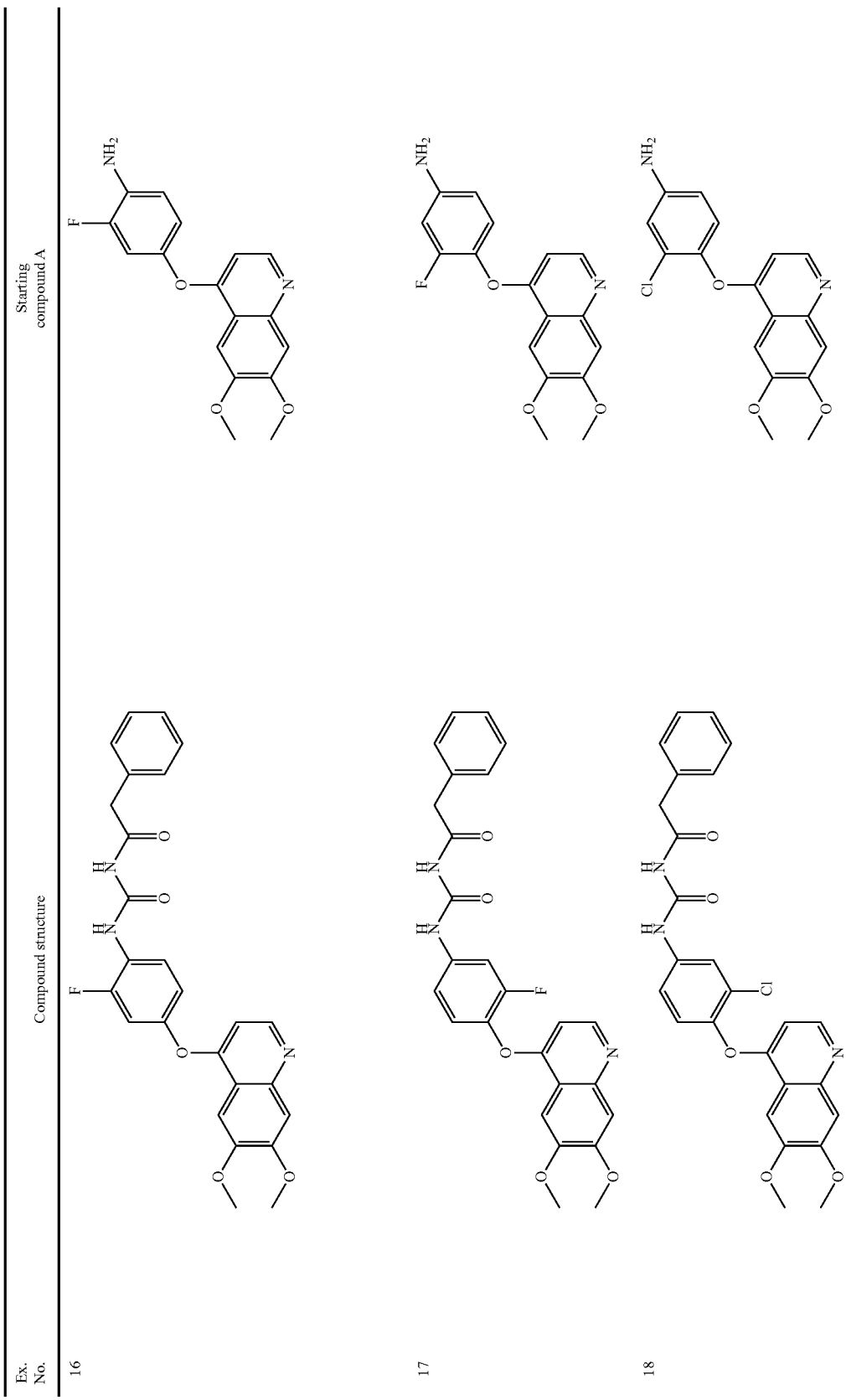

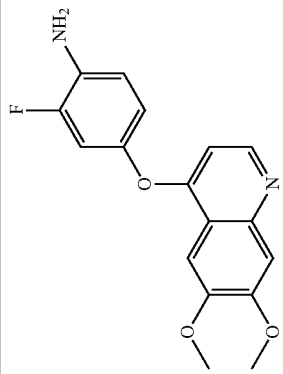
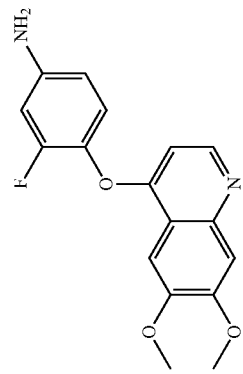
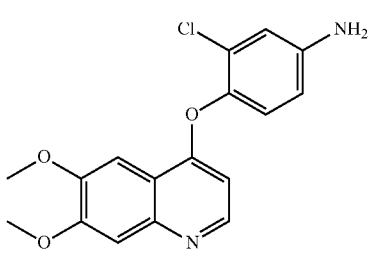
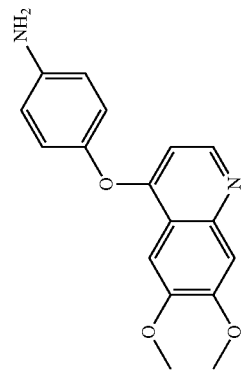

-continued
| 23 | 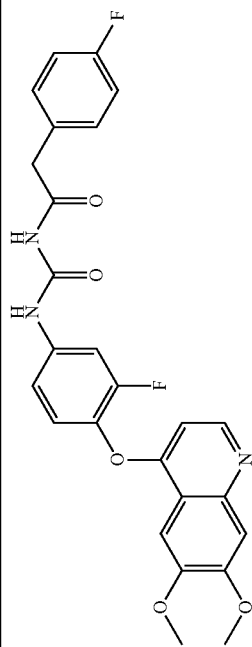 |
| 24 | 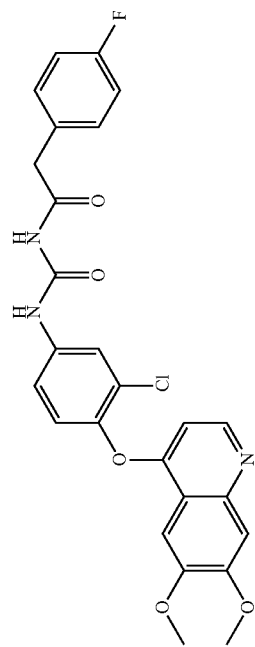 |
| 25 | 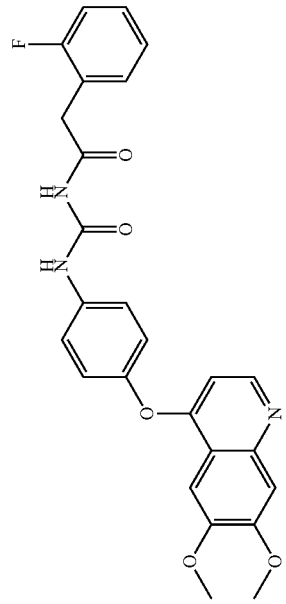 |
| 26 | 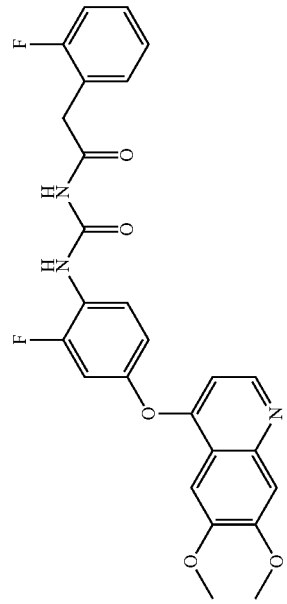 |

-continued
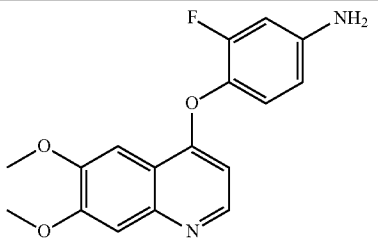
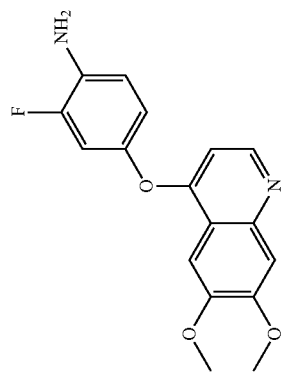
27
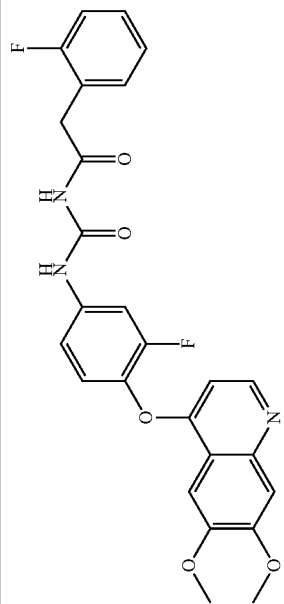
28
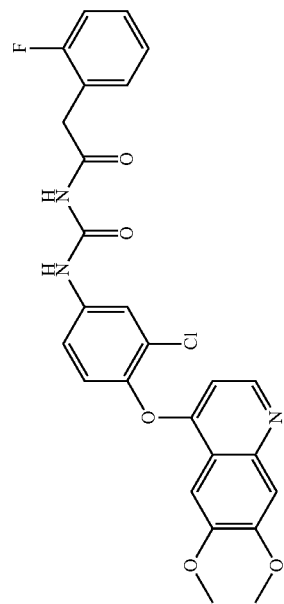
29
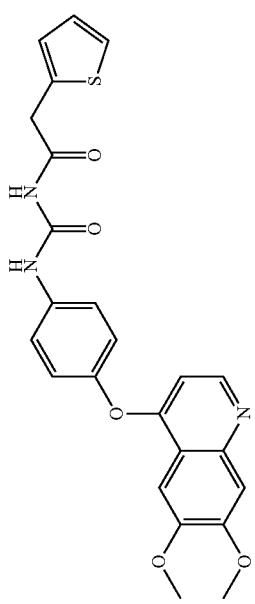
30
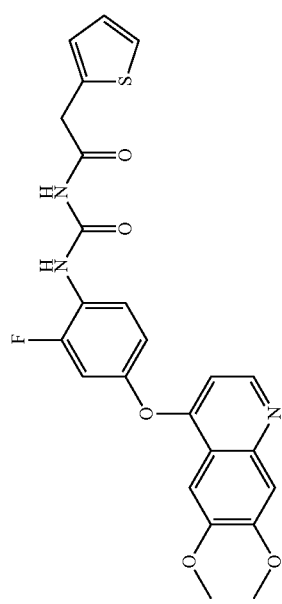

-continued
| | | |
|---|---|---|
| 31 | 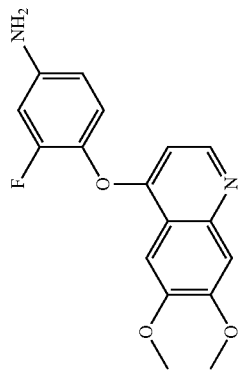 | |
| 32 | 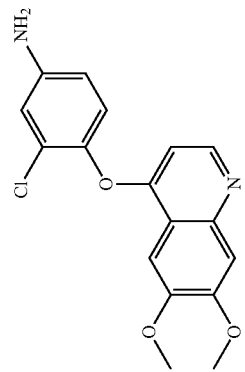 | |
| 33 | 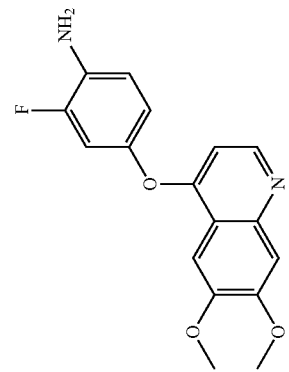 | |
| 34 | 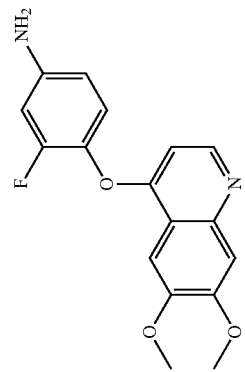 | |

-continued
| | |
|---|---|
| 35 | 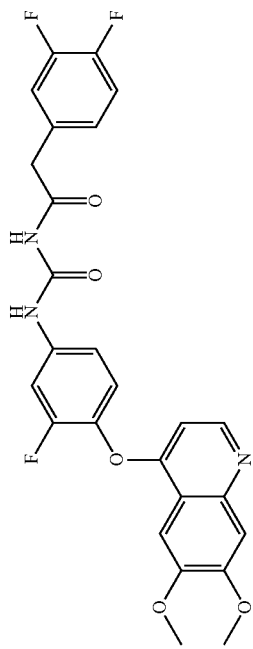 |
| 36 | 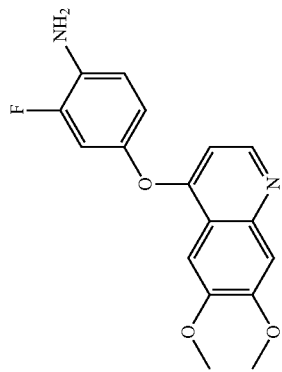 |
| 37 |  |
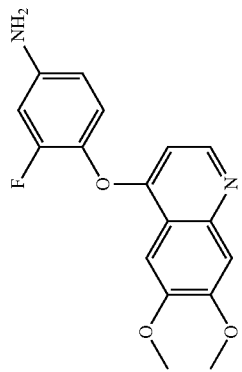

-continued
| | | |
|---|---|---|
| 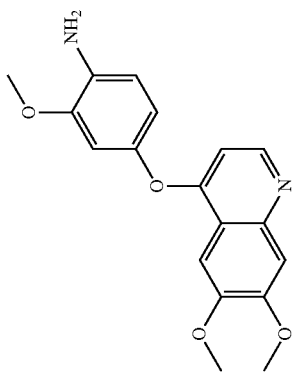 | 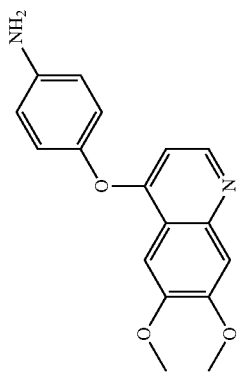 | 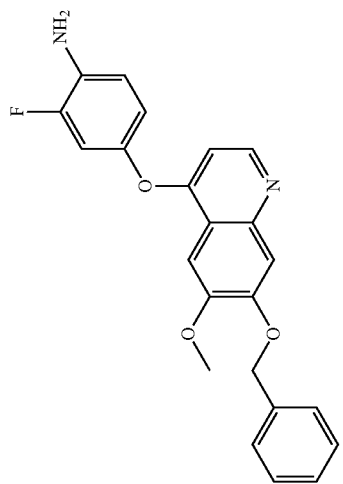 |
| 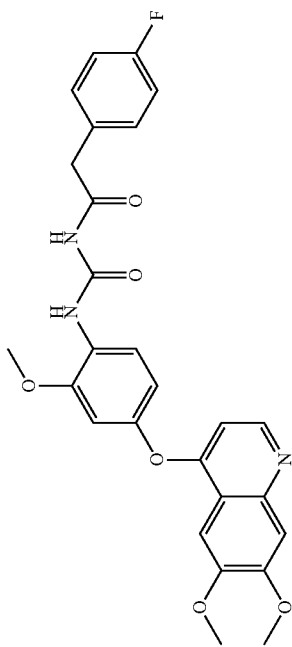 | 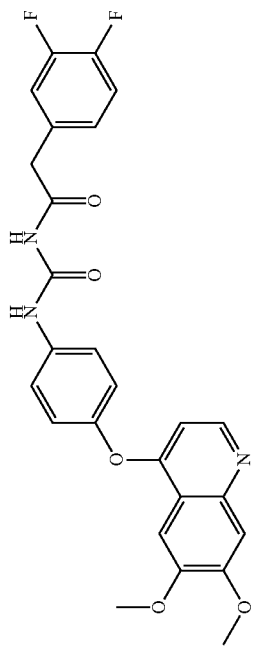 |  |
| 38 | 39 | 40 |

-continued
| 41 | 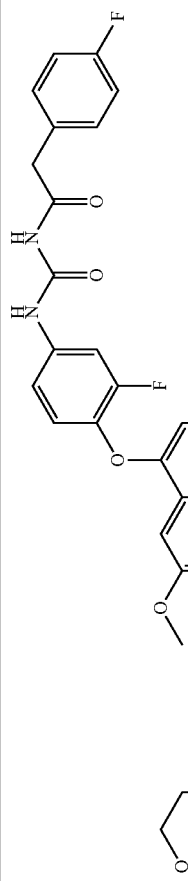 | 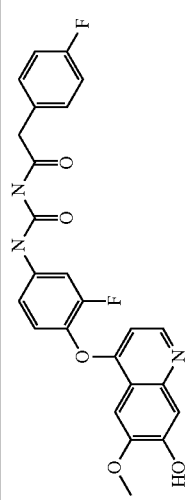 |
| 42 | 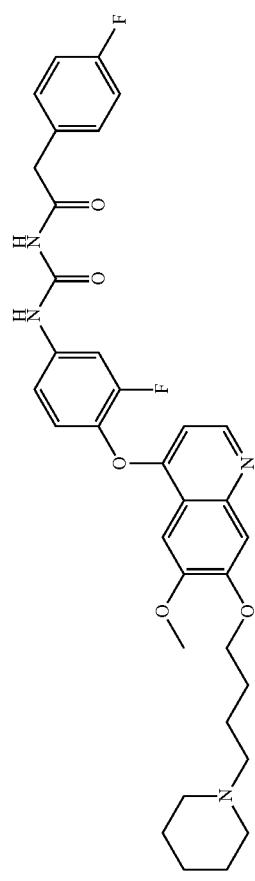 | 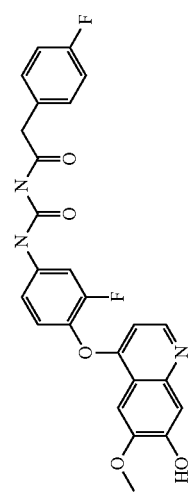 |
| 43 | 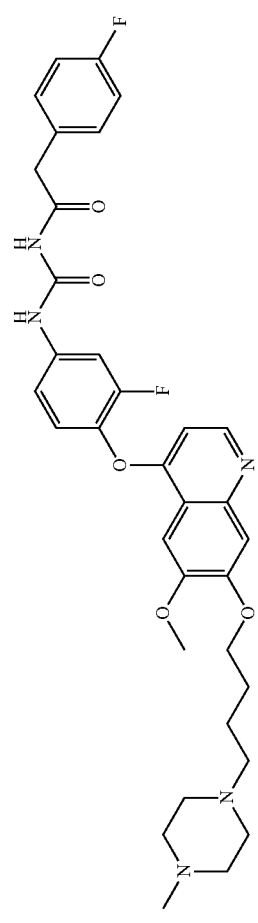 | 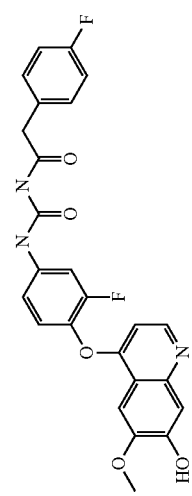 |
| 44 | 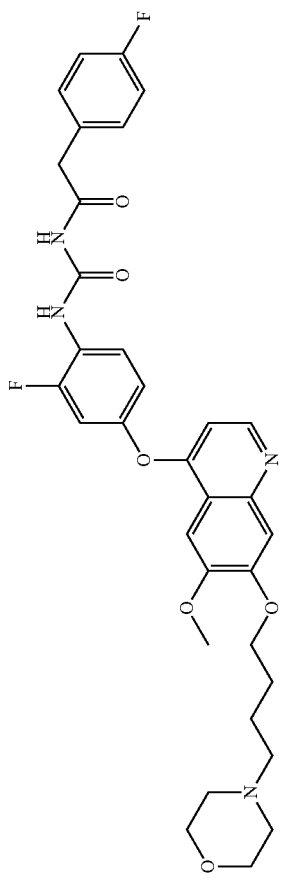 | 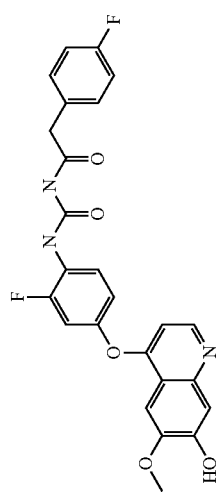 |

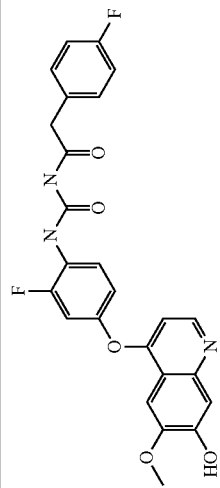
45
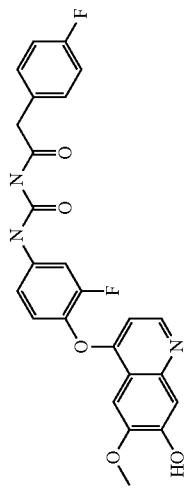
46
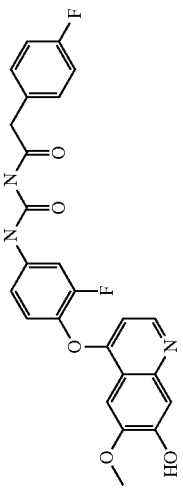
47

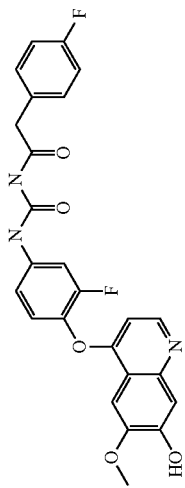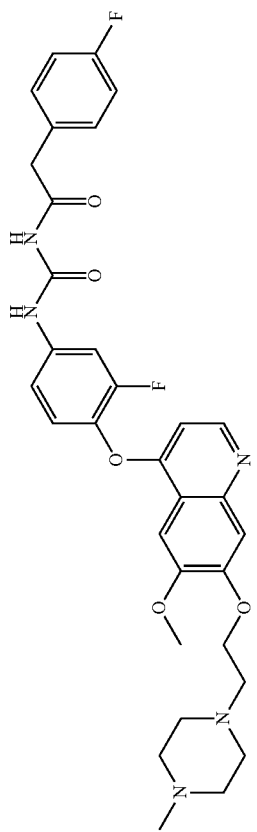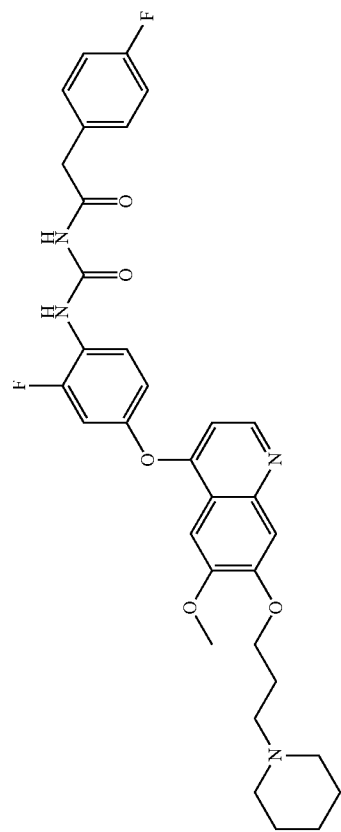

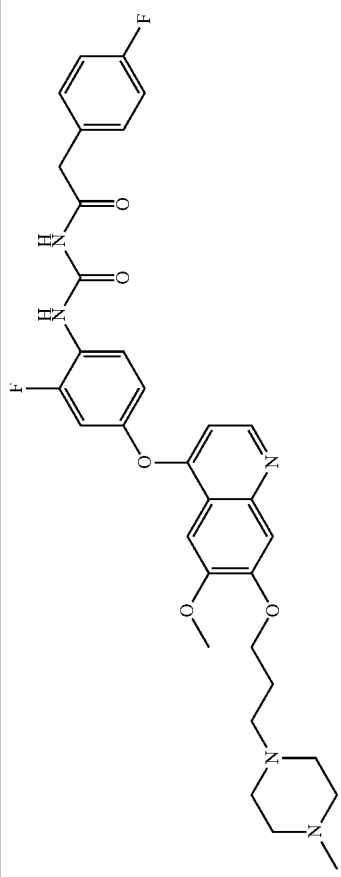
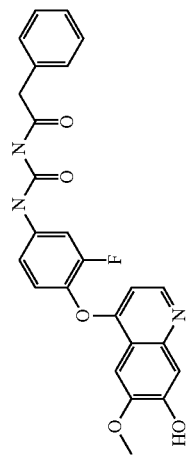
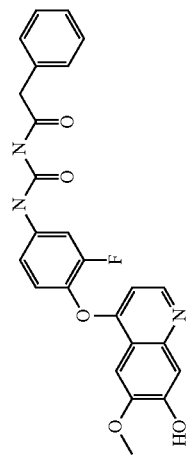

-continued
| 54 | 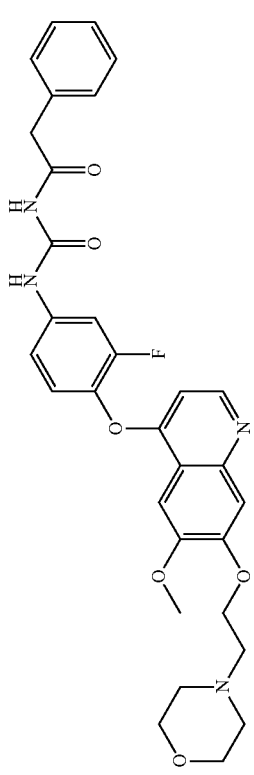 | 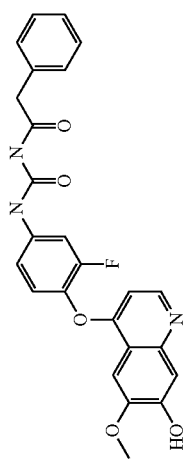 |
| --- | --- | --- |
| 55 | 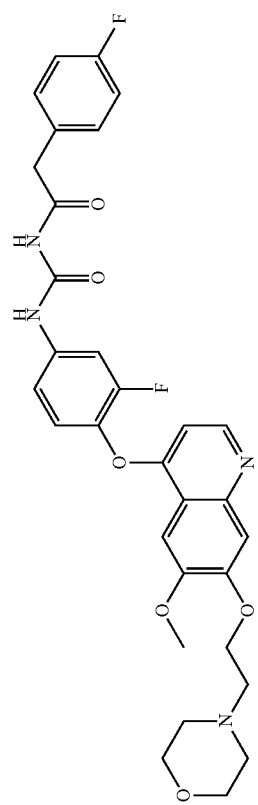 | 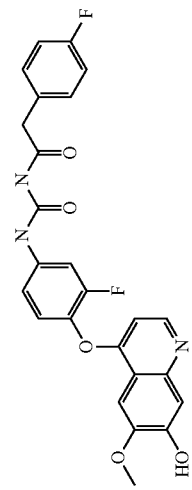 |
| 56 | 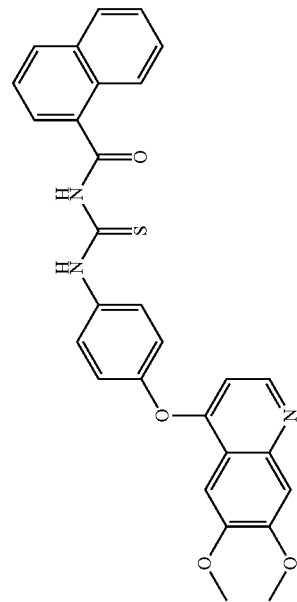 | 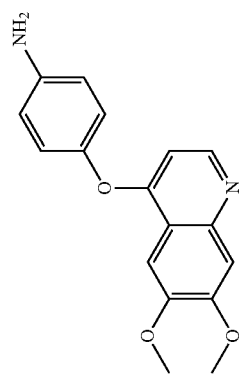 |
| 57 | 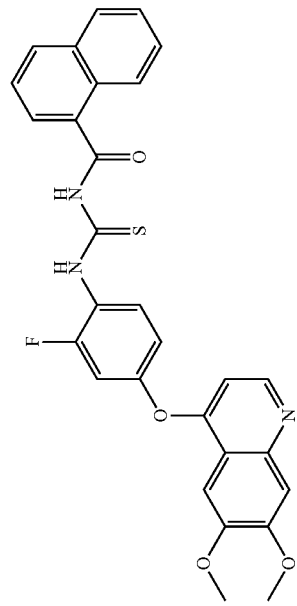 | 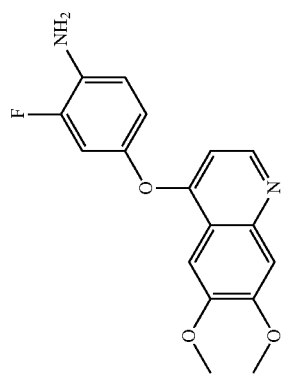 |

-continued
| | |
|---|---|
| 58 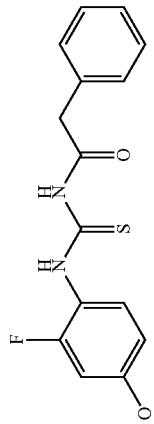 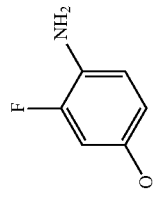 | 59 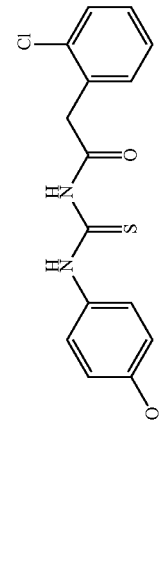 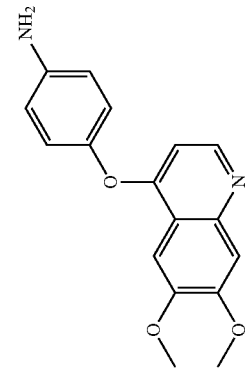 |
| 60 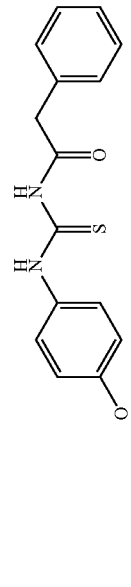 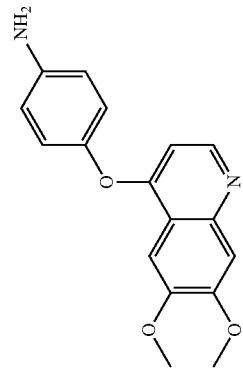 | 61 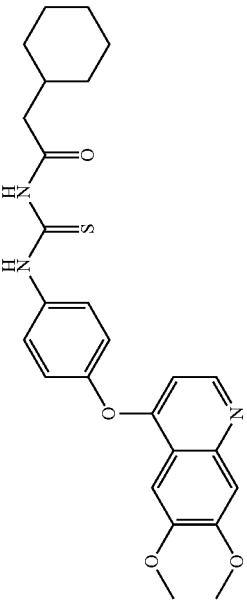 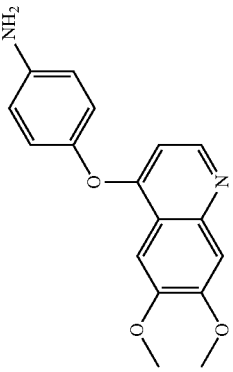 |

-continued
| | | |
|---|---|---|
| 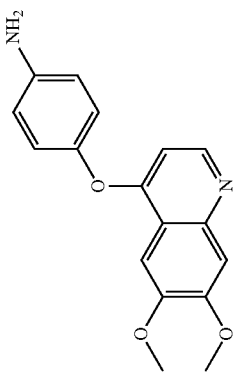 | 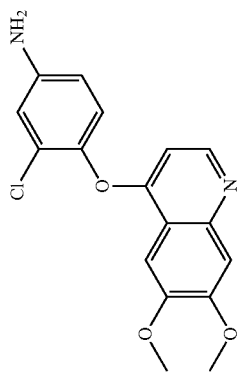 | 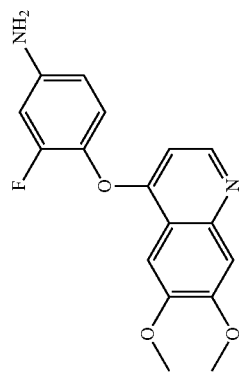 |
| 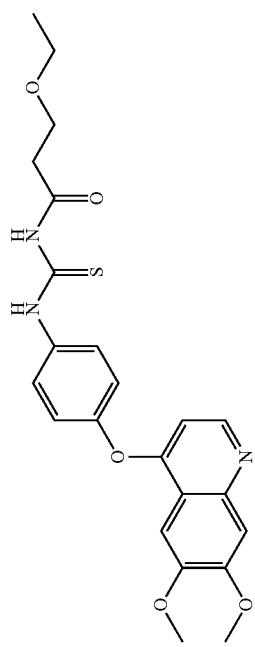 | 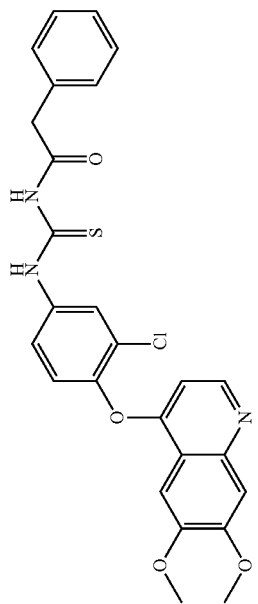 | 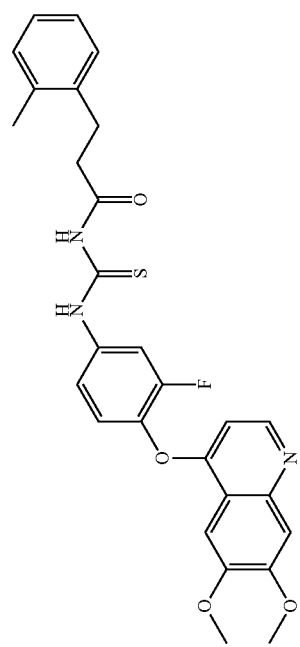 |
| 62 | 63 | 64 |

-continued
| | |
|---|---|
| 65 | 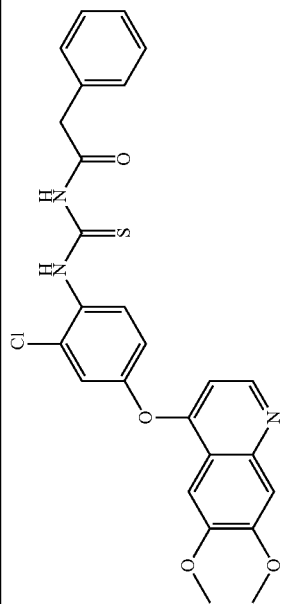 |
| 66 | 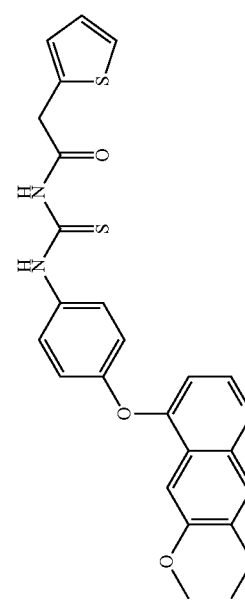 |
| 67 | 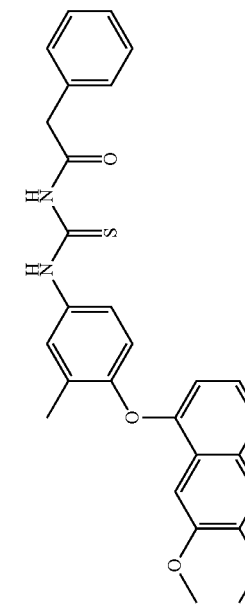 |
| 68 | 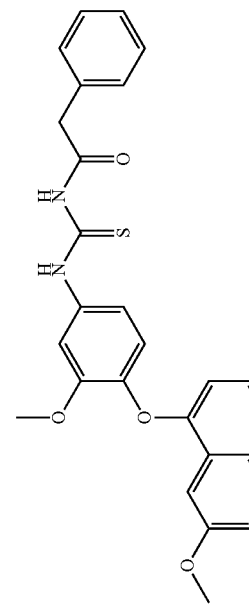 |
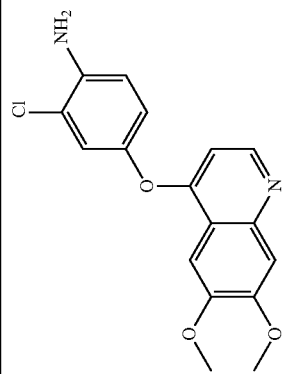
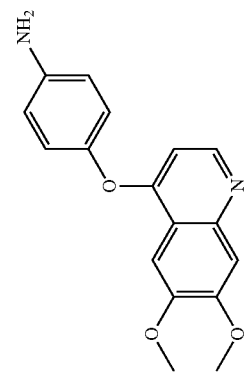
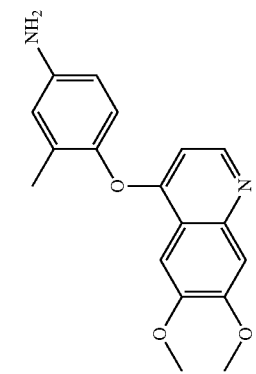
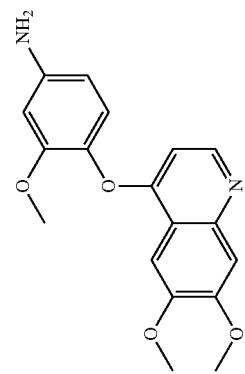

-continued
| | |
|---|---|
| 69 | 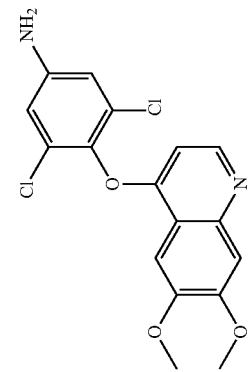 |
| 70 | 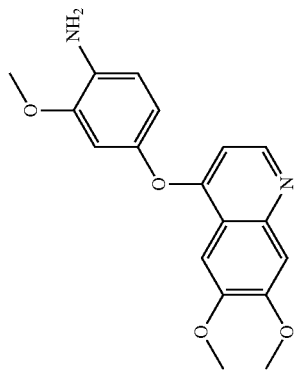 |
| 71 | 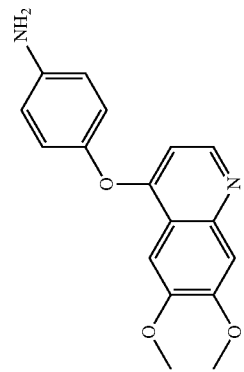 |
| 72 | 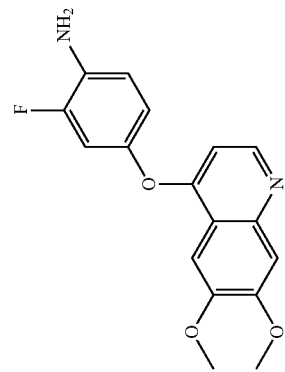 |

-continued
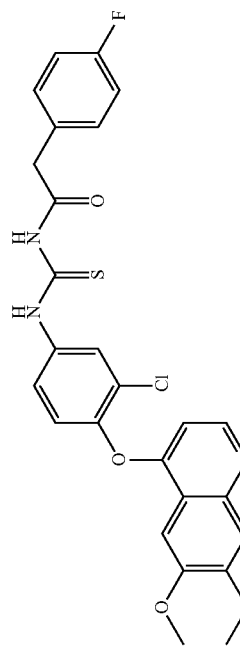
73
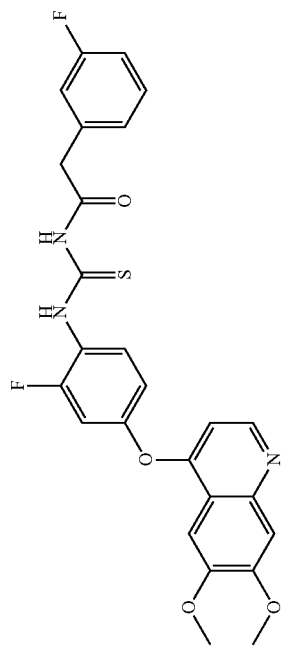
74
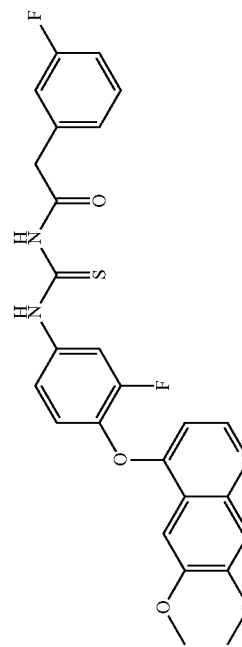
75
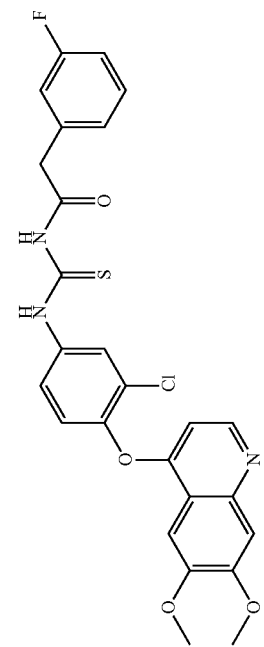
76
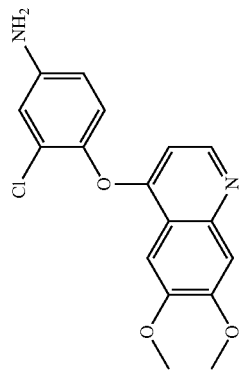
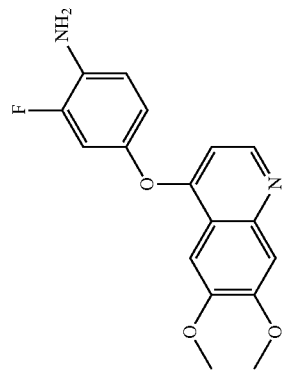
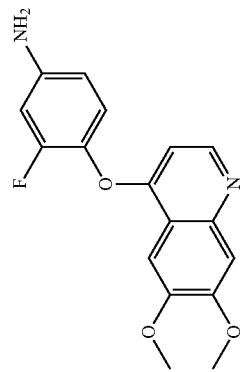
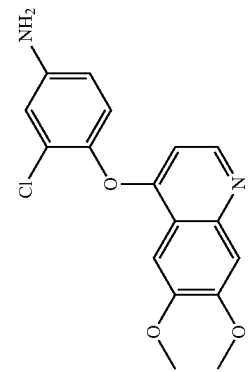

-continued
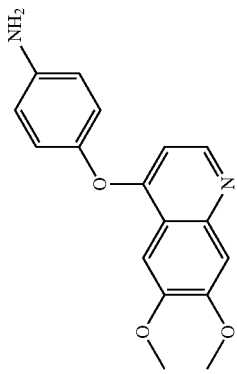
77
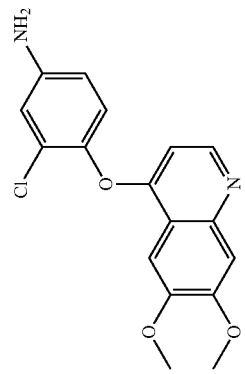
78
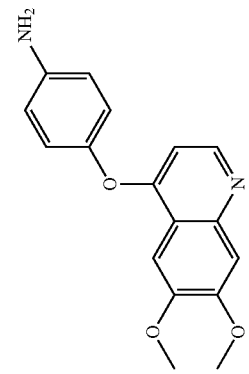
79
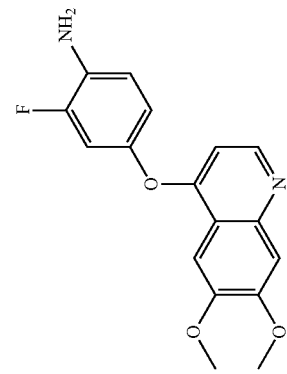
80

-continued
| | 101 | 102 |
|---|---|---|
| | 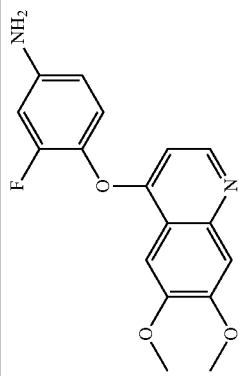 | 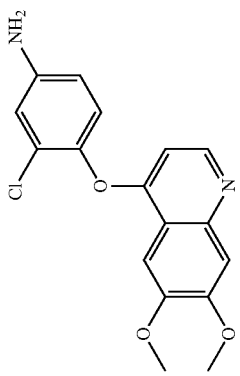 |
| | 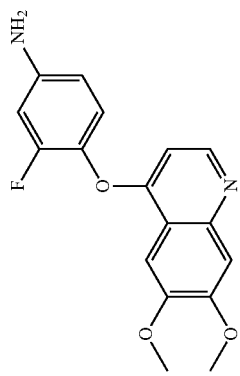 | |
| 81 | 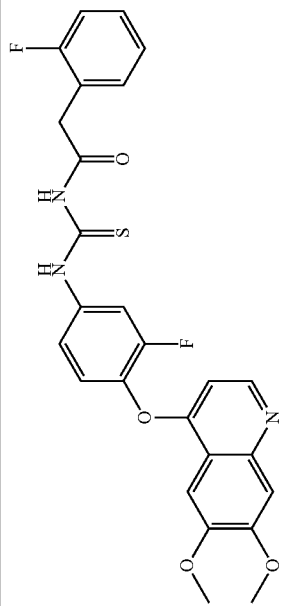 | |
| 82 | 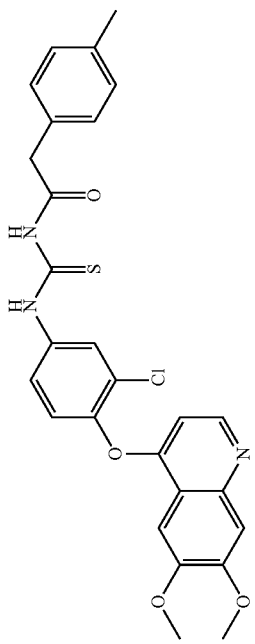 | |
| 83 | 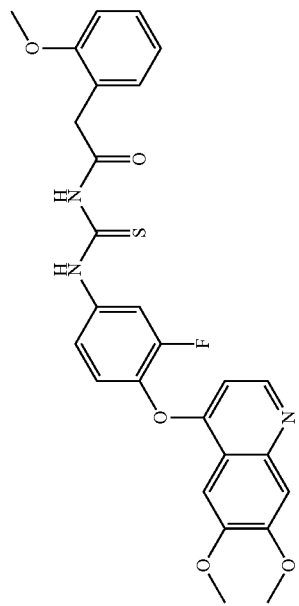 | |

| | |
|---|---|
| 84 | 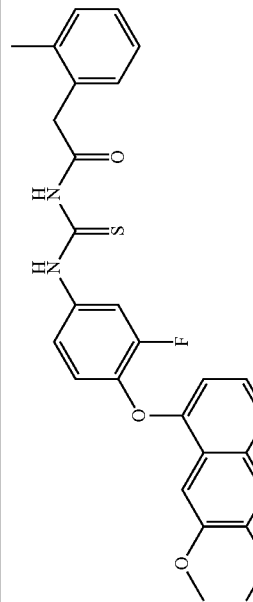 |
| 85 | 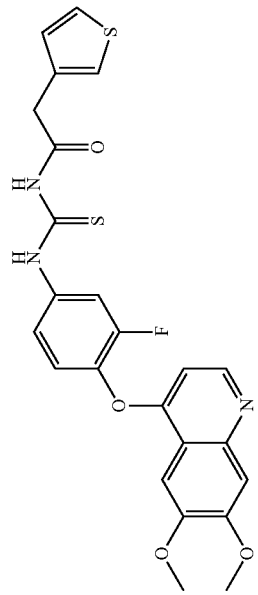 |
| 86 | 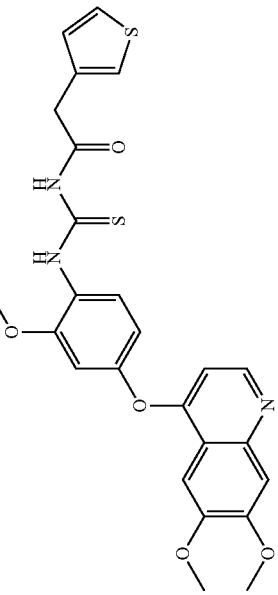 |
| 87 | 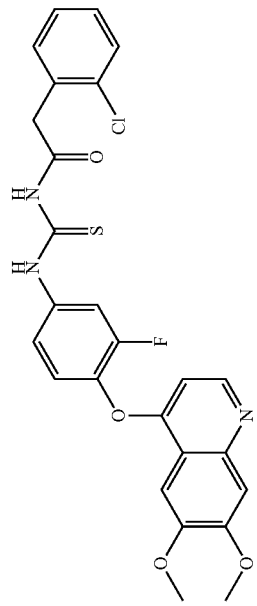 |

-continued
| | |
|---|---|
| 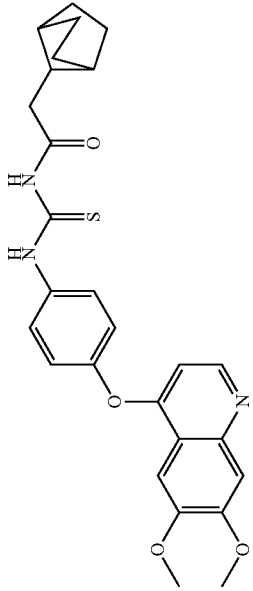 | 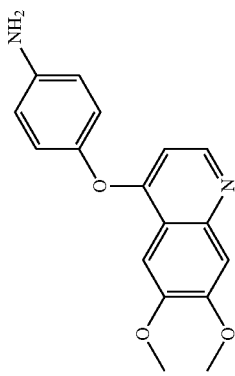 |
| 88 | |
| 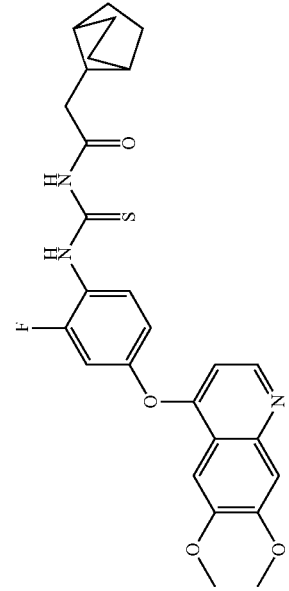 | 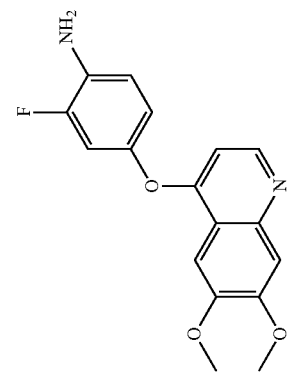 |
| 89 | |
| 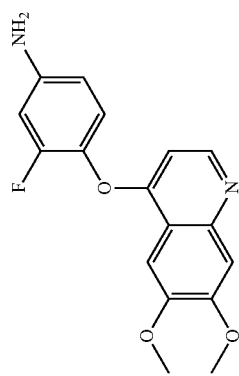 | |
| 90 | |
| 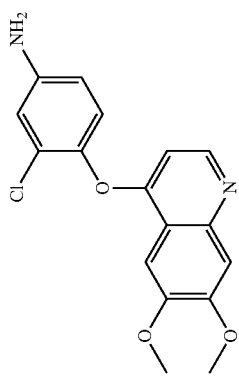 | |
| 91 | |

-continued
| 92 | 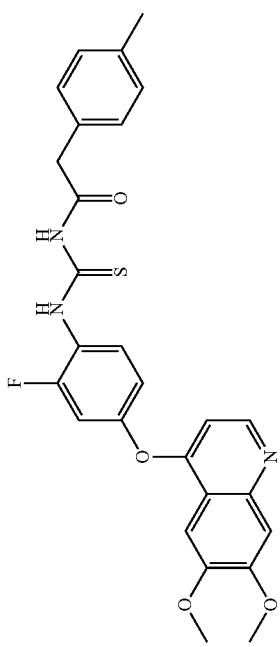 | 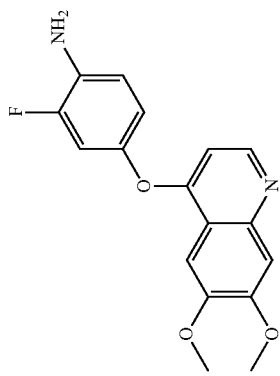 |
| 93 | 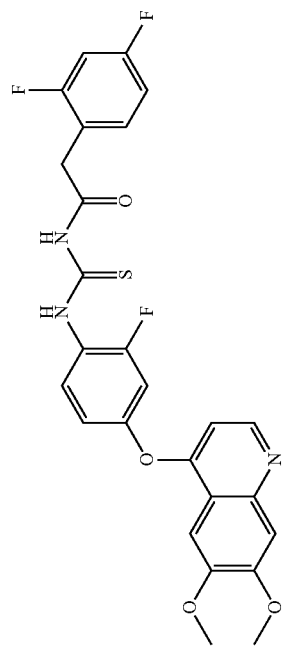 | 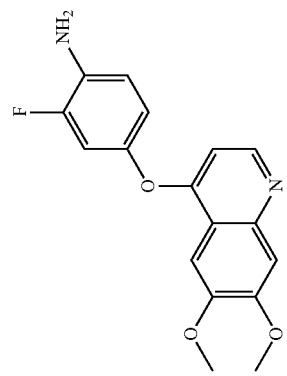 |
| 94 | 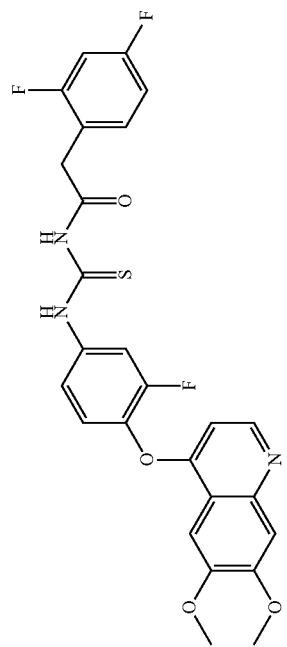 | 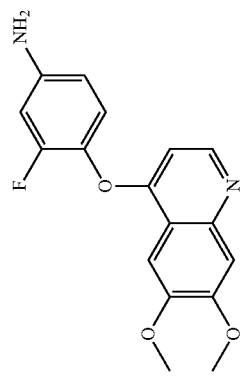 |

| 95 | 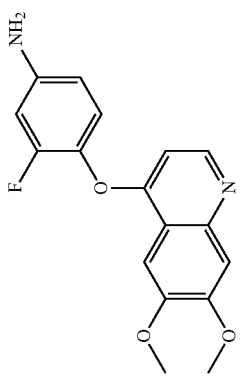 |
| 96 | 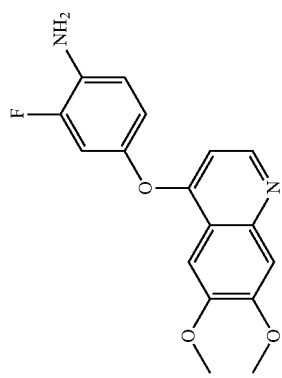 |
| 97 | 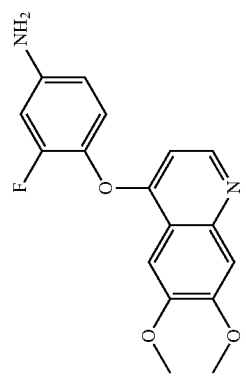 |

| | | | |
|---|---|---|---|
| 86 | 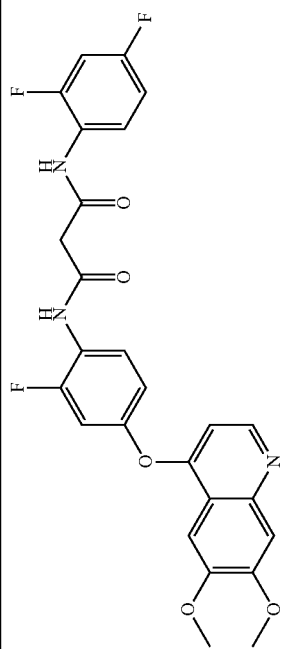 | | |
| 99 | 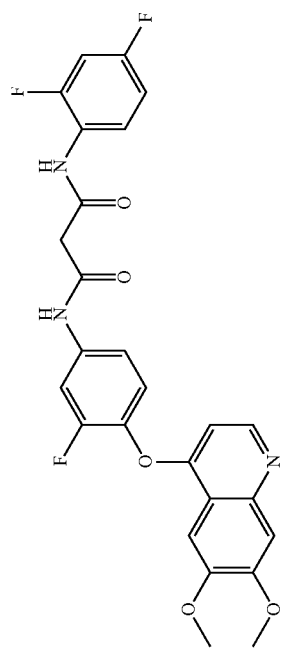 | | |
| 100 | 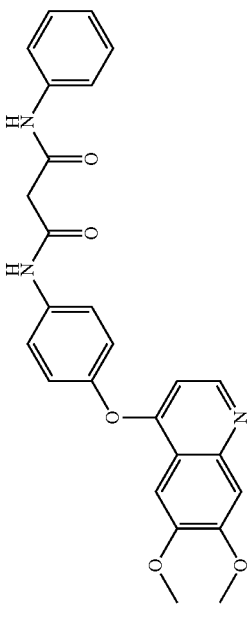 | | |
| 101 | 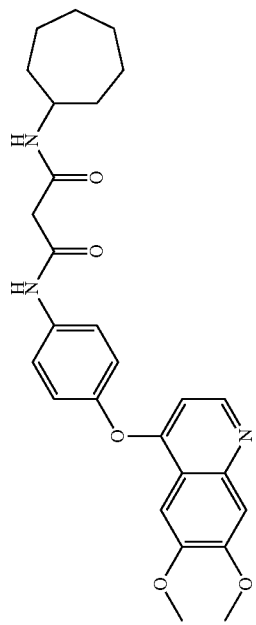 | | |

-continued
| 102 | 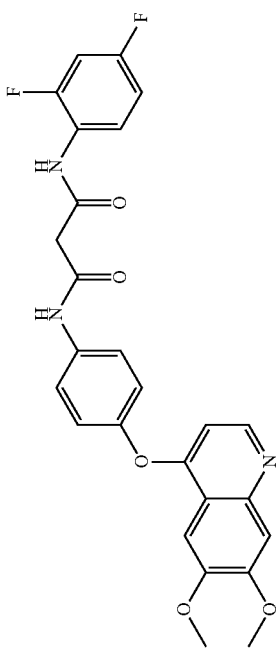 | 113 | 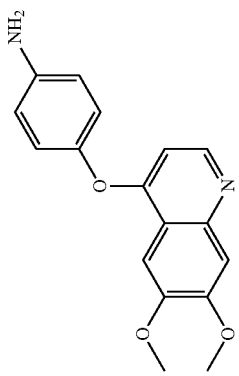 |
| 103 | 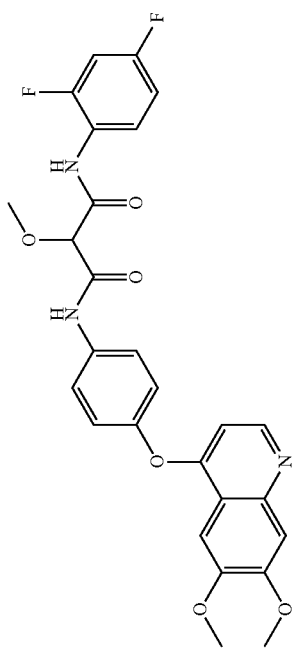 | | 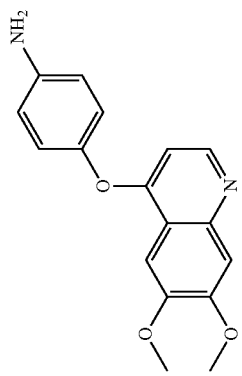 |
| 104 | 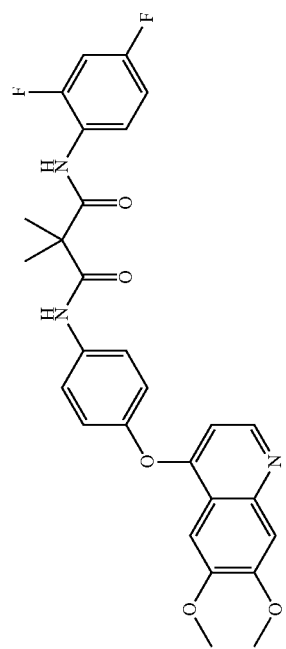 | | 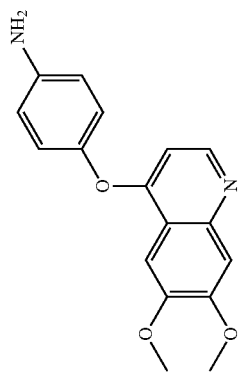 |

-continued
| | | | | | | |
|---|---|---|---|---|---|---|
| 105 | 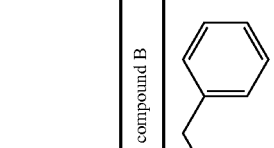 | | | | | |
| 106 | 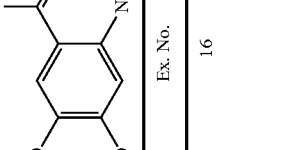 | | | | | |
| Ex. No. | Starting compound B | Starting compound C | Mass spectrometric value (m/z) | H$^1$-MNR | Synthesis method$^a$ |
|---|---|---|---|---|---|
| 16 | 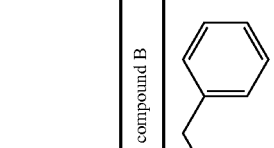 | | 476 [M + H]+ | (CDCl3, 400 MHz): δ 3.75 (s, 2H), 4.01 (s, 3H), 4.02 (s, 3H), 6.49 (d, J = 5.3 Hz, 1H), 6.95-7.00 (m, 2H), 7.28-7.48 (m, 5H), 7.41 (s, 1H), 7.50 (s, 1H), 8.01 (s, 1H), 8.18 (t, J = 9.1 Hz, 1H), 8.49 (d, J = 5.3 Hz, 1H), 10.74 (s, 1H) | Ex. 4 |
| 17 | 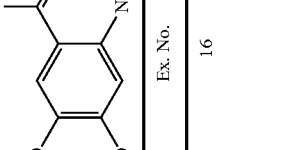 | | 476 [M + H]+ | (CDCl3, 400 MHz): δ 3.75 (s, 2H), 4.03 (s, 3H), 4.04 (s, 3H), 6.38 (d, J = 5.3 Hz, 1H), 6.97-7.42 (m, 7H), 7.40 (s, 1H), 7.55 (s, 1H), 7.65-7.68 (m, 1H), 8.09 (s, 1H), 8.46 (d, J = 5.3 Hz, 1H), 10.60 (s, 1H) | Ex. 4 |
| 18 | 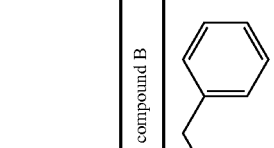 | | 492 [M + H]+ | (CDCl3, 400 MHz): δ 3.75 (s, 2H), 4.03 (s, 3H), 4.04 (s, 3H), 6.29 (d, J = 5.3 Hz, 1H), 7.17-7.43 (m, 7H), 7.41 (s, 1H), 7.56 (s, 1H), 7.82 (d, J = 2.5 Hz, 1H), 8.07 (br, 1H), 8.45 (d, J = 5.3 Hz, 1H), 10.62 (s, 1H) | Ex. 4 |
| 19 | 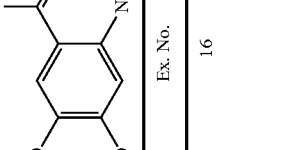 | | 482 [M + H]+ | (DMSO-d6, 400 MHz): δ 11.23 (br, 1H), 10.75 (br, 1H), 8.49 (d, J = 5.1 Hz, 1H), 8.22 (m, 1H), 7.52-7.37 (m, 3H), 7.23 (m, 1H), 7.10-7.02 (m, 2H), 6.87-6.85 (m, 1H), 6.56 (d, J = 5.4 Hz, 1H), 3.94 (s, 6H), 3.77 (s, 2H) | Ex. 3 |

| | | | |
|---|---|---|---|
| 20 | 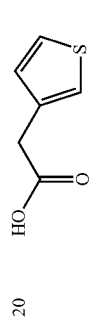 | 482 [M + H]+ | (DMSO-d6, 400 MHz): δ 11.00 (br, 1H), 10.63 (br, 1H), 8.48 (d, J = 5.1 Hz, 1H), 7.82 (d, J = 14.15 Hz, 1H), 7.52-7.38 (m, 5H), 7.23 (m, 1H), 7.02 (d, J = 6.1 Hz, 1H), 6.45 (d, J = 5.4 Hz, 1H), 3.95 (s, 6H), 3.77 (s, 2H) | Ex. 3 |
| 21 | 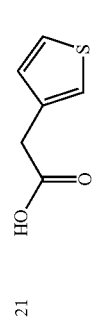 | 498 [M + H]+ | (DMSO-d6, 400 MHz): δ 10.63 (br, 1H), 8.47 (d, J = 5.1 Hz, 1H), 8.01 (s, 1H), 7.59-7.38 (m, 5H), 7.23 (s, 1H), 7.09 (d, J = 4.8 Hz, 1H), 7.02 (d, J = 4.8 Hz, 1H), 6.35 (d, J = 5.4 Hz, 1H), 3.94 (s, 6H), 3.77 (s, 2H) | Ex. 3 |
| 22 | 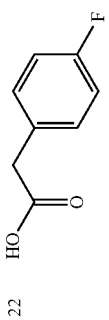 | 476 [M + H]+ | (DMSO-d6, 400 MHz): δ 10.96 (br, 1H), 10.50 (br, 1H), 8.31 (d, J = 5.4 Hz, 1H), 7.65 (d, J = 9.0 Hz, 2H), 7.38-7.08 (m, 8H), 6.45 (d, J = 5.1 Hz, 1H), 3.94 (s, 3H), 3.93 (s, 3H), 3.74 (s, 2H) | Ex. 3 |
| 23 | 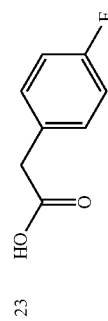 | 494 [M + H]+ | (DMSO-d6, 400 MHz): δ 11.03 (br, 1H), 10.61 (br, 1H), 8.47 (d, J = 5.4 Hz, 1H), 7.81 (d, J = 14.1 Hz, 1H), 7.52 (s, 1H), 7.42-7.08 (m, 6H), 6.85 (br, 1H), 6.44 (d, J = 4.9 Hz, 1H), 3.94 (s, 6H), 3.75 (s, 2H) | Ex. 3 |
| 24 | 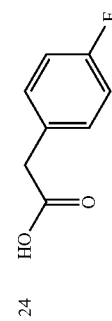 | 510 [M + H]+ | (DMSO-d6, 400 MHz): δ 11.08 (br, 1H), 10.62 (br, 1H), 8.46 (d, J = 5.1 Hz, 1H), 7.85 (d, J = 2.7 Hz, 1H), 7.59-7.57 (m, 1H), 7.52 (br, 1H), 7.42-7.09 (m, 5H), 6.87 (br, 1H), 6.34 (d, J = 5.1 Hz, 1H), 3.93 (s, 6H), 3.75 (s, 2H) | Ex. 3 |
| 25 | 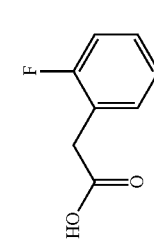 | 498 [M + Na]+ | (CDCl3, 400 MHz): δ 3.79 (s, 2H), 4.05 (s, 3H), 4.06 (s, 3H), 6.47 (d, J = 5.1 Hz, 1H), 7.13-7.42 (m, 6H), 7.46 (s, 1H), 7.55 (s, 1H), 7.60 (d, J = 9.0 Hz, 2H), 7.73 (s, 1H), 8.48 (d, J = 5.4 Hz, 1H), 10.47 (s, 1H) | Ex. 3 |
| 26 | 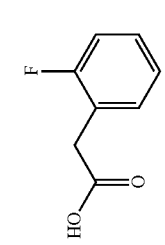 | 516 [M + Na]+ | (CDCl3, 400 MHz): δ 3.80 (s, 2H), 4.04 (s, 3H), 4.06 (s, 3H), 6.52 (d, J = 5.4 Hz, 1H), 6.96-7.02 (m, 2H), 7.13-7.42 (m, 4H), 7.46 (s, 1H), 7.49 (s, 1H), 7.76 (s, 1H), 8.20-8.26 (m, 1H), 8.51 (d, J = 5.4 Hz, 1H), 10.68 (s, 1H) | Ex. 3 |

| | Structure | MS | NMR | Ex. |
|---|---|---|---|---|
| 27 | 2-fluorophenylacetic acid | 494 [M + H]+ | (DMSO-d6, 400 MHz): δ 10.62 (br, 1H), 8.48 (d, J = 5.1 Hz, 1H), 7.82 (d, J = 13.9 Hz, 1H), 7.52-7.11 (m, 8H), 6.93 (br, 1H), 6.45 (d, J = 5.1 Hz, 1H), 3.85 (s, 2H), 3.44 (s, 6H) | Ex. 3 |
| 28 | 2-fluorophenylacetic acid | 532 [M + Na]+ | (CDCl3, 400 MHz): δ 3.79 (s, 2H), 4.06 (s, 3H), 4.07 (s, 3H), 6.34 (d, J = 5.4 Hz, 1H), 7.14-7.54 (m, 7H), 7.59 (s, 1H), 7.70 (s, 1H), 7.84 (d, J = 2.7 Hz, 1H), 8.48 (d, J = 5.4 Hz, 1H), 10.55 (s, 1H) | Ex. 3 |
| 29 | thiopheneacetic acid | 464 [M + H]+ | (DMSO-d6, 400 MHz): δ 10.97 (br, 1H), 10.47 (br, 1H), 8.47 (d, J = 5.4 Hz, 1H), 7.67-7.65 (m, 2H), 7.50 (s, 1H), 7.44 (d, J = 6.6 Hz, 1H), 7.39 (s, 1H), 7.25-7.23 (m, 2H), 7.01-6.99 (m, 2H), 6.46 (d, J = 5.4 Hz, 1H), 4.00 (s, 2H), 3.98 (s, 6H) | Ex. 3 |
| 30 | thiopheneacetic acid | 482 [M + H]+ | (DMSO-d6, 400 MHz): δ 11.17 (br, 1H), 10.69 (br, 1H), 8.47 (d, J = 5.1 Hz, 1H), 8.23-8.19 (m, 1H), 7.47-7.33 (m, 3H), 7.14 (d, J = 8.8 Hz, 1H), 7.02-6.89 (m, 3H), 6.55 (d, J = 5.1 Hz, 1H), 3.98 (s, 2H), 3.92 (s, 6H) | Ex. 3 |
| 31 | thiopheneacetic acid | 482 [M + H]+ | (DMSO-d6, 400 MHz): δ 8.48 (d, J = 5.1 Hz, 1H), 7.82 (d, J = 13.4 Hz, 1H), 7.53-7.33 (m, 4H), 7.01-6.89 (m, 5H), 6.45 (d, J = 5.1 Hz, 1H), 3.97 (s, 2H), 3.95 (s, 6H) | Ex. 3 |
| 32 | thiopheneacetic acid | 498 [M + H]+ | (DMSO-d6, 400 MHz): δ 11.04 (br, 1H), 10.54 (br, 1H), 8.47 (d, J = 5.1 Hz, 1H), 8.00 (s, 1H), 7.61-7.59 (m, 1H), 7.53 (s, 1H), 7.45-7.33 (m, 3H), 7.01-6.89 (m, 2H), 6.35 (d, J = 5.1 Hz, 1H), 3.99 (s, 2H), 3.94 (s, 6H) | Ex. 3 |
| 33 | 2,4-difluorophenylacetic acid | 512 [M + H]+ | (CDCl3, 400 MHz): δ 3.74 (s, 2H), 4.01 (s, 3H), 4.03 (s, 3H), 6.49 (d, J = 5.3 Hz, 1H), 6.86-6.99 (m, 4H), 7.21-7.32 (m, 1H), 7.41 (s, 1H), 7.47 (s, 1H), 8.15 (br, 1H), 8.20 (t, J = 9.5 Hz, 1H), 8.49 (d, J = 5.3 Hz, 1H), 10.63 (s, 1H) | Ex. 3 |

| # | Structure | MS | NMR | Ref |
|---|---|---|---|---|
| 34 | 2,4-difluorophenylacetic acid | 512 [M + H]+ | (CDCl3, 400 MHz): δ 3.74 (s, 2H), 4.02 (s, 3H), 4.04 (s, 3H), 6.39 (d, J = 5.3 Hz, 1H), 6.88-7.69 (m, 6H), 7.24 (s, 1H), 7.55 (s, 1H), 8.29 (br, 1H), 8.48 (d, J = 5.3 Hz, 1H), 10.56 (s, 1H) | Ex. 3 |
| 35 | 3,4-difluorophenylacetic acid | 512 [M + H]+ | (CDCl3, 400 MHz): δ 3.73 (s, 2H), 4.06 (s, 6H), 6.42 (d, J = 5.1 Hz, 1H), 7.03-7.08 (m, 1H), 7.14-7.26 (m, 4H), 7.49 (br, 1H), 7.58 (s, 1H), 7.67-7.72 (m, 1H), 8.13 (br, 1H), 8.51 (d, J = 5.1 Hz, 1H), 10.56 (s, 1H) | Ex. 3 |
| 36 | 3-fluorophenylacetic acid | 494 [M + H]+ | (CDCl3, 400 MHz): δ 3.74 (s, 2H), 4.01 (s, 3H), 4.03 (s, 3H), 6.50 (d, J = 5.3 Hz, 1H), 6.51-7.10 (m, 5H), 7.31-7.35 (m, 1H), 7.42 (s, 1H), 7.47 (s, 1H), 8.18 (t, J = 9.5 Hz, 1H), 8.50 (d, J = 5.3 Hz, 1H), 8.89 (s, 1H), 10.74 (s, 1H) | Ex. 3 |
| 37 | 3-fluorophenylacetic acid | 494 [M + H]+ | (CDCl3, 400 MHz): δ 3.74 (s, 2H), 4.03 (s, 3H), 4.04 (s, 3H), 6.39 (d, J = 5.3 Hz, 1H), 7.02-7.68 (m, 7H), 7.41 (s, 1H), 7.55 (s, 1H), 8.26 (s, 1H), 8.47 (d, J = 5.3 Hz, 1H), 10.60 (s, 1H) | Ex. 3 |
| 38 | 4-fluorophenylacetic acid | 506 [M + H]+ | (DMSO-d6, 400 MHz): δ 10.98 (br, 1H), 10.84 (br, 1H), 8.47 (d, J = 5.4 Hz, 1H), 8.25 (d, J = 8.8 Hz, 1H), 7.51 (s, 1H), 7.38-7.04 (m, 6H), 6.84-6.82 (m, 1H), 6.49 (d, J = 5.1 Hz, 1H), 3.95 (s, 3H), 3.93 (s, 3H), 3.84 (s, 3H), 3.72 (s, 2H) | Ex. 3 |
| 39 | 4-fluorophenylacetic acid | 516 [M + Na]+ | (CDCl3, 400 MHz): δ 3.72 (s, 2H), 4.04 (s, 3H), 4.05 (s, 3H), 6.47 (d, J = 5.4 Hz, 1H), 7.03-7.09 (m, 1H), 7.15-7.23 (m, 4H), 7.44 (s, 1H), 7.54 (s, 1H), 7.60 (d, J = 9.0 Hz, 2H), 8.49 (d, J = 5.4 Hz, 1H), 8.67 (s, 1H), 10.51 (s, 1H) | Ex. 3 |
| 40 | 4-fluorophenylacetic acid | 570 [M + H]+ | (DMSO-d6, 400 MHz): δ 11.16 (br, 1H), 10.75 (br, 1H), 8.49 (d, J = 4.9 Hz, 1H), 8.24-8.19 (m, 1H), 7.53-7.35 (m, 10H), 7.19-7.11 (m, 3H), 6.56 (d, J = 5.4 Hz, 1H), 5.31 (s, 2H), 3.94 (s, 3H), 3.75 (s, 2H) | Ex. 3[b] |

| | | | | | |
|---|---|---|---|---|---|
| 41 |  |  | 621 [M + H]+ | (DMSO-d6, 400 MHz): δ 11.03 (br, 1H), 10.60 (br, 1H), 8.46 (d, J = 5.1 Hz, 1H), 7.80 (d, J = 13.6 Hz, 1H), 7.51-7.07 (m, 5H), 6.85 (br, 3H), 6.43 (d, J = 5.1 Hz, 1H), 4.18-4.16 (m, 2H), 3.95 (s, 3H), 3.58-3.56 (m, 3H), 2.89 (s, 2H), 2.73 (s, 2H), 2.36 (s, 5H), 1.84 (m, 2H), 1.63 (m, 2H) | Ex. 12 |
| 42 | | | 619 [M + H]+ | (DMSO-d6, 400 MHz): δ 11.04 (br, 1H), 10.62 (br, 1H), 8.46 (d, J = 5.4 Hz, 1H), 7.81 (d, J = 13.4 Hz, 1H), 7.53 (s, 1H), 7.41-7.33 (m, 5H), 7.19-7.14 (m, 2H), 6.44 (d, J = 5.1 Hz, 1H), 4.19 (m, 2H), 3.95 (s, 2H), 3.75 (s, 2H), 3.29-3.27 (m, 3H), 3.29-3.28 (m, 4H), 2.50-2.49 (m, 4H), 2.36 (br, 2H), 2.18-2.17 (m, 1.90-1.85 (m, 3H), 1.69 (m, 9H) | Ex. 12 |
| 43 | 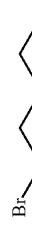 | | 634 [M + H]+ | (DMSO-d6, 400 MHz): δ 11.03 (br, 1H), 10.61 (br, 1H), 8.45 (d, J = 3.9 Hz, 1H), 7.81 (d, J = 13.4 Hz, 1H), 7.50 (s, 1H), 7.41-7.34 (m, 5H), 7.18-7.14 (m, 2H), 6.42 (d, J = 8.1 Hz, 1H), 4.18-4.15 (m, 2H), 3.94 (s, 3H), 3.74 (s, 2H), 3.29-3.28 (m, 4H), 2.50-2.49 (m, 4H), 2.36 (br, 2H), 1.61 (m, 2H) 3H), 1.83 (m, 2H), 1.61 (m, 2H) | Ex. 12 |
| 44 |  | | 621 [M + H]+ | (DMSO-d6, 400 MHz): δ 11.16 (br, 1H), 10.75 (br, 1H), 8.47 (d, J = 5.1 Hz, 1H), 8.22 (m, 1H), 7.95 (s, 1H), 7.46-7.08 (m, 3H), 6.86 (br, 4H), 6.55 (d, J = 5.4 Hz, 1H), 4.19-4.17 (m, 2H), 3.92 (s, 4H), 3.75 (s, 2H), 3.57 (br, 4H), 2.49 (br, 5H), 1.84 (m, 2H), 1.62 (m, 2H) | Ex. 12 |
| 45 | 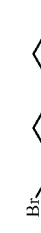 | | 619 [M + H]+ | (DMSO-d6, 400 MHz): δ 11.16 (br, 1H), 10.76 (br, 1H), 8.49 (d, J = 5.1 Hz, 1H), 8.25-8.20 (m, 1H), 7.48 (s, 1H), 7.42-7.34 (m, 4H), 7.19-7.10 (m, 3H), 6.56 (d, J = 5.4 Hz, 1H), 4.19 (br, 2H), 3.93 (s, 3H), 3.75 (s, 2H), 3.34-3.28 (m, 6H), 2.50-2.49 (m, 5H), 1.91-1.85 (m, 5H) | Ex. 12 |
| 46 |  | | 607 [M + H]+ | (DMSO-d6, 400 MHz): δ 11.21 (br, 1H), 10.54 (br, 1H), 8.31 (d, J = 5.2 Hz, 1H), 7.81 (d, J = 13.5 Hz, 1H), 7.48-7.06 (m, 5H), 6.51 (br, 3H), 6.31 (d, J = 5.1 Hz, 1H), 4.18-4.13 (m, 2H), 3.94 (s, 3H), 3.57-3.50 (m, 3H), 2.89 (s, 2H), 2.73 (s, 2H), 2.36 (br, 3H), 1.81 (m, 2H), 1.61 (m, 2H) | Ex. 11 |

| | | | | | |
|---|---|---|---|---|---|
| 47 | [piperidine NH] | [Br-CH2CH2CH2CH2-Br] | 605 [M + H]+ | (DMSO-d6, 400 MHz): δ 11.04 (br, 1H), 10.62 (br, 1H), 8.48 (d, J = 5.4 Hz, 1H), 7.81 (d, J = 13.2 Hz, 1H), 7.55 (s, 1H), 7.45-7.35 (m, 5H), 7.19-7.15 (m, 2H), 6.46 (d, J = 5.4 Hz, 1H), 4.18 (br, 2H), 3.96 (s, 3H), 3.75 (s, 3H), 3.51 (br, 1H), 3.29 (m, 5H), 2.50-2.49 (m, 4H), 2.26 (m, 2H), 1.83 (m, 1H), 1.70 (m, 1H) | Ex. 11 |
| 48 | [piperidine NH] | [Br-CH2CH2-Br] | 591 [M + H]+ | (DMSO-d6, 400 MHz): δ 11.04 (br, 1H), 10.62 (br, 1H), 8.48 (d, J = 5.1 Hz, 1H), 7.80 (d, J = 14.2 Hz, 1H), 7.55 (s, 1H), 7.48-7.34 (m, 5H), 7.18-7.14 (m, 2H), 6.45 (d, J = 4.9 Hz, 1H), 3.96 (s, 3H), 3.75 (s, 2H), 2.50-2.49 (m, 7H), 1.91-1.23 (m, 7H) | Ex. 13 |
| 49 | [piperazine N-Me] | [Br-CH2CH2-Br] | 606 [M + H]+ | (DMSO-d6, 400 MHz): δ 11.04 (br, 1H), 10.61 (br, 1H), 8.46 (d, J = 5.4 Hz, 1H), 7.80 (d, J = 13.6 Hz, 1H), 7.52 (s, 1H), 7.43-7.35 (m, 5H), 7.18-7.14 (m, 2H), 6.43 (d, J = 5.1 Hz, 1H), 4.27 (br, 2H), 3.94 (s, 3H), 3.74 (s, 2H), 2.89-2.38 (m, 8H), 1.27-1.39 (m, 5H) | Ex. 13 |
| 50 | [piperidine NH] | [Br-CH2CH2CH2CH2-Br] | 605 [M + H]+ | (DMSO-d6, 400 MHz): δ 11.16 (br, 1H), 10.77 (br, 1H), 8.51 (d, J = 5.3 Hz, 1H), 8.23 (m, 1H), 7.50-7.17 (m, 8H), 6.95 (d, J = 5.3 Hz, 4H), 4.26 (br, 2H), 3.93 (s, 4H), 3.75 (br, 2H), 3.50 (m, 1H), 3.29 (m, 3H), 2.94 (m, 1H), 2.67 (s, 1H), 2.49 (m, 3H), 2.32-2.25 (m, 2H), 1.83 (m, 1H), 1.69 (m, 1H) | Ex. 11 |
| 51 | [piperazine N-Me] | [Br-CH2CH2CH2CH2-Br] | 620 [M + H]+ | (DMSO-d6, 400 MHz): δ 11.10 (br, 1H), 10.76 (br, 1H), 8.50 (d, J = 5.1 Hz, 1H), 8.23 (m, 1H), 7.50-7.14 (m, 8H), 6.93 (d, J = 5.1 Hz, 1H), 4.22 (br, 2H), 3.94 (s, 3H), 3.75 (s, 2H), 3.29 (m, 6H), 2.67 (s, 1H), 2.52-2.49 (m, 7H), 2.32 (s, 1H) | Ex. 11 |
| 52 | [piperidine NH] | [Br-CH2CH2CH2-Br] | 587 [M + H]+ | (DMSO-d6, 400 MHz): δ 11.05 (br, 1H), 10.63 (br, 1H), 8.46 (d, J = 5.1 Hz, 1H), 7.81 (d, J = 13.9 Hz, 1H), 7.53 (s, 3H), 7.43-7.27 (m, 8H), 6.44 (d, J = 5.1 Hz, 1H), 4.23 (m, 1H), 3.95 (s, 1H), 3.74 (s, 2H), 3.28-3.26 (m, 4H), 2.89 (s, 1H), 2.73 (s, 1H), 2.50-2.48 (m, 5H), 1.67-1.23 (m, 4H) | Ex. 11 |

| | | | | |
|---|---|---|---|---|
| 53 | ![piperazine with methyl] H-N(piperazine)-N-CH3 | Br-(CH2)4-Br | 602 [M + H]+ | (DMSO-d6, 400 MHz): δ 11.04 (br, 1H), 10.63 (br, 1H), 8.45 (d, J = 5.4 Hz, 1H), 7.95 (d, J = 11.2 Hz, 1H), 7.80 (d, J = 13.9 Hz, 1H), 7.50 (s, 1H), 7.39-7.28 (m, 5H), 6.41 (d, J = 5.1 Hz, 1H), 4.19-4.16 (m, 2H), 3.94 (s, 3H), 3.74 (s, 2H), 3.36-3.27 (m, 7H), 2.89 (s, 1H), 2.73 (s, 1H), 2.32-2.19 (m, 6H), 1.98-1.95 (m, 2H) | Ex. 11 |
| 54 | morpholine (H-N, O) | Br-(CH2)2-Br | 575 [M + H]+ | (DMSO-d6, 400 MHz): δ 11.12 (br, 1H), 10.51 (br, 1H), 8.45 (d, J = 5.3 Hz, 1H), 7.80 (d, J = 13.9 Hz, 1H), 7.52 (s, 1H), 7.43-7.28 (m, 8H), 6.41 (d, J = 5.3 Hz, 1H), 4.29 (br, 2H), 3.94 (s, 3H), 3.89 (s, 2H), 3.61-3.56 (m, 4H), 2.52-2.49 (m, 6H) | Ex. 13 |
| 55 | morpholine (H-N, O) | Br-(CH2)3-Br | 593 [M + H]+ | (DMSO-d6, 400 MHz): δ 11.10 (br, 1H), 10.75 (br, 1H), 8.49 (d, J = 5.3 Hz, 1H), 8.21 (m, 1H), 7.53-7.09 (m, 8H), 6.44 (d, J = 5.3 Hz, 1H), 4.28 (br, 2H), 3.94 (s, 3H), 3.88 (s, 2H), 3.60-3.51 (m, 4H), 3.25-3.24 (m, 2H), 2.51-2.48 (m, 4H) | Ex. 13 |
| 56 | 1-naphthoic acid | | 510 [M + H]+ | (DMSO-d6, 400 MHz): δ 12.69 (br, 1H), 12.04 (br, 1H), 8.72 (d, J = 5.9 Hz, 1H), 8.25 (d, J = 8.5 Hz, 1H), 8.17 (d, J = 8.3 Hz, 1H), 8.05 (d, J = 8.8 Hz, 1H), 7.97 (d, J = 8.8 Hz, 1H), 7.84 (d, J = 7.1 Hz, 1H), 7.68-7.61 (m, 4H), 7.48-7.43 (m, 4H), 6.79 (d, J = 5.9 Hz, 1H), 4.00 (s, 6H) | Ex. 2 |
| 57 | 1-naphthoic acid | | 528 [M + H]+ | (DMSO-d6, 400 MHz): δ 12.54 (br, 1H), 12.21 (br, 1H), 8.57 (d, J = 5.4 Hz, 1H), 8.23-8.14 (m, 3H), 8.05 (d, J = 7.6 Hz, 1H), 7.86 (d, J = 6.1 Hz, 1H), 7.69-7.52 (m, 3H), 7.48-7.41 (m, 3H), 7.19 (m, 1H), 6.69 (d, J = 5.1 Hz, 1H), 3.98 (s, 3H), 3.93 (s, 3H) | Ex. 2 |
| 58 | phenylacetyl chloride | | 492 [M + H]+ | (DMSO-d6, 400 MHz): δ 12.26 (br, 1H), 11.89 (br, 1H), 8.55 (d, J = 5.1 Hz, 1H), 8.05 (t, J = 8.7 Hz, 1H), 7.46 (s, 1H), 7.41 (s, 1H), 7.29-7.36 (m, 6H), 7.13 (d, J = 9.5 Hz, 1H), 6.64 (d, J = 5.1 Hz, 1H), 3.95 (s, 3H), 3.92 (s, 3H), 3.83 (s, 2H) | Ex. 1 |

| | Structure | MS | NMR | Ex. |
|---|---|---|---|---|
| 59 | 2-chlorophenylacetic acid | 508 [M + H]+ | (DMSO-d6, 400 MHz): δ 3.92 (s, 3H), 3.95 (s, 3H), 4.04 (s, 2H), 6.54 (d, J = 5.1 Hz, 1H), 7.27-7.50 (m, 7H), 7.74-7.79 (m, 2H), 8.31 (s, 1H), 8.51 (d, J = 5.1 Hz, 1H), 11.80-11.83 (br, 1H) | Ex. 2 |
| 60 | phenylacetyl chloride | 474 [M + H]+ | (DMSO-d6, 400 MHz): δ 12.47 (br, 1H), 11.81 (br, 1H), 8.14-8.16 (m, 1H), 7.69 (m, 1H), 7.51 (s, 1H), 7.48 (d, J = 8.8 Hz, 1H), 7.44 (s, 1H), 7.25-7.35 (m, 7H), 6.51 (d, J = 6.1 Hz, 1H), 3.98 (s, 3H), 3.96 (s, 3H), 3.82 (s, 2H) | Ex. 1 |
| 61 | cyclohexylacetic acid | 480 [M + H]+ | (DMSO-d6, 400 MHz): δ 12.41 (br, 1H), 11.48 (br, 1H), 8.63 (m, 1H), 7.81-7.84 (m, 2H), 7.59 (s, 1H), 7.44 (s, 1H), 7.34-7.36 (m, 2H), 6.67 (m, 1H), 3.95 (s, 6H), 2.37 (d, J = 6.8 Hz, 2H), 1.69 (m, 3H), 1.19-1.25 (m, 6H), 0.86-1.00 (m, 2H) | Ex. 2 |
| 62 | 3-ethoxypropanoic acid | 456 [M + H]+ | (DMSO-d6, 400 MHz): δ 12.48 (br, 1H), 10.09 (br, 1H), 8.54 (d, J = 6.3 Hz, 1H), 8.09 (s, 1H), 7.90 (d, J = 8.8 Hz, 1H), 7.62 (s, 1H), 7.26-7.25 (m, 3H), 6.74 (d, J = 6.1 Hz, 1H), 4.22 (s, 3H), 4.16 (s, 3H), 3.79-3.77 (m, 2H), 3.66-3.62 (m, 2H), 2.65-2.64 (m, 2H), 1.23-1.18 (m, 3H) | Ex. 2 |
| 63 | phenylacetyl chloride | 508 [M + H]+ | (CDCl3, 400 MHz): δ 3.76 (s, 2H), 4.05 (s, 3H), 4.06 (s, 3H), 6.39 (d, J = 5.1 Hz, 1H), 7.23-7.47 (m, 6H), 7.51 (s, 1H), 7.57 (s, 1H), 7.61-7.64 (m, 1H), 8.00 (d, J = 2.4 Hz, 1H), 8.53 (d, J = 5.4 Hz, 1H) | Ex. 1 |
| 64 | 3-(2-methylphenyl)propanoic acid | 520 [M + H]+ | (DMSO-d6, 400 MHz): δ 12.62 (br, 1H), 11.64 (br, 1H), 8.51 (d, J = 5.4 Hz, 1H), 8.64 (d, J = 11.5 Hz, 1H), 7.57-7.42 (m, 4H), 7.16-7.13 (m, 4H), 6.51 (d, J = 5.4 Hz, 1H), 3.96 (s, 8H), 2.91-2.88 (m, 1H), 2.79-7.75 (m, 1H), 2.31 (s, 3H) | Ex. 2 |
| 65 | phenylacetyl chloride | 508 [M + H]+ | (DMSO-d6, 400 MHz): δ 12.37 (br, 1H), 11.89 (br, 1H), 8.54 (d, J = 5.1 Hz, 1H), 8.07 (d, J = 8.9 Hz, 1H), 7.56 (d, J = 2.7 Hz, 1H), 7.46 (s, 1H), 7.41 (s, 1H), 7.37-7.23 (m, 6H), 6.63 (d, J = 5.1 Hz, 1H), 3.94 (s, 3H), 3.91 (s, 3H), 3.84 (s, 2H) | Ex. 1 |

| | | | | |
|---|---|---|---|---|
| 66 | 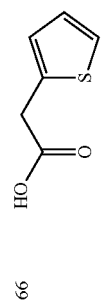 | 480 [M + H]+ | (DMSO-d6, 400 MHz): δ 12.4 (br, 1H), 11.69 (br, 1H), 8.53 (d, J = 5.1 Hz, 1H), 8.49-7.00 (m, 9H), 6.56 (d, J = 5.1 Hz, 1H), 3.95 (s, 3H), 3.94 (s, 3H), 3.84 (s, 2H) | Ex. 2 |
| 67 | 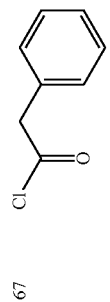 | 488 [M + H]+ | (DMSO-d6, 400 MHz): δ 12.42 (br, 1H), 11.73 (br, 1H), 8.47 (d, J = 5.4 Hz, 1H), 8.30 (s, 1H), 7.66-7.63 (m, 2H), 7.55 (s, 1H), 7.39 (s, 1H), 7.35-7.19 (m, 8H), 6.34 (d, J = 5.4 Hz, 1H), 3.94 (s, 6H), 3.82 (s, 2H) | Ex. 1 |
| 68 | 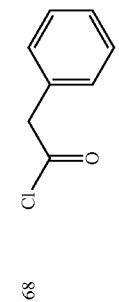 | 504 [M + H]+ | (DMSO-d6, 400 MHz): δ 11.76 (br, 1H), 10.95 (br, 1H), 8.44 (d, J = 5.4 Hz, 1H), 8.30 (s, 1H), 7.63 (s, 2H), 7.51 (s, 1H), 7.38-7.22 (m, 6H), 6.31 (d, J = 5.4 Hz, 1H), 3.94 (s, 3H), 3.82 (s, 6H), 3.69 (s, 2H) | Ex. 1 |
| 69 | 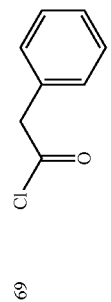 | 504 [M + H]+ | (DMSO-d6, 400 MHz): δ 12.71 (br, 1H), 11.71 (br, 1H), 8.63 (d, J = 8.8 Hz, 1H), 8.49 (d, J = 5.1 Hz, 1H), 7.50 (s, 1H), 7.40 (s, 1H), 7.38-7.11 (m, 5H), 7.03 (s, 1H), 6.87 (d, J = 11.5 Hz, 1H), 6.57 (d, J = 5.1 Hz, 1H), 3.95 (s, 9H), 3.83 (s, 2H) | Ex. 1 |
| 70 | 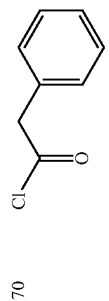 | 543 [M + H]+ | (DMSO-d6, 400 MHz): δ 12.43 (br, 1H), 11.89 (br, 1H), 8.48 (d, J = 5.1 Hz, 1H), 8.07 (s, 2H), 7.55 (s, 1H), 7.42 (s, 1H), 7.35-7.28 (m, 5H), 6.33 (d, J = 5.3 Hz, 1H), 3.95 (s, 6H), 3.83 (s, 2H) | Ex. 1 |
| 71 | 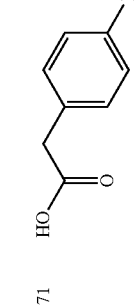 | 492 [M + H]+ | (DMSO-d6, 400 MHz): δ 12.39 (br, 1H), 11.73 (br, 1H), 8.53 (d, J = 5.4 Hz, 1H), 7.75 (d, J = 9.0 Hz, 2H), 7.51 (s, 1H), 7.41-7.16 (m, 7H), 6.56 (d, J = 5.4 Hz, 1H), 3.95 (s, 3H), 3.93 (s, 3H), 3.83 (s, 2H) | Ex. 2 |
| 72 | 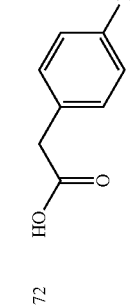 | 510 [M + H]+ | (DMSO-d6, 400 MHz): δ 12.22 (br, 1H), 11.89 (br, 1H), 8.58 (d, J = 5.4 Hz, 1H), 8.04 (t, J = 8.8 Hz, 1H), 7.65 (s, 1H), 7.43-7.11 (m, 7H), 6.68 (d, J = 5.4 Hz, 1H), 3.96 (s, 3H), 3.93 (s, 3H), 3.57 (s, 2H) | Ex. 2 |

| No. | Structure | MS | NMR | Source |
|---|---|---|---|---|
| 73 | 4-fluorophenylacetic acid | 527 [M + H]+ | (DMSO-d6, 400 MHz): δ 12.43 (br, 1H), 11.83 (br, 1H), 8.61 (d, J = 5.6 Hz, 1H), 8.15 (s, 1H), 7.73-7.70 (m, 1H), 7.60 (s, 1H), 7.53-7.10 (m, 6H), 6.55 (d, J = 5.1 Hz, 1H), 3.97 (s, 6H), 3.84 (s, 2H) | Ex. 2 |
| 74 | 3-fluorophenylacetic acid | 510 [M + H]+ | (DMSO-d6, 400 MHz): δ 3.88 (s, 2H), 3.91 (s, 3H), 3.95 (s, 3H), 6.64 (d, J = 5.1 Hz, 1H), 7.12-7.22 (m, 4H), 7.35-7.37 (m, 4H), 7.99-8.04 (m, 1H), 8.55 (d, J = 5.3 Hz, 1H), 11.90 (s, 1H), 12.18 (s, 1H) | Ex. 2 |
| 75 | 3-fluorophenylacetic acid | 510 [M + H]+ | (DMSO-d6, 400 MHz): δ 3.87 (s, 2H), 3.94 (s, 3H), 3.95 (s, 3H), 6.49 (d, J = 4.9 Hz, 1H), 7.08-7.23 (m, 3H), 7.34-7.56 (m, 5H), 8.00-8.03 (m, 1H), 8.50 (d, J = 5.1 Hz, 1H), 11.82 (s, 1H), 12.44 (s, 1H) | Ex. 2 |
| 76 | 3-fluorophenylacetic acid | 526 [M + H]+ | (DMSO-d6, 400 MHz): δ 3.87 (s, 2H), 3.93 (s, 3H), 3.95 (s, 3H), 6.40 (d, J = 5.4 Hz, 1H), 7.09-7.24 (m, 3H), 7.35-7.54 (m, 4H), 7.65-7.71 (m, 1H), 8.09-8.13 (m, 1H), 8.50 (d, J = 5.4 Hz, 1H), 11.82 (s, 1H), 12.38 (s, 1H) | Ex. 2 |
| 77 | 3-methylphenylacetic acid | 488 [M + H]+ | (DMSO-d6, 400 MHz): δ 2.31 (s, 3H), 3.78 (s, 2H), 3.93 (s, 3H), 3.95 (s, 3H), 6.39 (d, J = 5.1 Hz, 1H), 7.05-7.27 (m, 5H), 7.41 (s, 1H), 7.45 (d, J = 8.8 Hz, 1H), 7.51 (s, 1H), 7.67 (dd, J = 2.4, 8.5 Hz, 1H), 8.11 (d, J = 2.4 Hz, 1H), 8.49 (d, J = 5.1 Hz, 1H), 11.79 (s, 1H), 12.44 (s, 1H) | Ex. 2 |
| 78 | 3-methylphenylacetic acid | 522 [M + H]+ | (DMSO-d6, 400 MHz): δ 2.30 (s, 3H), 3.77 (s, 2H), 3.92 (s, 3H), 3.94 (s, 3H), 6.53 (d, J = 5.1 Hz, 1H), 7.08-7.31 (m, 5H), 7.40 (s, 1H), 7.48 (s, 1H), 7.74 (d, J = 8.7 Hz, 2H), 8.49 (d, J = 5.1 Hz, 1H), 11.71 (s, 1H), 12.42 (s, 1H) | Ex. 2 |
| 79 | 2-methylphenylacetic acid | 488 [M + H]+ | (DMSO-d6, 400 MHz): δ 2.29 (s, 3H), 3.89 (s, 2H), 4.02 (s, 3H), 4.04 (s, 3H), 6.87 (d, J = 6.6 Hz, 1H), 7.12-7.30 (m, 4H), 7.44 (d, J = 9.0 Hz, 2H), 7.51 (s, 1H), 7.74 (s, 1H), 7.88 (d, J = 9.0 Hz, 2H), 8.12 (d, J = 6.4 Hz, 1H), 11.77 (s, 1H), 12.49 (s, 1H) | Ex. 2 |

| | | | | |
|---|---|---|---|---|
| 80 | [2-fluorophenyl acetic acid] | 510 [M + H]+ | (DMSO-d6, 400 MHz): δ 12.45 (br, 1H), 11.87 (br, 1H), 8.56 (d, J = 5.6 Hz, 1H), 8.05-8.02 (m, 1H), 7.56-7.18 (m, 8H), 6.57 (d, J = 5.4 Hz, 1H), 3.96 (s, 8H) | Ex. 2 |
| 81 | [2-fluorophenyl acetic acid] | 510 [M + H]+ | (DMSO-d6, 400 MHz): δ 12.19 (br, 1H), 11.95 (br, 1H), 8.62 (d, J = 5.6 Hz, 1H), 8.07-8.05 (m, 1H), 7.51 (s, 1H), 7.43-7.18 (m, 7H), 6.72 (d, J = 5.4 Hz, 1H), 3.97 (s, 8H) | Ex. 2 |
| 82 | [4-methylphenyl acetic acid] | 522 [M + H]+ | (DMSO-d6, 400 MHz): δ 2.29 (s, 3H), 3.77 (s, 2H), 3.93 (s, 3H), 3.95 (s, 3H), 6.39 (d, J = 5.1 Hz, 1H), 7.16 (d, J = 8.1 Hz, 2H), 7.23 (d, J = 8.1 Hz, 2H), 7.41 (s, 1H), 7.46 (dd, J = 8.8 Hz, 1H), 7.51 (s, 1H), 7.66 (dd, J = 2.7, 9.0 Hz, 1H), 8.11 (d, J = 2.4 Hz, 1H), 8.49 (d, J = 5.1 Hz, 1H), 11.78 (s, 1H), 12.44 (s, 1H) | Ex. 2 |
| 83 | [2-methoxyphenyl acetic acid] | 522 [M + H]+ | (DMSO-d6, 400 MHz): δ 3.79 (s, 3H), 3.81 (s, 2H), 3.94 (s, 3H), 3.95 (s, 3H), 6.49 (d, J = 5.1 Hz, 1H), 6.88-7.03 (m, 2H), 7.20-7.32 (m, 2H), 7.41 (s, 1H), 7.44-7.58 (m, 3H), 8.05 (d, J = 12.4 Hz, 1H), 8.51 (d, J = 2.1 Hz, 1H), 11.71 (s, 1H), 12.55 (s, 1H) | Ex. 2 |
| 84 | [2-methylphenyl acetic acid] | 506 [M + H]+ | (CDCl3, 400 MHz): δ 2.36 (s, 3H), 3.77 (s, 2H), 4.05 (s, 6H), 6.46 (d, J = 5.1 Hz, 1H), 7.22-7.34 (m, 5H), 7.41 (d, J = 8.8 Hz, 1H), 7.46 (s, 1H), 7.55 (s, 1H), 7.95 (dd, J = 2.4, 11.7 Hz, 1H), 8.37 (s, 1H), 8.51 (d, J = 5.4 Hz, 1H), 12.50 (s, 1H) | Ex. 2 |
| 85 | [3-thienyl acetic acid] | 498 [M + H]+ | (DMSO-d6, 400 MHz): δ 12.50 (br, 1H), 11.78 (br, 1H), 8.56 (d, J = 5.1 Hz, 1H), 7.56-7.28 (m, 3H), 7.11-7.00 (m, 5H), 6.57 (m, 1H), 3.95 (s, 6H), 3.84 (s, 2H) | Ex. 2 |
| 86 | [3-thienyl acetic acid] | 510 [M + H]+ | (DMSO-d6, 400 MHz): δ 12.71 (br, 1H), 11.67 (br, 1H), 8.64 (d, J = 5.1 Hz, 1H), 8.52-8.48 (m, 1H), 7.52-7.40 (m, 4H), 7.12-7.04 (m, 3H), 6.59 (d, J = 5.1 Hz, 1H), 3.95 (s, 6H), 3.85 (s, 5H) | Ex. 2 |

| # | Structure | MS | NMR | Source |
|---|---|---|---|---|
| 87 | 2-chlorophenylacetic acid | 527 [M + H]+ | (DMSO-d6, 400 MHz): δ 12.45 (br, 1H), 11.91 (br, 1H), 8.53 (d, J = 5.1 Hz, 1H), 8.05-8.03 (m, 1H), 7.54-7.33 (m, 8H), 6.56-6.54 (m, 1H), 4.04 (s, 2H), 3.95 (s, 6H) | Ex. 2 |
| 88 | bicyclic acetic acid | 492 [M + H]+ | (DMSO-d6, 400 MHz): δ 12.57 (br, 1H), 11.45 (br, 1H), 8.52 (d, J = 5.1 Hz, 1H), 7.79-7.76 (m, 2H), 7.57 (s, 1H), 7.45 (s, 1H), 7.31-7.28 (m, 2H), 6.54 (d, J = 5.1 Hz, 1H), 3.97 (s, 3H), 3.95 (s, 3H), 3.31 (s, 2H), 2.49-2.30 (m, 2H), 1.52-1.08 (m, 9H) | Ex. 2 |
| 89 | bicyclic acetic acid | 510 [M + H]+ | (DMSO-d6, 400 MHz): δ 12.41 (br,1H), 11.93 (br, 1H), 8.56 (d, J = 5.1 Hz, 1H), 8.15-8.07 (m, 1H), 7.47 (s, 1H), 7.42 (s, 1H), 7.34 (d, J = 13.6 Hz, 1H), 7.15 (d, J = 8.8 Hz, 1H), 6.65 (d, J = 5.1 Hz, 1H), 3.96 (s, 3H), 3.92 (s, 3H), 3.31 (s, 2H), 2.45-2.31 (m, 2H), 1.51-1.07 (m, 9H) | Ex. 2 |
| 90 | bicyclic acetic acid | 510 [M + H]+ | (DMSO-d6, 400 MHz): δ 12.66 (br, 1H), 11.54 (br, 1H), 8.54 (d, J = 5.1 Hz, 1H), 8.08 (m, 1H), 7.55-7.43 (m, 4H), 6.54 (d, J = 5.6 Hz, 1H), 3.96 (s, 6H), 3.31 (s, 2H), 2.43-2.30 (m, 2H), 1.48-1.06 (m, 9H) | Ex. 2 |
| 91 | bicyclic acetic acid | 527 [M + H]+ | (DMSO-d6, 400 MHz): δ 12.59 (br, 1H), 11.54 (br, 1H), 8.51 (d, J = 5.1 Hz, 1H), 8.17-8.15 (m, 1H), 7.70-7.68 (m, 1H), 7.53 (s, 1H), 7.47 (d, J = 8.8 Hz, 1H), 7.43 (s, 1H), 6.42 (d, J = 5.1 Hz, 1H), 3.94 (s, 6H), 3.31 (s, 2H), 2.42-2.31 (m, 2H), 1.47-1.05 (m, 9H) | Ex. 2 |
| 92 | 4-methylphenylacetic acid | 506 [M + H]+ | (DMSO-d6, 400 MHz): δ 12.32 (br, 1H), 11.89 (br, 1H), 8.73 (d, J = 5.9 Hz, 1H), 7.62 (s, 1H), 7.51-7.48 (m, 2H), 7.24-7.12 (m, 6H), 6.84 (d, J = 6.1 Hz, 1H), 4.01 (s, 6H), 3.78 (s, 2H), 2.28 (s, 3H) | Ex. 2 |
| 93 | 2,4-difluorophenylacetic acid | ND[c] | (DMSO-d6, 400 MHz): δ 3.92 (s, 5H), 3.95 (s, 3H), 6.65 (d, J = 5.4 Hz, 1H), 7.06-7.50 (m, 7H), 7.99-8.05 (m, 1H), 8.55 (d, J = 5.1 Hz, 1H), 11.94 (s, 1H), 12.12 (s, 1H) | Ex. 2 |

-continued

| # | Structure 1 | Structure 2 | MS | NMR | Ex. |
|---|---|---|---|---|---|
| 94 | 2,4-difluorophenylacetic acid | | 528 [M + H]+ | (DMSO-d6, 400 MHz): δ 3.92 (s, 2H), 3.95 (s, 3H), 3.96 (s, 3H), 6.51 (d, J = 5.1 Hz, 1H), 7.04-7.12 (m, 2H), 7.20-7.29 (m, 2H), 7.41-7.57 (m, 3H), 7.99-8.05 (m, 1H), 8.52 (d, J = 5.1 Hz, 1H), 11.87 (s, 1H), 12.39 (s, 1H) | Ex. 2 |
| 95 | 2,6-difluorophenylacetic acid | | 528 [M + H]+ | (DMSO-d6, 400 MHz): δ 12.32 (br, 1H), 11.94 (br, 1H), 8.51 (d, J = 5.1 Hz, 1H), 8.02-7.99 (m, 1H), 7.54-7.41 (m, 4H), 7.15-7.11 (m, 3H), 6.49 (d, J = 5.4 Hz, 1H), 3.97 (s, 2H), 3.94 (s, 6H) | Ex. 2 |
| 96 | 2,5-difluorophenylacetic acid | | 528 [M + H]+ | (DMSO-d6, 400 MHz): δ 12.38 (br, 1H), 11.88 (br, 1H), 8.51 (d, J = 4.9 Hz, 1H), 8.02-7.99 (m, 1H), 7.53-7.19 (m, 7H), 6.50 (d, J = 5.1 Hz, 1H), 3.94 (s, 8H) | Ex. 2 |
| 97 | 2,6-dichlorophenylacetic acid | | 561 [M + H]+ | (DMSO-d6, 400 MHz): δ 12.33 (br, 1H), 11.85 (br, 1H), 8.52 (d, J = 4.9 Hz, 1H), 8.06-7.93 (m, 4H), 7.63-7.43 (m, 4H), 6.46 (d, J = 5.1 Hz, 1H), 3.94 (s, 8H) | Ex. 2 |
| 98 | methyl malonyl chloride | 2,4-difluoroaniline | ND^c | (CDCl3, 400 MHz): δ 3.64 (s, 2H), 4.04 (s, 3H), 4.05 (s, 3H), 6.53 (d, J = 5.1 Hz, 1H), 6.87-6.94 (m, 2H), 6.98-7.04 (m, 2H), 7.43 (s, 1H), 7.49 (s, 1H), 8.16-8.24 (m, 1H), 8.31-8.37 (m, 1H), 8.52 (d, J = 5.4 Hz, 1H), 8.81 (br, 1H), 9.04 (br, 1H) | Ex. 6 |
| 99 | methyl malonyl chloride | 2,4-difluoroaniline | ND^c | (CDCl3, 400 MHz): δ 3.62 (s, 2H), 4.05 (s, 3H), 4.06 (s, 3H), 6.40 (d, J = 5.1 Hz, 1H), 6.87-6.96 (m, 2H), 7.20-7.34 (m, 2H), 7.43 (s, 1H), 7.58 (s, 1H), 7.76-7.82 (m, 1H), 8.10-8.18 (m, 1H), 8.49 (d, J = 5.4 Hz, 1H), 8.72 (br, 1H), 9.38 (br, 1H) | Ex. 6 |

-continued

| # | Structure 1 | Structure 2 | MS | NMR | Ex. |
|---|---|---|---|---|---|
| 100 | (acid chloride methyl ester) | aniline (H2N–Ph) | 458 [M + H]+ | (DMSO-d6, 400 MHz): δ 3.49 (s, 2H), 3.92 (s, 3H), 3.93 (s, 3H), 6.44 (d, J = 5.4 Hz, 1H), 7.04-7.08 (m, 2H), 7.24 (d, J = 9.0 Hz, 2H), 7.28-7.34 (m, 2H), 7.38 (s, 1H), 7.50 (s, 1H), 7.61 (d, J = 7.6 Hz, 2H), 7.74 (d, J = 9.0 Hz, 2H), 8.45 (d, J = 5.4 Hz, 1H), 10.19 (s, 1H), 10.34 (s, 1H) | Ex. 5 |
| 101 | (acid chloride methyl ester) | cycloheptylamine | 478 [M + H]+ | (CDCl3, 400 MHz): δ 1.24-2.04 (m, 12H), 3.30 (s, 2H), 3.90-4.01 (m, 1H), 4.05 (s, 6H), 6.45 (d, J = 5.4 Hz, 1H), 7.14-7.17 (m, 2H), 7.42 (s, 1H), 7.55 (s, 1H), 7.65-7.68 (m, 2H), 8.48 (d, J = 5.1 Hz, 1H) | Ex. 5 |
| 102 | (acid chloride methyl ester) | 2,4-difluoroaniline | ND[c] | (CDCl3, 400 MHz): δ 3.60 (s, 2H), 4.05 (s, 3H), 4.06 (s, 3H), 6.47 (d, J = 5.4 Hz, 1H), 6.88-6.94 (m, 2H), 7.18 (d, J = 9.0 Hz, 2H), 7.45 (s, 1H), 7.55 (s, 1H), 7.68 (d, J = 9.0 Hz, 2H), 8.14-8.20 (m, 1H), 8.49 (d, J = 5.4 Hz, 1H), 8.78 (br, 1H), 8.91 (br, 1H) | Ex. 5 |
| 103 | (dimethyl methoxymalonate) | 2,4-difluoroaniline | 524 [M + H]+ | (CDCl3, 400 MHz): δ 3.81 (s, 3H), 4.05 (s, 3H), 4.07 (s, 3H), 4.50 (s, 1H), 6.48 (d, J = 5.6 Hz, 1H), 6.87-6.94 (m, 2H), 7.19 (d, J = 9.0 Hz, 2H), 7.52 (s, 1H), 7.55 (s, 1H), 7.70 (d, J = 9.0 Hz, 2H), 8.21-8.29 (m, 1H), 8.48 (d, J = 5.6 Hz, 1H), 8.79 (br, 1H), 8.93 (br, 1H) | Ex. 15 |
| 104 | (dimethyl 2,2-dimethylmalonate) | 2,4-difluoroaniline | 522 [M + H]+ | (CDCl3, 400 MHz): δ 1.73 (s, 6H), 4.05 (s, 3H), 4.05 (s, 3H), 6.44 (d, J = 5.1 Hz, 1H), 6.87-6.94 (m, 2H), 7.18 (d, J = 9.0 Hz, 2H), 7.43 (s, 1H), 7.55 (s, 1H), 7.65 (d, J = 9.0 Hz, 2H), 8.14-8.21 (m, 1H), 8.48 (d, J = 5.1 Hz, 1H), 8.56 (br, 1H), 8.70 (br, 1H) | Ex. 15 |
| 105 | (ClC(O)NCO) | 3-methyl-2-aminopyridine | 472 [M − H]− | (CDCl3, 400 MHz): δ 2.37 (s, 3H), 4.06 (s, 6H), 6.49 (d, J = 5.1 Hz, 1H), 6.88 (d, J = 5.1 Hz, 1H), 7.2 (m, 2H), 7.43 (s, 1H), 7.58 (s, 1H), 7.7 (m, 2H), 8.2 (m, 2H), 8.49 (d, J = 5.2 Hz, 1H) | Ex. 10 |
| 106 | | | 462 [M + H]+ | (CDCl3, 400 MHz): δ 8.43 (d, 1H, J = 5.1 Hz), 7.82-7.79 (m, 1H), 7.49-7.08 (m, 12H), 6.36 (d, 1H, J = 5.1 Hz), 3.95 (s, 3H), 3.75 (s, 2H) | Ex. 10[b] |

[a] Synthesized as in Examples described below.
[b] Synthesized as described in indicated Synthesis Example.
[c] No data

| Ex. No. | Compound structure | Starting compound A |
|---|---|---|
| 107 | 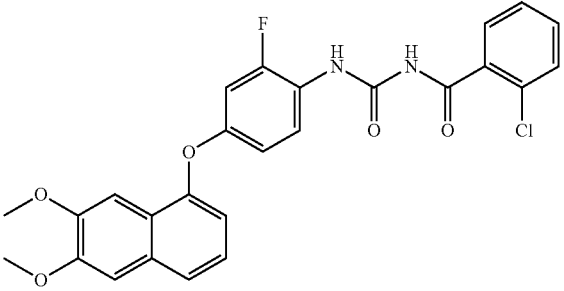 | 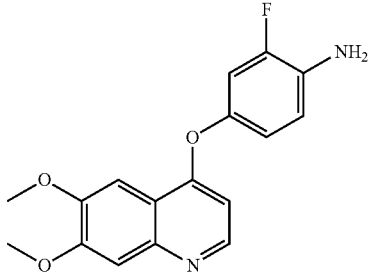 |
| 108 | 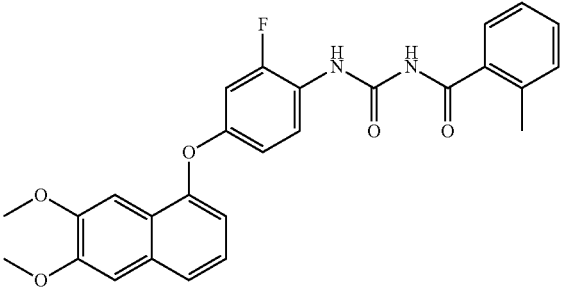 | 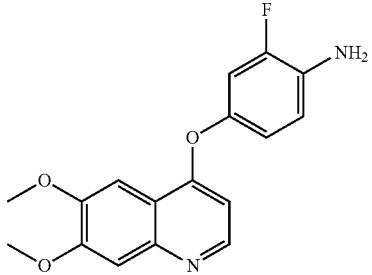 |
| 109 | 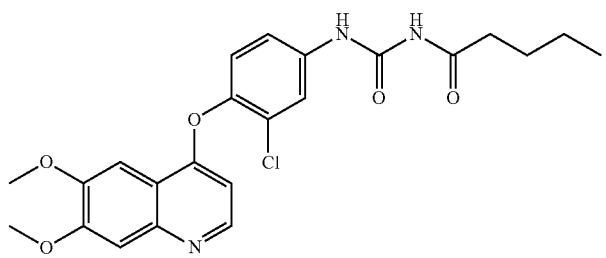 | 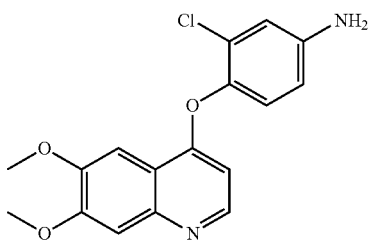 |
| 110 | 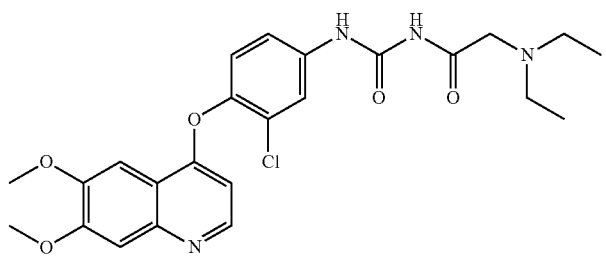 | 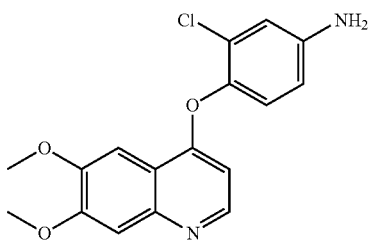 |
| 111 | 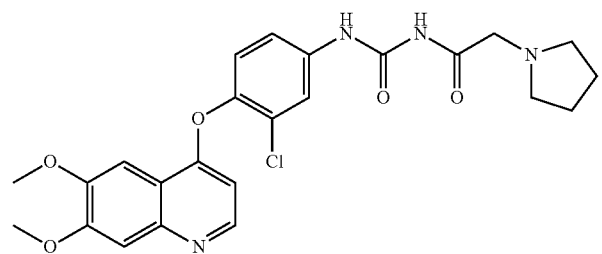 | 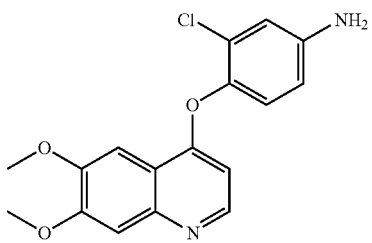 |

| | | |
|---|---|---|
| 112 | 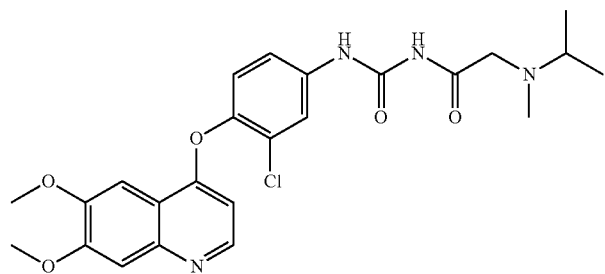 | 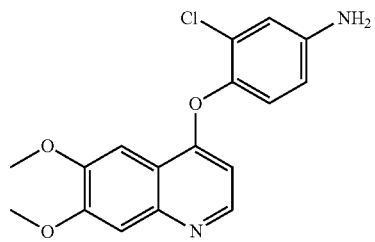 |
| 113 | 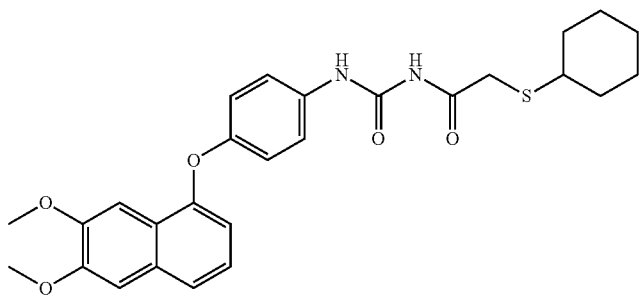 | 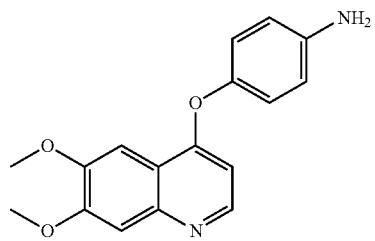 |
| 114 | 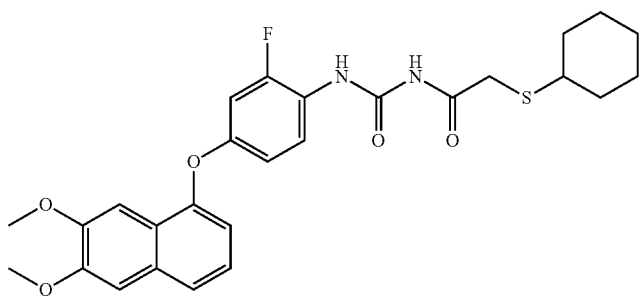 | 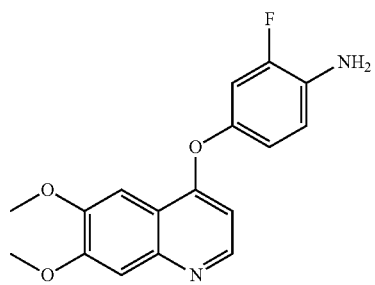 |
| 115 | 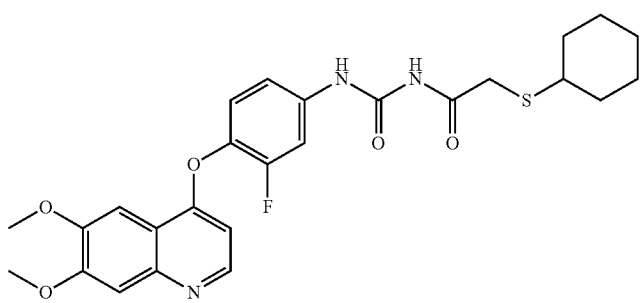 | 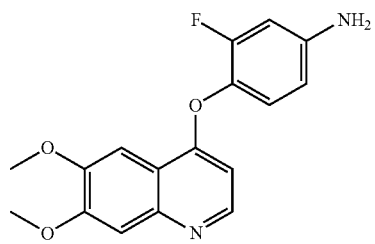 |
| 116 | 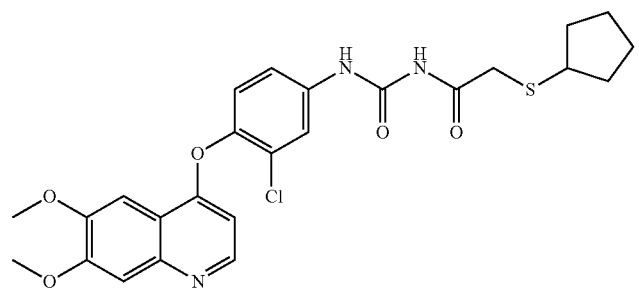 | 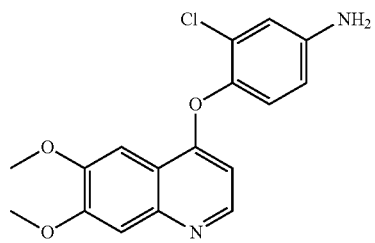 |

117 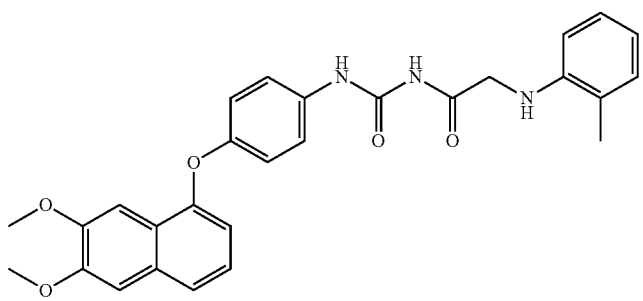 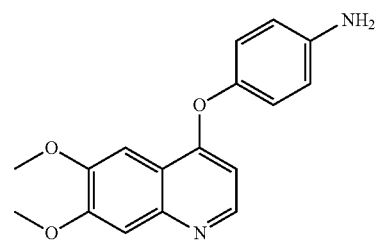
118 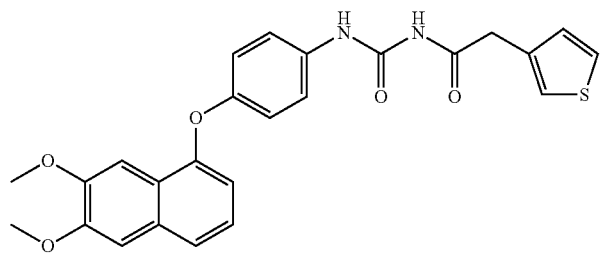 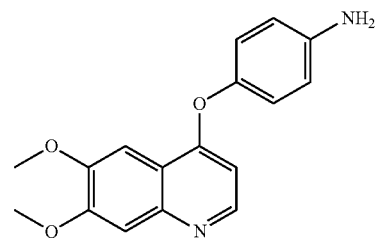
119 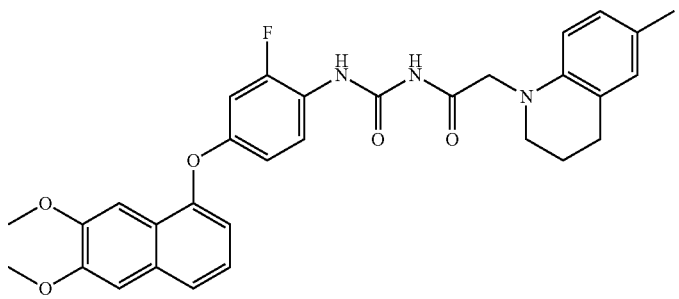 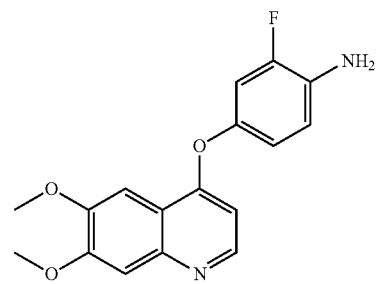
120 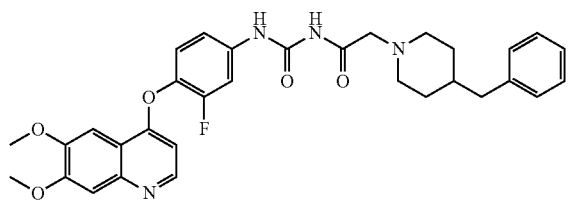 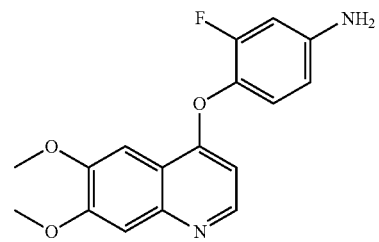
121 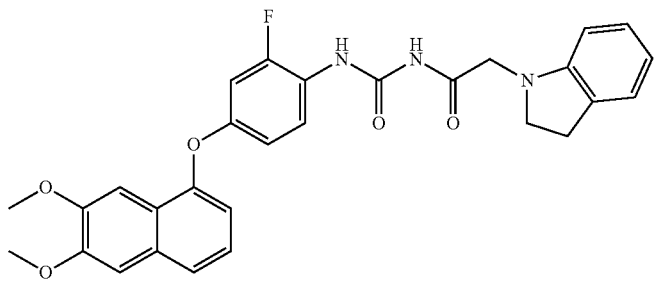 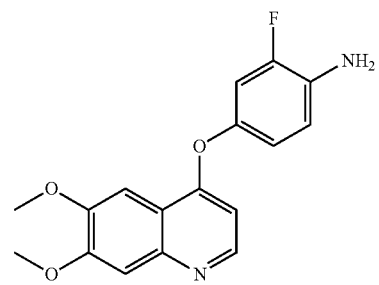

| 122 | 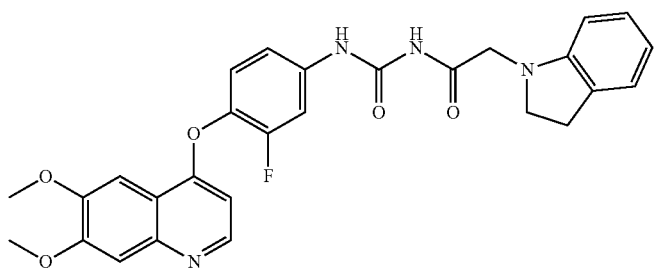 | 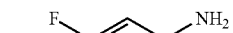 |
| 123 | 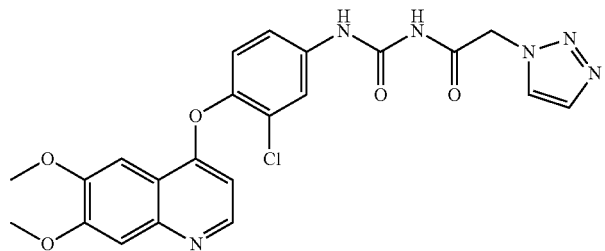 | 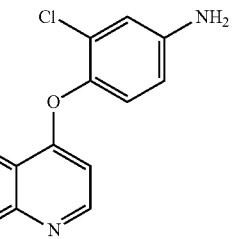 |
| 124 | 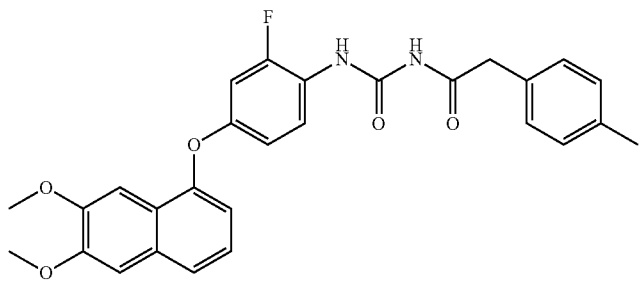 | 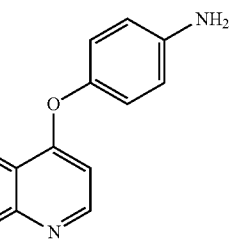 |
| 125 | 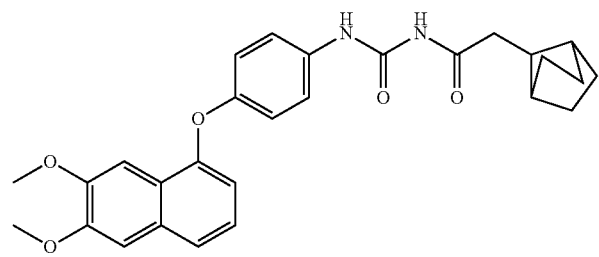 | 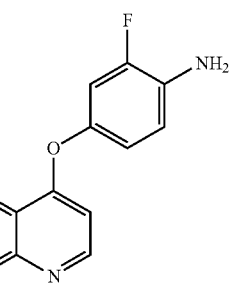 |
| 126 | 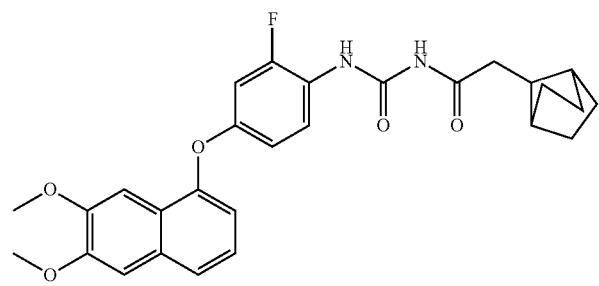 | 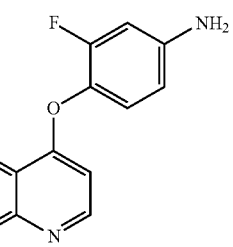 |
| 127 | 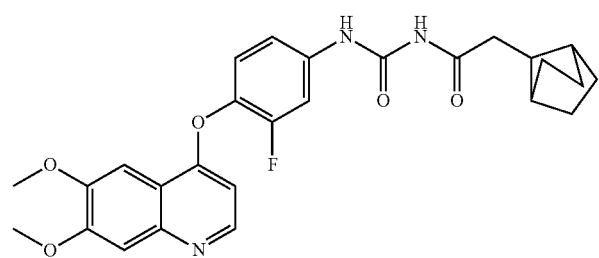 | |

| 151 | 152 |
|---|---|
| 128 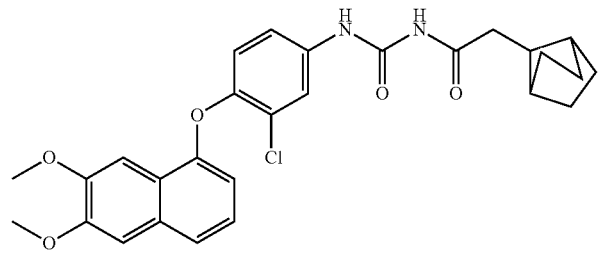 | 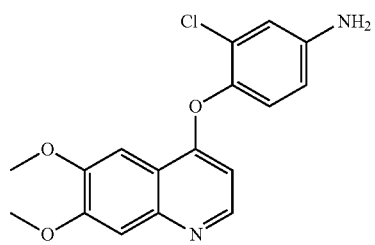 |
| 129 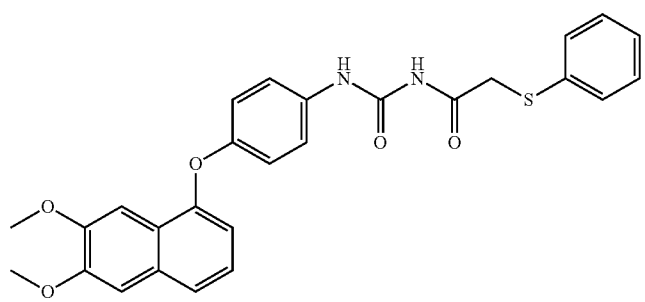 | 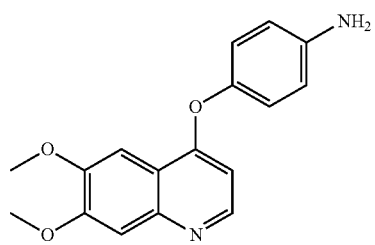 |
| 130 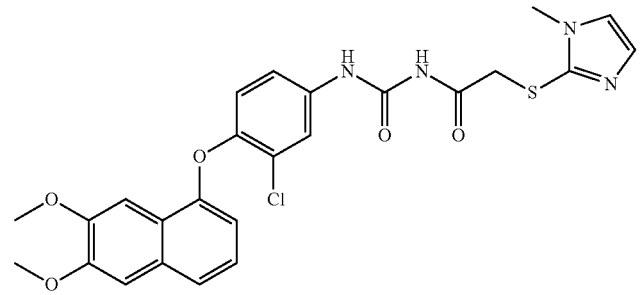 | 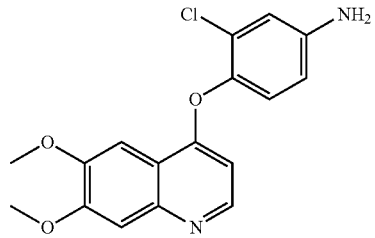 |
| 131 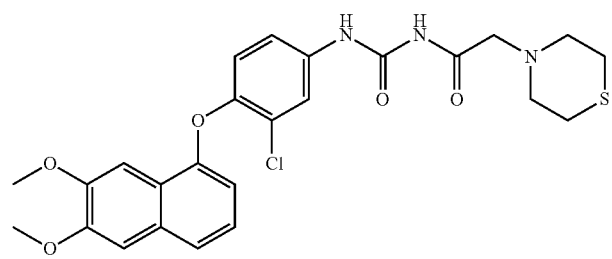 | 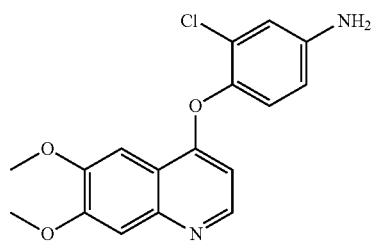 |
| 132 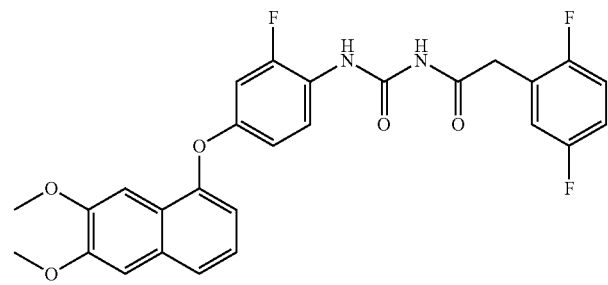 | 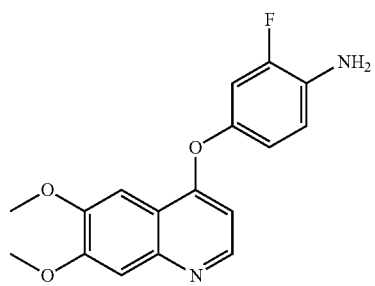 |

| 133 | 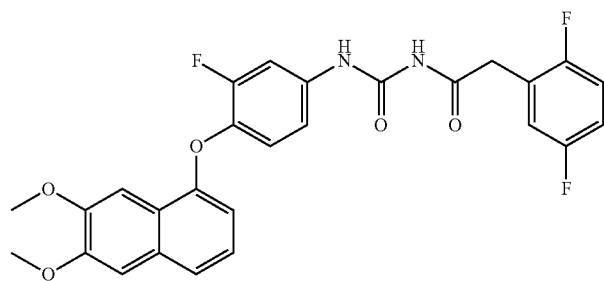 | 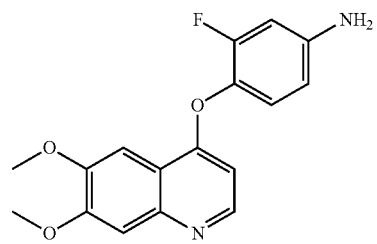 |
| 134 | 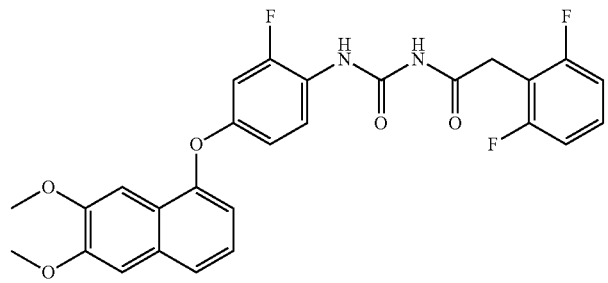 | 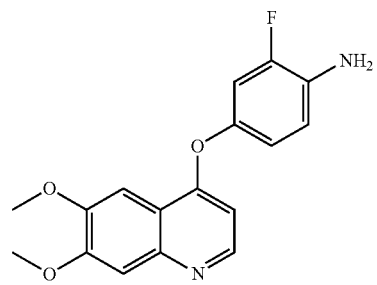 |
| 135 | 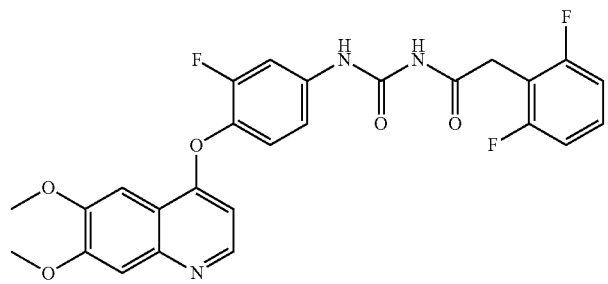 | 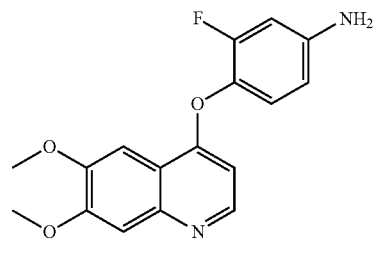 |
| 136 | 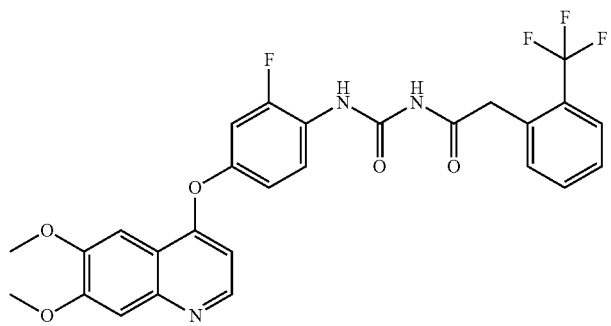 | 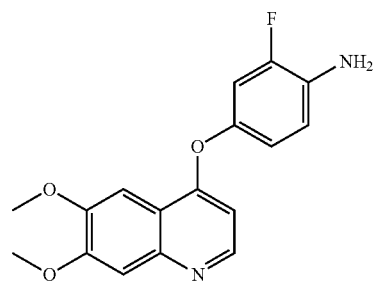 |
| 137 | 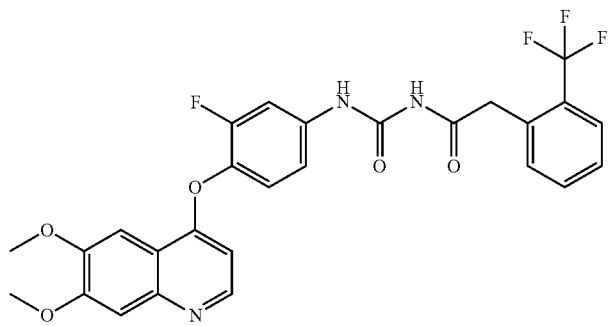 | 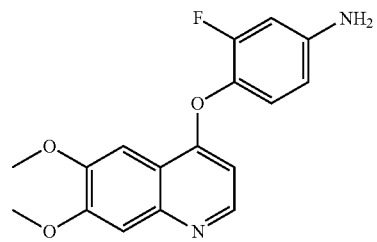 |

| | | |
|---|---|---|
| 138 | 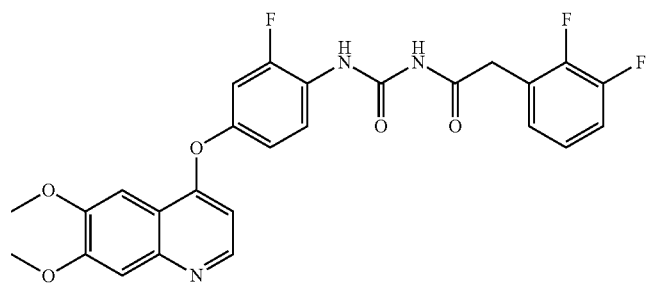 | 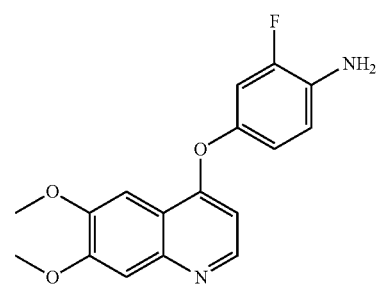 |
| 139 | 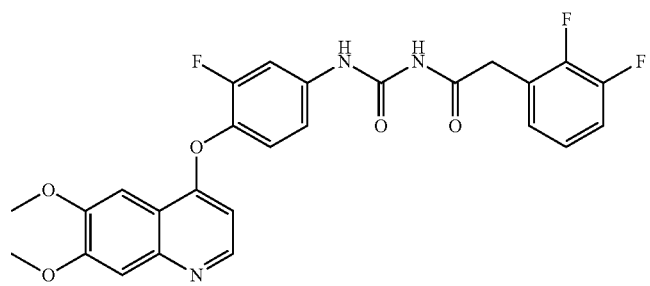 | 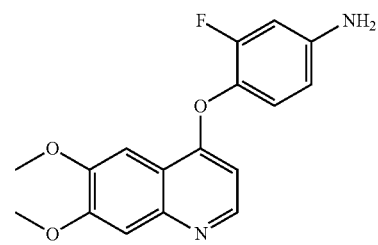 |
| 140 | 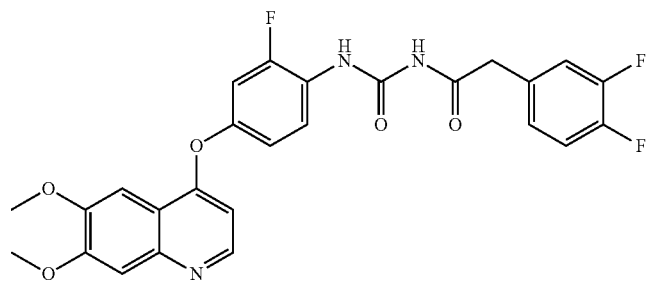 | 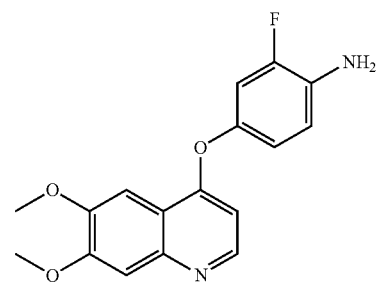 |
| 141 | 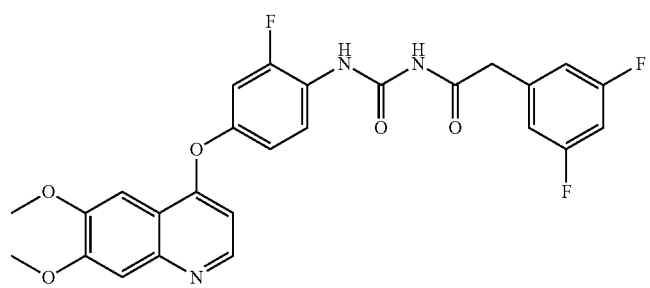 | 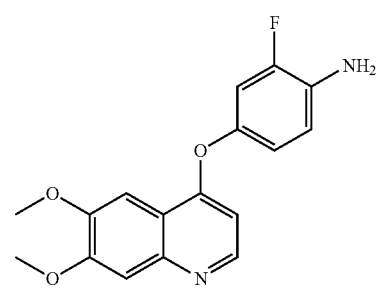 |
| 142 | 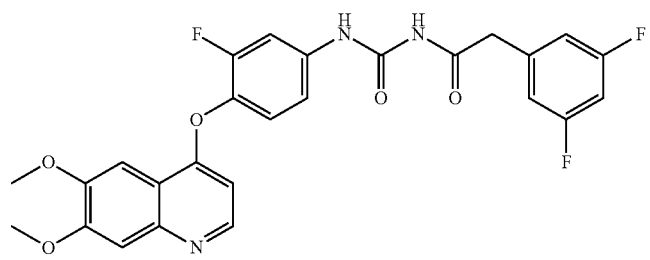 | 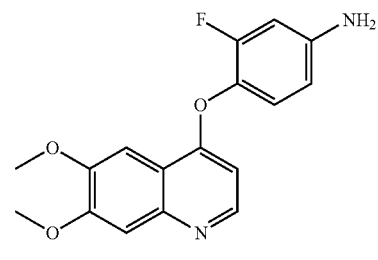 |

| | | | |
|---|---|---|---|
| 143 | 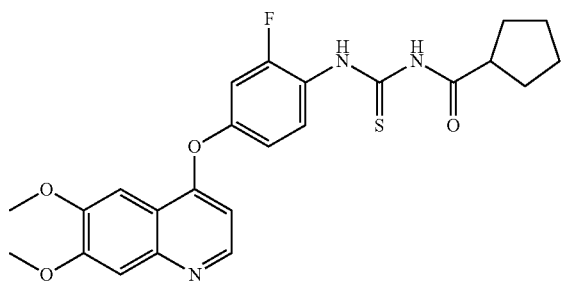 | | |
| 144 | 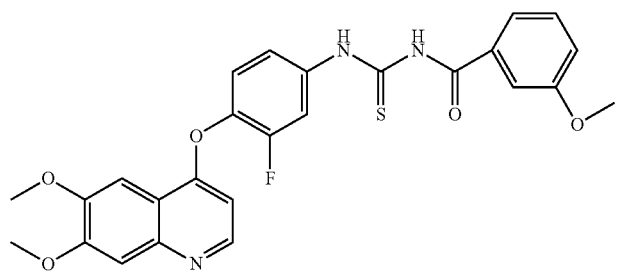 | 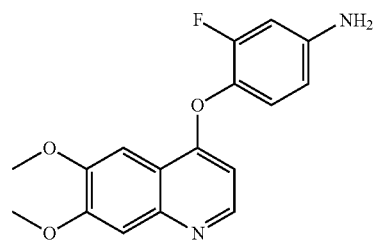 | |
| 145 | 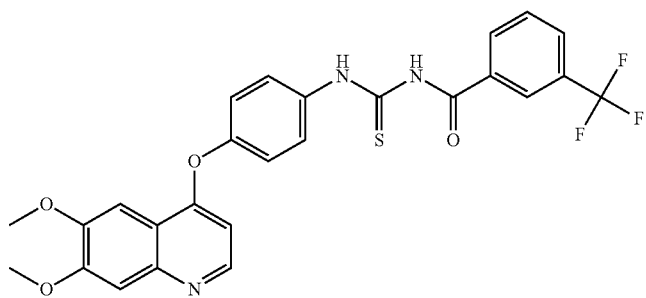 | 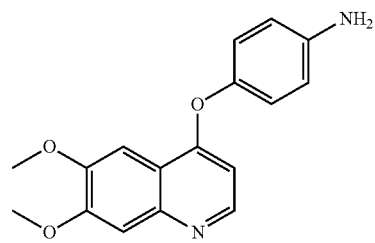 | |
| 146 | 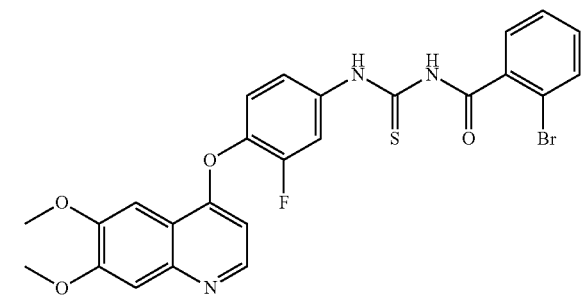 | 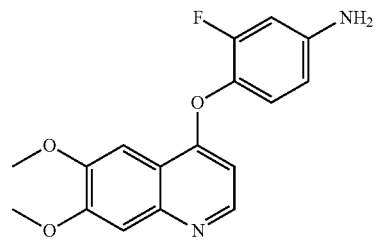 | |
| 147 | 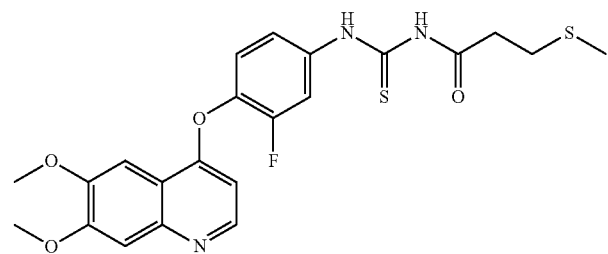 | 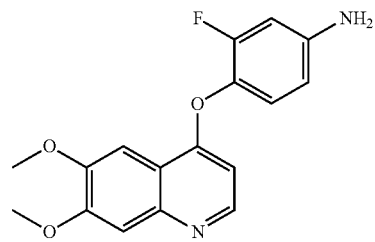 | |

| 148 | 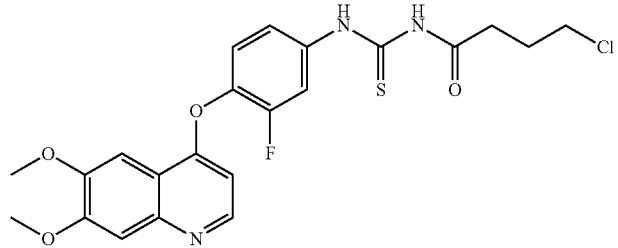 | 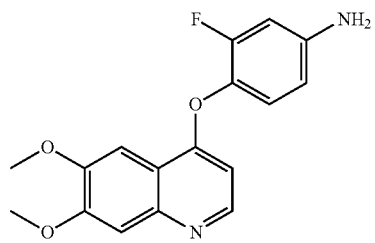 |
| 149 | 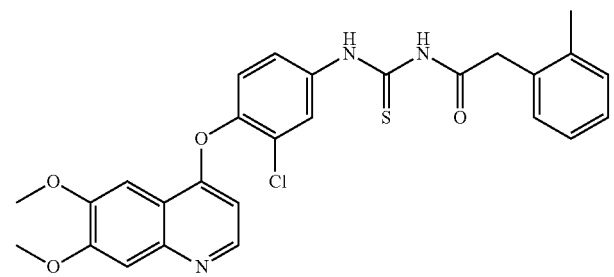 | 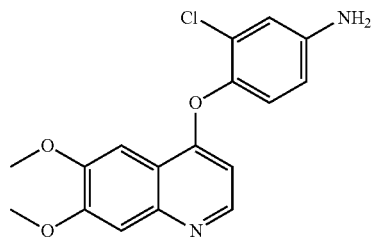 |
| 150 | 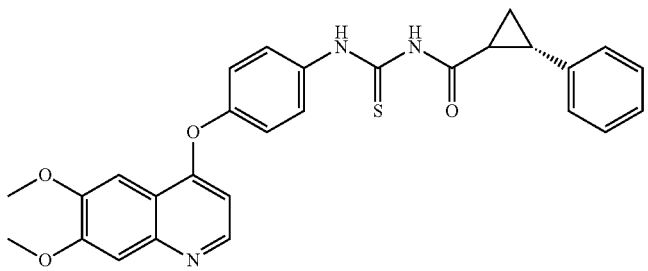 | 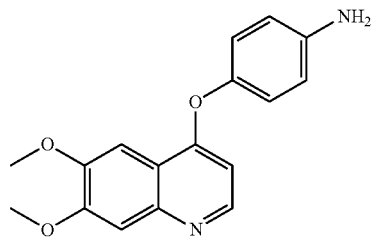 |
| 151 | 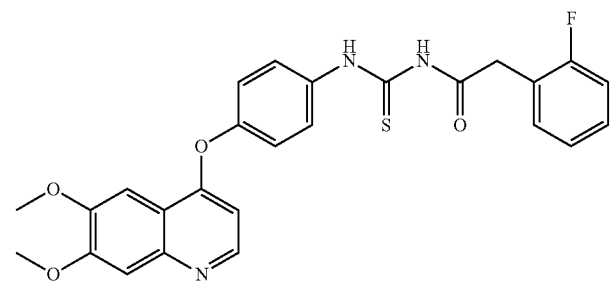 | 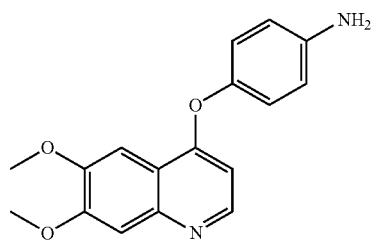 |
| 152 | 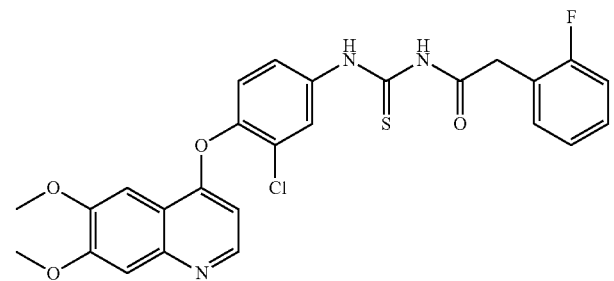 | 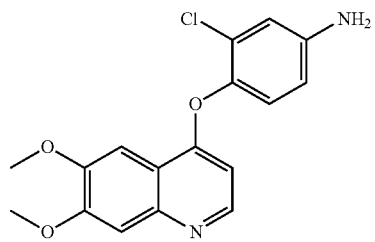 |

| 153 | 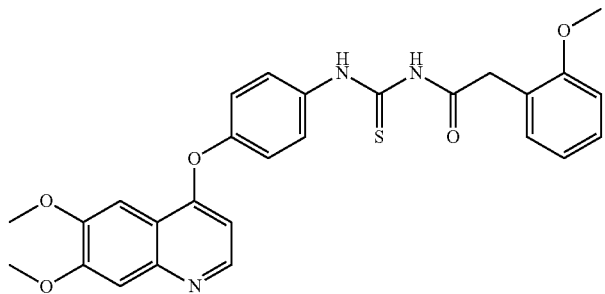 | 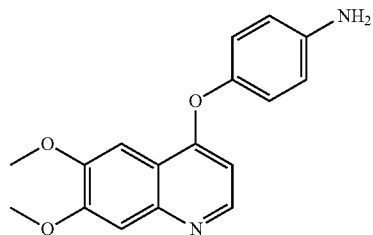 |
| --- | --- | --- |
| 154 | 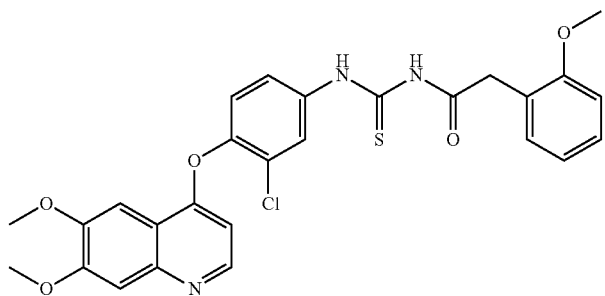 | 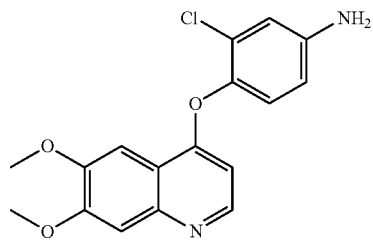 |
| 155 | 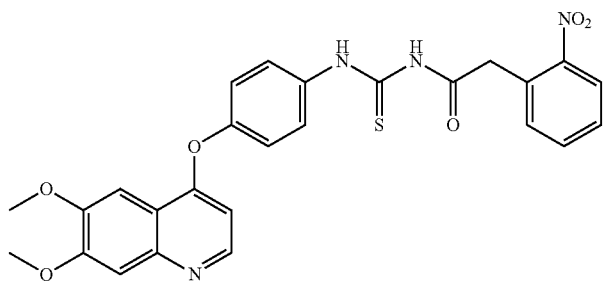 | 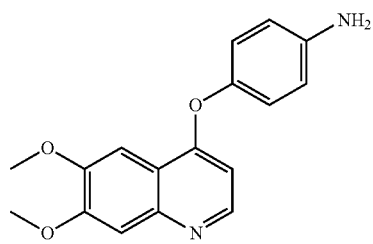 |
| 156 | 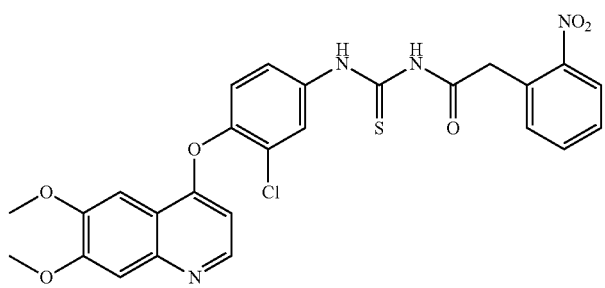 | 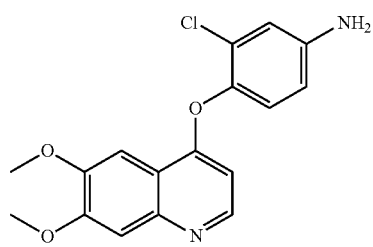 |
| 157 | 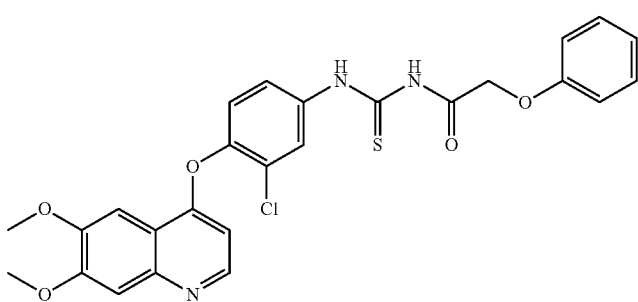 | 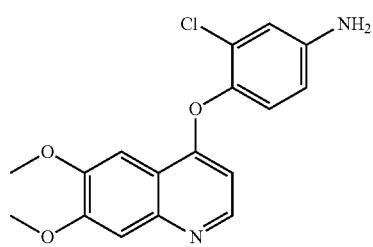 |

| | | |
|---|---|---|
| 158 | 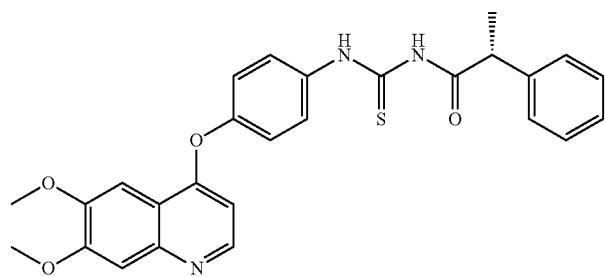 | 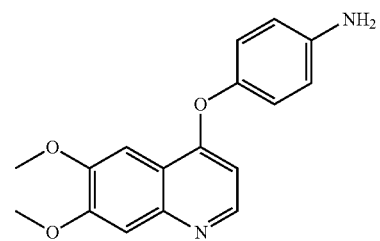 |
| 159 | 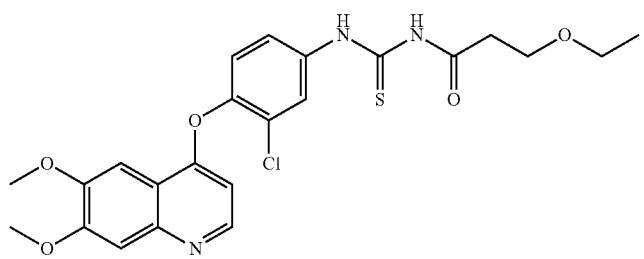 | 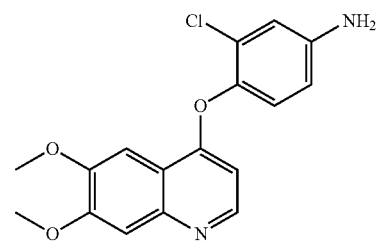 |
| 160 | 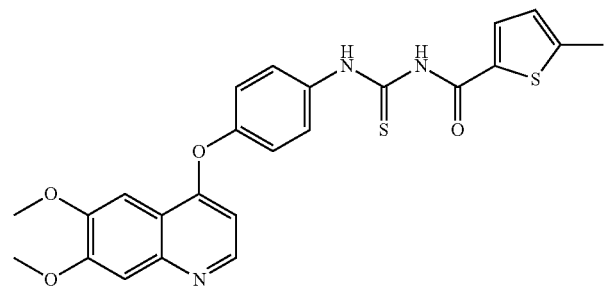 | 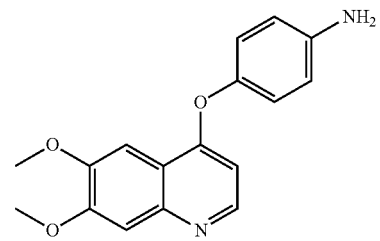 |
| 161 | 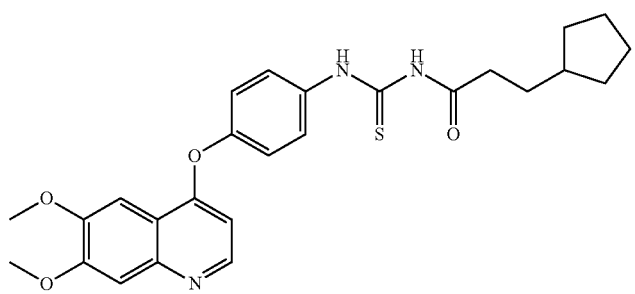 | 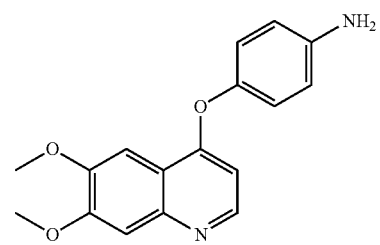 |
| 162 | 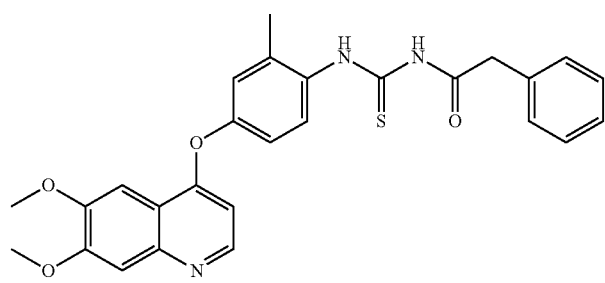 | 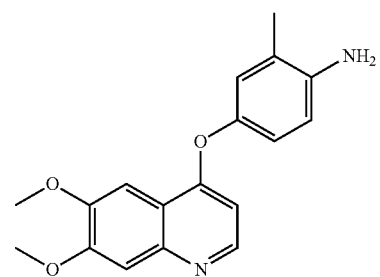 |

| 165 | 166 |
|---|---|
| 163 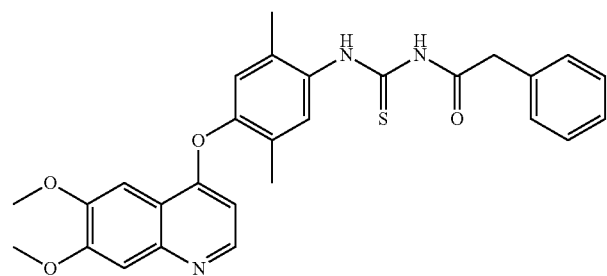 | 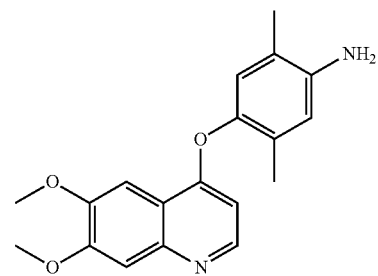 |
| 164 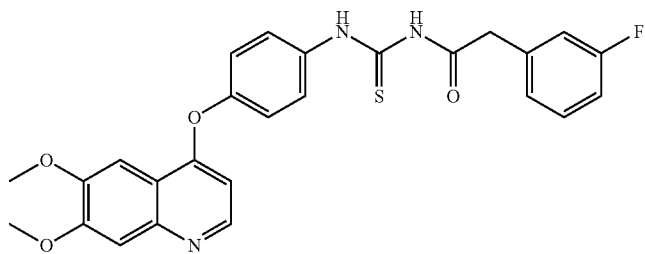 | 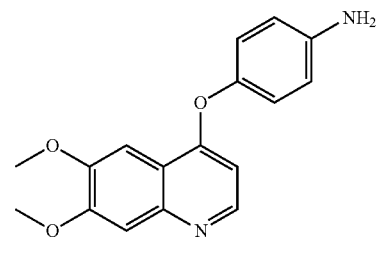 |
| 165 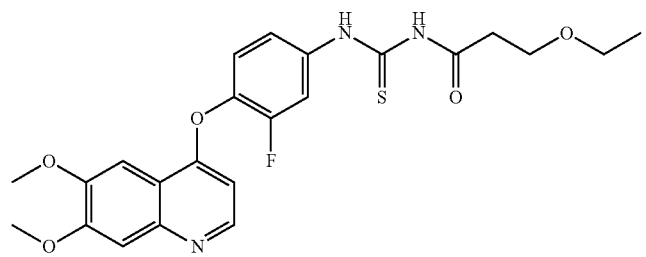 | 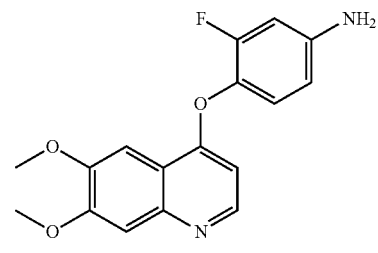 |
| 166 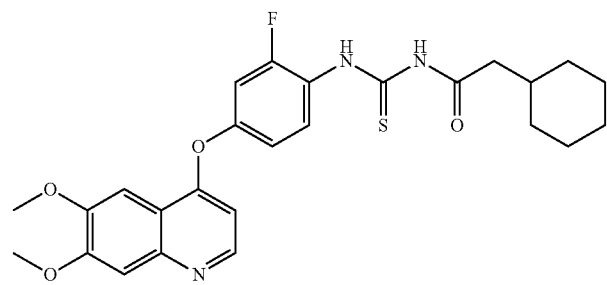 | 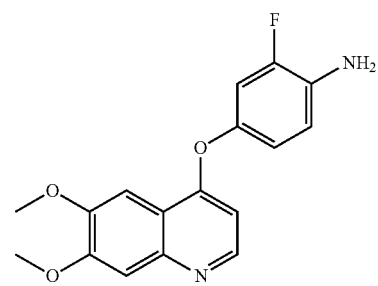 |
| 167 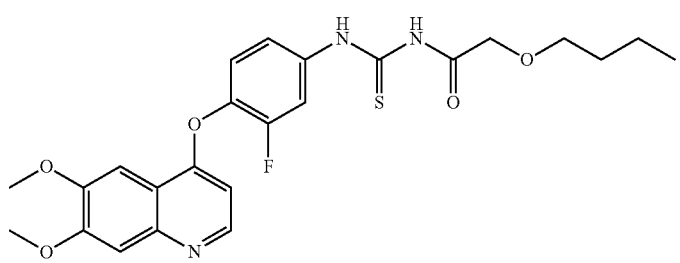 | 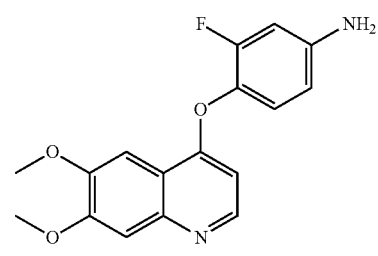 |
| 168 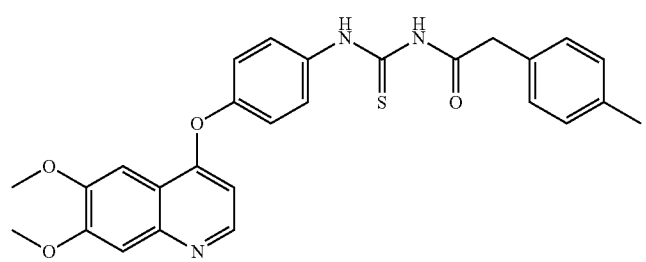 | 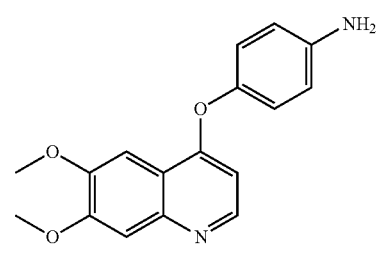 |

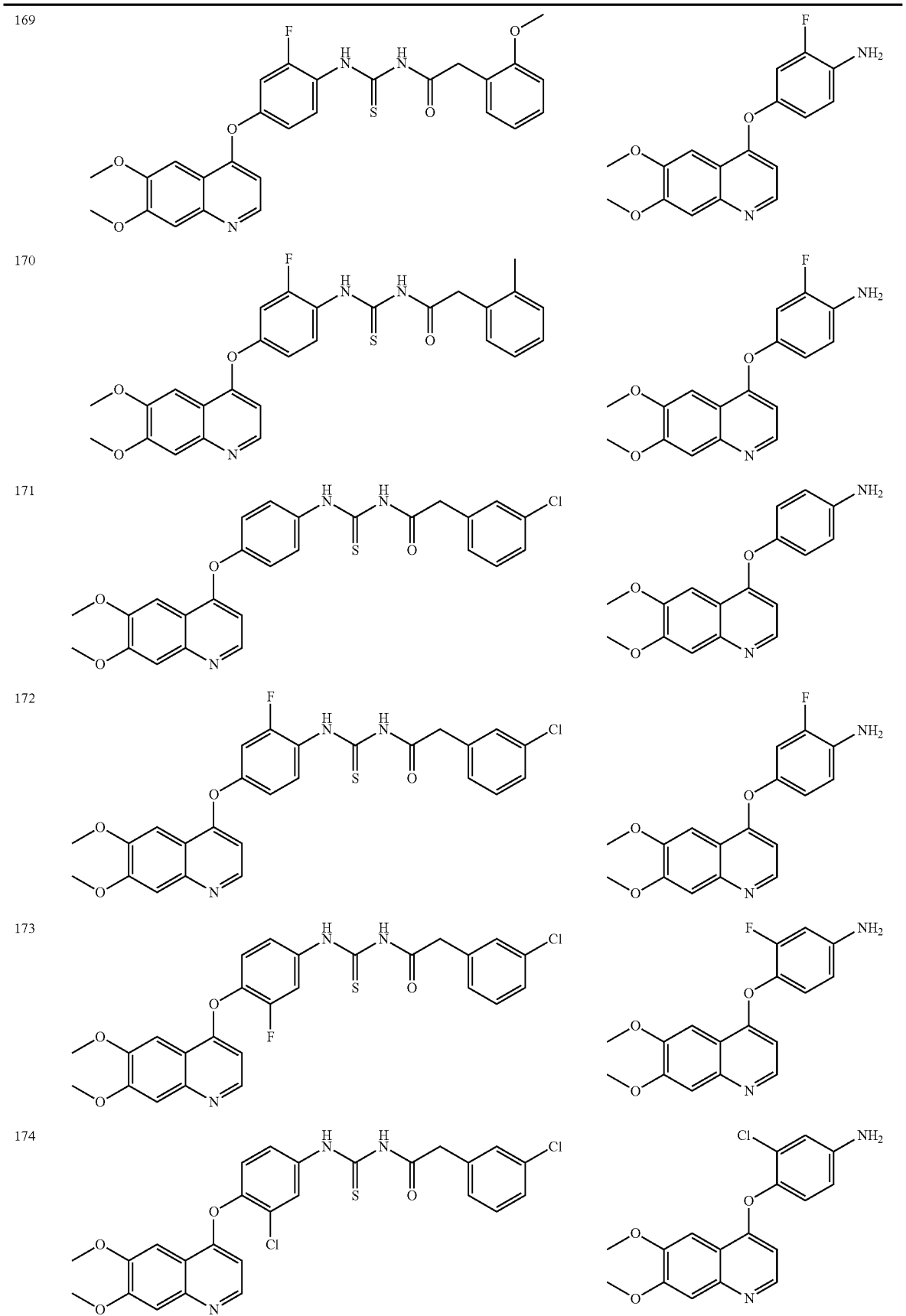

| 175 | 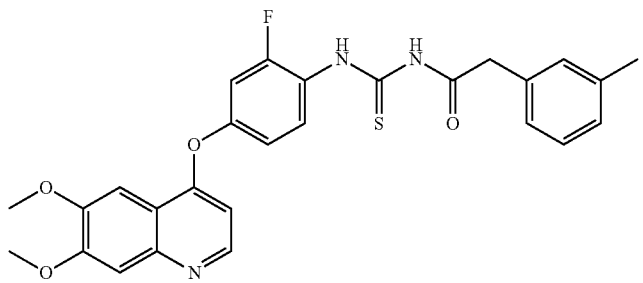 | 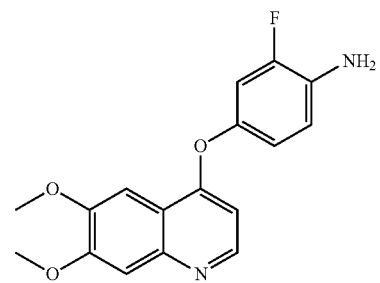 |
|---|---|---|
| 176 | 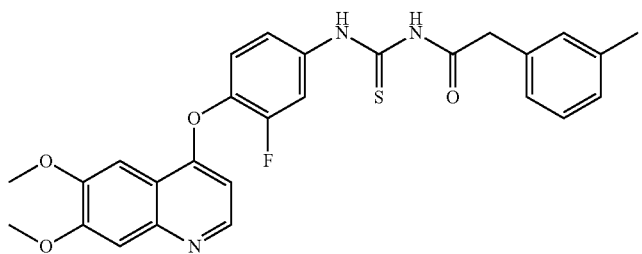 | 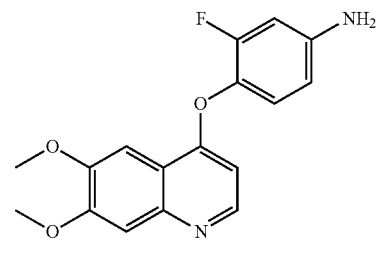 |
| 177 | 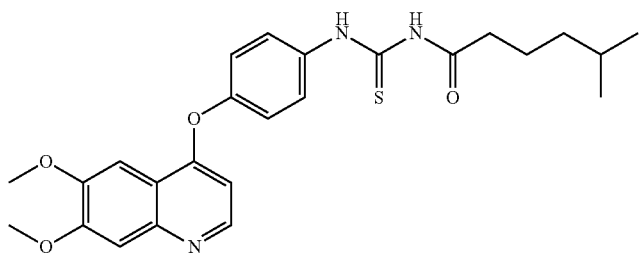 | 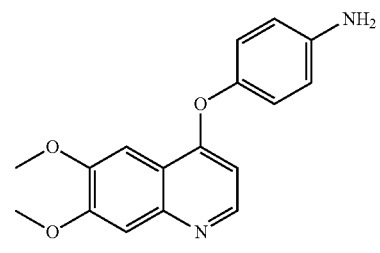 |
| 178 | 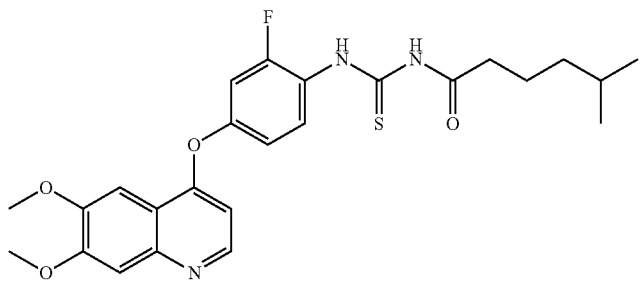 | 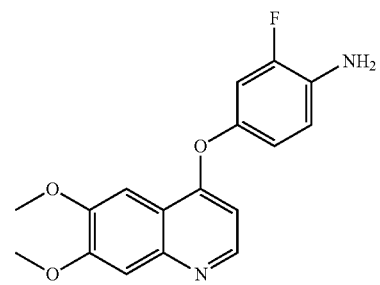 |
| 179 | 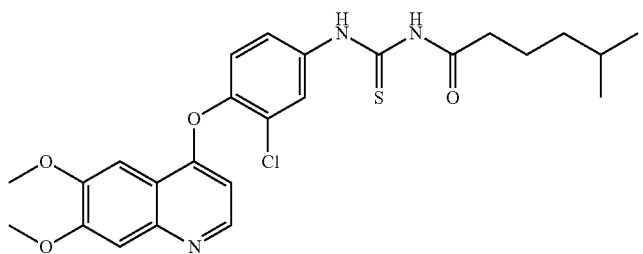 | 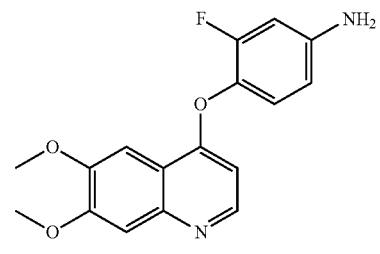 |
| 180 | 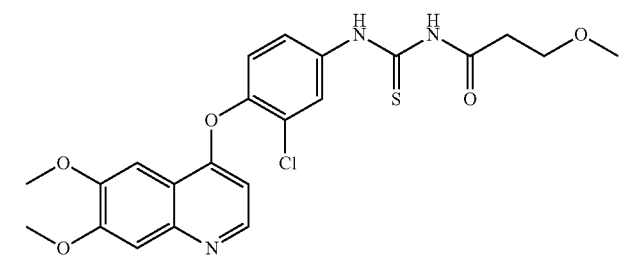 | 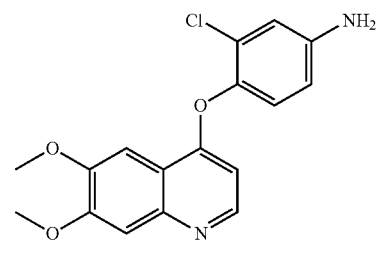 |

| 181 | 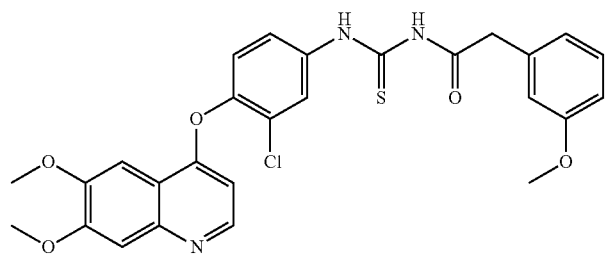 |
| 182 | 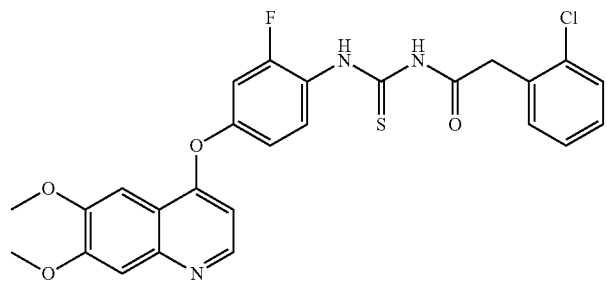 |
| 183 | 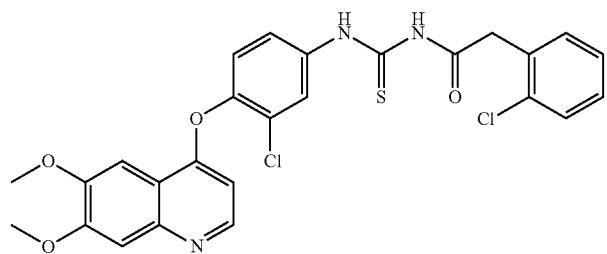 |
| 184 | 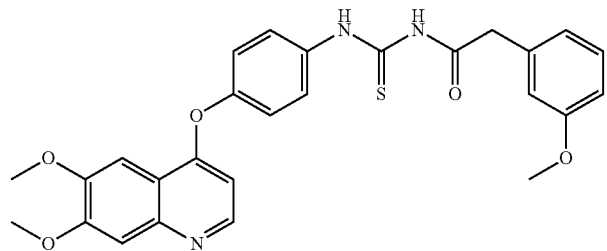 |
| 185 | 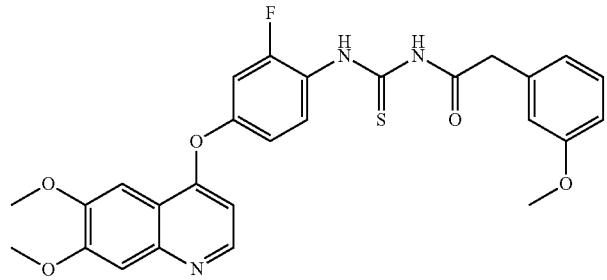 |
| 186 | 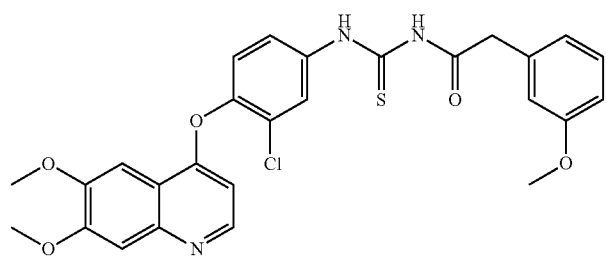 |

-continued
| | 173 | 174 |
|---|---|---|
| 187 | 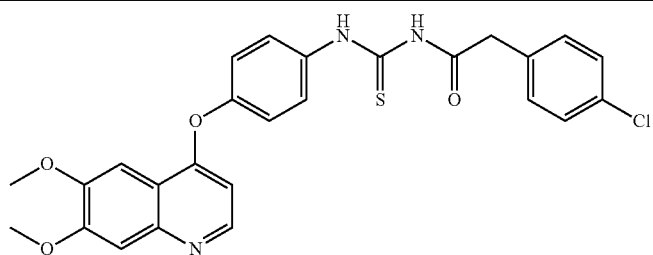 | 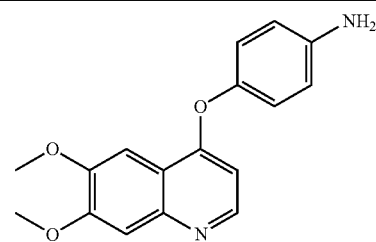 |
| 188 | 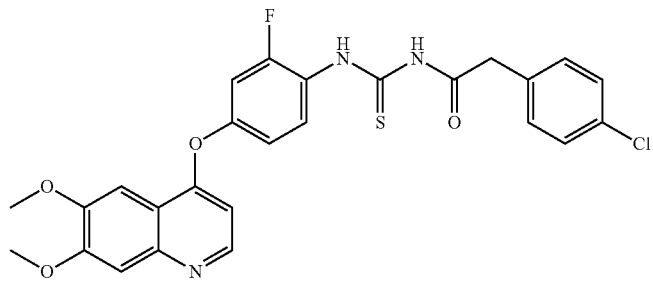 | 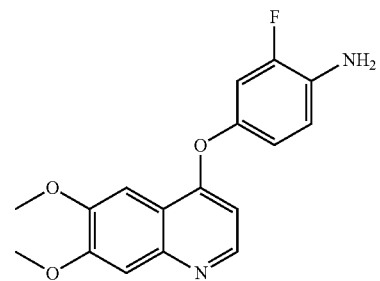 |
| 189 | 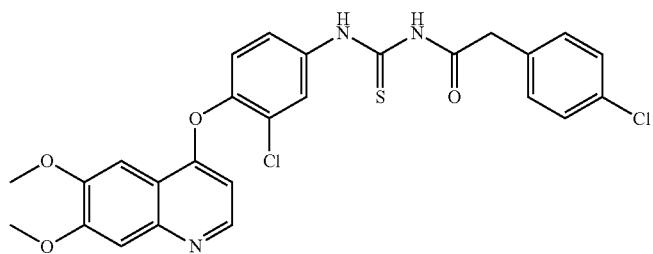 | 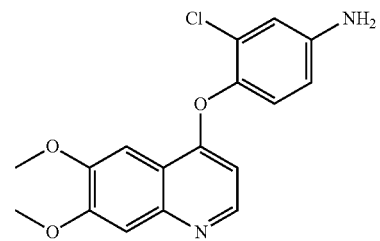 |
| 190 | 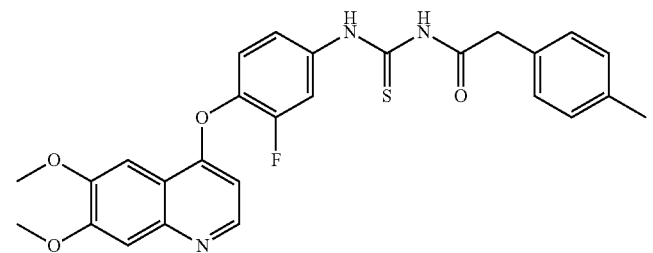 | 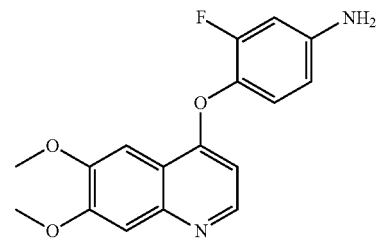 |
| 191 | 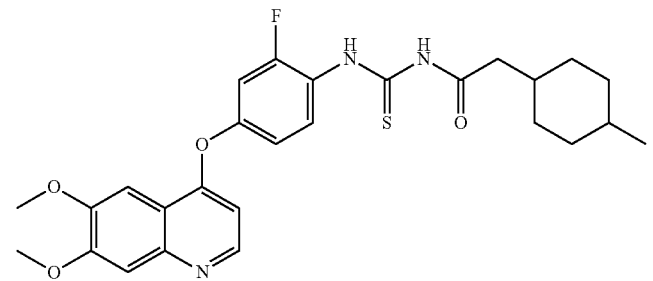 | 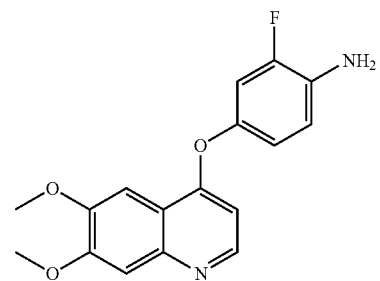 |
| 192 | 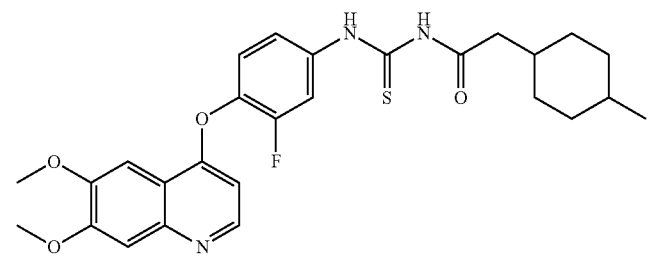 | 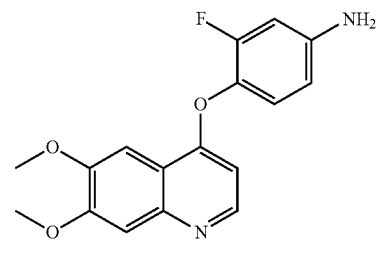 |

| 175 | 176 |
|---|---|
| 193 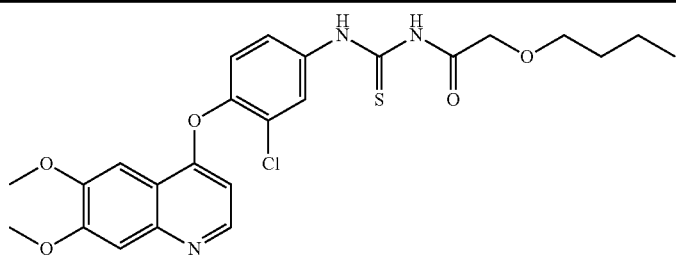 | 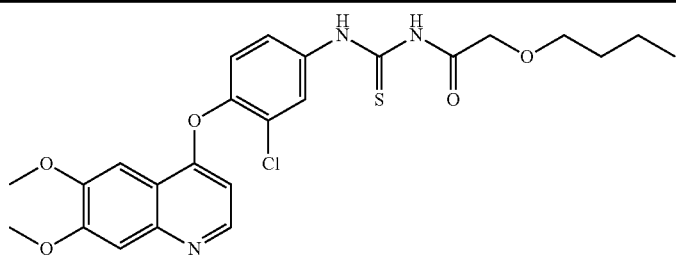 |
| 194 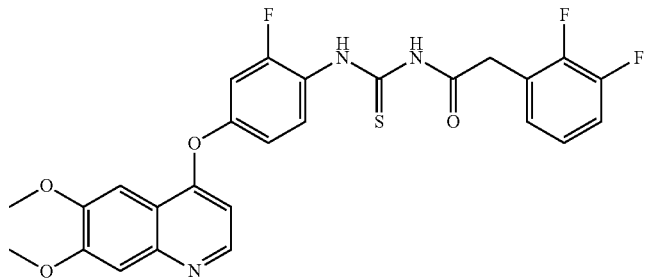 | 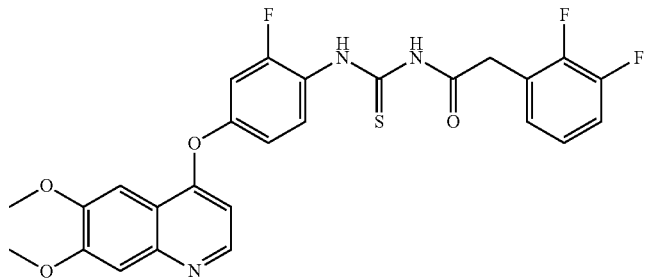 |
| 195 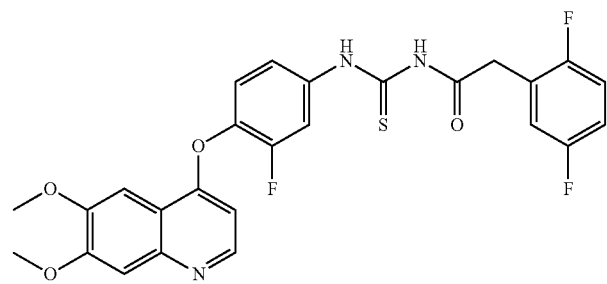 | 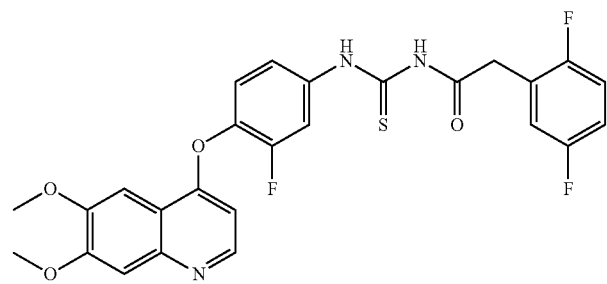 |
| 196 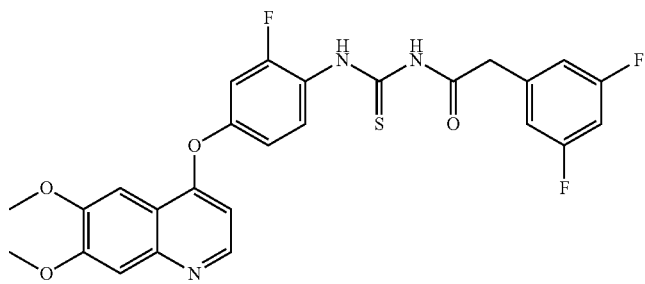 | 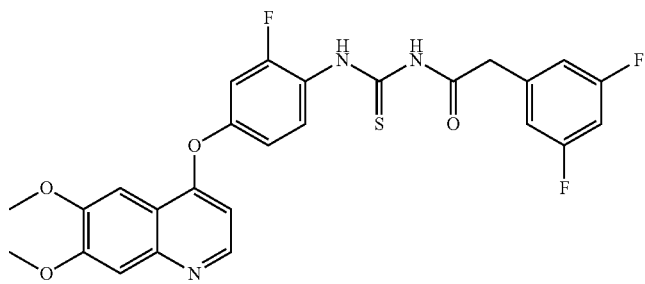 |
| 197 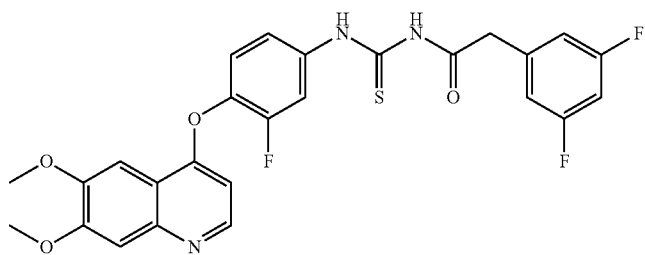 | 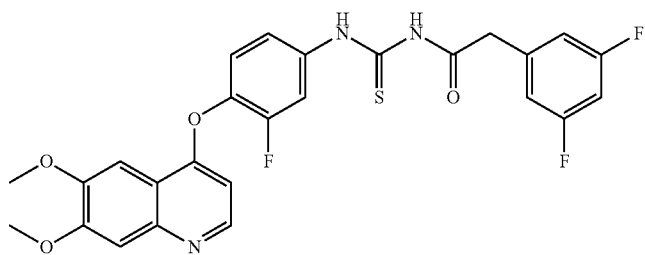 |
| 198 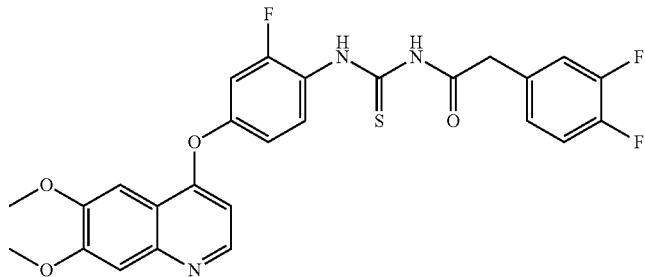 | 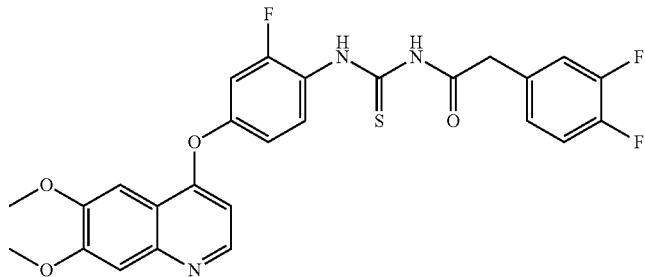 |

| | | |
|---|---|---|
| 199 | 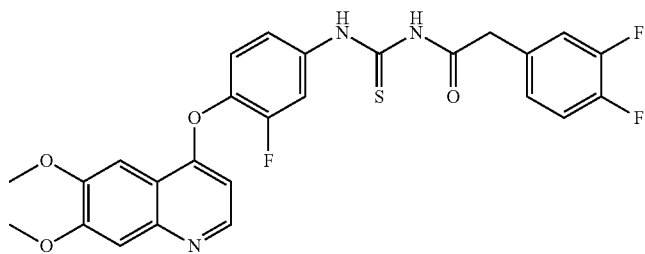 | 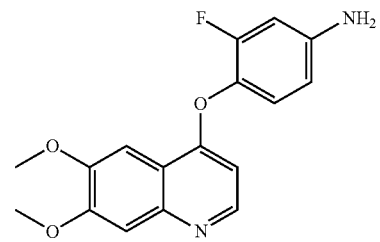 |
| 200 | 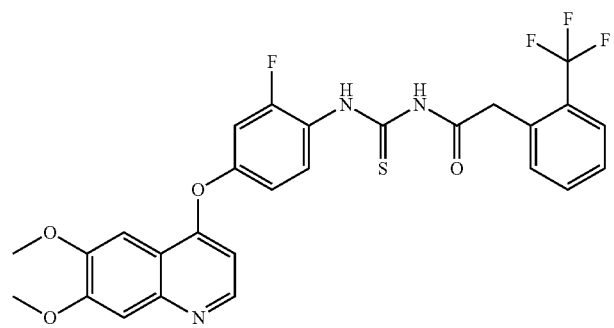 | 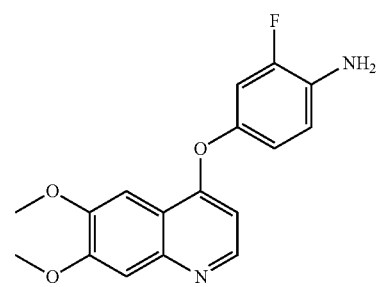 |
| 201 | 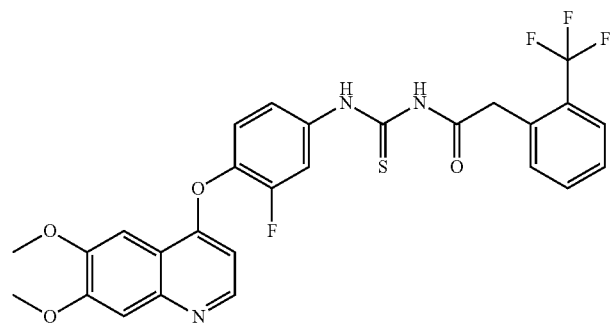 | 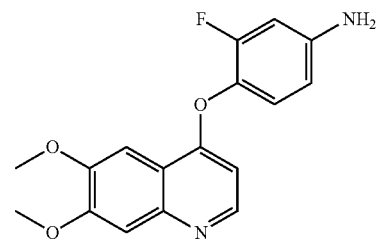 |
| 202 | 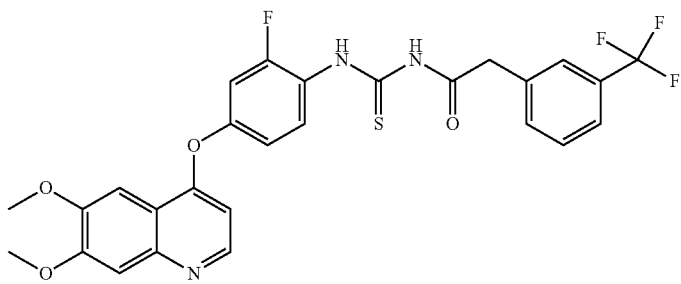 | 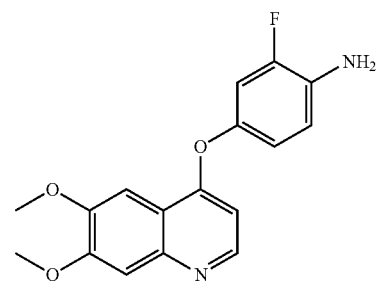 |
| 203 | 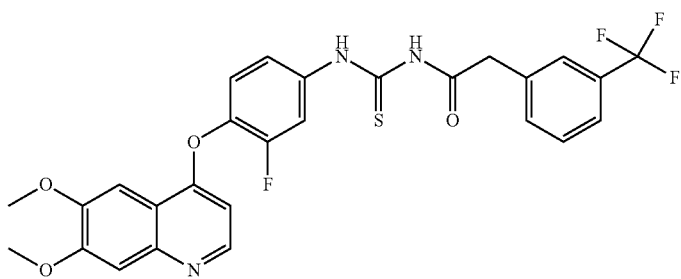 | 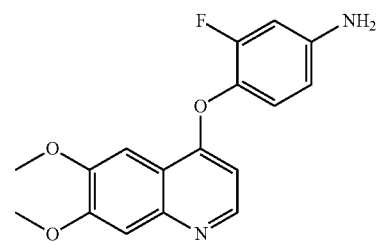 |

| | | |
|---|---|---|
| 204 | 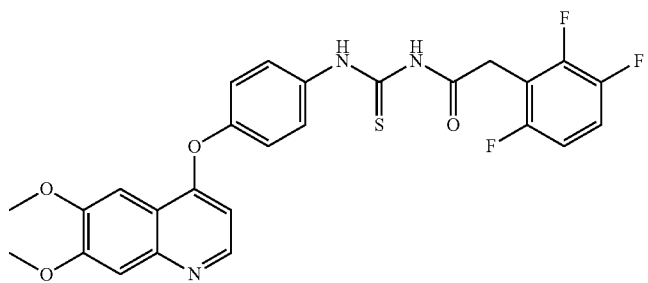 | 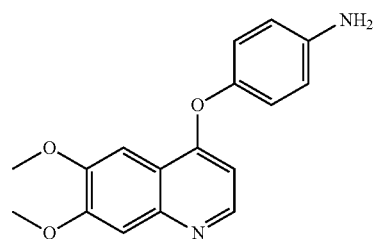 |
| 205 | 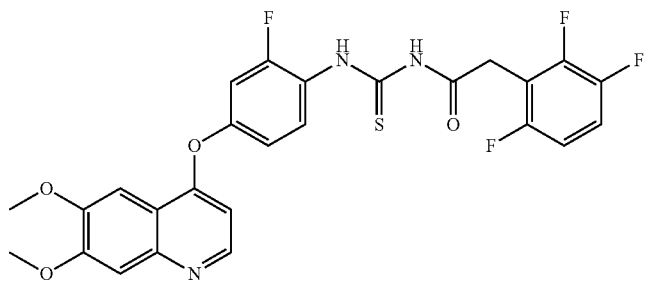 | 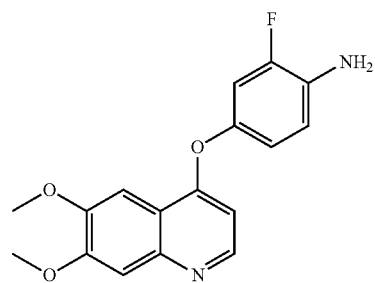 |
| 206 | 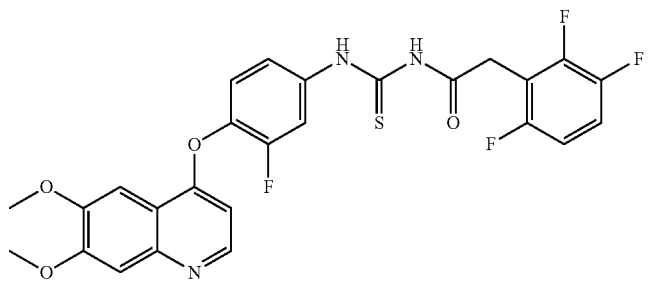 | 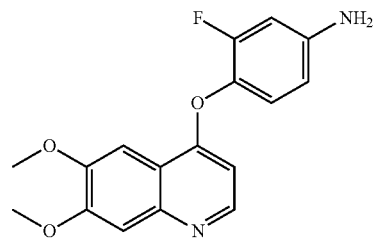 |
| 207 | 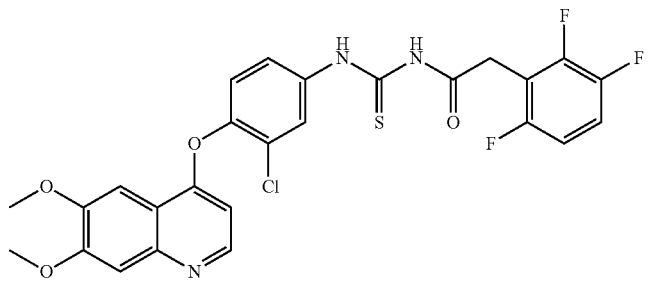 | 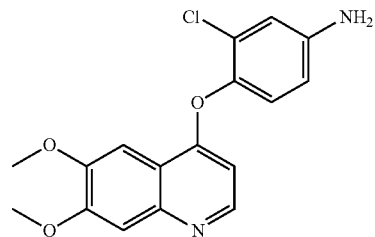 |
| 208 | 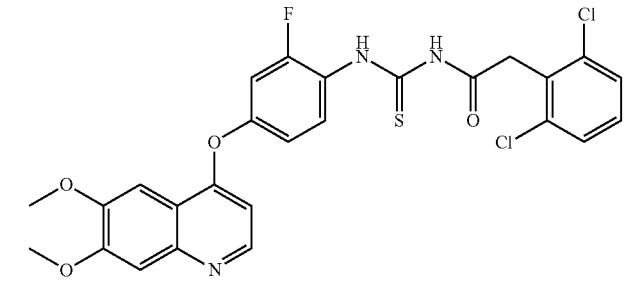 | 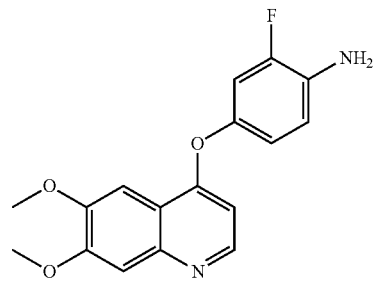 |

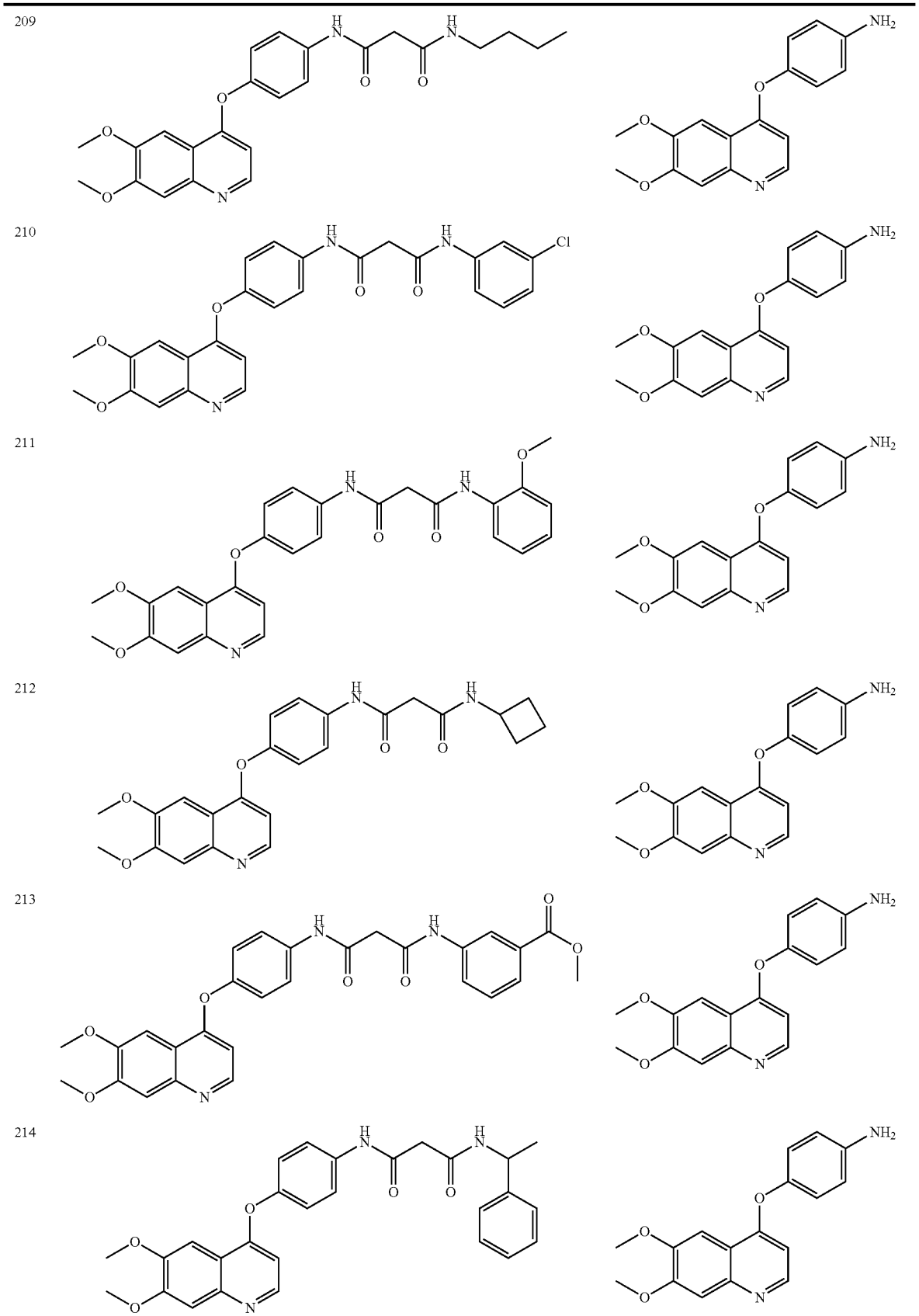

| | 183 | 184 |
|---|---|---|
| 215 | 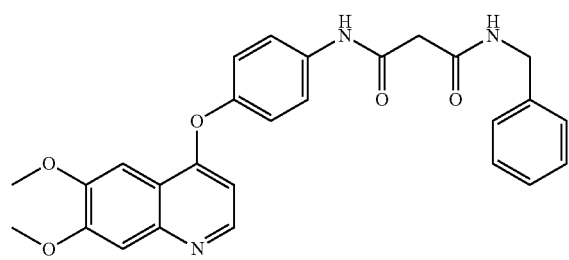 | 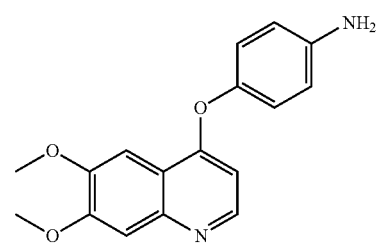 |
| 216 | 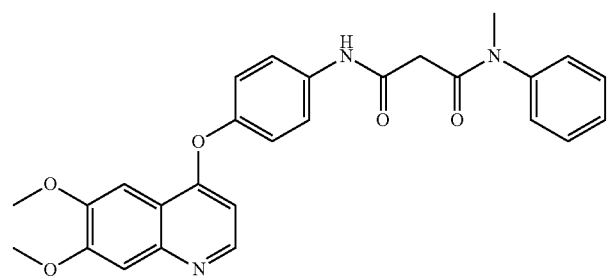 | 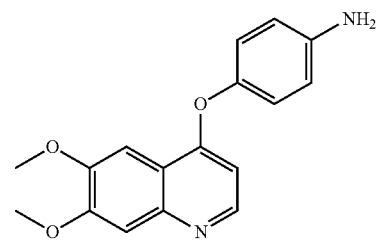 |
| 217 | 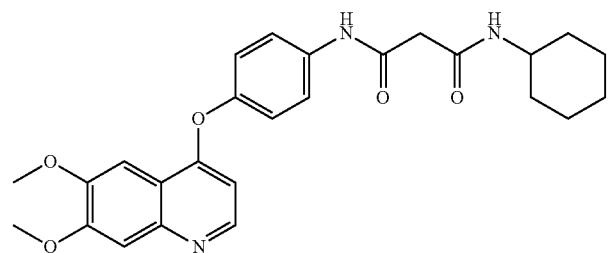 | 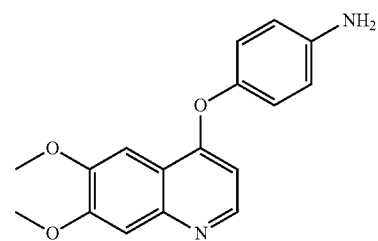 |
| 218 | 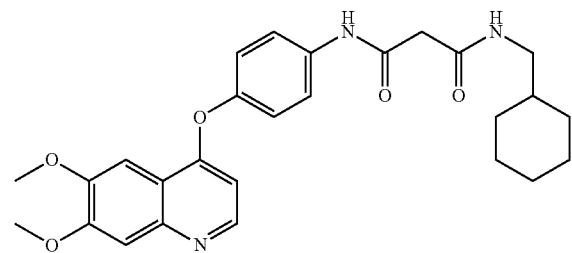 | 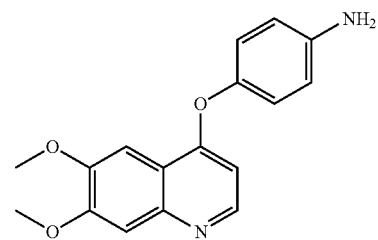 |
| 219 | 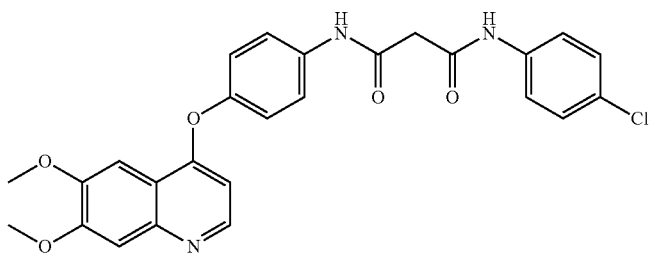 | 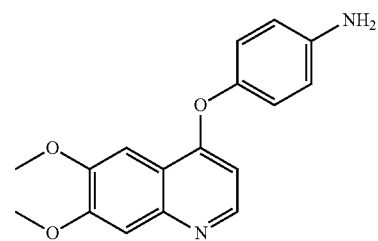 |
| 220 | 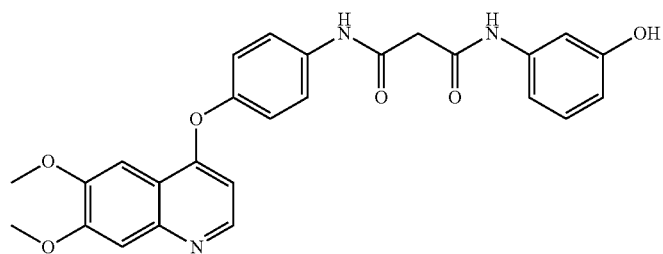 | 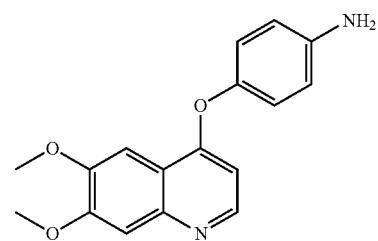 |

| 221 | 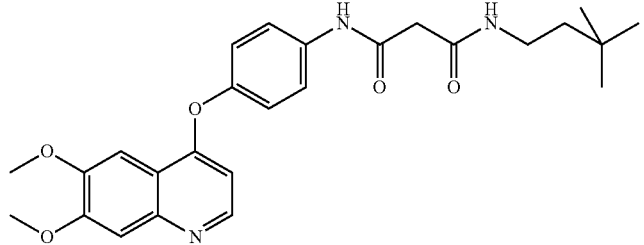 | 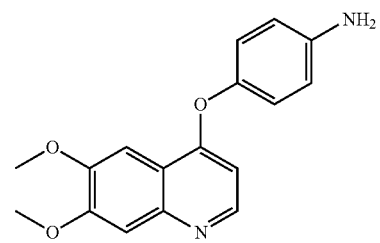 |
|---|---|---|
| 222 | 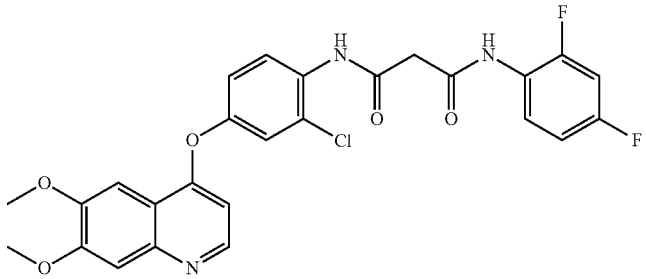 | 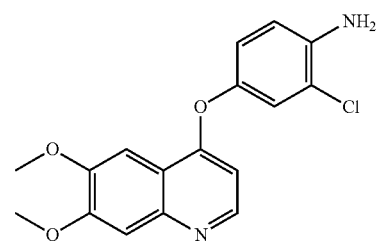 |
| 223 | 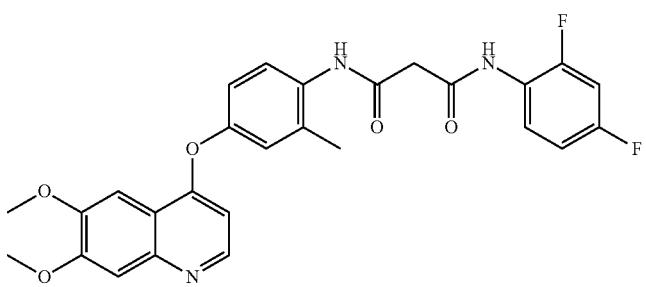 | 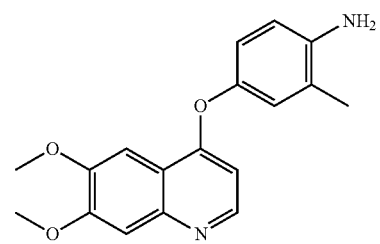 |
| 224 | 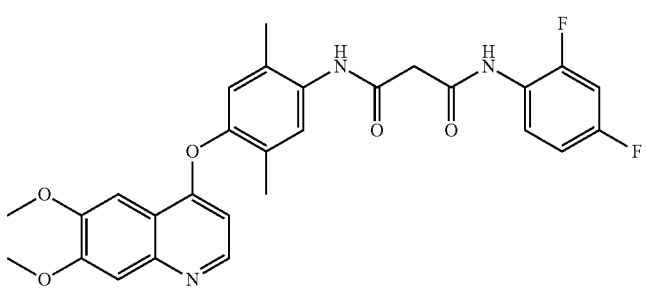 | 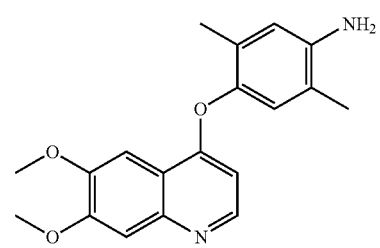 |
| 225 | 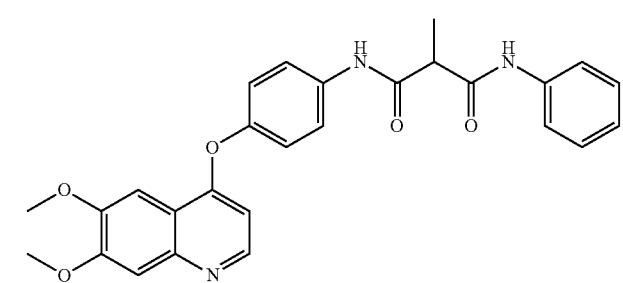 | 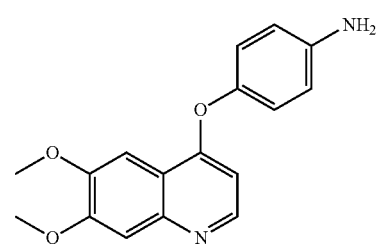 |

| 226 | 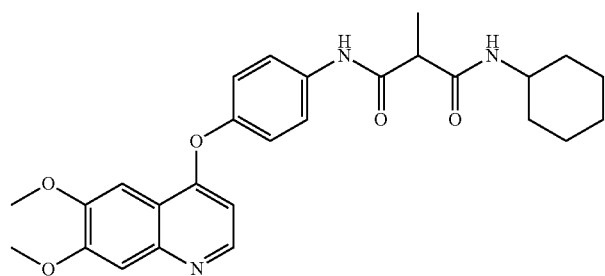 | 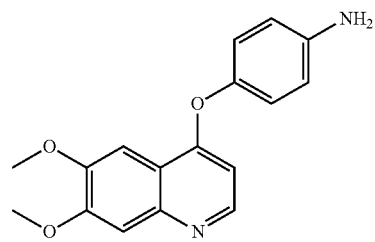 |
| 227 | 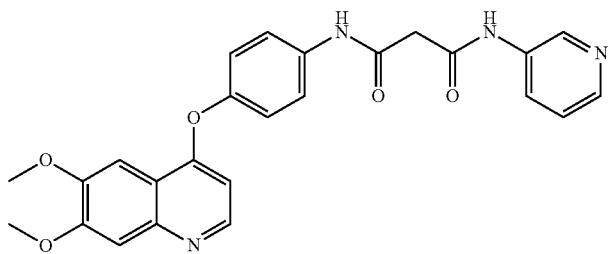 | 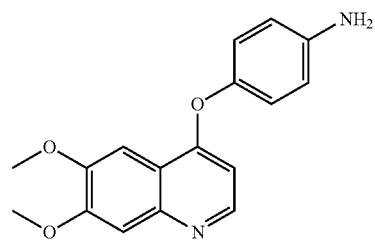 |
| 228 | 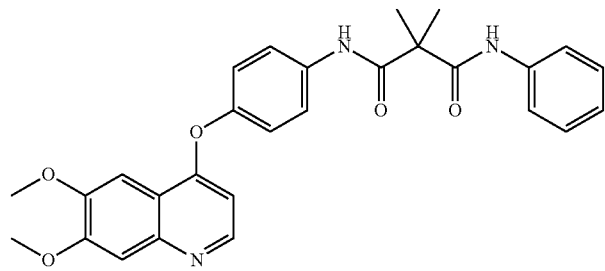 | 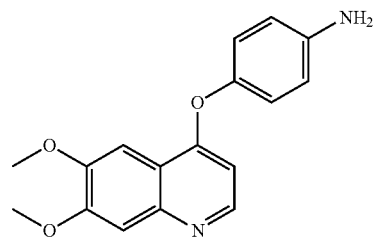 |
| 229 | 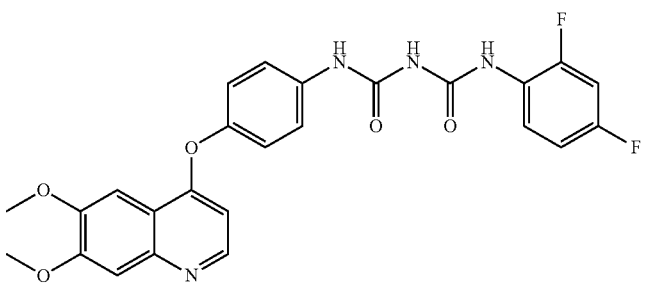 | 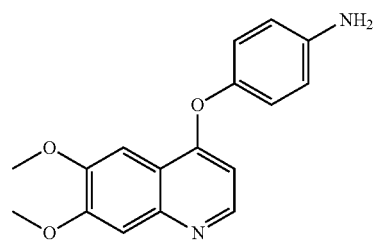 |
| 230 | 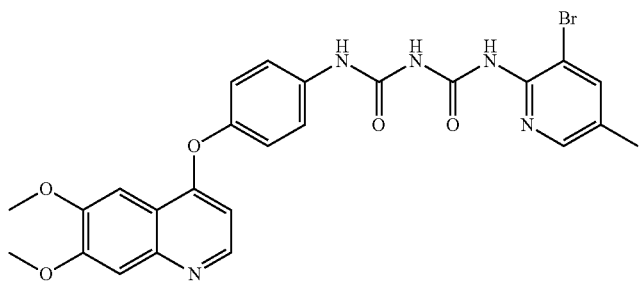 | 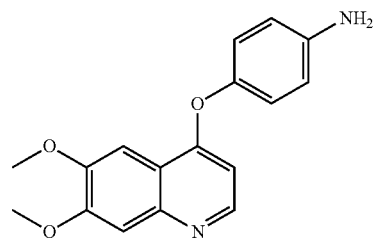 |
| 231 | 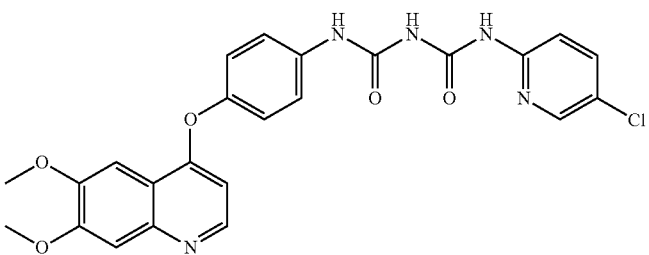 | 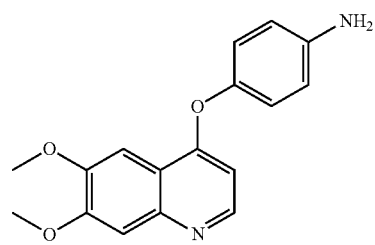 |

| 232 | 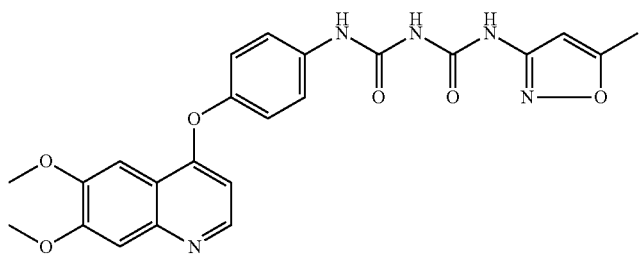 | 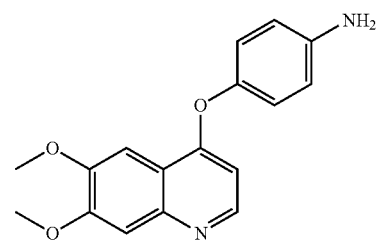 |
| --- | --- | --- |
| 233 | 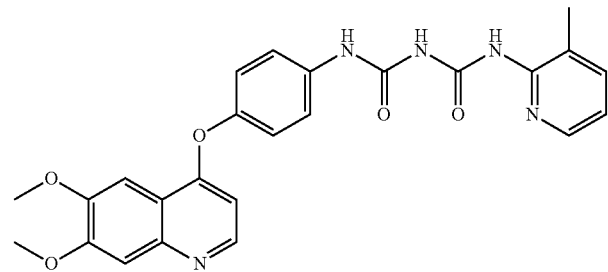 | 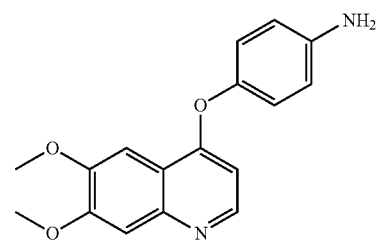 |
| 234 | 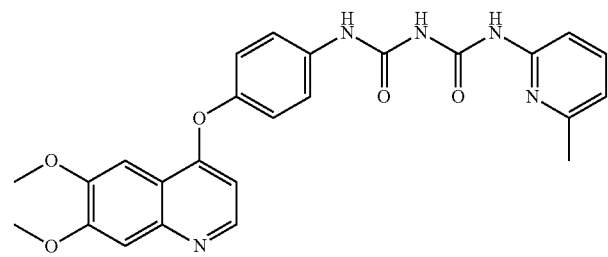 | 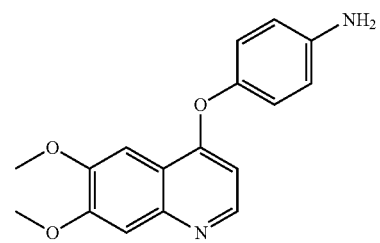 |
| 235 | 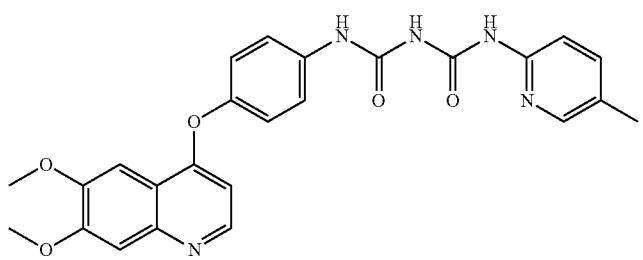 | 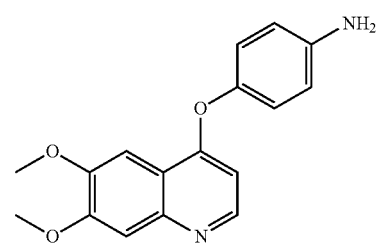 |
| 236 | 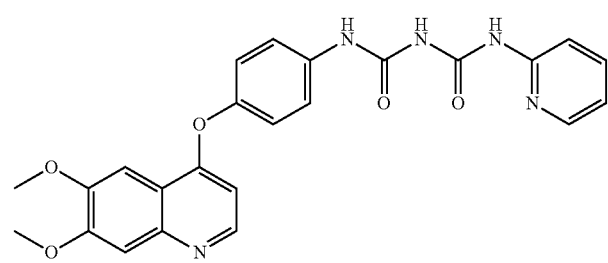 | 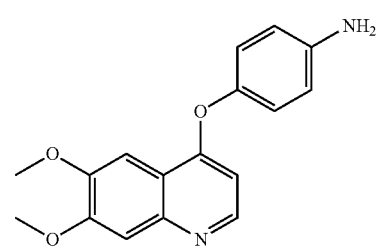 |
| 237 | 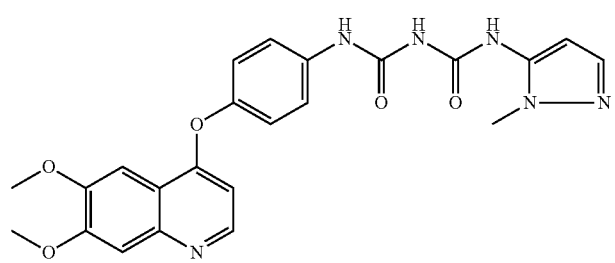 | 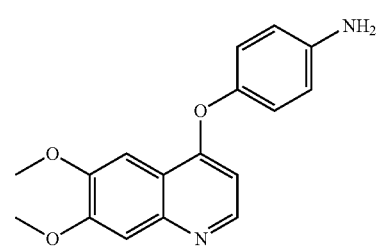 |

| 191 | 192 |
|---|---|
| 238 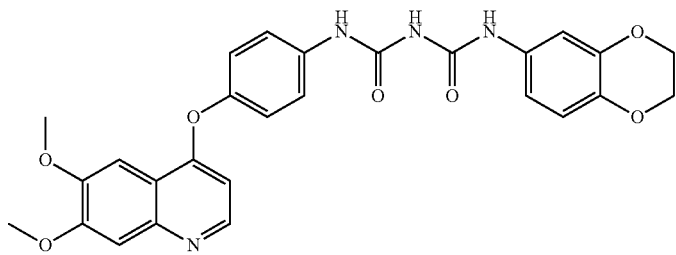 | |
| 239 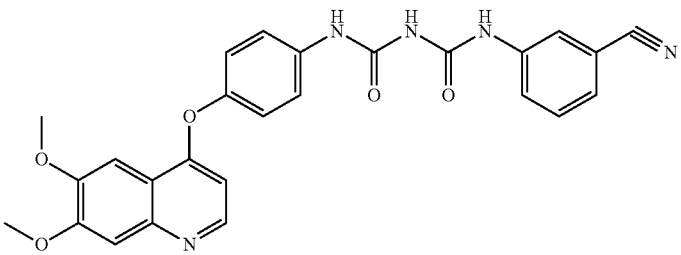 | |
| 240 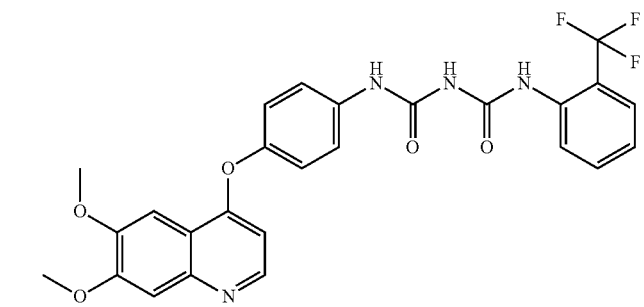 | |
| 241 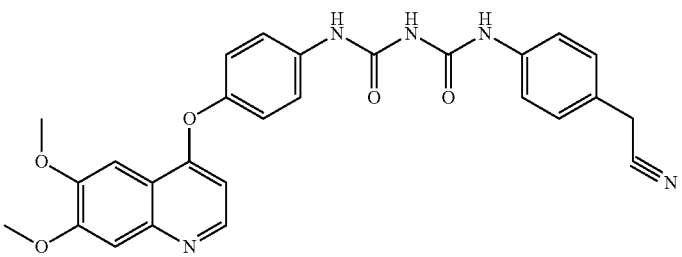 | |
| 242 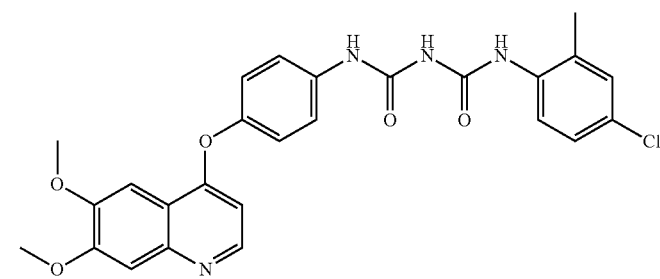 | |
| 243 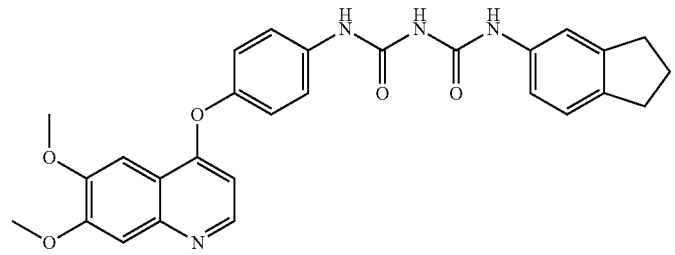 | |

-continued
| | 193 | 194 |
|---|---|---|
| 244 | 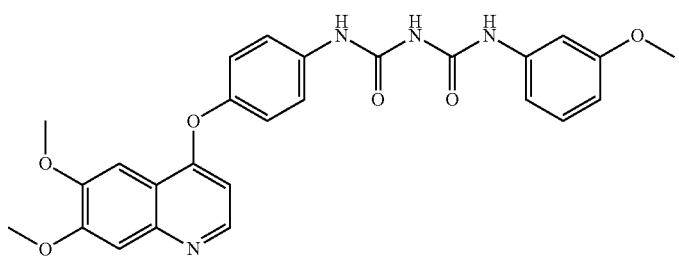 | 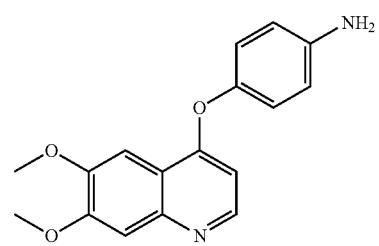 |
| 245 | 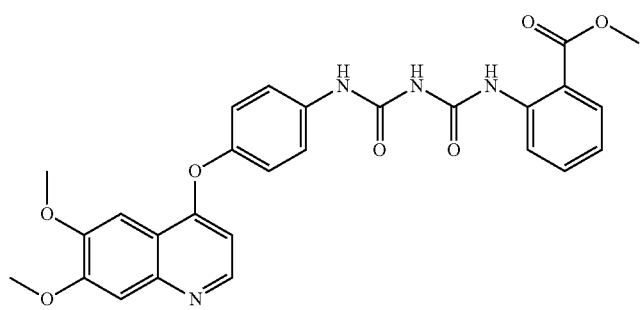 | 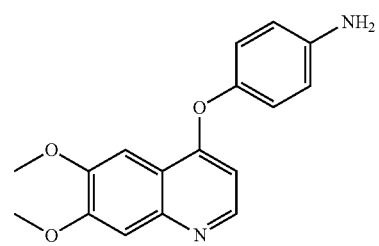 |
| 246 | 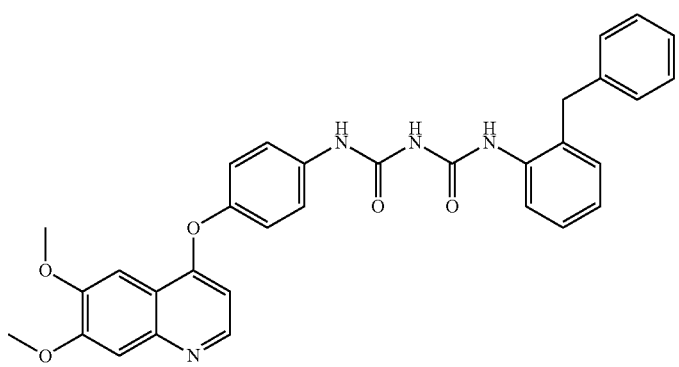 | 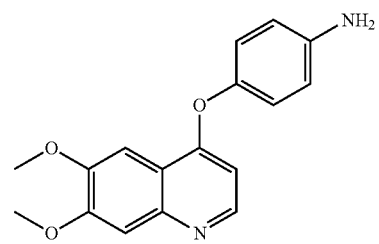 |
| 247 | 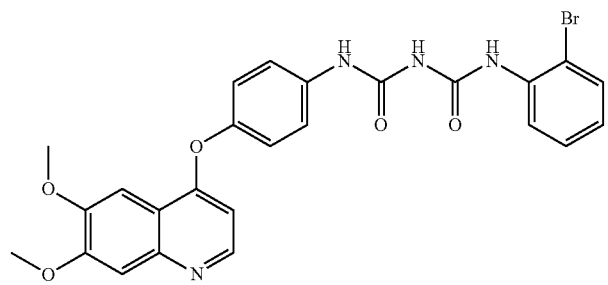 | 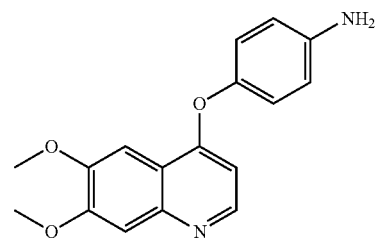 |
| 248 | 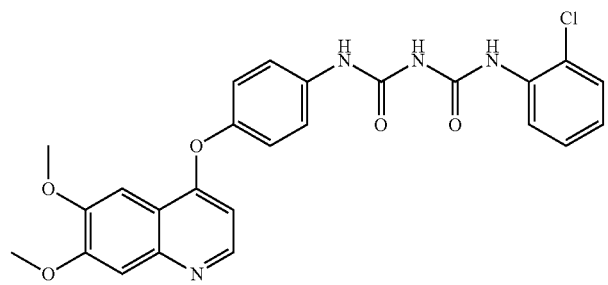 | 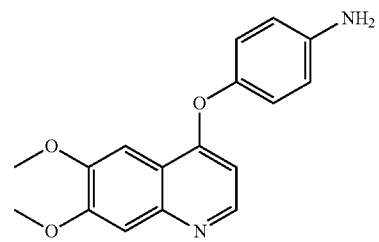 |

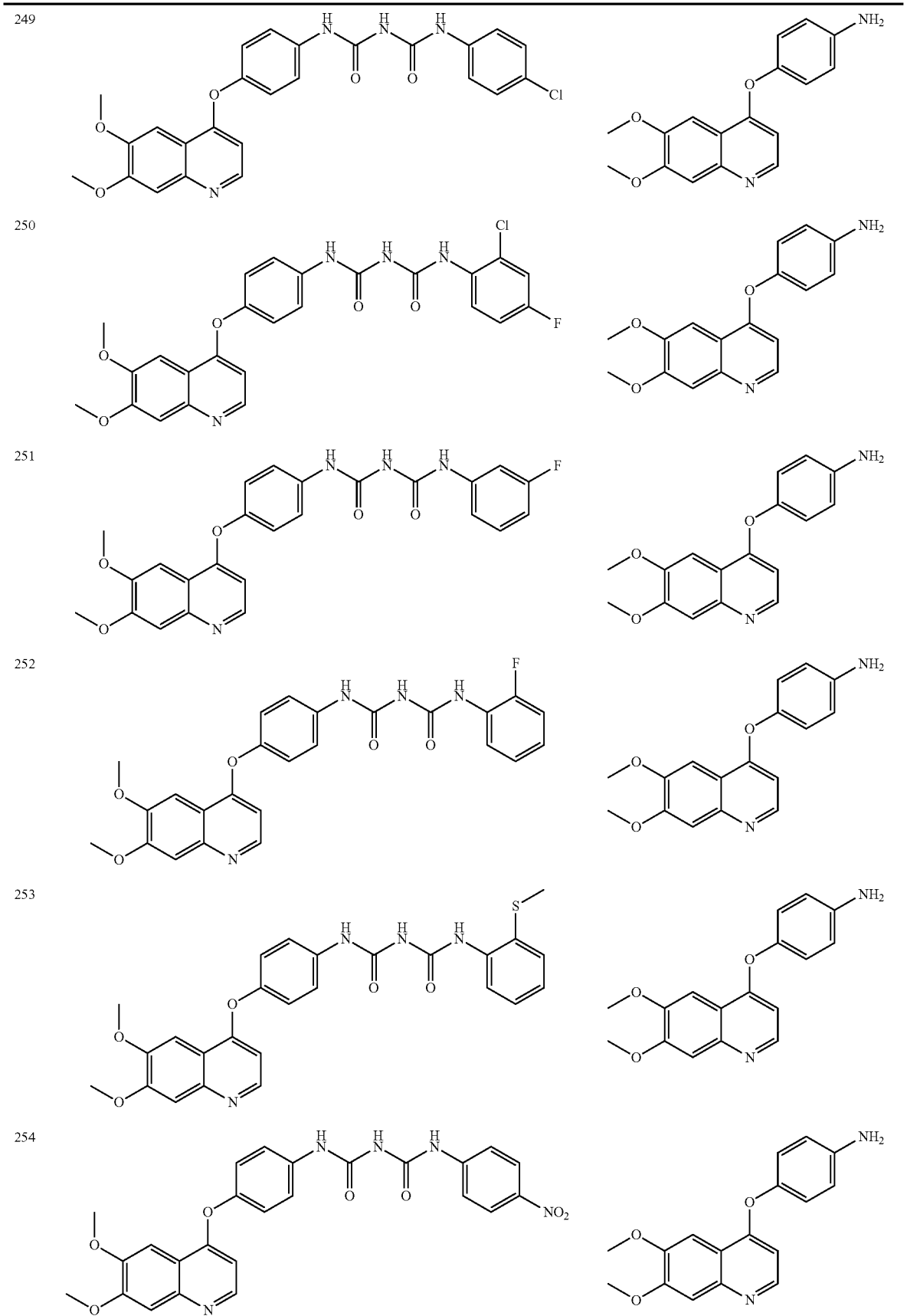

| 255 | 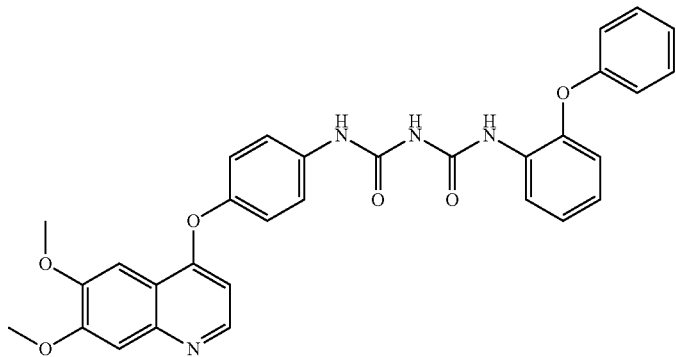 | 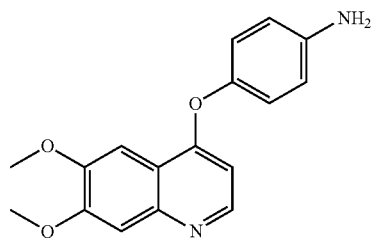 |
|---|---|---|
| 256 | 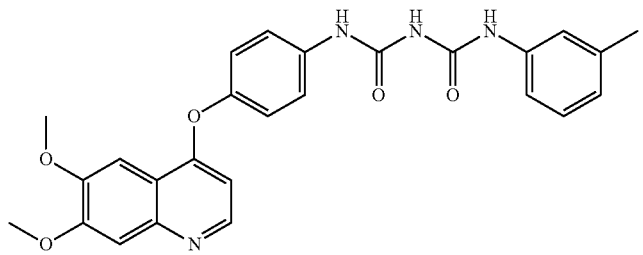 | 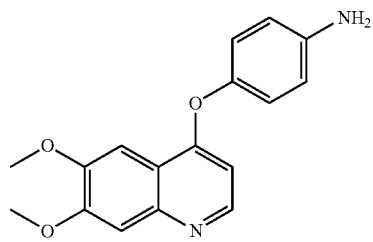 |
| 257 | 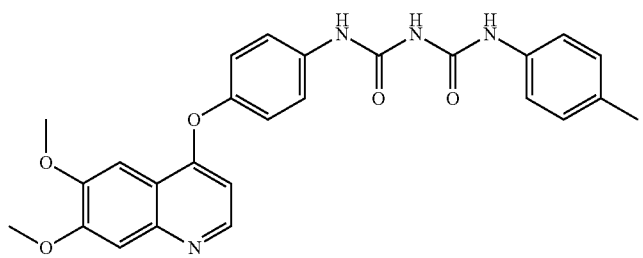 | 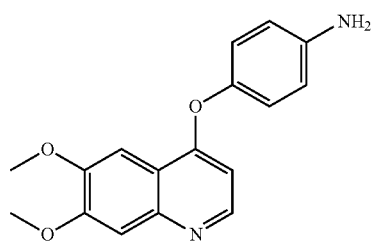 |
| 258 | 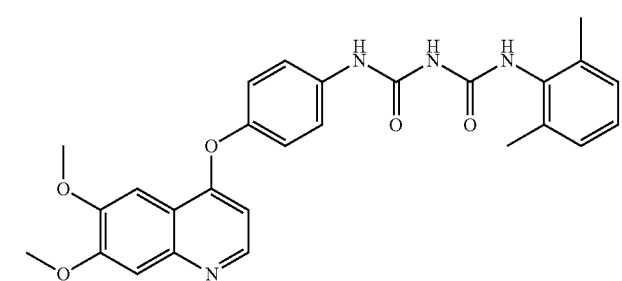 | 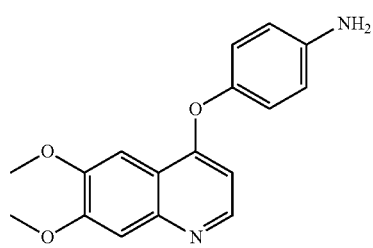 |
| 259 | 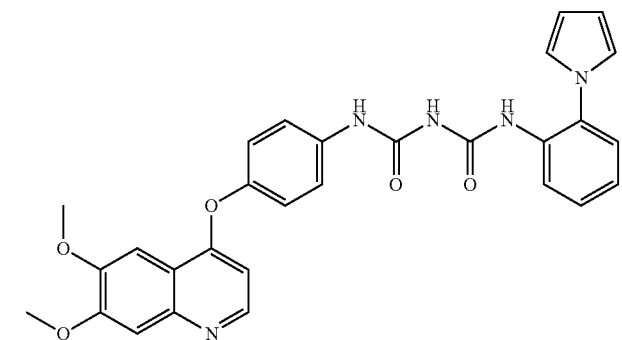 | 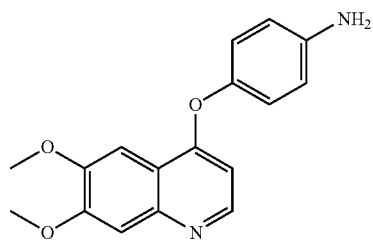 |

| 199 | 200 |
|---|---|
| 260 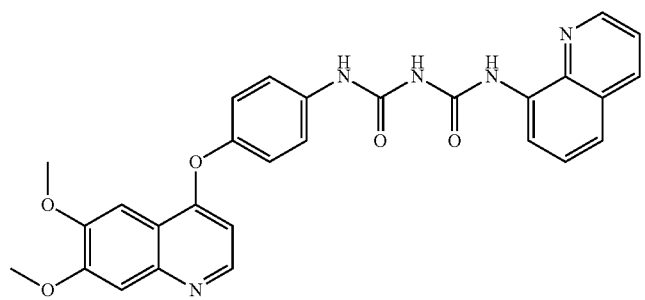 | 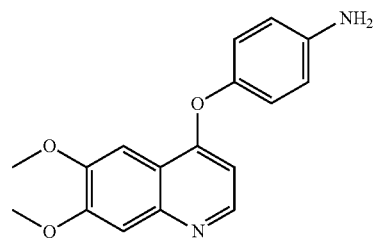 |
| 261 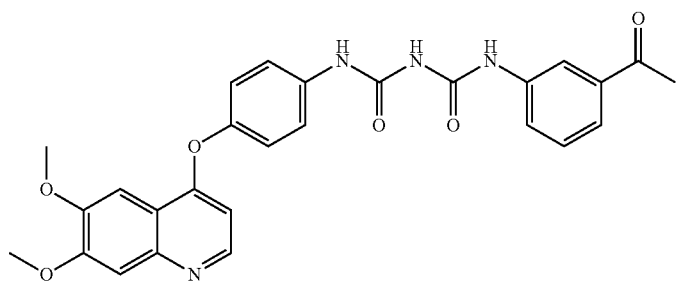 | 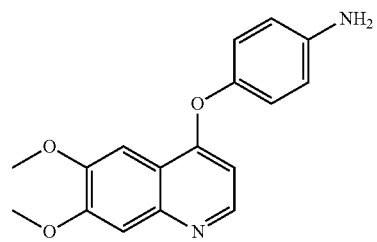 |
| 262 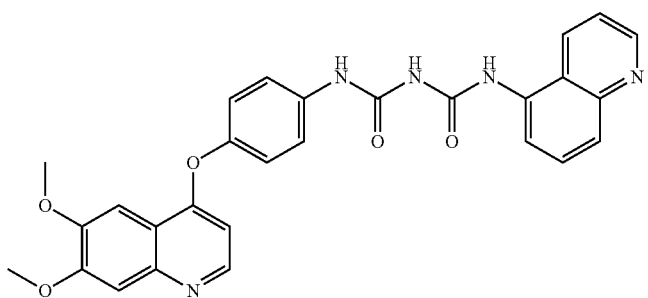 | 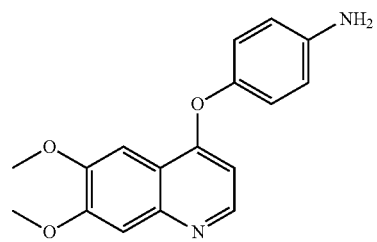 |
| 263 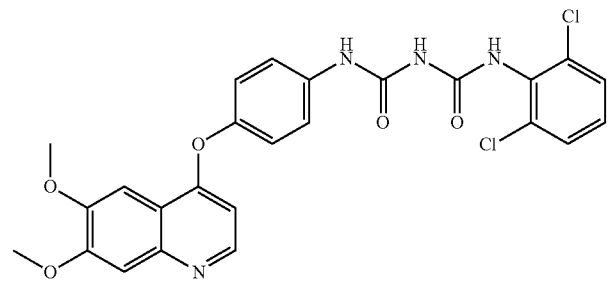 | 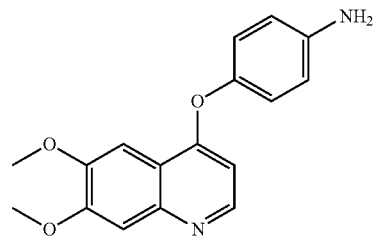 |
| 264 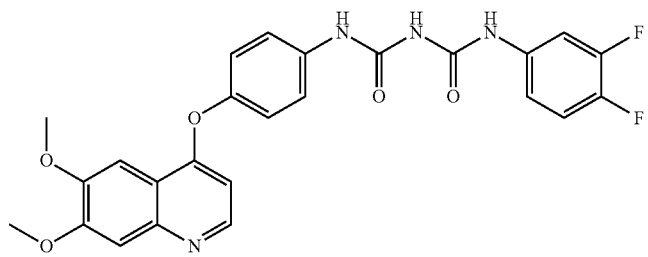 | 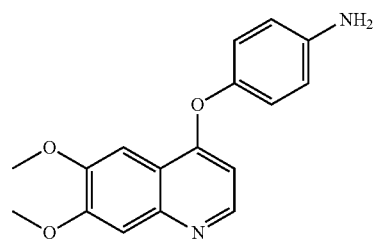 |

265 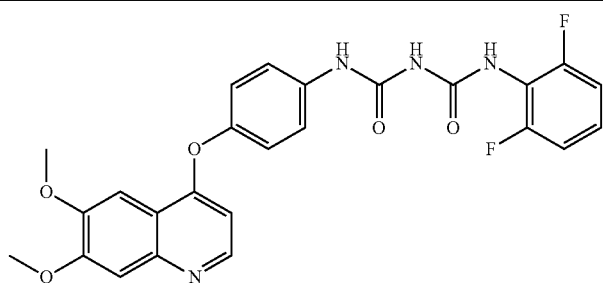 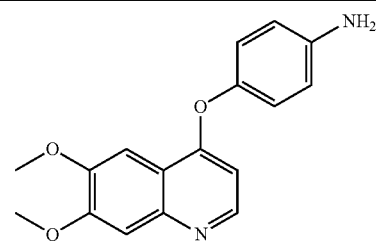
266 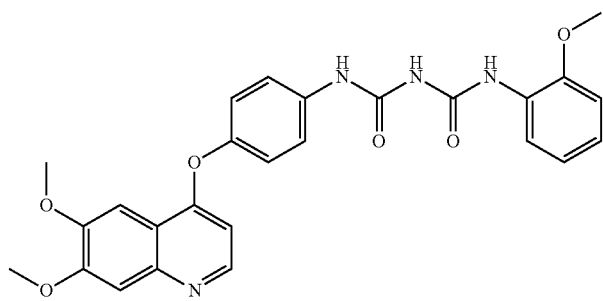 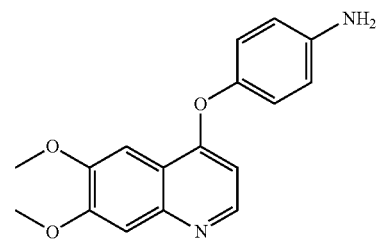
267 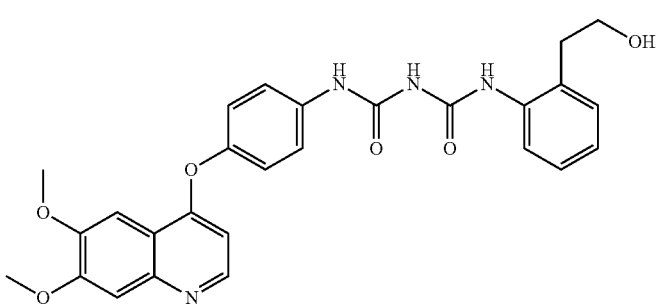 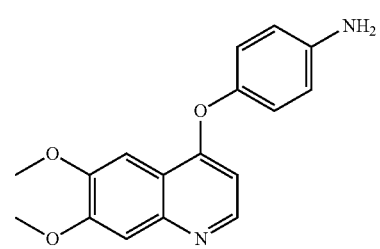
| Ex. No. | Starting compound B | Starting compound C | Mass spectrometric value (m/z) | Synthesis method[a] |
|---|---|---|---|---|
| 107 | 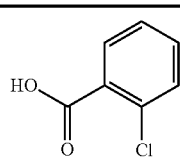 | | 496 [M + H]+ | Ex. 3 |
| 108 | 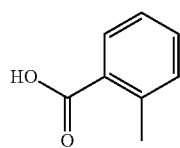 | | 476 [M + H]+ | Ex. 3 |
| 109 | 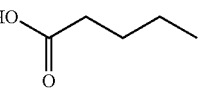 | | 458 [M + H]+ | Ex. 3 |
| 110 | 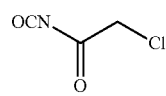 | 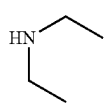 | 487 [M + H]+ | Ex. 8 |
| 111 | 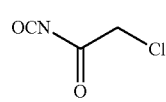 | 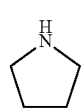 | 485 [M + H]+ | Ex. 8 |

-continued
| | | | | |
|---|---|---|---|---|
| 112 | 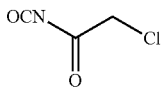 | 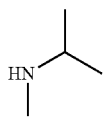 | 487 [M + H]+ | Ex. 8 |
| 113 | 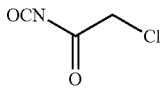 | 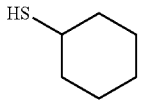 | 496 [M + H]+ | Ex. 7 |
| 114 | 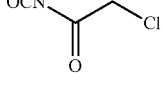 | 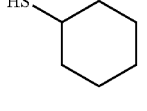 | 514 [M + H]+ | Ex. 7 |
| 115 | 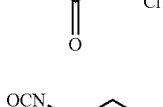 | 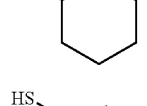 | 514 [M + H]+ | Ex. 7 |
| 116 | 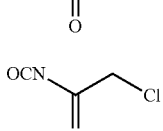 | 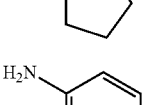 | 516 [M + H]+ | Ex. 7 |
| 117 | 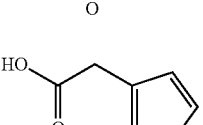 | 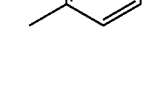 | 488 [M + H]+ | Ex. 8 |
| 118 | 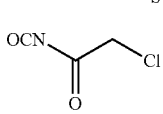 | | 463 [M + H]+ | Ex. 3 |
| 119 | 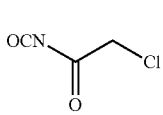 | 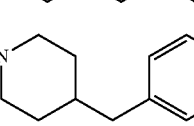 | 545 [M + H]+ | Ex. 8 |
| 120 | 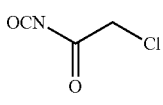 | 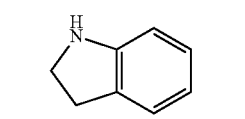 | 573 [M + H]+ | Ex. 8 |
| 121 | 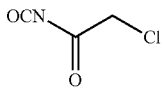 | 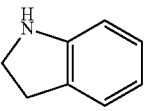 | 517 [M + H]+ | Ex. 8 |
| 122 | 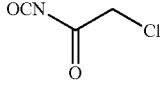 | 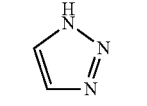 | 517 [M + H]+ | Ex. 8 |
| 123 | 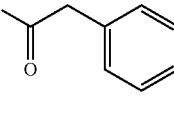 |  | 483 [M + H]+ | Ex. 8 |
| 124 | 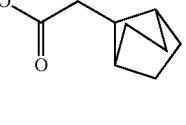 | | 490 [M + H]+ | Ex. 3 |
| 125 |  | | 476 [M + H]+ | Ex. 3 |

-continued
| | | | | |
|---|---|---|---|---|
| 126 | 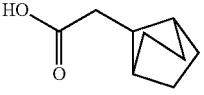 | | 494 [M + H]+ | Ex. 3 |
| 127 | 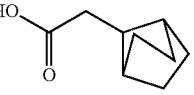 | | 494 [M + H]+ | Ex. 3 |
| 128 | 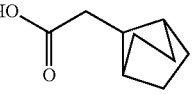 | | 511 [M + H]+ | Ex. 3 |
| 129 | 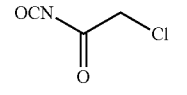 | 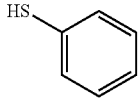 | 490 [M + H]+ | Ex. 7 |
| 130 | 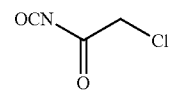 | 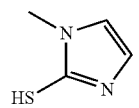 | 528 [M + H]+ | Ex. 7 |
| 131 | 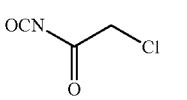 | 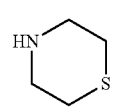 | 517 [M + H]+ | Ex. 8 |
| 132 | 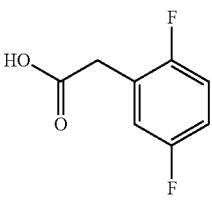 | | 512 [M + H]+ | Ex. 3 |
| 133 | 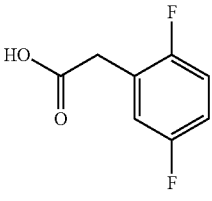 | | 512 [M + H]+ | Ex. 3 |
| 134 | 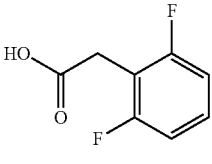 | | 512 [M + H]+ | Ex. 3 |
| 135 | 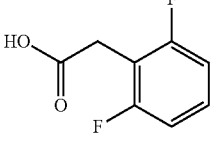 | | 512 [M + H]+ | Ex. 3 |
| 136 | 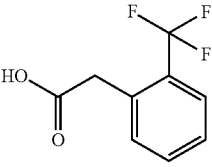 | | 544 [M + H]+ | Ex. 3 |

-continued
| | | | |
|---|---|---|---|
| 137 | 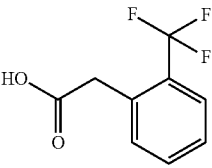 | 544 [M + H]+ | Ex. 3 |
| 138 | 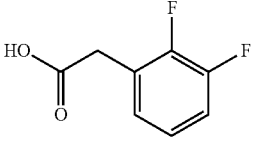 | 512 [M + H]+ | Ex. 3 |
| 139 | 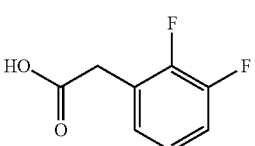 | 512 [M + H]+ | Ex. 3 |
| 140 | 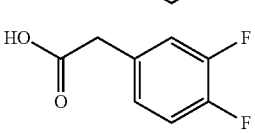 | 512 [M + H]+ | Ex. 3 |
| 141 | 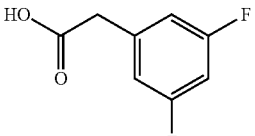 | 512 [M + H]+ | Ex. 3 |
| 142 | 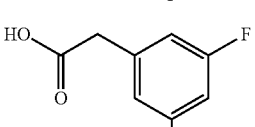 | 512 [M + H]+ | Ex. 3 |
| 143 | 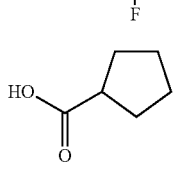 | 470 [M + H]+ | Ex. 2 |
| 144 | 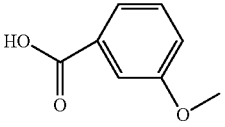 | 508 [M + H]+ | Ex. 2 |
| 145 | 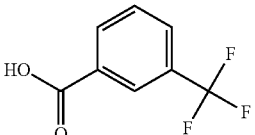 | 528 [M + H]+ | Ex. 2 |
| 146 | 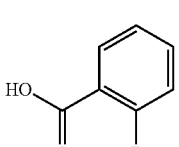 | 557 [M + H]+ | Ex. 2 |
| 147 | 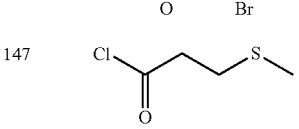 | 476 [M + H]+ | Ex. 1 |

-continued

| # | Structure | Mass | Ex. |
|---|---|---|---|
| 148 | Cl-C(=O)-CH₂CH₂CH₂-Cl | 478 [M + H]+ | Ex. 1 |
| 149 | 2-methylphenylacetic acid | 522 [M + H]+ | Ex. 2 |
| 150 | trans-2-phenylcyclopropanecarboxylic acid | 500 [M + 1]+ | Ex. 2 |
| 151 | 2-fluorophenylacetic acid | 492 [M + H]+ | Ex. 2 |
| 152 | 2-fluorophenylacetic acid | 526 [M + H]+ | Ex. 2 |
| 153 | 2-methoxyphenylacetic acid | 504 [M + 1]+ | Ex. 2 |
| 154 | 2-methoxyphenylacetic acid | 539 [M + 1]+ | Ex. 2 |
| 155 | 2-nitrophenylacetic acid | 519 [M + 1]+ | Ex. 2 |
| 156 | 2-nitrophenylacetic acid | 353 [M + 1]+ | Ex. 2 |
| 157 | phenoxyacetic acid | 524 [M + 1]+ | Ex. 2 |

| | | | |
|---|---|---|---|
| 158 | 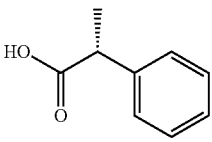 | 488 [M + 1]+ | Ex. 2 |
| 159 | 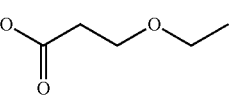 | 490 [M + 1]+ | Ex. 2 |
| 160 | 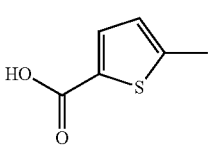 | 480 [M + 1]+ | Ex. 2 |
| 161 | 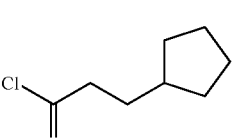 | 480 [M + 1]+ | Ex. 1 |
| 162 | 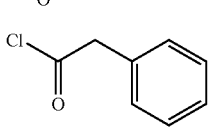 | 488 [M + H]+ | Ex. 1 |
| 163 | 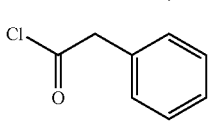 | 502 [M + H]+ | Ex. 1 |
| 164 | 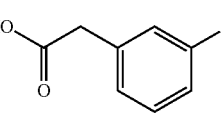 | 492 [M + H]+ | Ex. 2 |
| 165 | 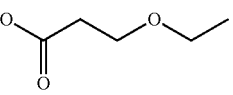 | 474 [M + H]+ | Ex. 2 |
| 166 | 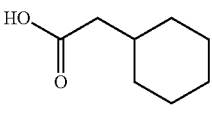 | 498 [M + H]+ | Ex. 2 |
| 167 | 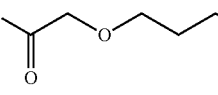 | 488 [M + H]+ | Ex. 2 |
| 168 | 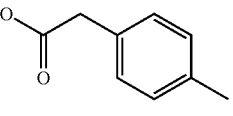 | 488 [M + H]+ | Ex. 2 |
| 169 | 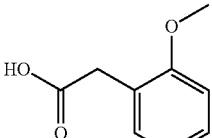 | 522 [M + H]+ | Ex. 2 |
| 170 | 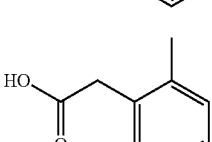 | 506 [M + H]+ | Ex. 2 |

-continued
| | | | |
|---|---|---|---|
| 171 | 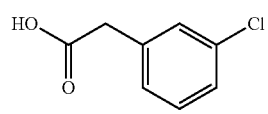 | 506 [M + H]+ | Ex. 2 |
| 172 | 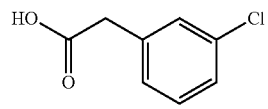 | 526 [M + H]+ | Ex. 2 |
| 173 | 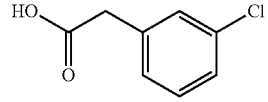 | 526 [M + H]+ | Ex. 2 |
| 174 | 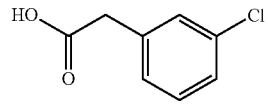 | 542 [M + H]+ | Ex. 2 |
| 175 | 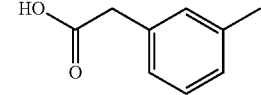 | 506 [M + H]+ | Ex. 2 |
| 176 | 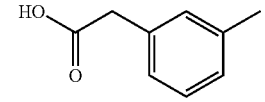 | 506 [M + H]+ | Ex. 2 |
| 177 | 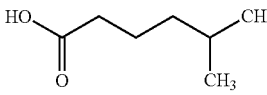 | 468 [M + H]+ | Ex. 2 |
| 178 | 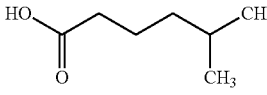 | 486 [M + H]+ | Ex. 2 |
| 179 | 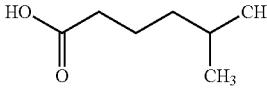 | 486 [M + H]+ | Ex. 2 |
| 180 | 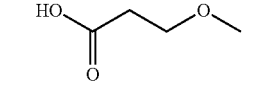 | 476 [M + H]+ | Ex. 2 |
| 181 | 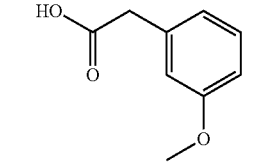 | 522 [M + H]+ | Ex. 2 |
| 182 | 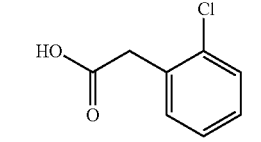 | 526 [M + H]+ | Ex. 2 |
| 183 | 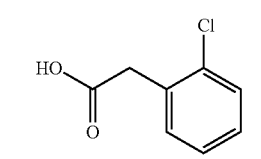 | 543 [M + H]+ | Ex. 2 |

-continued

| | | | |
|---|---|---|---|
| 184 | 3-methoxyphenylacetic acid | 504 [M + H]+ | Ex. 2 |
| 185 | 3-ethoxyphenylacetic acid | 522 [M + H]+ | Ex. 2 |
| 186 | 3-propoxyphenylacetic acid | 539 [M + H]+ | Ex. 2 |
| 187 | 4-chlorophenylacetic acid | 508 [M + H]+ | Ex. 2 |
| 188 | 4-chlorophenylacetic acid | 526 [M + H]+ | Ex. 2 |
| 189 | 4-chlorophenylacetic acid | 543 [M + H]+ | Ex. 2 |
| 190 | 4-methylphenylacetic acid | 506 [M + H]+ | Ex. 2 |
| 191 | 4-methylcyclohexylacetic acid | 512 [M + H]+ | Ex. 2 |
| 192 | 4-methylcyclohexylacetic acid | 512 [M + H]+ | Ex. 2 |
| 193 | butoxyacetic acid | 505 [M + H]+ | Ex. 2 |
| 194 | 2,3-difluorophenylacetic acid | 528 [M + H]+ | Ex. 2 |

-continued

| | | | |
|---|---|---|---|
| 195 | 2,5-difluorophenylacetic acid | 528 [M + H]+ | Ex. 2 |
| 196 | 3,5-difluorophenylacetic acid | 528 [M + H]+ | Ex. 2 |
| 197 | 3,5-difluorophenylacetic acid | 528 [M + H]+ | Ex. 2 |
| 198 | 3,4-difluorophenylacetic acid | 528 [M + H]+ | Ex. 2 |
| 199 | 3,4-difluorophenylacetic acid | 528 [M + H]+ | Ex. 2 |
| 200 | 2-(trifluoromethyl)phenylacetic acid | 560 [M + H]+ | Ex. 2 |
| 201 | 2-(trifluoromethyl)phenylacetic acid | 560 [M + H]+ | Ex. 2 |
| 202 | 3-(trifluoromethyl)phenylacetic acid | 560 [M + H]+ | Ex. 2 |
| 203 | 3-(trifluoromethyl)phenylacetic acid | 560 [M + H]+ | Ex. 2 |
| 204 | 2,3,6-trifluorophenylacetic acid | 528 [M + H]+ | Ex. 2 |

| | | | | |
|---|---|---|---|---|
| 205 | 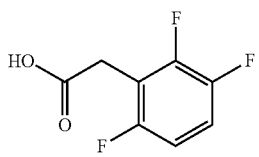 | | 546 [M + H]+ | Ex. 2 |
| 206 | 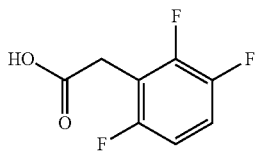 | | 546 [M + H]+ | Ex. 2 |
| 207 | 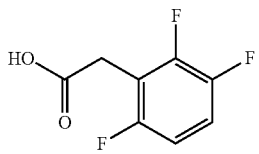 | | 562 [M + H]+ | Ex. 2 |
| 208 | 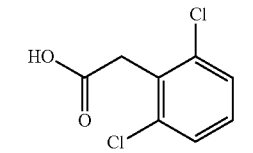 | | 561 [M + H]+ | Ex. 2 |
| 209 | 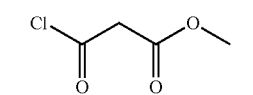 | 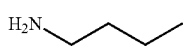 | 438 [M + H]+ | Ex. 5 |
| 210 | 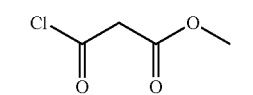 | 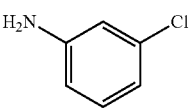 | 492 [M + H]+ | Ex. 5 |
| 211 | 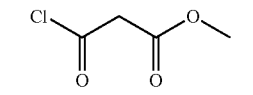 | 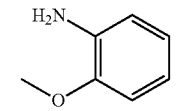 | 488 [M + H]+ | Ex. 5 |
| 212 | 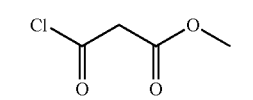 | 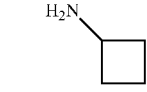 | 436 [M + H]+ | Ex. 5 |
| 213 | 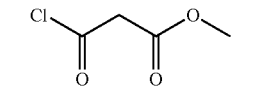 | 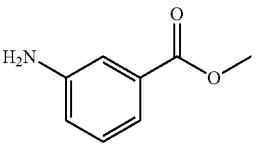 | 516 [M + H]+ | Ex. 5 |
| 214 | 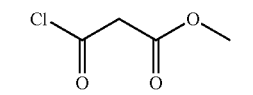 | 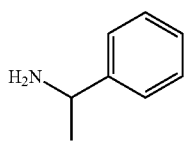 | 486 [M + H]+ | Ex. 5 |
| 215 | 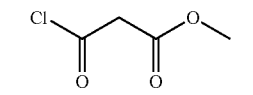 | 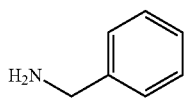 | 472 [M + H]+ | Ex. 5 |

-continued
| | | | | |
|---|---|---|---|---|
| 216 | 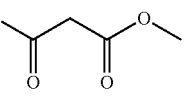 | 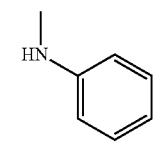 | 472 [M + H]+ | Ex. 5 |
| 217 | 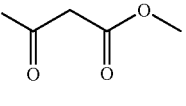 | 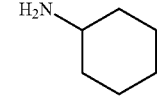 | 464 [M + H]+ | Ex. 5 |
| 218 | 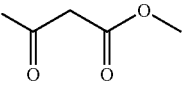 | 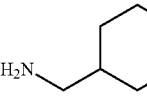 | 478 [M + H]+ | Ex. 5 |
| 219 | 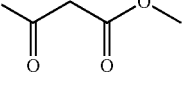 | 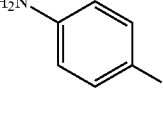 | 492 [M + H]+ | Ex. 5 |
| 220 | 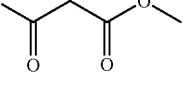 | 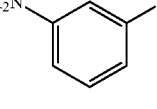 | 474 [M + H]+ | Ex. 5 |
| 221 | 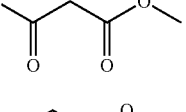 | 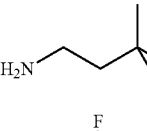 | 466 [M + H]+ | Ex. 5 |
| 222 | 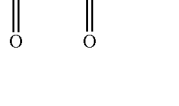 | 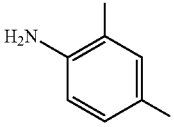 | 528 [M + H]+ | Ex. 6 |
| 223 | 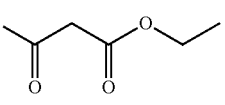 | 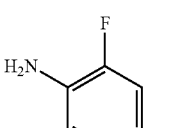 | 508 [M + H]+ | Ex. 6 |
| 224 | 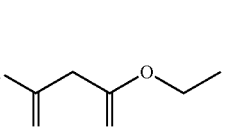 | 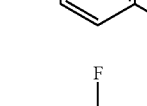 | 522 [M + H]+ | Ex. 6 |
| 225 | 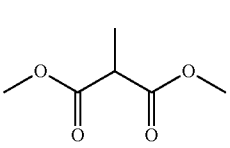 | 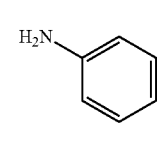 | 472 [M + H]+ | Ex. 15 |
| 226 | 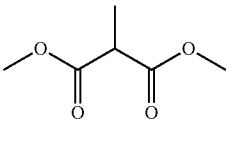 | 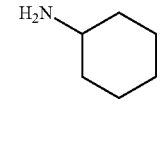 | 478 [M + H]+ | Ex. 15 |
| 227 | 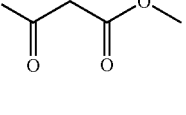 | 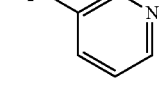 | 459 [M + H]+ | Ex. 5 |

-continued

| # | Reagent 1 | Reagent 2 | MS | Ex. |
|---|---|---|---|---|
| 228 | dimethyl 2,2-dimethylmalonate | aniline | 486 [M + H]+ | Ex. 15 |
| 229 | Cl-C(O)-NCO | 2,4-difluoroaniline | 493 [M − H]− | Ex. 9 |
| 230 | Cl-C(O)-NCO | 3-bromo-5-methylpyridin-2-amine | 550 [M − H]− | Ex. 9 |
| 231 | Cl-C(O)-NCO | 5-chloropyridin-2-amine | 492 [M − H]− | Ex. 9 |
| 232 | Cl-C(O)-NCO | 5-methylisoxazol-3-amine | 462 [M − H]− | Ex. 9 |
| 233 | Cl-C(O)-NCO | 3-methylpyridin-2-amine | 472 [M − H]− | Ex. 9 |
| 234 | Cl-C(O)-NCO | 6-methylpyridin-2-amine | 472 [M − H]− | Ex. 9 |
| 235 | Cl-C(O)-NCO | 5-methylpyridin-2-amine | 472 [M − H]− | Ex. 9 |
| 236 | Cl-C(O)-NCO | pyridin-2-amine | 458 [M − H]− | Ex. 9 |
| 237 | Cl-C(O)-NCO | 1-methyl-1H-pyrazol-5-amine | 461 [M − H]− | Ex. 9 |
| 238 | Cl-C(O)-NCO | 2,3-dihydrobenzo[b][1,4]dioxin-6-amine | 515 [M − H]− | Ex. 9 |
| 239 | Cl-C(O)-NCO | 3-aminobenzonitrile | 482 [M − H]− | Ex. 9 |

-continued
| | | | | |
|---|---|---|---|---|
| 240 | 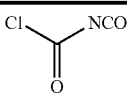 | 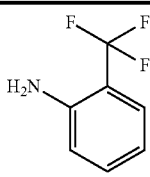 | 525 [M − H]− | Ex. 9 |
| 241 | 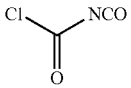 | 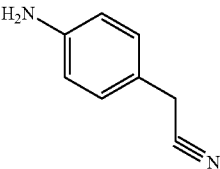 | 496 [M − H]− | Ex. 9 |
| 242 | 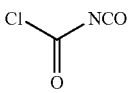 | 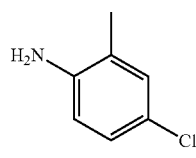 | 505 [M − H]− | Ex. 9 |
| 243 | 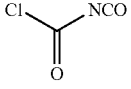 | 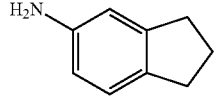 | 497 [M − H]− | Ex. 9 |
| 244 | 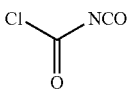 | 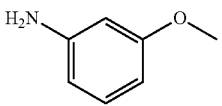 | 487 [M − H]− | Ex. 9 |
| 245 | 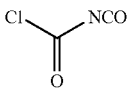 | 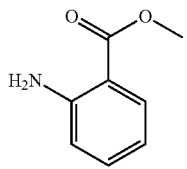 | 515 [M − H]− | Ex. 9 |
| 246 | 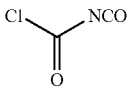 | 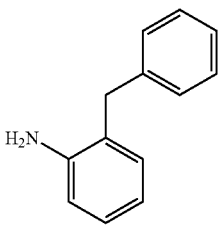 | 547 [M − H]− | Ex. 9 |
| 247 | 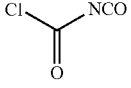 | 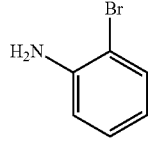 | 535 [M − H]− | Ex. 9 |
| 248 | 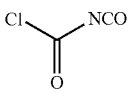 | 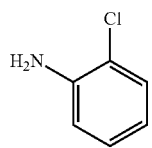 | 491 [M − H]− | Ex. 9 |
| 249 | 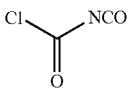 | 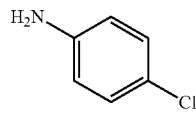 | 491 [M − H]− | Ex. 9 |

| | | | | |
|---|---|---|---|---|
| 250 | 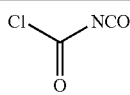 | 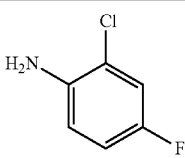 | 509 [M − H]− | Ex. 9 |
| 251 | 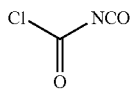 | 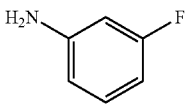 | 475 [M − H]− | Ex. 9 |
| 252 | 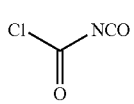 | 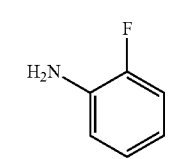 | 475 [M − H]− | Ex. 9 |
| 253 | 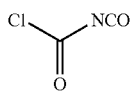 | 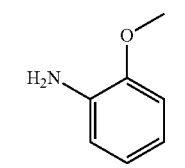 | 503 [M − H]− | Ex. 9 |
| 254 | 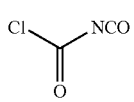 | 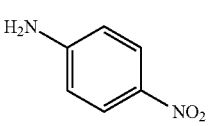 | 502 [M − H]− | Ex. 9 |
| 255 | 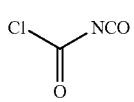 | 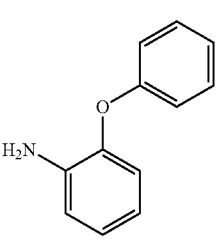 | 549 [M − H]− | Ex. 9 |
| 256 | 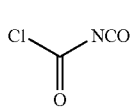 | 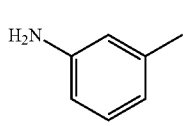 | 471 [M − H]− | Ex. 9 |
| 257 | 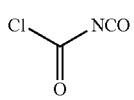 | 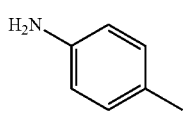 | 571 [M − H]− | Ex. 9 |
| 258 | 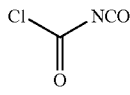 | 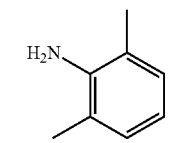 | 485 [M − H]− | Ex. 9 |
| 259 | 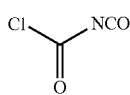 | 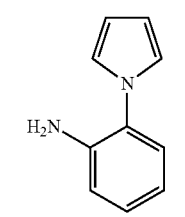 | 522 [M − H]− | Ex. 9 |

-continued

| | | | | | |
|---|---|---|---|---|---|
| 260 | 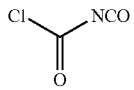 | 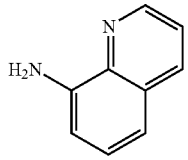 | 508 [M − H]− | Ex. 9 | |
| 261 | 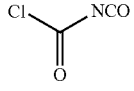 | 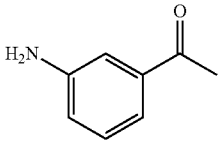 | 499 [M − H]− | Ex. 9 | |
| 262 | 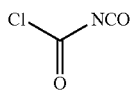 | 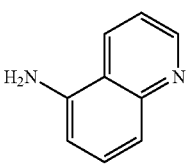 | 508 [M − H]− | Ex. 9 | |
| 263 | 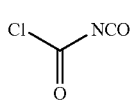 | 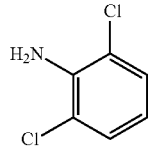 | 525 [M − H]− | Ex. 9 | |
| 264 | 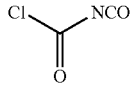 | 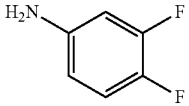 | 493 [M − H]− | Ex. 9 | |
| 265 | 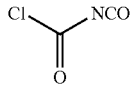 | 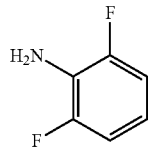 | 493 [M − H]− | Ex. 9 | |
| 266 | 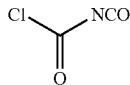 | 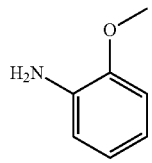 | 487 [M − H]− | Ex. 9 | |
| 267 | 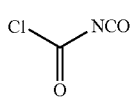 | 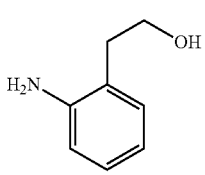 | 501 [M − H]− | Ex. 9 | | a)Synthesized as in Examples described below.

Example 277

1-{3-Fluoro-4-[6-methoxy-7-(2-morpholin-4-yl-ethoxy)-quinolin-4-yloxy]-phenyl}-3-[2-(4-fluorophenyl)-acetyl]-thiourea 1) Synthesis of 3-fluoro-4-[(7-(3-bromoethyl)-6-methoxy-4-quinolyl)oxy]aniline)

3-Fluoro-4-[(7-benzyloxy-6-methoxy-4-quinolyl)-oxy]aniline (7.8 g), together with trifluoroacetic acid (80 ml) and methanesulfonic acid (1 ml), was stirred at 80° C. for 2 hr. After the removal of the solvent by evaporation, the residue was neutralized with an aqueous saturated sodium hydrogencarbonate solution, and the precipitated crystal was collected by suction filtration to give a crude crystal (8.8 g) (starting compound A). This crude crystal (5 g) was dissolved in dimethylformamide (120 ml). Potassium carbonate (9.2 g) and dibromoethane (12.5 g) (starting compound C) were added to the solution, and the mixture was stirred at room temperature for about 90 hr. The reaction solution was filtered through Celite, and the solvent was removed from the filtrate by evaporation under the reduced pressure. The residue was purified by column chromatography on silica gel [chloroform:methanol] to give 3-fluoro-4-[(7-(3-bromoethyl)-6-methoxy-4-quinolyl)oxy]aniline) (1.88 g, yield 29%).

2) Synthesis of 1-{3-fluoro-4-[7-(3-bromoethyl)-6-methoxy-quinolin-4-yloxy]-phenyl}-3-[2-(4-fluoro-phenyl)-acetyl]-thiourea 4-Fluorophenylacetic acid (2.37 g) (starting compound D) was dissolved in thionyl chloride (8 ml) to prepare a solution which was then stirred at 40° C. for one hr. The solvent was removed by evaporation under the reduced pressure. Acetonitrile (300 ml) was added to the residue to dissolve the residue. Potassium thiocyanate (1.87 g) was added to the solution, and the mixture was stirred at 40° C. for 50 min. The solvent was removed by evaporation under the reduced pressure. Ethyl acetate (50 ml) and an aqueous saturated sodium hydrogencarbonate solution (50 ml) were added to the residue, and the mixture was stirred at room temperature for 10 min. The reaction solution was filtered through Celite, and the filtrate was extracted with ethyl acetate, followed by washing with saturated brine. The extract was dried over anhydrous sodium sulfate. The solvent was removed by evaporation under the reduced pressure. The residue was dissolved in ethanol:toluene (1:1=10 ml). 3-Fluoro-4-[(7-(3-bromoethyl)-6-methoxy-4-quinolyl)oxy]aniline (1.4 g) synthesized in step 1) was added to the solution, and the mixture was stirred at room temperature for 18 hr. The precipitated crystal was collected by filtration to give the title compound (1.58 g, yield 73%).

$^1$H-NMR (DMSO, 400 MHz): δ 3.85 (s, 2H), 3.96 (t, J=5.4 Hz, 2H), 4.06 (s, 3H), 4.62 (t, J=5.4 Hz, 2H), 6.98 (d, J=6.3 Hz, 1H), 7.15-7.23 (m, 2H), 7.37-7.43 (m, 2H), 7.55 (s, 1H), 7.60-7.68 (m, 1H), 7.79 (s, 1H), 8.15-8.18 (m, 1H), 8.85 (d, J=6.3 Hz, 1H), 11.86 (s, 1H), 12.54 (s, 1H)

3) Synthesis of 1-{3-fluoro-4-[6-methoxy-7-(2-morpholin-4-yl-ethoxy)-quinolin-4-yloxy]-phenyl}-3-[2-(4-fluorophenyl)-acetyl]-thiourea (Example 277)

Dimethylformamide (3 ml) was added to the compound (200 mg) prepared in step 2) to dissolve the compound. Morpholine (29 mg) (starting compound B) and potassium carbonate (46 mg) were added to the solution, and the mixture was stirred at room temperature for 18 hr. Ethyl acetate:water was added thereto, and the mixture was extracted with ethyl acetate, followed by washing with saturated brine. The extract was dried over anhydrous sodium sulfate. The solvent was removed by evaporation under the reduced pressure. The residue was purified by TLC preparation [chloroform:methanol] to give the title compound (Example 277) (92 mg, yield 46%).

$^1$H-NMR (CDCl$_3$, 400 MHz): δ 2.89 (s, 4H), 2.95 (s, 4H), 3.73 (s, 2H), 3.73-3.78 (m, 2H), 4.03 (s, 3H), 4.34 (t, J=6.1 Hz, 2H), 6.43 (d, J=5.1 Hz, 1H), 7.12 (t, J=8.8 Hz, 1H), 7.23-7.32 (m, 6H), 7.43 (s, 1H), 7.94 (dd, J=2.4, 11.5 Hz, 1H), 8.50 (d, J=5.1 Hz, 1H), 8.66 (br, 1H), 12.44 (s, 1H)

ESI-MS: m/z=607 (M−1)

Example 285

1-[2-(2-Chloro-phenyl)-acetyl]-3-{3-fluoro-4-[6-methoxy-7-(3-morpholin-4-yl-propoxy)-quinolin-4-yloxy]-phenyl}-thiourea 2-Chlorophenylacetic acid (96 mg) (starting compound D) was dissolved in thionyl chloride (0.5 ml) to prepare a solution which was then stirred at 40° C. for one hr. The solvent was removed by evaporation under the reduced pressure. Acetonitrile (30 ml) was added to the residue to dissolve the residue. Potassium thiocyanate (68 mg) was added to the solution, and the mixture was stirred at 40° C. for 50 min. The solvent was removed by evaporation under the reduced pressure. Ethyl acetate (15 ml) and an aqueous saturated sodium hydrogencarbonate solution (15 ml) were added to the residue, and the mixture was stirred at room temperature for 20 min. The reaction solution was extracted with ethyl acetate, followed by washing with saturated brine. The extract was dried over anhydrous sodium sulfate. The solvent was removed by evaporation under the reduced pressure. The residue was dissolved in ethanol:toluene (1:1=6 ml). Starting compound 12 (60 mg) (starting compound A) was added to the solution, and the mixture was stirred at room temperature for 18 hr. The solvent was removed by evaporation under the reduced pressure, and the residue was purified by TLC preparation [chloroform:methanol] to give the title compound (44 mg, yield 49%).

$^1$H-NMR (CDCl$_3$, 400 MHz): δ 2.10-2.18 (m, 2H), 2.47-2.54 (m, 4H), 2.59 (t, J=7.2 Hz, 2H), 3.73 (t, J=4.5 Hz, 4H), 3.89 (s, 2H), 4.03 (s, 3H), 4.28 (t, J=6.7 Hz, 2H), 6.44 (dd, J=1.0, 5.4 Hz, 1H), 7.31-7.52 (m, 6H), 7.54 (s, 1H), 7.95 (dd, J=2.4, 11.5 Hz, 1H), 8.50 (d, J=5.4 Hz, 1H), 8.64 (s, 1H), 12.42 (s, 1H)

ESI-MS: m/z=639 (M+1), 637 (M−1)

Example 287

1-{2-Fluoro-4-[(6-methoxy-7-(3-morpholin-4-yl-propoxy)-quinolin-4-yloxy]-phenyl}-3-phenyl-acetyl-urea 1) Synthesis of 2-fluoro-4-[(7-(3-chloropropyl)-6-methoxy-4-quinolyl)oxy]aniline)

2-Fluoro-4-[(7-benzyloxy-6-methoxy-4-quinolyl)-oxy]aniline (4.2 g) (starting compound 2), together with trifluoroacetic acid (20 ml) and methanesulfonic acid (1 ml), was heated under reflux for one hr. The solvent was removed by evaporation, and the residue was then neutralized with a 10% aqueous sodium hydroxide solution. The precipitated crystal was collected by suction filtration to give a crude crystal (3.8 g) (starting compound A). This crude crystal (2 g) was dissolved in dimethylformamide (80 ml). Potassium carbonate (4.9 g) and 1-bromo-3-chloro-propane (5.6 g) (starting compound C) were added to the solution, and the mixture was stirred at room temperature for 16 hr. The reaction solution was extracted with ethyl acetate, followed by washing with saturated brine. The extract was dried over anhydrous sodium sulfate, and the solvent was removed by evaporation under the reduced pressure. The residue was purified by column chromatography on silica gel, and the title compound (1.65 g, yield 77%) was obtained from the fraction of chloroform:methanol (99:1).

$^1$H-NMR (CDCl$_3$, 400 MHz): δ 2.36-2.43 (m, 2H), 3.75 (s, 2H), 3.79-3.83 (m, 2H), 3.96 (s, 3H), 4.32-4.36 (m, 2H), 6.44 (d, J=5.3 Hz, 1H), 6.80-6.92 (m, 3H), 7.43 (s, 1H), 7.52 (s, 1H), 8.48 (d, J=5.3 Hz, 1H)

2) Synthesis of 2-fluoro-4-[(6-methoxy-7-(3-morpholinopropyl)-4-quinolyl)oxy]aniline The aniline compound (0.7 g) prepared in step 1) was dissolved in dimethylformamide (40 ml) to prepare a solution. Potassium carbonate (1.4 g), sodium iodide (0.6 g) and morpholine (0.85 g) (starting compound B) were added to the solution, and the mixture was stirred at 70° C. for 20 hr. The reaction solution was extracted with ethyl acetate, followed by washing with saturated brine. The extract was dried over anhydrous sodium sulfate, and the solvent was removed by evaporation under the reduced pressure. The residue was purified by column chromatography on silica gel, and the title compound (0.64 g, yield 76%) was obtained from the fraction of chloroform:methanol (95:5).

$^1$H-NMR (CDCl$_3$, 400 MHz): δ 2.01-2.11 (m, 2H), 2.37-2.50 (m, 4H), 2.44-2.57 (m, 2H), 3.64-3.74 (m, 4H), 3.67 (s, 2H), 3.95 (s, 3H), 4.13-4.22 (m, 2H), 6.36 (d, J=5.4 Hz, 1H), 6.73-6.84 (m, 3H), 7.35 (s, 1H), 7.46 (s, 1H), 8.40 (d, J=5.4 Hz, 1H)

3) Synthesis of 1-{2-fluoro-4-[6-methoxy-7-(3-morpholin-4-yl-propoxy)-quinolin-4-yloxy]-phenyl}-3-phenyl-acetyl-urea (Example 287)

Phenylacetamide (95 mg) (starting compound D) was suspended in anhydrous dichloroethane (10 ml). Oxalyl chloride (0.09 ml) was added to the suspension, and the mixture was heated under reflux for 17 hr. The solvent was removed by evaporation under the reduced pressure to give a crude crystal. The crude crystal was suspended in anhydrous chloroform (10 ml). The suspension was added at room temperature to a solution of the aniline compound (100 mg) prepared in step 2) and triethylamine (330 mg) in anhydrous chloroform (10 ml), and the mixture was stirred at room temperature for 5 hr. A 2% aqueous sodium hydroxide solution was added thereto, and the chloroform layer was separated. The separated chloroform layer was dried over anhydrous sodium sulfate. The solvent was removed by evaporation under the reduced pressure. The residue was purified by column chromatography on silica gel, and the title compound (Example 287) (115 mg, yield 84%) was obtained from the fraction of chloroform:methanol (97:3).

$^1$H-NMR (CDCl$_3$, 400 MHz): δ 2.07-2.15 (m, 2H), 2.44-2.51 (m, 4H), 2.55 (t, J=7.0 Hz, 2H), 3.69-3.75 (m, 4H), 3.75 (s, 2H), 3.98 (s, 3H), 4.24 (t, J=6.5 Hz, 2H), 6.48 (d, J=5.1 Hz, 1H), 6.94-7.00 (m, 4H), 7.24-7.40 (m, 5H), 7.36 (s, 1H), 7.40 (s, 1H), 8.18 (t, J=8.8 Hz, 1H), 8.48 (d, J=5.1 Hz, 1H), 8.49 (s, 1H), 10.76 (s, 1H)

Mass spectrometric value (ESI-MS, m/z): 589 (M$^+$+1)

Example 313

1-{3-Fluoro-4-[7-(2-hydroxy-3-morpholin-4-yl-propoxy)-6-methoxy-quinolin-4-yloxy]-phenyl}-3-[2-(4-fluorophenyl)-acetyl]-thiourea

1) Synthesis of 1-{[4-(4-aminophenoxy)-6-methoxy-7-quinolyl]oxy}-3-morpholino-2-propanol Starting compound 2 (10 g), together with trifluoroacetic acid (100 ml) and methanesulfonic acid (1 ml), was heated under reflux for one hr. The temperature of the reaction solution was returned to room temperature, and the solvent was removed by evaporation. The residue was then made weakly alkaline with an aqueous saturated sodium hydrogencarbonate solution to precipitate a solid. The solid was collected by filtration, was washed with water, and was then dried to give a crude crystal (9.6 g) (starting compound A). Dimethylformamide (300 ml) was added to the crude crystal to dissolve the crystal. Potassium carbonate (23.5 g) and epibromohydrin (3.1 ml) (starting compound C) were then added to the solution, and the mixture was stirred at room temperature overnight. Further, potassium carbonate (2.3 g) and epibromohydrin (0.3 ml) (starting compound C) were added thereto, and the mixture was stirred at room temperature overnight. Morpholine (14.8 ml) (starting compound B) was added thereto, and the mixture was stirred at 70° C. overnight. The temperature of the reaction solution was returned to room temperature, and water was added thereto. The mixture was then extracted with ethyl acetate. The organic layer was washed with saturated brine and was dried over sodium sulfate, and the dried organic layer was then concentrated. The residue was purified by column chromatography on silica gel using chloroform:methanol for development to give 6.9 g of the title compound.

$^1$H-NMR (CDCl$_3$, 400 MHz): δ 2.48-2.54 (m, 2H), 2.62-2.64 (m, 2H), 2.67-2.73 (m, 2H), 3.52 (brs, 1H), 3.73-3.76 (m, 4H), 3.82 (brs, 2H), 4.16-4.23 (m, 2H), 4.26-4.32 (m, 1H), 6.42 (dd, J=1.0, 5.4 Hz, 1H), 6.50 (ddd, J=1.0, 2.7, 8.5 Hz, 1H), 6.57 (dd, J=2.7, 12.0 Hz, 1H), 7.04 (t, J=8.5 Hz, 1H), 7.45 (s, 1H), 7.58 (s, 1H), 8.47 (d, J=5.4 Hz, 1H)

Mass spectrometric value (ESI-MS, m/z): 442 (M$^+$-1)

2) 1-{3-Fluoro-4-[7-(2-hydroxy-3-morpholin-4-yl-propoxy)-6-methoxy-quinolin-4-yloxy]-phenyl}-3-[2-(4-fluoro-phenyl)-acetyl]-thiourea (Example 313)

4-Fluorophenylacetic acid (4.3 g) (starting compound D) was added to thionyl chloride (10 ml). The mixture was stirred at 40° C. for one hr and was then concentrated, and the residue was then dried by means of a vacuum pump. Acetonitrile (250 ml) was added thereto, and potassium isothiocyanate (3.4 g) was added to the mixture. The mixture was stirred at 40° C. for 50 min, followed by concentration. An aqueous saturated sodium hydrogencarbonate solution was added to the concentrate, and the mixture was extracted with ethyl acetate. The organic layer was washed with saturated brine and was dried over sodium sulfate, and the solvent was then removed by evaporation. A mixed solvent composed of toluene (50 ml) and ethanol (50 ml) was added to the residue, and amine (3.0 g) was added thereto. The mixture was stirred at room temperature overnight. An aqueous saturated sodium hydrogencarbonate solution was added to the reaction solution, and the mixture was extracted with a mixed solvent composed of chloroform and methanol. The organic layer was washed with saturated brine and was dried over sodium sulfate. The dried organic layer was then concentrated, and the residue was purified by column chromatography on silica gel using chloroform:methanol for development to give the title compound (1.4 g, yield 44%).

$^1$H-NMR (CDCl$_3$, 400 MHz): δ 2.48-2.55 (m, 2H), 2.60-2.73 (m, 4H), 3.72-3.77 (m, 6H), 4.02 (s, 3H), 4.16-4.32 (m, 3H), 6.45 (d, J=4.4 Hz, 1H), 7.12 (t, J=8.5 Hz, 2H), 7.23-7.32 (m, 3H), 7.40 (d, J=8.8 Hz, 1H), 7.45 (s, 1H), 7.54 (s, 1H), 7.93 (dd, J=2.6, 11.5 Hz, 1H), 8.50 (d, J=5.4 Hz, 1H), 8.65 (s, 1H), 12.44 (s, 1H)

ESI-MS: m/z=639 (M+1)

Compounds of Examples 277, 285, 287, and 313 had the following respective structures.

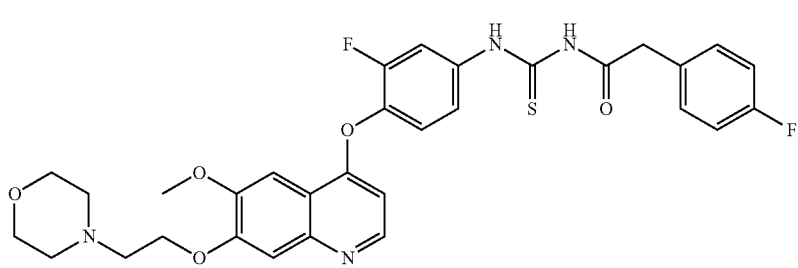
Example 277
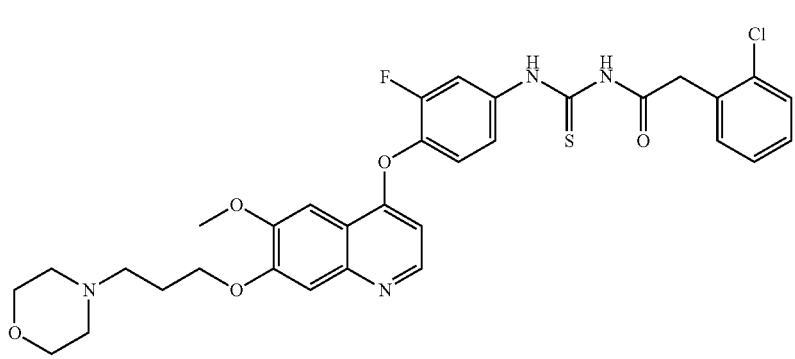
Example 285
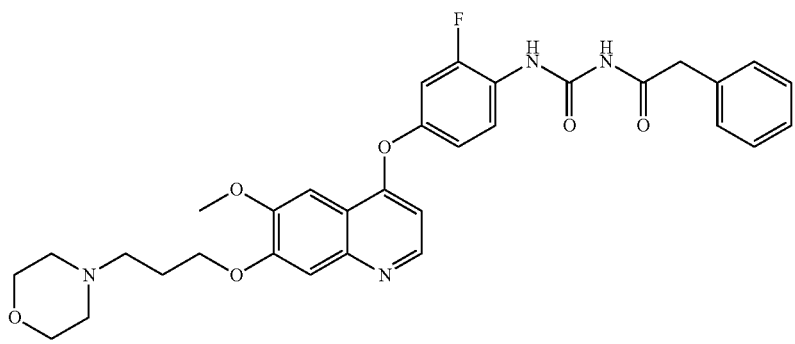
Example 287
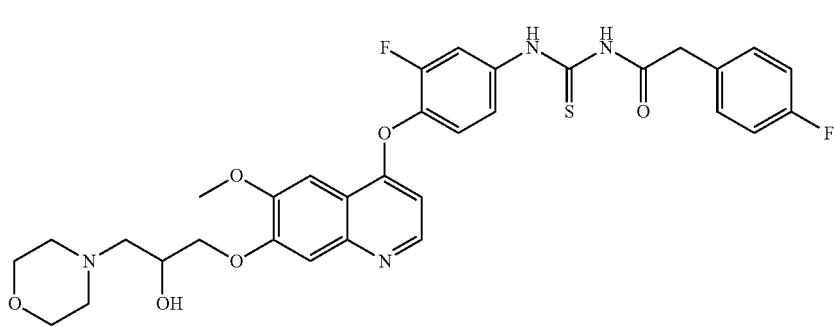
Example 313

Compounds of Examples 270 to 276, 278 to 284, 286, 288 to 312, and 314 to 337 were synthesized as described in Examples 277, 285, 287, and 313. For these compounds, chemical structural formulae, starting compounds, synthesis methods, and data for identifying the compounds are as follows.

| Ex. No. | Compound structure |
|---|---|
| 270 | 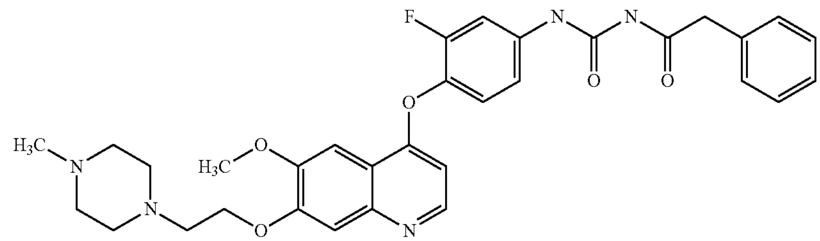 |
| 271 | 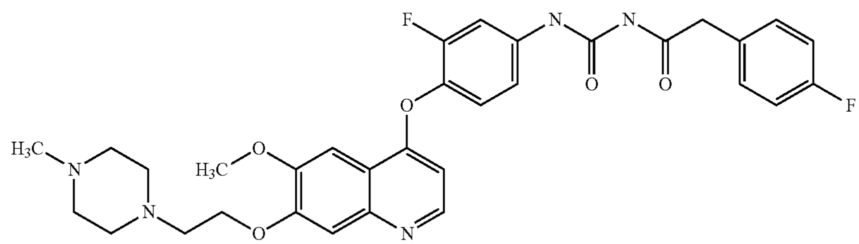 |
| 272 | 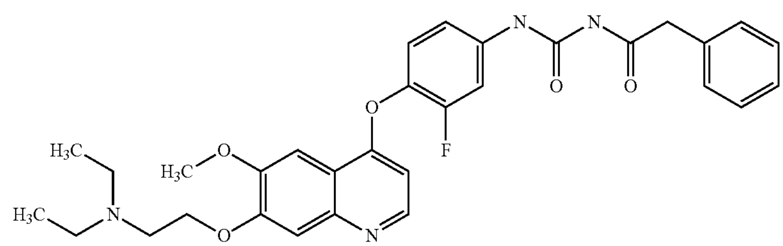 |
| 273 | 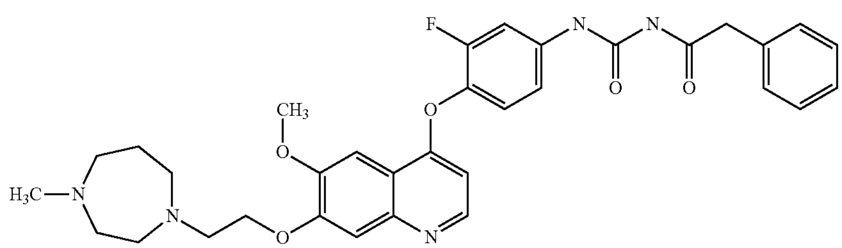 |
| 275 | 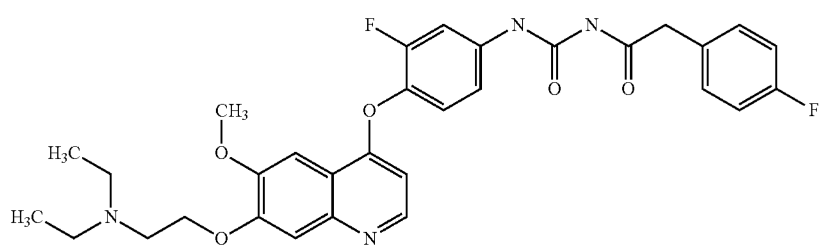 |
| 276 | 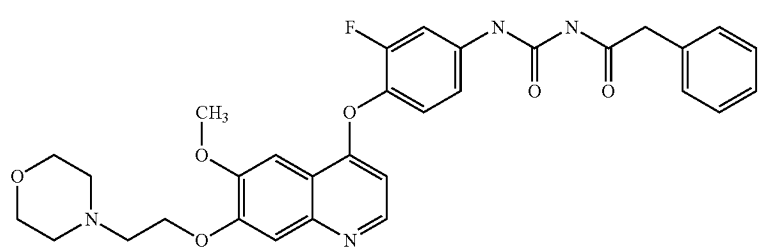 |

277 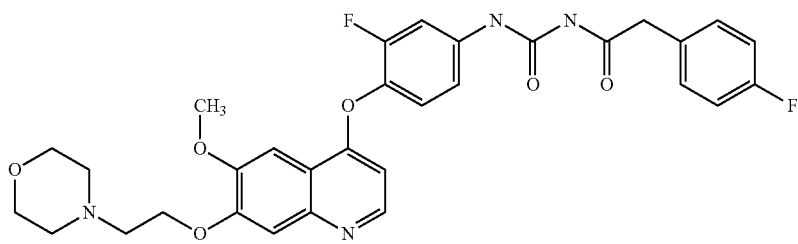
278 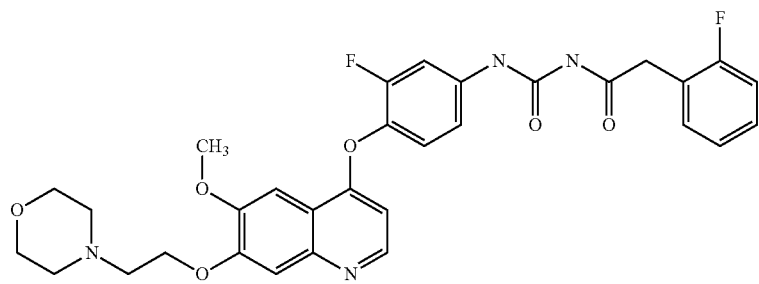
279 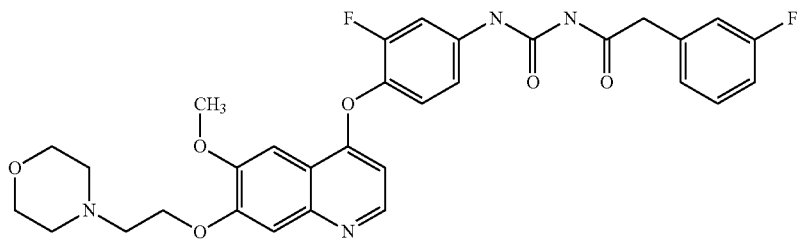
282 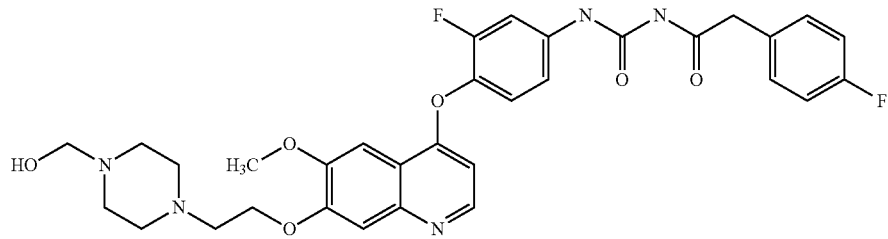
283 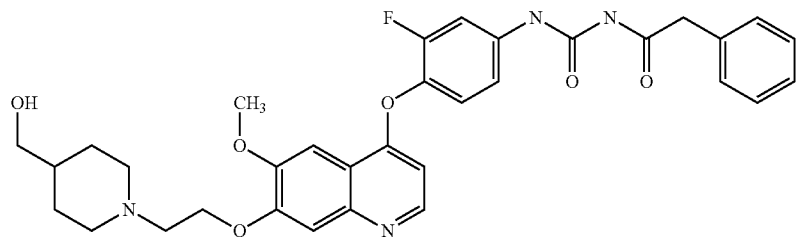
284 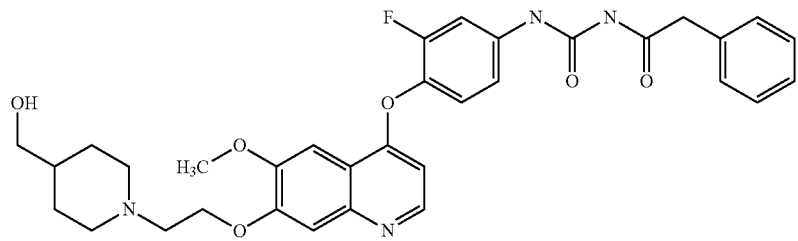

286 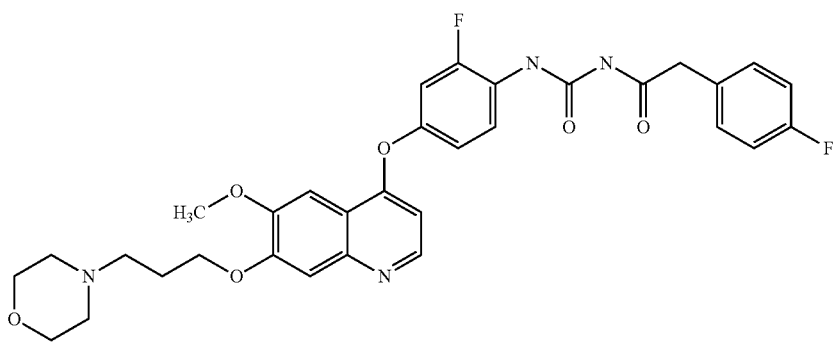
288 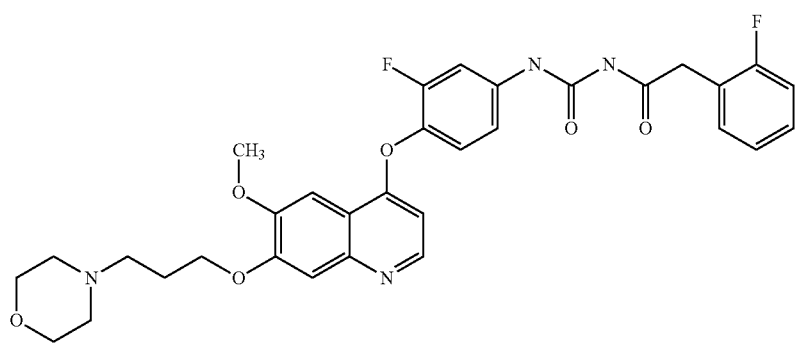
289 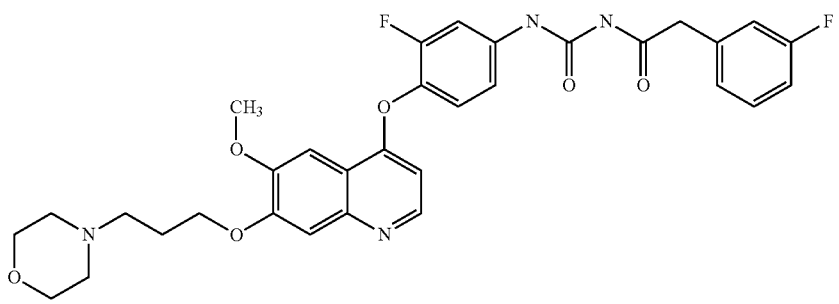
291 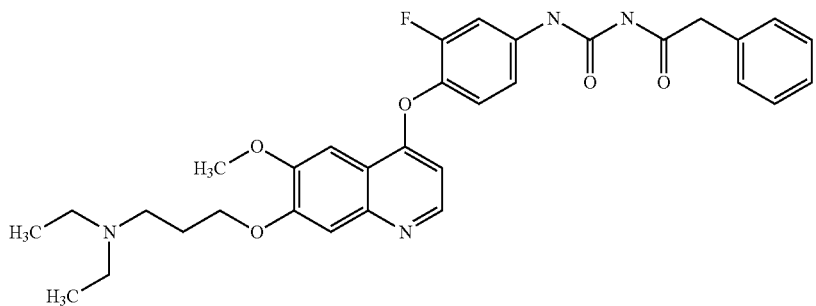
292 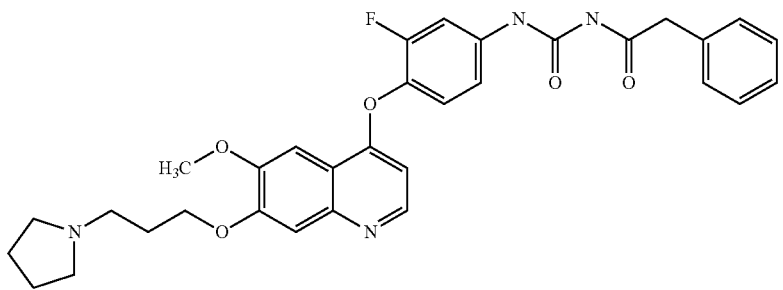

293
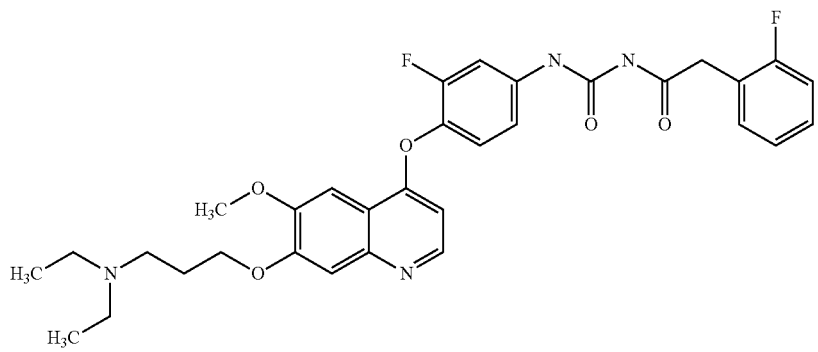
294
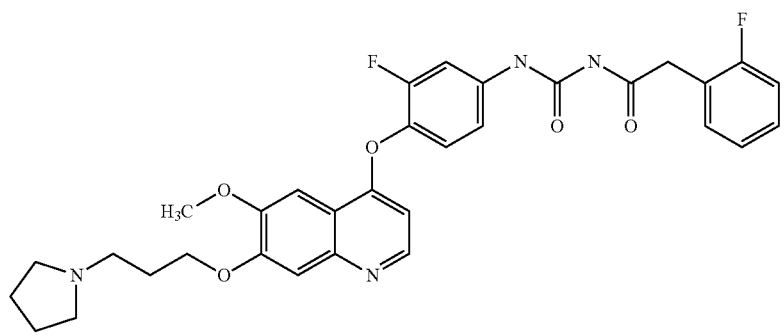
295
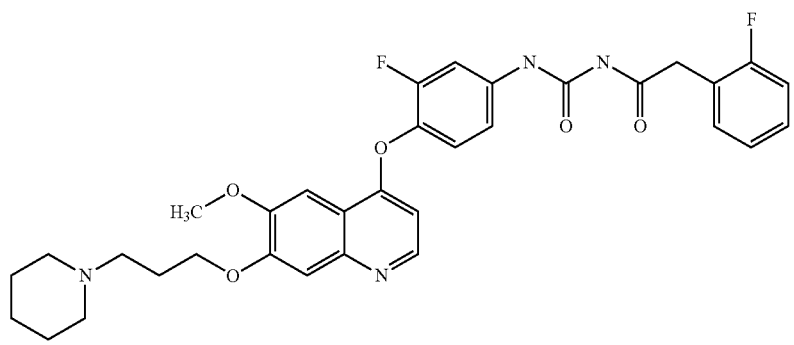
296
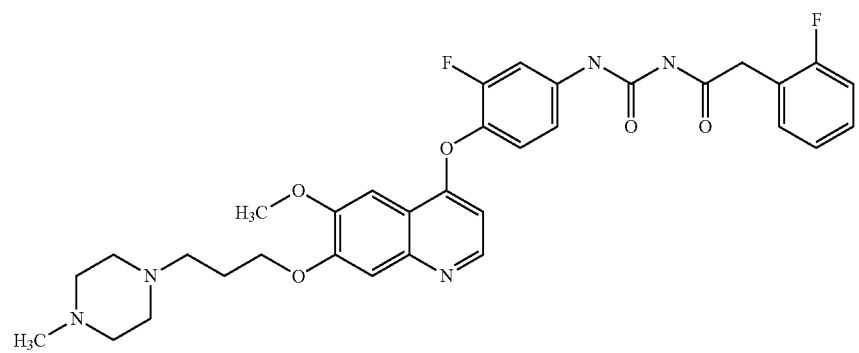

297 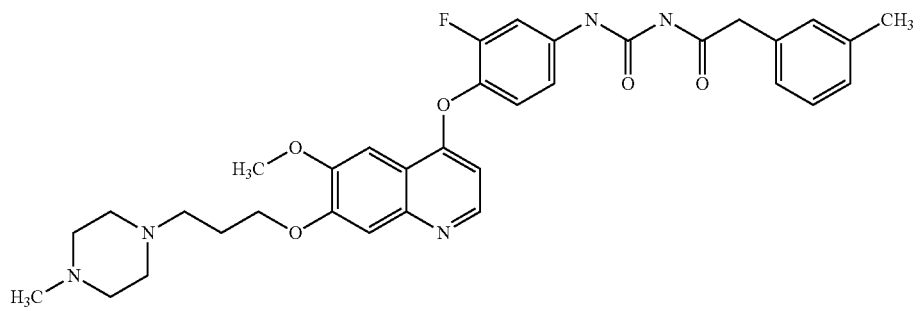
298 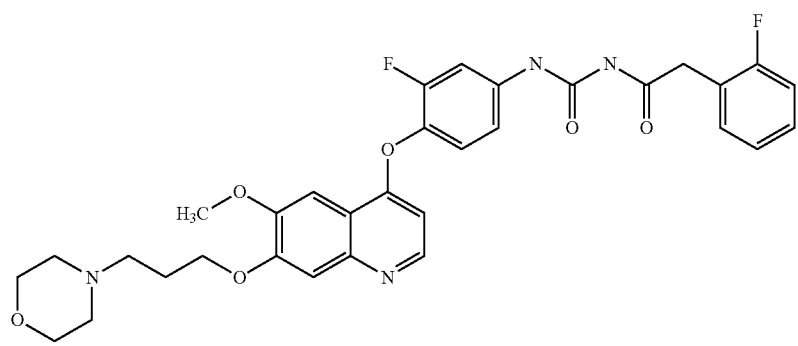
299 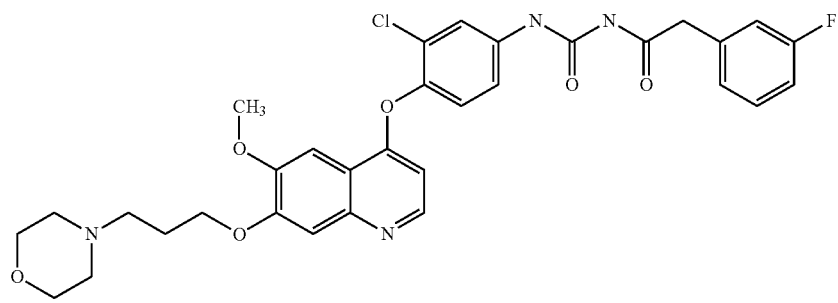
300 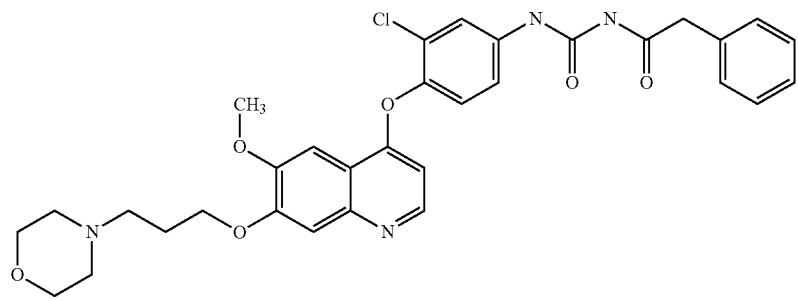
301 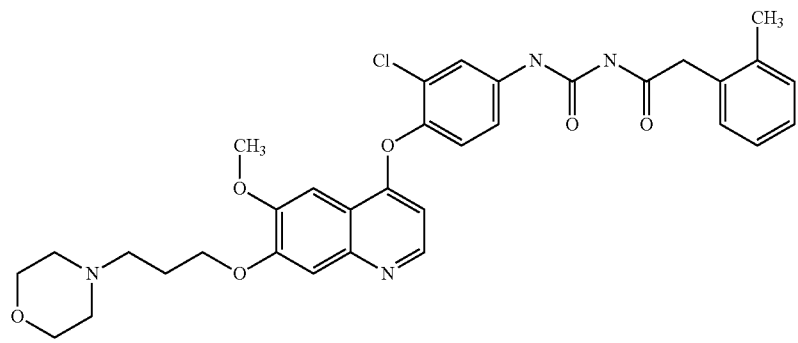

302 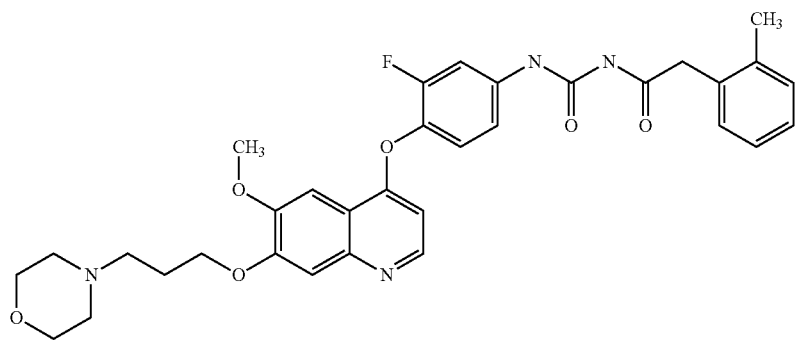
303 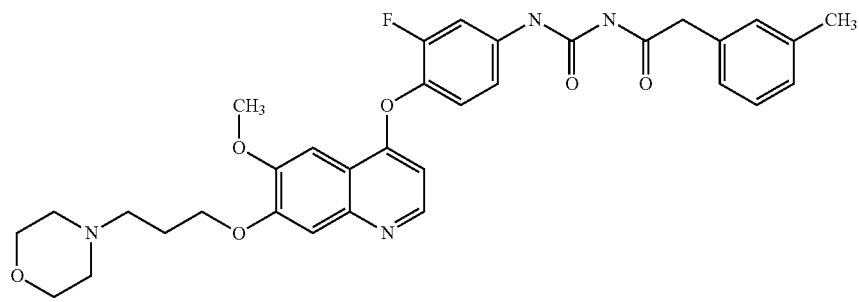
304 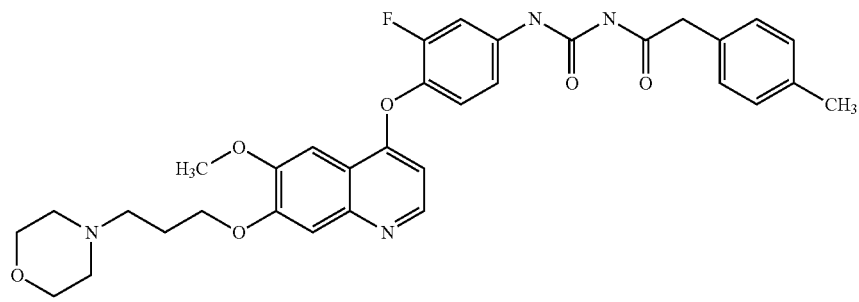
305 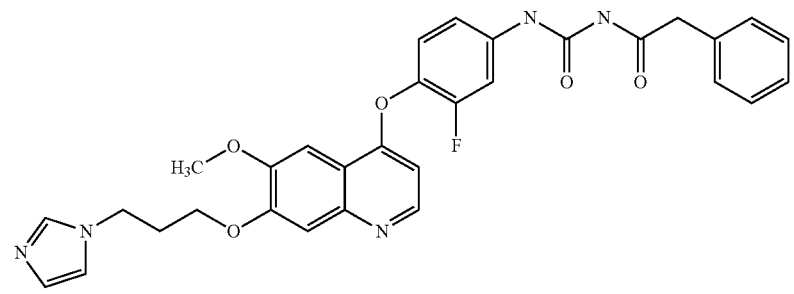
306 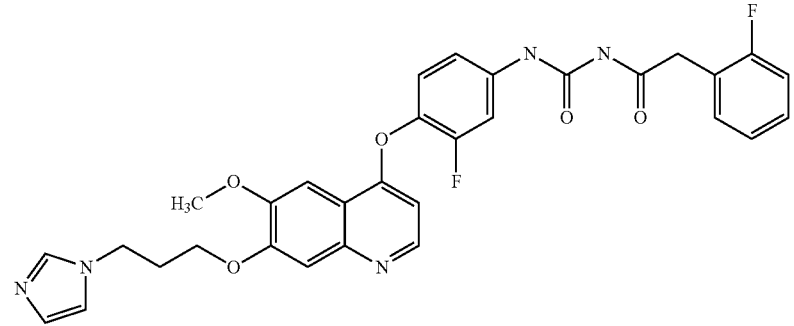

307 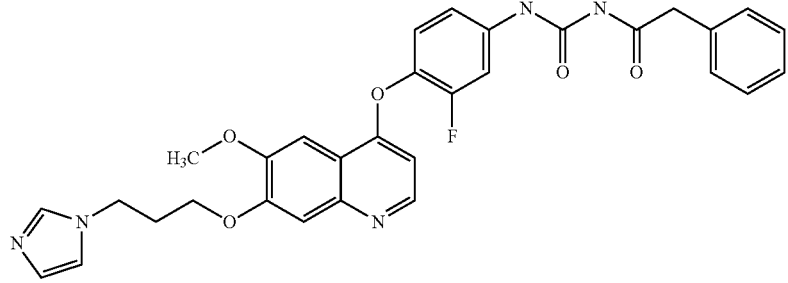
308 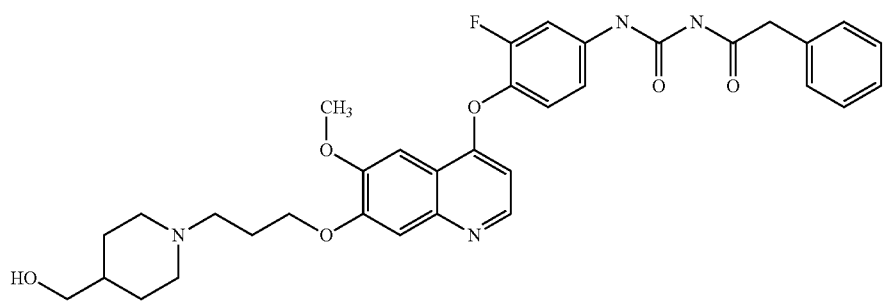
309 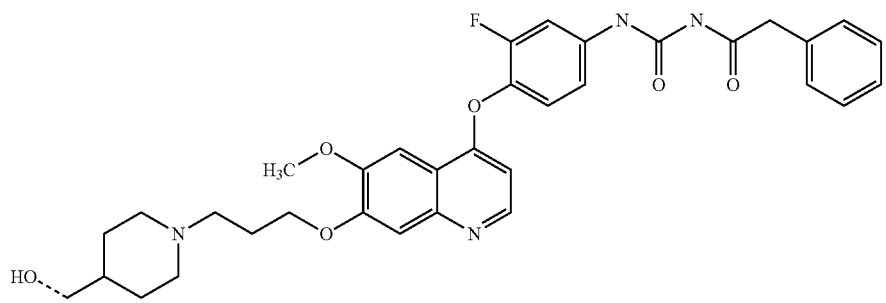
310 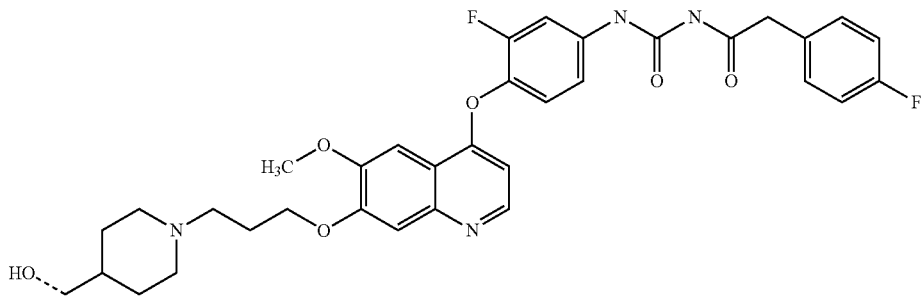
311 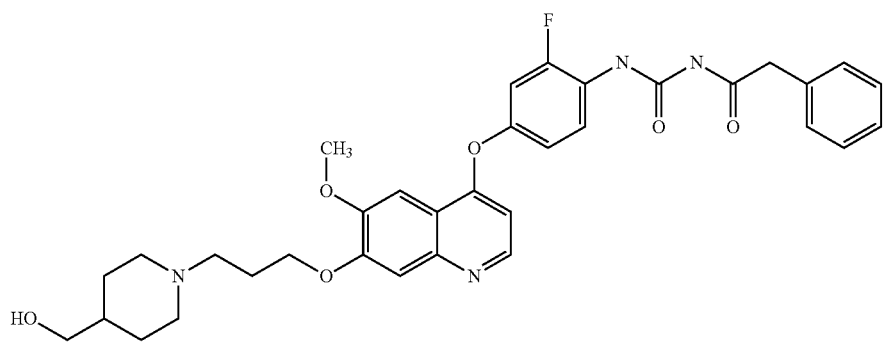

312
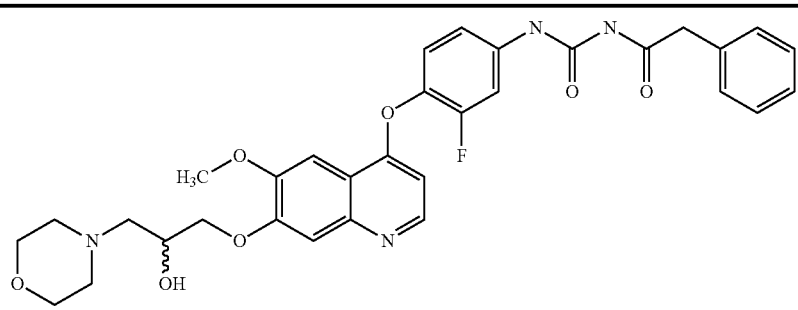
314
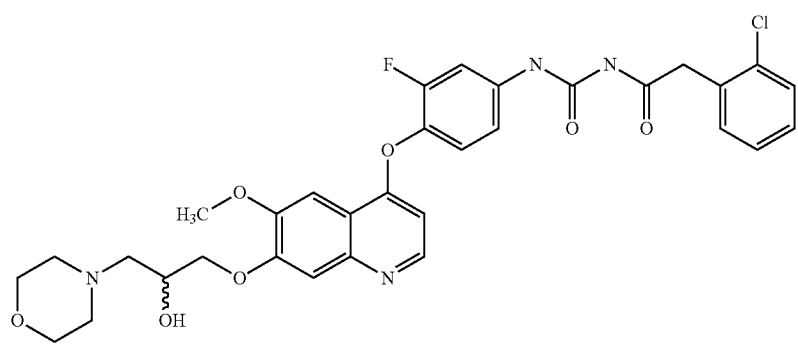
315
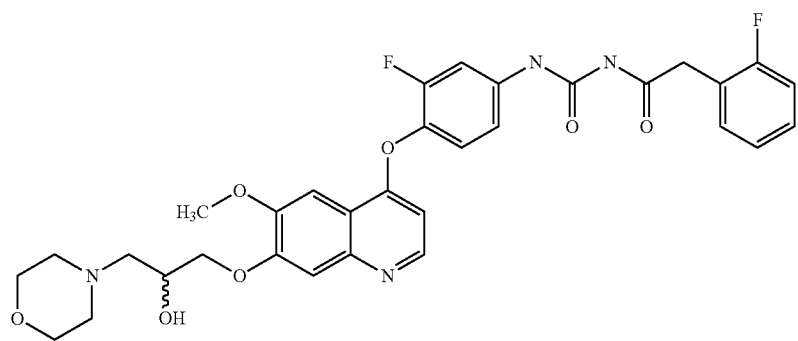
316
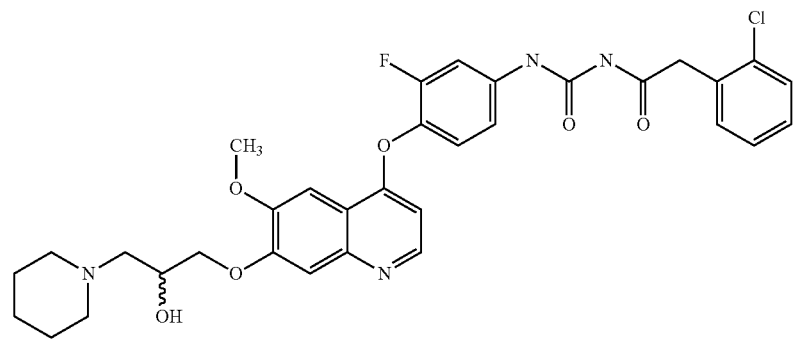

317 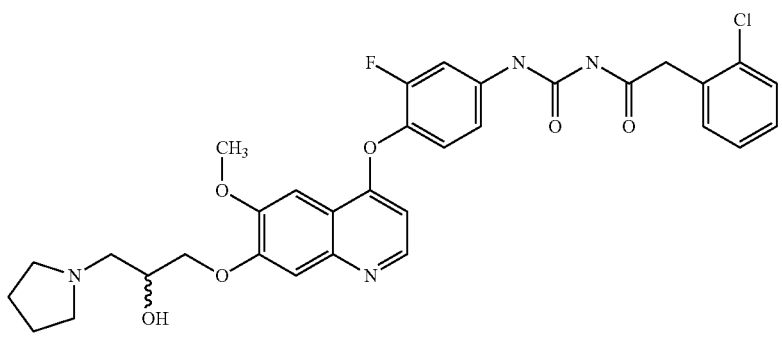
318 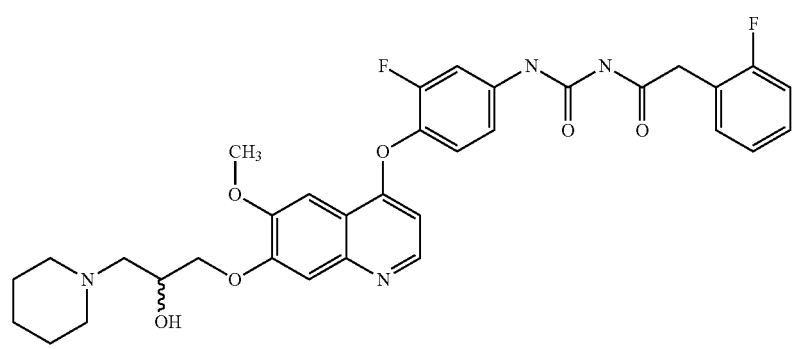
319 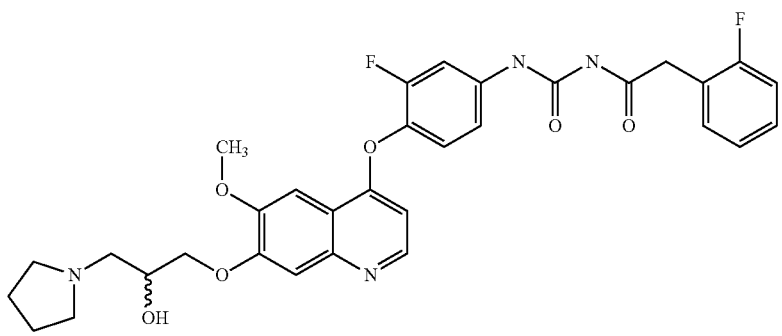
320 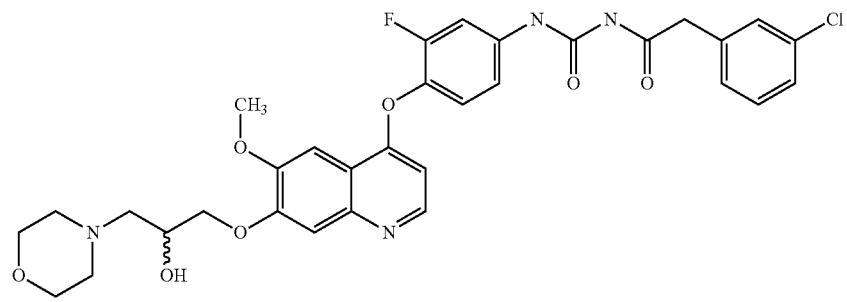
321 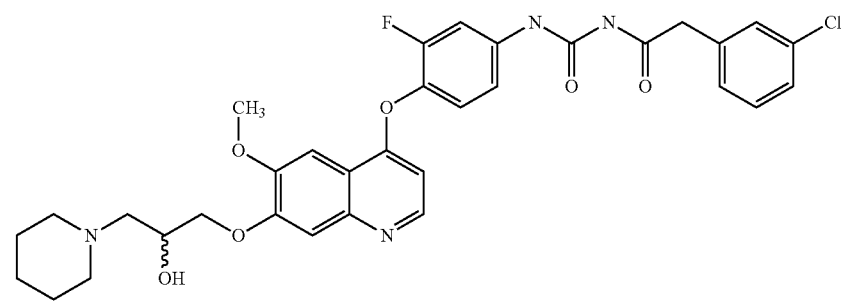

322 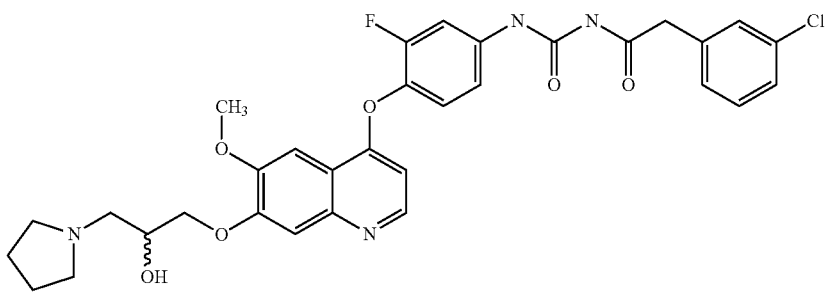
323 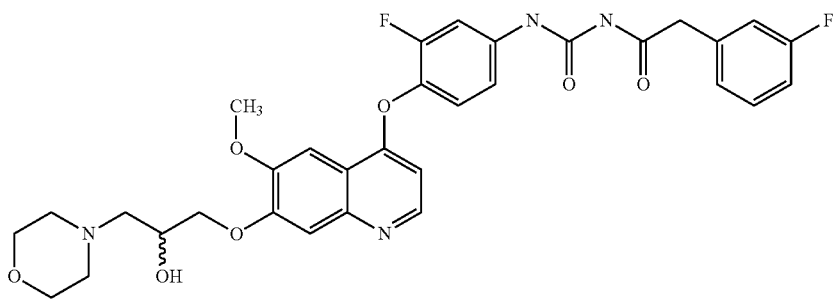
324 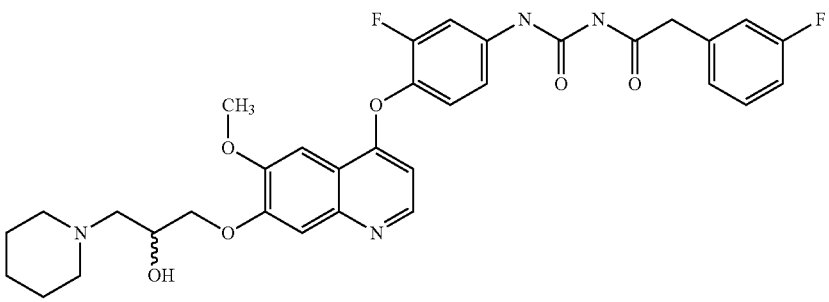
325 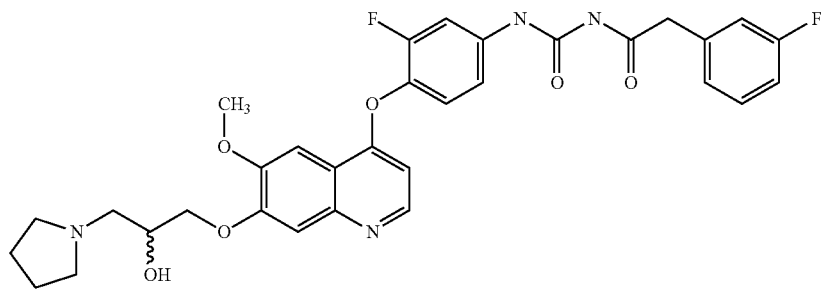
326 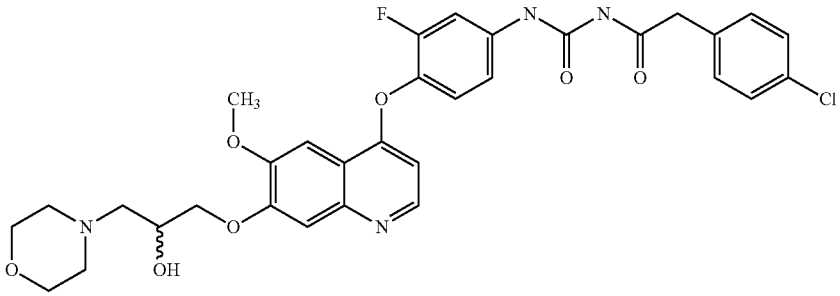

327 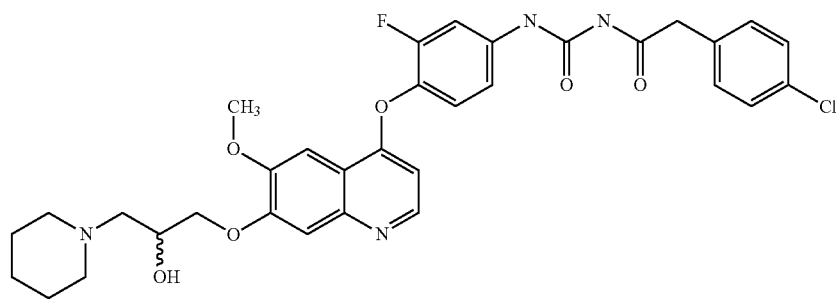
328 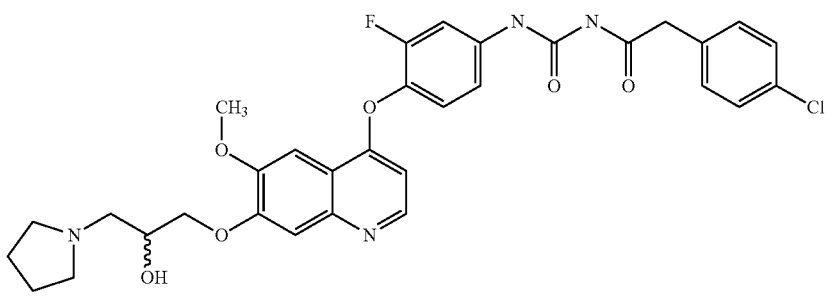
329 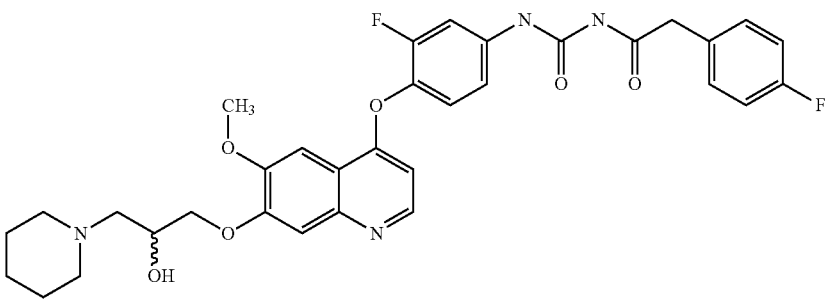
330 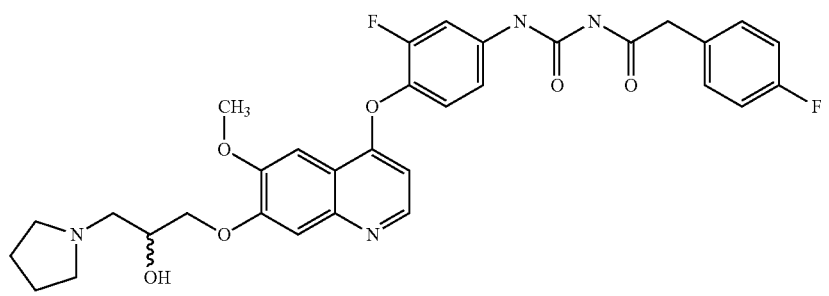
331 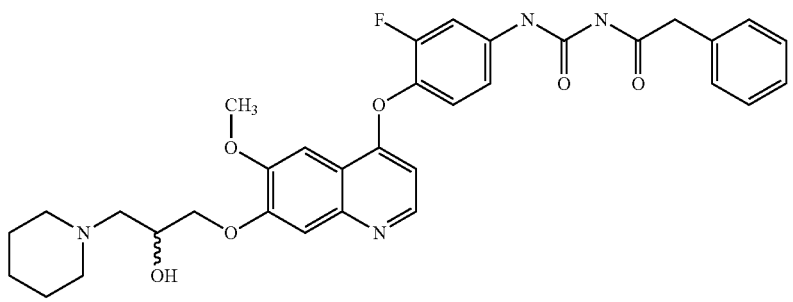

332 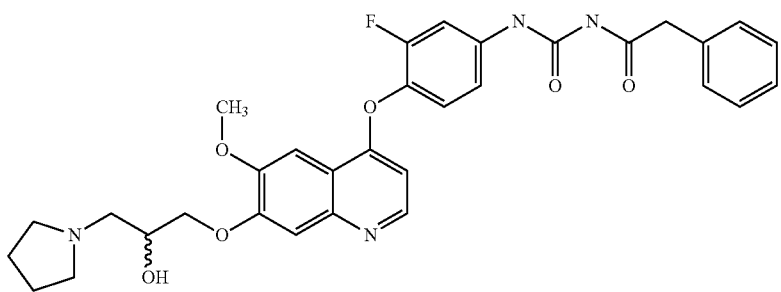
333 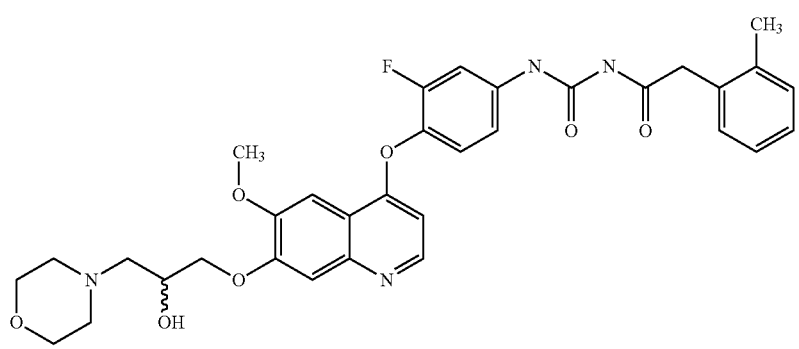
334 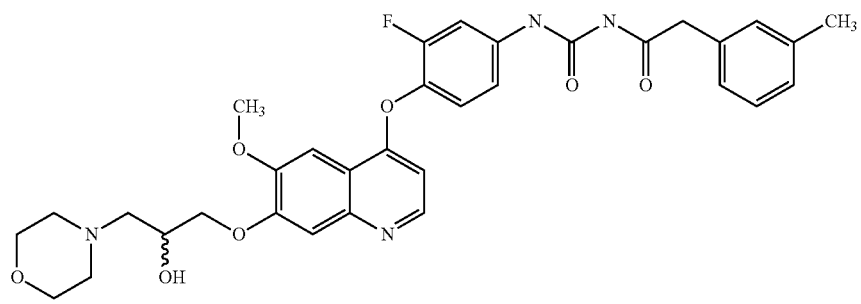
335 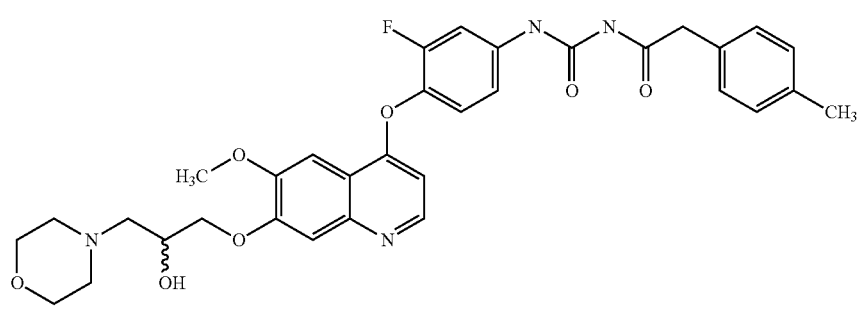
336 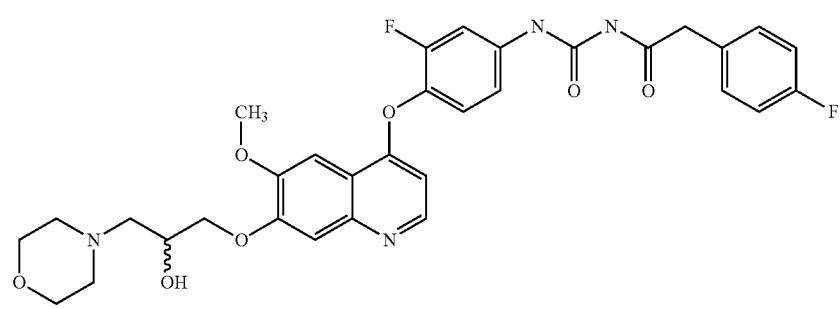

-continued
| 337 | 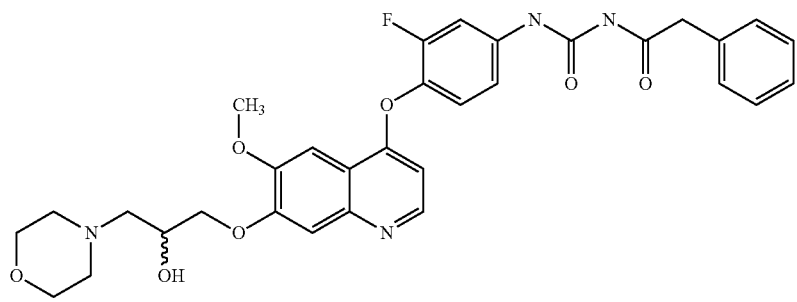 | |
|---|---|---|
| Ex. No. | Starting compound A | Starting compound B |
| 270 | 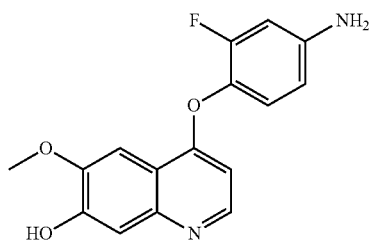 | 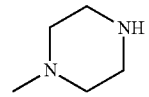 |
| 271 | 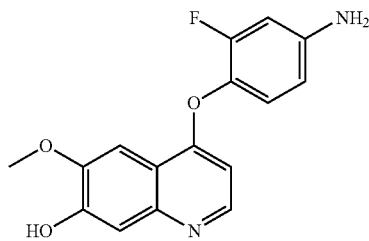 | 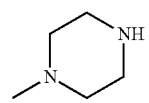 |
| 272 | 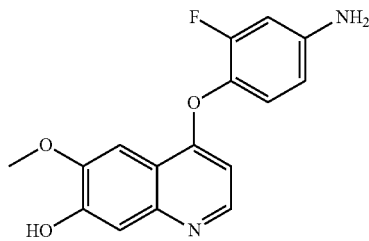 | 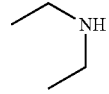 |
| 273 | 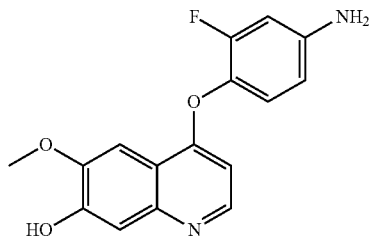 | 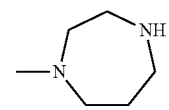 |
| 275 | 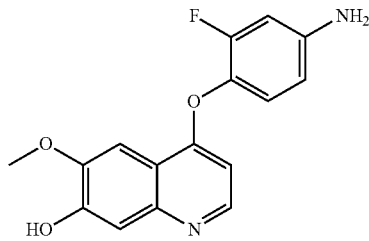 | 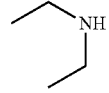 |

263 264
-continued
276 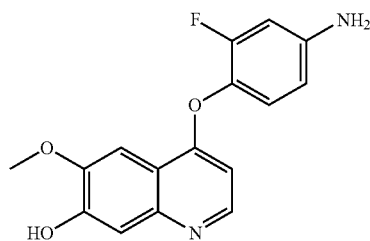 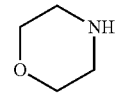
277 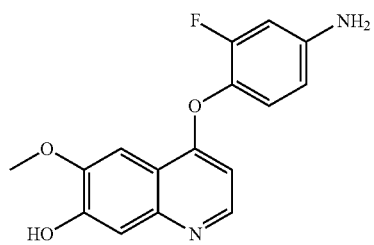 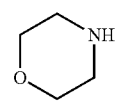
278 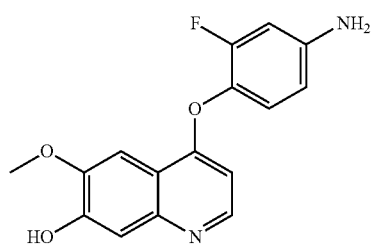 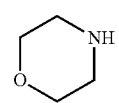
279 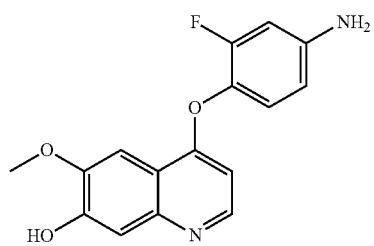 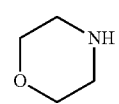
282 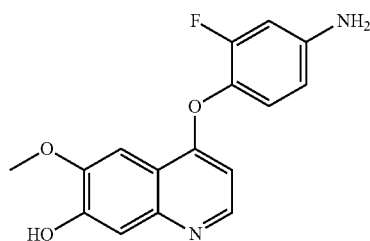 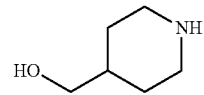
283 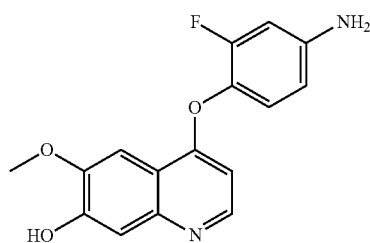 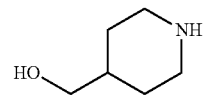

-continued
| 265 | 266 |
|---|---|
| 284 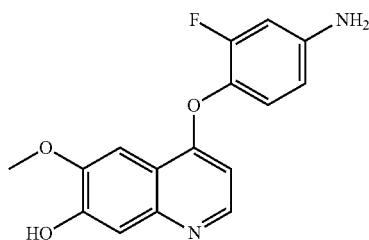 | 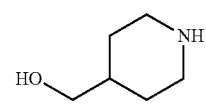 |
| 286 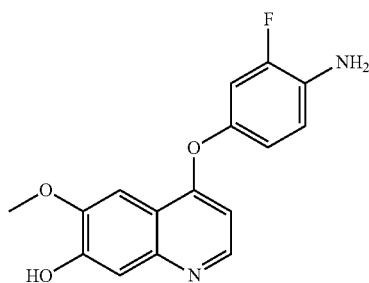 | 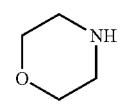 |
| 288 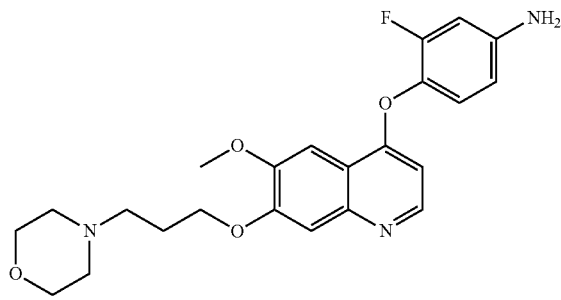 | |
| 289 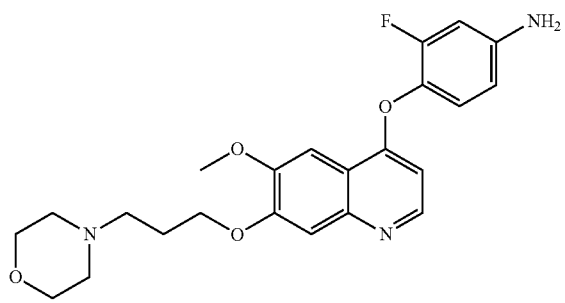 | |
| 291 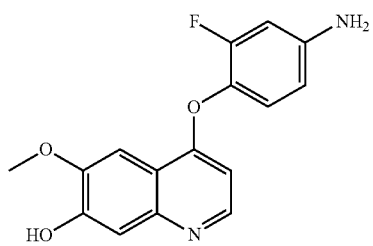 | 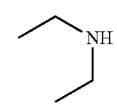 |
| 292 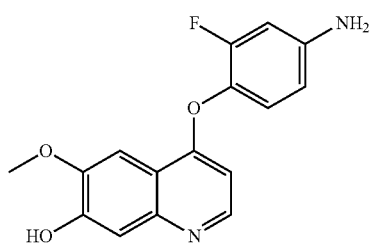 | 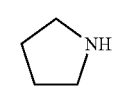 |

| | | |
|---|---|---|
| 293 | 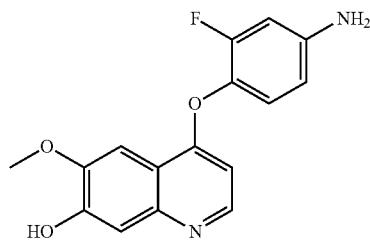 | 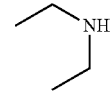 |
| 294 | 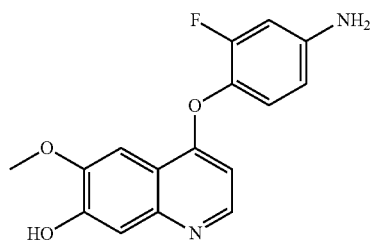 | 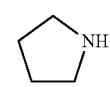 |
| 295 | 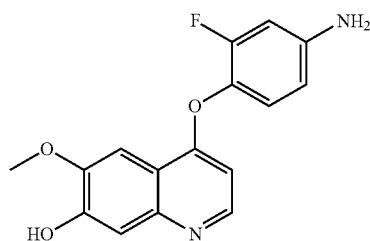 | 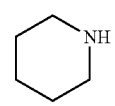 |
| 296 | 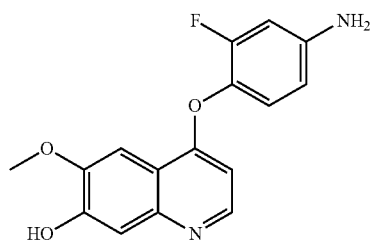 | 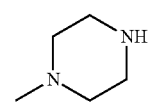 |
| 297 | 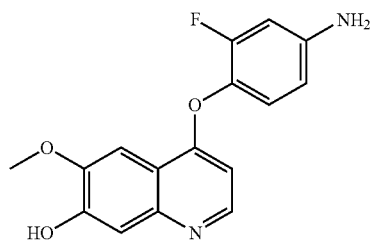 | 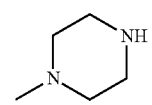 |
| 298 | 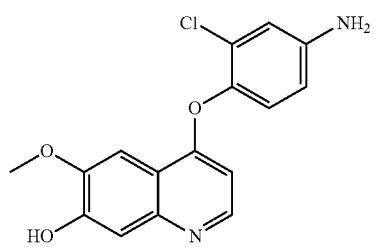 | 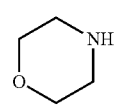 |

-continued
| | 269 | 270 |
|---|---|---|
| 299 | 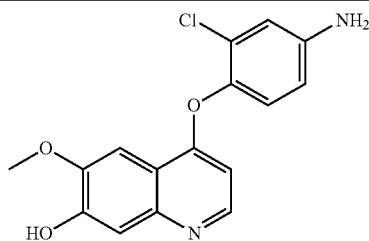 | 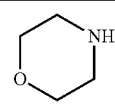 |
| 300 | 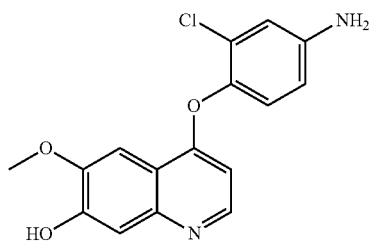 | 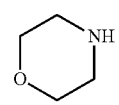 |
| 301 | 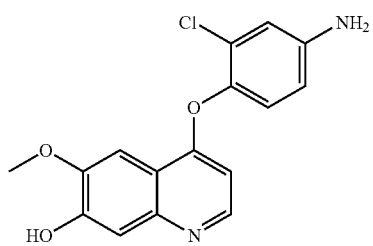 | 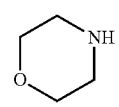 |
| 302 | 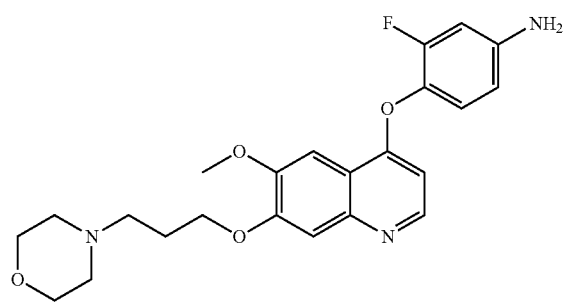 | |
| 303 | 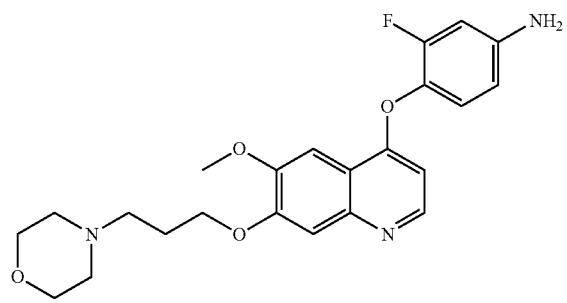 | |
| 304 | 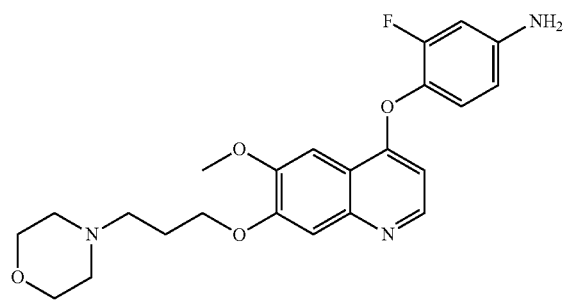 | |

| | | |
|---|---|---|
| 305 | 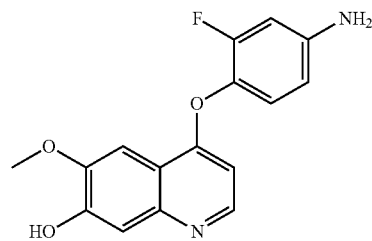 | 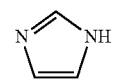 |
| 306 | 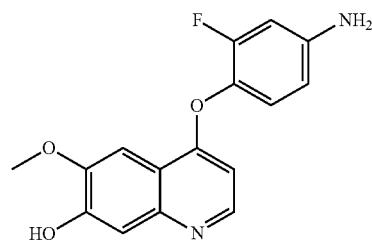 | 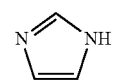 |
| 307 | 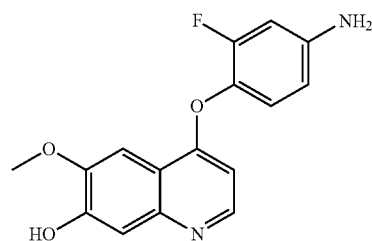 | 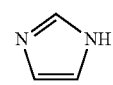 |
| 308 | 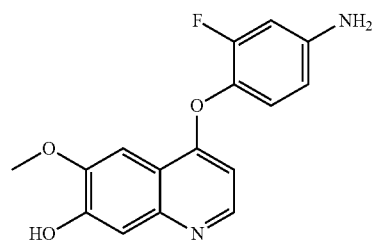 | 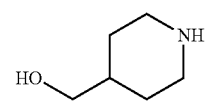 |
| 309 | 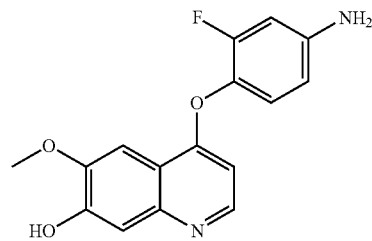 | 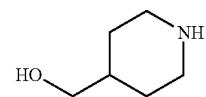 |
| 310 | 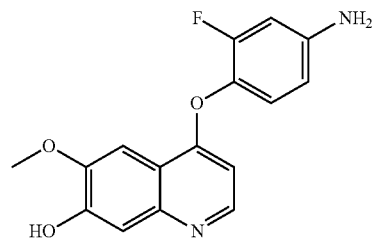 | 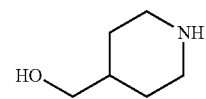 |

-continued
| | | |
|---|---|---|
| 311 | 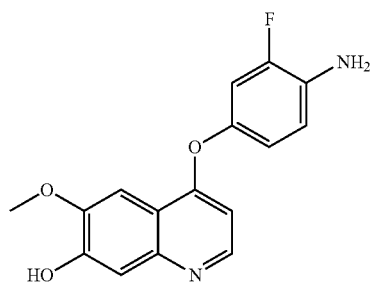 | 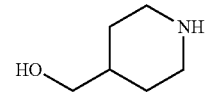 |
| 312 | 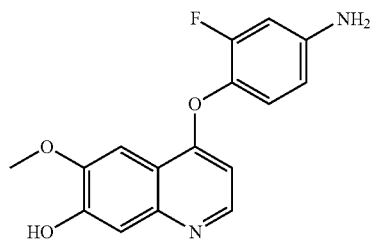 | 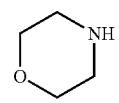 |
| 314 | 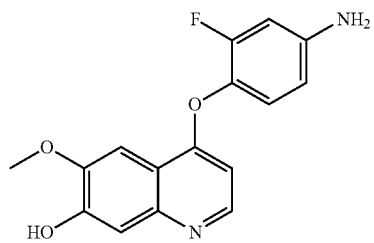 | 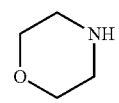 |
| 315 | 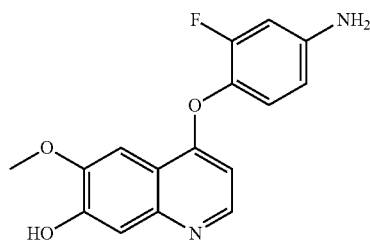 | 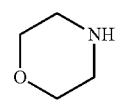 |
| 316 | 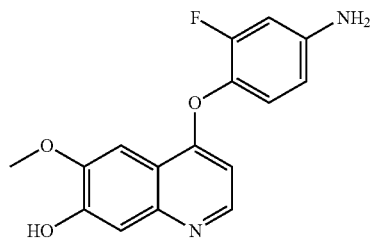 | 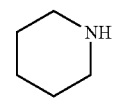 |
| 317 | 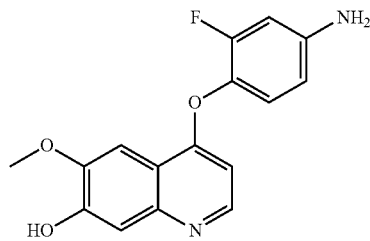 | 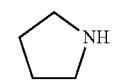 |

| | | |
|---|---|---|
| 318 | 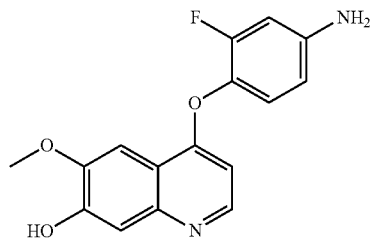 | 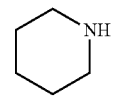 |
| 319 | 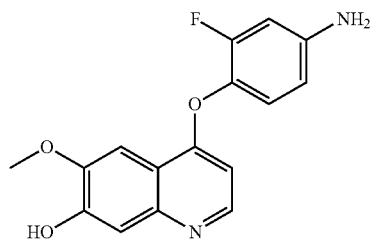 |  |
| 320 | 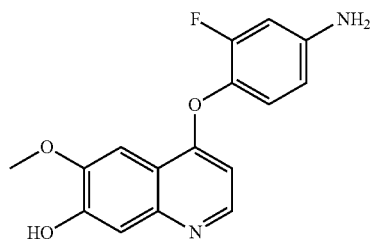 | 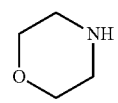 |
| 321 | 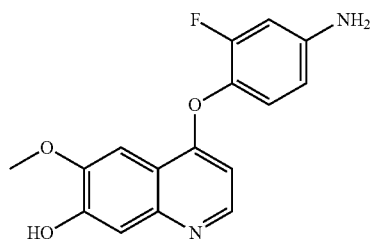 | 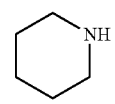 |
| 322 | 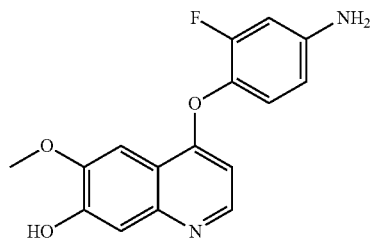 |  |
| 323 | 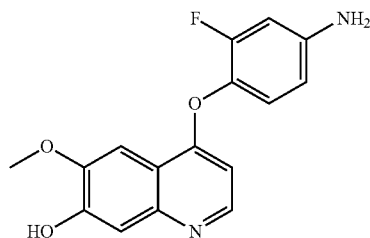 | 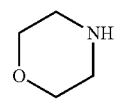 |

-continued
| | | |
|---|---|---|
| 324 | 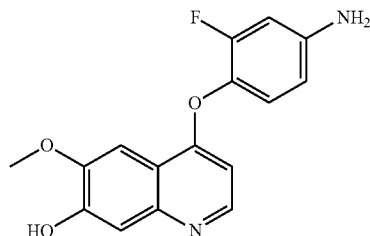 | 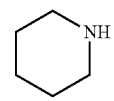 |
| 325 | 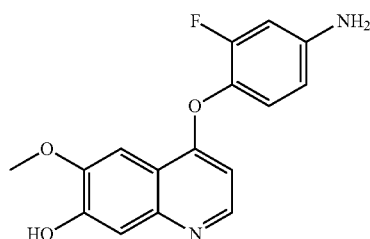 |  |
| 326 | 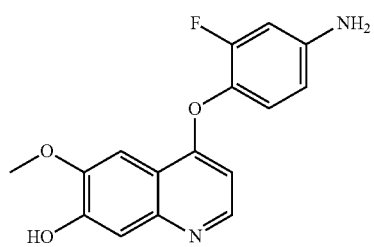 | 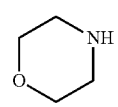 |
| 327 | 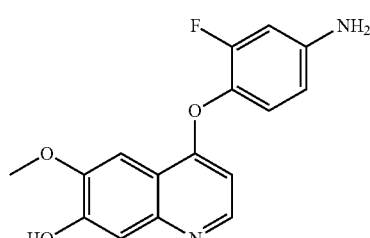 | 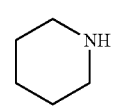 |
| 328 | 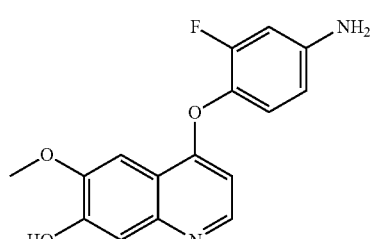 | 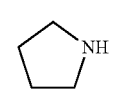 |
| 329 | 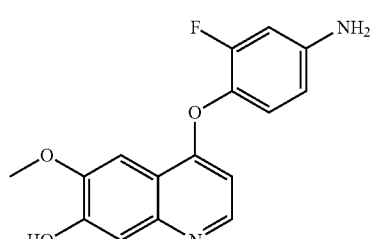 | 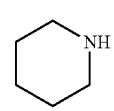 |

-continued
| | | |
|---|---|---|
| 330 | 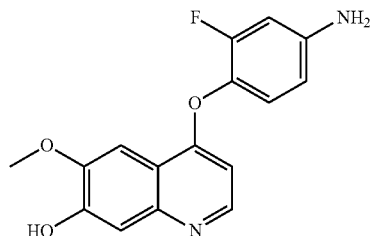 | 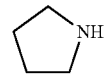 |
| 331 | 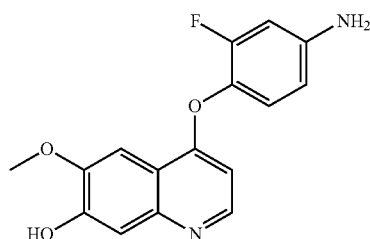 | 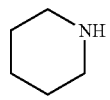 |
| 332 | 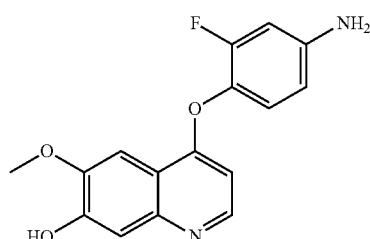 | 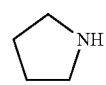 |
| 333 | 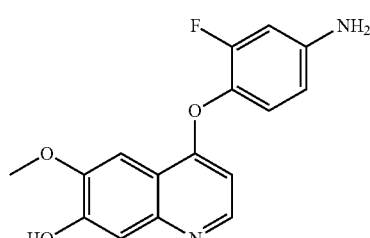 | 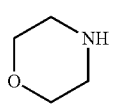 |
| 334 | 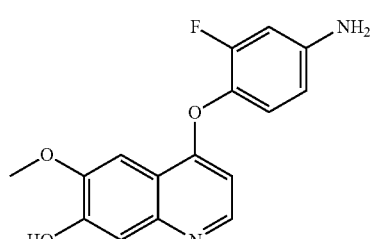 | 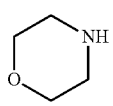 |
| 335 | 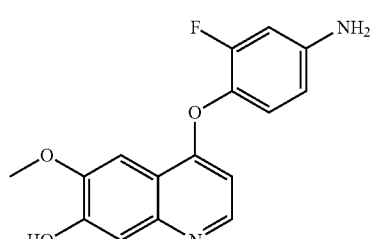 | 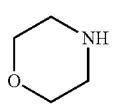 |

-continued
| | | | |
|---|---|---|---|
| 336 | 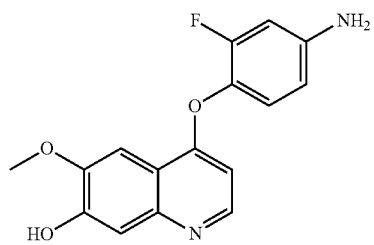 | 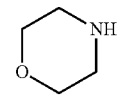 | |
| 337 | 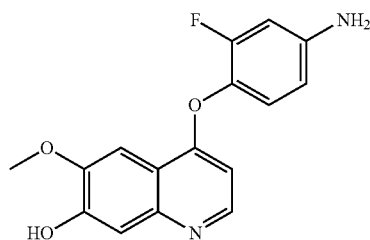 | 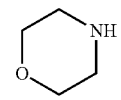 | |
| Ex. No. | Starting compound C | Starting Compound D | Synthesis method<sup>a</sup> |
|---|---|---|---|
| 270 | Cl-CH₂CH₂-Br | HOOC-CH₂-C₆H₅ | Ex. 277 |
| 271 | Cl-CH₂CH₂-Br | HOOC-CH₂-C₆H₄-F (4-F) | Ex. 277 |
| 272 | Cl-CH₂CH₂-Br | HOOC-CH₂-C₆H₅ | Ex. 277 |
| 273 | Br-CH₂CH₂-Br | HOOC-CH₂-C₆H₅ | Ex. 277 |
| 275 | Br-CH₂CH₂-Br | HOOC-CH₂-C₆H₄-F (4-F) | Ex. 277 |
| 276 | Cl-CH₂CH₂-Br | HOOC-CH₂-C₆H₅ | Ex. 277 |
| 277 | Cl-CH₂CH₂-Br | HOOC-CH₂-C₆H₄-F (4-F) | Ex. 277 |
| 278 | Cl-CH₂CH₂-Br | HOOC-CH₂-C₆H₄-F (2-F) | Ex. 277 |

-continued

| | | | |
|---|---|---|---|
| 279 | Cl~~Br | 3-F-C6H4-CH2-COOH | Ex. 277 |
| 282 | Cl~~Br | 4-F-C6H4-CH2-COOH | Ex. 277 |
| 283 | Cl~~Br | C6H5-CH2-C(O)NH2 | Ex. 287 |
| 284 | Cl~~Br | C6H5-CH2-COOH | Ex. 277 |
| 286 | Cl~~~Br | 4-F-C6H4-CH2-C(O)NH2 | Ex. 287 |
| 288 | | 2-F-C6H4-CH2-COOH | Ex. 285 |
| 289 | | 3-F-C6H4-CH2-COOH | Ex. 285 |
| 291 | Cl~~~Br | C6H5-CH2-COOH | Ex. 287 |
| 292 | Cl~~~Br | C6H5-CH2-C(O)NH2 | Ex. 287 |
| 293 | Cl~~~Br | 2-F-C6H4-CH2-C(O)NH2 | Ex. 287 |
| 294 | Cl~~~Br | 2-F-C6H4-CH2-C(O)NH2 | Ex. 287 |
| 295 | Cl~~~Br | 2-F-C6H4-CH2-C(O)NH2 | Ex. 287 |

-continued

| | | | |
|---|---|---|---|
| 296 | Cl~~~Br | 2-F-C6H4-CH2-C(O)-NH2 | Ex. 287 |
| 297 | Cl~~~Br | 3-Me-C6H4-CH2-COOH | Ex. 277 |
| 298 | Cl~~~Br | 2-F-C6H4-CH2-COOH | Ex. 277 |
| 299 | Cl~~~Br | 3-F-C6H4-CH2-COOH | Ex. 277 |
| 300 | Cl~~~Br | C6H5-CH2-COOH | Ex. 277 |
| 301 | Cl~~~Br | 2-Me-C6H4-CH2-COOH | Ex. 277 |
| 302 | | 2-Me-C6H4-CH2-COOH | Ex. 285 |
| 303 | | 3-Me-C6H4-CH2-COOH | Ex. 285 |
| 304 | | 4-Me-C6H4-CH2-COOH | Ex. 285 |
| 305 | Cl~~~Br | C6H5-CH2-C(O)-NH2 | Ex. 287 |
| 306 | Cl~~~Br | 2-F-C6H4-CH2-COOH | Ex. 287 |
| 307 | Cl~~~Br | C6H5-CH2-COOH | Ex. 277 |

| | | | |
|---|---|---|---|
| 308 | 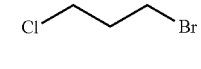 Cl~~~Br | 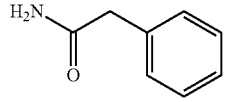 H₂N-C(O)-CH₂-Ph | Ex. 287 |
| 309 | Cl~~~Br | HO-C(O)-CH₂-Ph | Ex. 277 |
| 310 | Cl~~~Br | HO-C(O)-CH₂-C₆H₄-F (4-F) | Ex. 277 |
| 311 | Cl~~~Br | H₂N-C(O)-CH₂-Ph | Ex. 287 |
| 312 | epoxide-CH₂Br | HO-C(O)-CH₂-Ph | Ex. 313 |
| 314 | epoxide-CH₂Br | HO-C(O)-CH₂-C₆H₄-Cl (2-Cl) | Ex. 313 |
| 315 | epoxide-CH₂Br | HO-C(O)-CH₂-C₆H₄-F (2-F) | Ex. 313 |
| 316 | epoxide-CH₂Br | HO-C(O)-CH₂-C₆H₄-Cl (2-Cl) | Ex. 313 |
| 317 | epoxide-CH₂Br | HO-C(O)-CH₂-C₆H₄-Cl (2-Cl) | Ex. 313 |
| 318 | epoxide-CH₂Br | HO-C(O)-CH₂-C₆H₄-F (2-F) | Ex. 313 |
| 319 | epoxide-CH₂Br | HO-C(O)-CH₂-C₆H₄-F (2-F) | Ex. 313 |

-continued
| 320 | 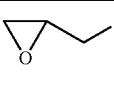 | 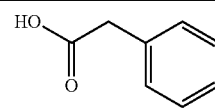 | Ex. 313 |
| 321 | 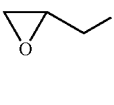 | 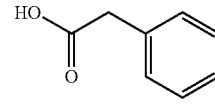 | Ex. 313 |
| 322 | 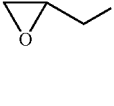 | 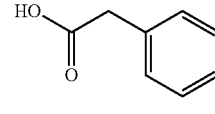 | Ex. 313 |
| 323 | 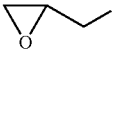 | 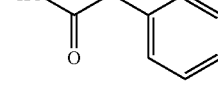 | Ex. 313 |
| 324 | 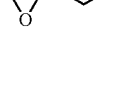 | 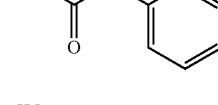 | Ex. 313 |
| 325 | 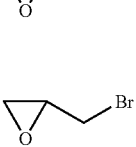 | 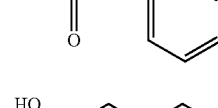 | Ex. 313 |
| 326 |  | 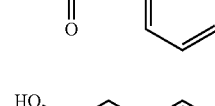 | Ex. 313 |
| 327 |  | 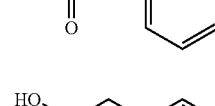 | Ex. 313 |
| 328 |  | 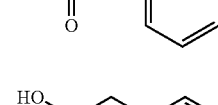 | Ex. 313 |
| 329 | 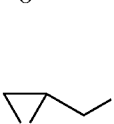 | 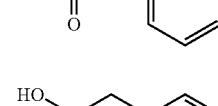 | Ex. 313 |
| 330 | 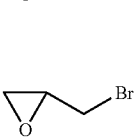 | 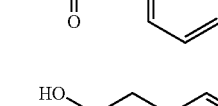 | Ex. 285 |
| 331 |  | 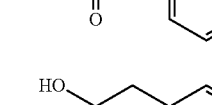 | Ex. 285 |
| 332 |  | 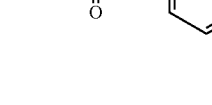 | Ex. 285 |

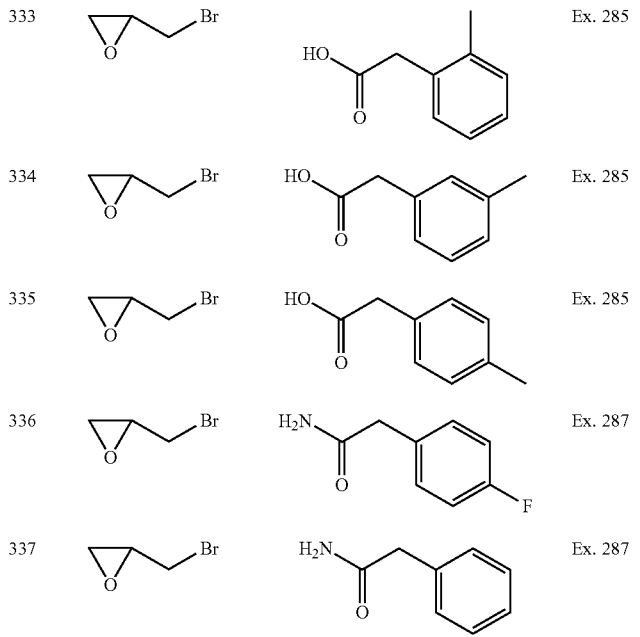

Example 270

1-(3-Fluoro-4-{6-methoxy-7-[2-(4-methyl-piperazin-1-yl)-ethoxy]-quinolin-4-yloxy}-phenyl)-3-phenylacetyl-thiourea $^1$H-NMR (DMSO, 400 MHz): δ 2.20 (s, 3H), 2.33-2.57 (m, 8H), 2.79 (t, J=5.6 Hz, 2H), 3.83 (s, 2H), 3.94 (s, 3H), 4.26 (t, J=5.9 Hz, 2H), 6.48 (d, J=5.1 Hz, 1H), 7.23-7.57 (m, 9H), 8.01 (dd, J=2.2, 12.2 Hz, 1H), 8.49 (d, J=5.1 Hz, 1H), 11.82 (br, 1H), 12.50 (br, 1H)

ESI-MS: m/z=604 (M+1), 602 (M−1)

Example 271

1-(3-Fluoro-4-{6-methoxy-7-[2-(4-methyl-piperazin-1-yl)-ethoxy]-quinolin-4-yloxy}-phenyl)-3-[2-(4-fluoro-phenyl)-acetyl]-thiourea $^1$H-NMR (DMSO, 400 MHz): δ 2.16 (s, 3H), 2.28-2.62 (m, 8H), 2.78 (t, J=5.9 Hz, 2H), 3.83 (s, 2H), 3.94 (s, 3H), 4.26 (t, J=5.9 Hz, 2H), 6.48 (dd, J=1.0, 5.1 Hz, 1H), 7.10-7.41 (m, 6H), 7.44 (s, 1H), 7.52 (s, 1H), 8.00 (dd, J=2.2, 12.2 Hz, 1H), 8.49 (d, J=5.1 Hz, 1H), 11.81 (br, 1H), 12.47 (br, 1H)

Example 272

1-{4-[7-(2-Diethylamine-ethoxy)-6-methoxy-quinolin-4-yloxy]-3-fluoro-phenyl}-3-phenylacetyl-thiourea $^1$H-NMR (DMSO-$d_6$, 400 MHz): δ 1.01 (t, J=7.1 Hz, 6H), 2.50-2.70 (m, 4H), 2.80-3.00 (m, 2H), 3.81 (s, 2H), 3.92 (s, 3H), 4.20 (t, J=5.9 Hz, 2H), 6.46 (d, J=5.1 Hz, 1H), 7.07-7.57 (m, 9H), 7.93-8.10 (m, 1H), 8.48 (d, J=5.1 Hz, 1H), 11.80 (s, 1H), 12.50 (s, 1H)

Mass spectrometric value (ESI-MS, m/z): 577 (M+1)$^+$

Example 273

1-(3-Fluoro-4-{6-methoxy-7-[2-(4-methyl-[1,4]diazepan-1-yl)-ethoxy]-3-quinolin-4-yloxy}-phenyl)-3-phenylacetyl-thiourea $^1$H-NMR (CDCl$_3$:CD$_3$OD=20:1, 400 MHz): δ 1.84-1.94 (m, 2H), 2.42 (s, 3H), 2.68-2.78 (m, 4H), 2.88-2.97 (m, 4H), 3.12 (t, J=6.4 Hz, 2H), 3.76 (s, 2H), 4.02 (s, 3H), 4.29 (t, J=6.4 Hz, 2H), 6.44 (d, J=5.1 Hz, 1H), 7.24-7.49 (m, 8H), 7.54 (s, 1H), 7.93 (dd, J=2.4, 11.7 Hz, 1H), 8.51 (d, J=5.1 Hz, 1H)

ESI-MS: m/z=618 (M+1), 616 (M−1)

Example 275

1-{4-[7-(2-Diethylamino-ethoxy)-6-methoxy-quinolin-4-yloxy]-3-fluoro-phenyl}-3-[2-(4-fluoro-phenyl)-acetyl]-thiourea $^1$H-NMR (CDCl$_3$, 400 MHz): δ 1.11 (t, J=7.1 Hz, 6H), 2.66-2.74 (m, 4H), 3.02-3.08 (m, 2H), 3.73 (s, 2H), 4.02 (s, 3H), 4.29 (t, J=6.5 Hz, 2H), 6.44 (d, J=5.1 Hz, 1H), 7.09-7.46 (m, 7H), 7.53 (s, 1H), 7.93 (dd, J=2.4, 11.5 Hz, 1H), 8.50 (d, J=5.1 Hz, 1H), 8.51 (br, 1H), 12.42 (s, 1H)

ESI-MS: m/z=595 (M+1), 593 (M−1)

Example 276

1-{3-Fluoro-4-[(6-methoxy-7-(2-morpholin-4-yl-ethoxy)-quinolin-4-yloxy]-phenyl}-3-phenylacetyl-thiourea $^1$H-NMR (CDCl$_3$, 400 MHz): δ 2.62-2.72 (m, 4H), 2.98 (t, J=5.7 Hz, 2H), 3.70-3.78 (m, 6H), 4.02 (s, 3H), 4.35 (t, J=5.7 Hz, 2H), 6.46 (d, J=5.4 Hz, 1H), 7.21-7.45 (m, 8H), 7.55 (s, 1H), 7.93 (dd, J=2.4, 11.5 Hz, 1H), 8.52 (d, J=5.4 Hz, 1H), 9.33 (s, 1H), 12.57 (s, 1H)

ESI-MS: m/z=591 (M+1), 589 (M−1)

Example 278

1-{3-Fluoro-4-[6-methoxy-7-(2-morpholin-4-yl-ethoxy)-quinolin-4-yloxy]-phenyl}-3-[2-(2-fluoro-phenyl)-acetyl]-thiourea $^1$H-NMR (CDCl$_3$, 400 MHz): δ 2.63-2.78 (m, 4H), 2.98 (t, J=5.8 Hz, 2H), 3.75-3.82 (m, 4H), 3.80 (s, 2H), 4.03 (s, 3H), 4.37 (t, J=5.8 Hz, 2H), 6.46 (d, J=5.4 Hz, 1H), 7.05-7.43 (m, 6H), 7.47 (s, 1H), 7.55 (s, 1H), 7.94 (dd, J=2.4, 11.7 Hz, 1H), 8.50 (d, J=5.4 Hz, 1H), 8.92 (s, 1H), 12.45 (s, 1H)
ESI-MS: m/z=607 (M−1)

Example 279

1-{3-Fluoro-4-[6-methoxy-7-(2-morpholin-4-yl-ethoxy)-quinolin-4-yloxy]-phenyl}-3-[2-(3-fluoro-phenyl)-acetyl]-thiourea $^1$H-NMR (CDCl$_3$, 400 MHz): δ 2.66-3.06 (m, 6H), 3.70-3.85 (m, 6H), 4.03 (s, 3H), 4.39 (t, J=5.8 Hz, 2H), 6.48 (d, J=5.4 Hz, 1H), 7.04-7.14 (m, 3H), 7.25-7.45 (m, 3H), 7.50 (s, 1H), 7.56 (s, 1H), 7.94 (dd, J=2.4, 11.7 Hz, 1H), 8.51 (d, J=5.4 Hz, 1H), 8.74 (s, 1H), 12.44 (s, 1H)
ESI-MS: m/z=607 (M−1)

Example 282

1-(3-Fluoro-4-{7-[2-(4-hydroxymethyl-piperidin-1-yl)ethoxy]-6-methoxy-quinolin-4-yloxy}-phenyl)-3-[2-(4-fluoro-phenyl)-acetyl]-thiourea $^1$H-NMR (CDCl$_3$:CD$_3$OD=20:1, 400 MHz): δ 1.58-1.99 (m, 5H), 2.43-2.62 (m, 2H), 3.16-3.40 (m, 4H), 3.50-3.54 (m, 2H), 3.73 (s, 2H), 4.03 (s, 3H), 4.45-4.51 (m, 2H), 6.47 (d, J=5.4 Hz, 1H), 7.06-7.15 (m, 2H), 7.22-7.34 (m, 4H), 7.42 (s, 1H), 7.57 (s, 1H), 7.94 (dd, J=2.4, 11.7 Hz, 1H), 8.47 (d, J=5.4 Hz, 1H)
ESI-MS: m/z=637 (M+1), 635 (M−1)

Example 283

1-(3-Fluoro-4-{7-[(2-(4-hydroxymethyl-piperidin-1-yl)-ethoxy]-6-methoxy-quinolin-4-yloxy}-phenyl)-3-phenylacetyl-urea $^1$H-NMR (CDCl$_3$, 400 MHz): δ 1.13-1.76 (m, 7H), 2.11-2.26 (m, 2H), 2.87-3.11 (m, 4H), 3.37-3.48 (m, 2H), 3.70 (s, 2H), 3.95 (s, 3H), 4.26-4.33 (m, 2H), 6.32 (d, J=5.1 Hz, 1H), 7.07-7.50 (m, 7H), 7.35 (s, 1H), 7.48 (s, 1H), 7.57-7.65 (m, 1H), 8.13 (s, 1H), 8.40 (d, J=5.1 Hz, 1H), 10.59 (s, 1H)
Mass spectrometric value (ESI-MS, m/z): 603 (M+1)

Example 284

1-(3-Fluoro-4-{7-[2-(4-hydroxymethyl-piperidin-1-yl)-ethoxy]-6-methoxy-quinolin-4-yloxy}-phenyl)-3-phenylacetyl-thiourea $^1$H-NMR (CDCl$_3$:CD$_3$OD=10:1, 400 MHz): δ 1.45-1.88 (m, 5H), 2.37-2.50 (m, 2H), 3.08-3.18 (m, 2H), 3.26-3.34 (m, 2H), 3.50-3.54 (m, 2H), 3.76 (s, 2H), 4.02 (s, 3H), 4.41-4.47 (m, 2H), 6.47 (d, J=5.1 Hz, 1H), 7.22-7.47 (m, 7H), 7.56 (s, 1H), 7.94 (dd, J=2.4, 11.7 Hz, 1H), 8.48 (d, J=5.1 Hz, 1H)
ESI-MS: m/z=619 (M+1), 617 (M−1)

Example 286

1-{2-Fluoro-4-[6-methoxy-7-(3-morpholin-4-yl-propoxy)-quinolin-4-yloxy]-phenyl}-3-[2-(4-fluoro-phenyl)-acetyl]-urea $^1$H-NMR (CDCl$_3$, 400 MHz): δ 2.02-2.25 (m, 2H), 2.40-2.49 (m, 4H), 2.51 (t, J=7.1 Hz, 2H), 3.64-3.67 (m, 4H), 3.67 (s, 2H), 3.93 (s, 3H), 4.19 (t, J=6.7 Hz, 2H), 6.44 (d, J=5.4 Hz, 1H), 6.89-7.02 (m, 4H), 7.20-7.25 (m, 2H), 7.36 (s, 1H), 7.39 (s, 1H), 8.13 (t, J=8.5 Hz, 1H), 8.43 (d, J=5.4 Hz, 1H), 9.30 (s, 1H), 10.74 (s, 1H)
Mass spectrometric value (ESI-MS, m/z): 607 (M$^+$+1)

Example 288

1-{3-Fluoro-4-[6-methoxy-7-(3-morpholin-4-yl-propoxy)-quinolin-4-yloxy]-phenyl}-3-[2-(2-fluoro-phenyl)-acetyl]-thiourea $^1$H-NMR (CDCl$_3$, 400 MHz): δ 2.12-2.19 (m, 2H), 2.50-2.66 (m, 6H), 3.72-3.81 (m, 6H), 4.03 (s, 3H), 4.28 (t, J=6.6 Hz, 2H), 6.45 (d, J=5.4 Hz, 1H), 7.16-7.42 (m, 6H), 7.45 (s, 1H), 7.54 (s, 1H), 7.94 (dd, J=2.4, 11.5 Hz, 1H), 8.51 (d, J=5.4 Hz, 1H), 8.61 (s, 1H), 12.41 (s, 1H)
ESI-MS: m/z=623 (M+1), 621 (M−1)

Example 289

1-{3-Fluoro-4-[(6-methoxy-7-(3-morpholin-4-yl-propoxy)-quinolin-4-yloxy]-phenyl}-3-[2-(3-fluoro-phenyl)-acetyl]-thiourea $^1$H-NMR (CDCl$_3$, 400 MHz): δ 2.10-2.18 (m, 2H), 2.44-2.56 (m, 4H), 2.59 (t, J=7.2 Hz, 2H), 3.70-3.76 (m, 6H), 4.03 (s, 3H), 4.28 (t, J=6.6 Hz, 2H), 6.45 (d, J=5.4 Hz, 1H), 7.01-7.13 (m, 3H), 7.26-7.44 (m, 3H), 7.44 (s, 1H), 7.54 (s, 1H), 7.93 (dd, J=2.4, 11.5 Hz, 1H), 8.50 (d, J=5.4 Hz, 1H), 8.55 (s, 1H), 12.41 (s, 1H)
ESI-MS: m/z=623 (M+1), 621 (M−1)

Example 291

1-{4-[7-(3-Diethylamino-propoxy)-6-methoxy-quinolin-4-yloxy]-3-fluoro-phenyl}-3-phenylacetyl-urea $^1$H-NMR (CDCl$_3$, 400 MHz): δ 1.31 (t, J=7.3 Hz, 6H), 2.29-2.39 (m, 2H), 2.93-3.02 (m, 4H), 3.06-3.17 (m, 2H), 3.80 (s, 2H), 4.01 (s, 3H), 4.26 (t, J=6.0 Hz, 2H), 6.38 (d, J=5.1 Hz, 1H), 7.18-7.44 (m, 8H), 7.56 (s, 1H), 7.68 (dd, J=2.4, 12.2 Hz, 1H), 8.46 (d, J=5.1 Hz, 1H), 8.85 (br, 1H), 10.72 (s, 1H)
ESI-MS: m/z=575 (M+1)

Example 292

1-{3-Fluoro-4-[6-methoxy-7-(3-pyrrolidin-1-yl-propoxy)-quinolin-4-yloxy]-phenyl}-3-phenylacetyl-urea $^1$H-NMR (CDCl$_3$, 400 MHz): δ 1.94-2.05 (m, 4H), 2.30-2.40 (m, 2H), 2.80-3.15 (m, 6H), 3.78 (s, 2H), 4.02 (s, 3H), 4.27 (t, J=6.1 Hz, 2H), 6.38 (d, J=1.0, 5.4 Hz, 1H), 7.16-7.44

(m, 8H), 7.56 (s, 1H), 7.68 (dd, J=2.4, 12.7 Hz, 1H), 8.45 (br, 1H), 8.47 (d, J=5.4 Hz, 1H), 10.69 (s, 1H)

Example 293

1-{4-[7-(3-Diethylamino-propoxy)-6-methoxy-quinolin-4-yloxy]-3-fluoro-phenyl}-3-[2-(2-fluoro-phenyl)-acetyl]-urea $^1$H-NMR (CDCl$_3$, 400 MHz): δ 1.27 (t, J=7.2 Hz, 6H), 2.25-2.35 (m, 2H), 2.87-3.10 (m, 6H), 3.84 (s, 2H), 4.01 (s, 3H), 4.26 (t, J=6.1 Hz, 2H), 6.38 (d, J=5.4 Hz, 1H), 7.10-7.25 (m, 4H), 7.29-7.40 (m, 2H), 7.41 (s, 1H), 7.56 (s, 1H), 7.67 (dd, J=2.2, 12.7 Hz, 1H), 8.47 (d, J=5.4 Hz, 1H), 8.91 (br, 1H), 10.67 (s, 1H)
ESI-MS: m/z=593 (M+1)

Example 294

1-{3-Fluoro-4-[6-methoxy-7-(3-pyrrolidin-1-yl-propoxy)-quinolin-4-yloxy]-phenyl}-3-[2-(2-fluoro-phenyl)-acetyl]-urea $^1$H-NMR (CDCl$_3$, 400 MHz): δ 1.93-2.00 (m, 4H), 2.28-2.36 (m, 2H), 2.75-3.09 (m, 6H), 3.83 (s, 2H), 4.02 (s, 3H), 4.27 (t, J=6.3 Hz, 2H), 6.38 (dd, J=1.0, 5.1 Hz, 1H), 7.10-7.28 (m, 4H), 7.30-7.39 (m, 2H), 7.41 (s, 1H), 7.55 (s, 1H), 7.68 (dd, J=2.2, 11.7 Hz, 1H), 8.46 (d, J=5.1 Hz, 1H), 8.85 (br, 1H), 10.66 (s, 1H)
ESI-MS: m/z=593 (M+1)

Example 295

1-{3-Fluoro-4-[6-methoxy-7-(3-piperidin-1-yl-propoxy)-quinolin-4-yloxy]-phenyl}-3-[2-(2-fluoro-phenyl)-acetyl]-urea $^1$H-NMR (CDCl$_3$, 400 MHz): δ 1.45-1.55 (m, 2H), 1.68-1.79 (m, 4H), 2.09-2.16 (m, 2H), 2.54-2.82 (m, 6H), 3.83 (s, 2H), 4.02 (s, 3H), 4.25 (t, J=6.6 Hz, 2H), 6.38 (dd, J=0.7, 5.4 Hz, 1H), 7.10-7.31 (m, 4H), 7.30-7.39 (m, 2H), 7.41 (s, 1H), 7.55 (s, 1H), 7.68 (dd, J=2.2, 12.7 Hz, 1H), 8.46 (d, J=5.4 Hz, 1H), 9.00 (br, 1H), 10.68 (s, 1H)
ESI-MS: m/z=605 (M+1)

Example 296

1-(3-Fluoro-4-{6-methoxy-7-[3-(4-methyl-piperazin-1-yl)-propoxy]-quinolin-4-yloxy}-phenyl)-3-[2-(2-fluoro-phenyl)-acetyl]-urea $^1$H-NMR (CDCl$_3$, 400 MHz): δ 2.08-2.17 (m, 2H), 2.28-2.70 (m, 13H), 3.81 (s, 2H), 4.03 (s, 3H), 4.23-4.39 (m, 2H), 6.39 (d, J=5.4 Hz, 1H), 7.12-7.23 (m, 4H), 7.17-7.40 (m, 2H), 7.43 (s, 1H), 7.55 (s, 1H), 7.69 (dd, J=2.2, 12.1 Hz, 1H), 8.47 (d, J=5.4 Hz, 1H), 8.70 (br, 1H), 10.65 (s, 1H)

Example 297

1-(3-Fluoro-4-{6-methoxy-7-[3-(4-methyl-piperazin-1-yl)-propoxy]-quinolin-4-yloxy}-phenyl)-3-(2-m-toluoyl-acetyl)-thiourea $^1$H-NMR (CDCl$_3$, 400 MHz): δ 2.08-2.17 (m, 2H), 2.32-2.44 (m, 5H), 2.52-2.65 (m, 8H), 3.71 (s, 2H), 4.02 (s, 3H), 4.26 (t, J=6.3 Hz, 2H), 6.44 (d, J=5.4 Hz, 1H), 7.01-7.55 (m, 8H), 7.93 (dd, J=2.7, 11.5 Hz, 1H), 8.48-8.54 (m, 2H), 12.49 (s, 1H)
ESI-MS: m/z=632 (M+1)

Example 298

1-{3-Chloro-4-[6-methoxy-7-(3-morpholin-4-yl-propoxy)-quinolin-4-yloxy]-phenyl}-3-[2-(2-fluoro-phenyl)-acetyl]-thiourea $^1$H-NMR (CDCl$_3$, 400 MHz): δ 2.15-2.22 (m, 2H), 2.52-2.58 (m, 4H), 2.63 (t, J=7.1 Hz, 2H), 3.76 (t, J=4.6 Hz, 4H), 3.80 (s, 2H), 4.03 (s, 3H), 4.28 (t, J=6.6 Hz, 2H), 6.38 (d, J=5.1 Hz, 1H), 7.13-7.25 (m, 3H), 7.29-7.42 (m, 2H), 7.46 (s, 1H), 7.55 (s, 1H), 7.62 (dd, J=2.4, 8.8 Hz, 1H), 8.00 (d, J=2.4 Hz, 1H), 8.50 (d, J=5.1 Hz, 1H) 8.97 (s, 1H), 12.39 (s, 1H)
ESI-MS: m/z=639 (M+1)

Example 299

1-{3-Chloro-4-[6-methoxy-7-(3-morpholin-yl-propoxy)-quinolin-4-yloxy]-phenyl}-3-[2-(3-fluoro-phenyl)-acetyl]-thiourea $^1$H-NMR (CDCl$_3$, 400 MHz): δ 2.15-2.26 (m, 2H), 2.55-2.75 (m, 6H), 3.77 (s, 2H), 3.78-3.83 (m, 4H), 4.03 (s, 3H), 4.29 (t, J=6.6 Hz, 2H), 6.39 (d, J=5.1 Hz, 1H), 7.02-7.13 (m, 4H), 7.36-7.44 (m, 1H), 7.48 (s, 1H), 7.55 (s, 1H), 7.62 (dd, J=2.4, 8.8 Hz, 1H), 8.00 (d, J=2.4 Hz, 1H), 8.50 (d, J=5.1 Hz, 1H), 8.85 (s, 1H), 12.39 (s, 1H)
ESI-MS: m/z=639 (M+1)

Example 300

1-{3-Chloro-4-[6-methoxy-7-(3-morpholin-4-yl-propoxy)-quinolin-4-yloxy]-phenyl}-3-phenylacetyl-thiourea $^1$H-NMR (CDCl$_3$, 400 MHz): δ 2.14-2.24 (m, 2H), 2.53-2.72 (m, 6H), 3.76-3.80 (m, 6H), 4.03 (s, 3H), 4.28 (t, J=6.6 Hz, 2H), 6.38 (d, J=5.4 Hz, 1H), 7.22-7.45 (m, 7H), 7.55 (s, 1H), 7.62 (dd, J=2.4, 8.8 Hz, 1H), 8.00 (d, J=2.4 Hz, 1H), 8.50 (d, J=5.4 Hz, 1H), 8.72 (s, 1H), 12.44 (s, 1H)
ESI-MS: m/z=621 (M+1)

Example 301

1-{3-Chloro-4-[6-methoxy-7-(3-morpholin-yl-propoxy)-quinolin-4-yloxy]-phenyl}-3-(2-o-toluoyl-acetyl)-thiourea $^1$H-NMR (CDCl$_3$:CD$_3$OD=30:1, 400 MHz): δ 2.20-2.32 (m, 2H), 2.36 (s, 3H), 2.72-2.90 (m, 6H), 3.78 (s, 2H), 3.80-3.85 (m, 4H), 4.04 (s, 3H), 4.36 (t, J=6.1 Hz, 2H), 6.41 (d, J=5.4 Hz, 1H), 7.21-7.33 (m, 5H), 7.54-7.61 (m, 2H), 7.65 (dd, J=2.4, 8.6 Hz, 1H), 8.04 (d, J=2.4 Hz, 1H), 8.45 (br, 1H), 9.00 (br, 1H), 12.50 (br, 1H)
ESI-MS: m/z=635 (M+1)

Example 302

1-{3-Fluoro-4-[6-methoxy-7-(3-morpholin-4-yl-propoxy)-quinolin-4-yloxy]-phenyl}-3-(2-o-toluoyl-acetyl)-thiourea $^1$H-NMR (CDCl$_3$, 400 MHz): δ 2.20-2.33 (m, 2H), 2.36 (s, 3H), 2.50-2.59 (m, 6H), 3.79 (s, 2H), 3.81-3.90 (m, 4H), 4.03

(s, 3H), 4.29 (t, J=6.3 Hz, 2H), 6.47 (d, J=5.4 Hz, 1H), 7.22-7.34 (m, 5H), 7.42 (d, J=8.1 Hz, 1H), 7.49 (s, 1H), 7.55 (s, 1H), 7.96 (dd, J=2.4, 11.7 Hz, 1H), 8.44 (br, 1H), 8.50 (d, J=5.4 Hz, 1H), 12.52 (s, 1H)
ESI-MS: m/z=619 (M+1)

Example 303

1-{3-Fluoro-4-[6-methoxy-7-(3-morpholin-4-yl-propoxy)-quinolin-4-yloxy]-phenyl}-3-(2-m-toluoyl-acetyl)-thiourea $^1$H-NMR (CDCl$_3$, 400 MHz): δ 2.10-2.20 (m, 2H), 2.39 (s, 3H), 2.55-2.67 (m, 6H), 3.71 (s, 2H), 3.75-3.80 (m, 4H), 4.03 (s, 3H), 4.28 (t, J=6.6 Hz, 2H), 6.46 (d, J=4.6 Hz, 1H), 7.08-7.36 (m, 5H), 7.41 (d, J=8.8 Hz, 1H), 7.44 (s, 1H), 7.55 (s, 1H), 7.91-8.01 (m, 1H), 8.48-8.54 (m, 1H), 8.96 (br, 1H), 12.53 (s, 1H)
ESI-MS: m/z=619 (M+1)

Example 304

1-{3-Fluoro-4-[6-methoxy-7-(3-morpholin-4-yl-propoxy)-quinolin-4-yloxy]-phenyl}-3-(2-p-toluyl-acetyl)-thiourea $^1$H-NMR (CDCl$_3$, 400 MHz): δ 2.14-2.24 (m, 2H), 2.38 (s, 3H), 2.55-2.72 (m, 6H), 3.72 (s, 2H), 3.76-3.82 (m, 4H), 4.03 (s, 3H), 4.28 (t, J=6.4 Hz, 2H), 6.46 (d, J=5.4 Hz, 1H), 7.16-7.28 (m, 5H), 7.40 (d, J=8.8 Hz, 1H), 7.46 (s, 1H), 7.54 (s, 1H), 7.93 (dd, J=2.4, 11.5 Hz, 1H), 8.50 (d, J=5.4 Hz, 1H), 8.64 (s, 1H), 12.52 (s, 1H)
ESI-MS: m/z=619 (M+1)

Example 305

1-{3-Fluoro-4-[7-(3-imidazol-1-yl-propoxy)-6-methoxy-quinolin-4-yloxy]-phenyl}-3-phenylacetyl-urea $^1$H-NMR (DMSO-d$_6$, 400 MHz): δ 2.19-2.38 (m, 2H), 3.74 (s, 2H), 3.97 (s, 3H), 4.09 (t, J=6.3 Hz, 2H), 4.19 (t, J=6.8 Hz, 2H), 6.44 (d, J=5.4 Hz, 1H), 6.89 (s, 1H), 7.15-7.50 (m, 9H), 7.54 (s, 1H), 7.64 (s, 1H), 7.76-7.88 (m, 1H), 8.47 (d, J=5.4 Hz, 1H), 10.64 (s, 1H), 11.05 (s, 1H)
Mass spectrometric value (ESI-MS, m/z): 570 (M+1)$^+$ Example 306

1-{3-Fluoro-4-[7-(3-imidazol-1-yl-propoxy)-6-methoxy-quinolin-4-yloxy]-phenyl}-3-[2-(2-fluoro-phenyl)-acetyl]-urea $^1$H-NMR (DMSO-d$_6$, 400 MHz): δ 2.20-2.40 (m, 2H), 3.85 (s, 2H), 3.97 (s, 3H), 4.05-4.15 (m, 2H), 4.15-4.26 (m, 2H), 6.45 (d, J=5.1 Hz, 1H), 6.90 (s, 1H), 7.08-7.50 (m, 8H), 7.54 (s, 1H), 7.64 (s, 1H), 7.77-7.90 (m, 1H), 8.47 (d, J=5.1 Hz, 1H), 10.57 (s, 1H), 11.08 (s, 1H)
Mass spectrometric value (ESI-MS, m/z): 588 (M+1)$^+$ Example 307

1-{3-Fluoro-4-[7-(3-imidazol-1-yl-propoxy)-6-methoxy-quinolin-4-yloxy]-phenyl}-3-phenylacetyl-thiourea $^1$H-NMR (DMSO-d$_6$, 400 MHz): δ 2.21-2.39 (m, 2H), 3.83 (s, 2H), 3.97 (s, 3H), 4.00-4.20 (m, 2H), 4.15-4.30 (m, 2H), 6.50 (d, J=5.3 Hz, 1H), 6.91 (s, 1H), 7.17-7.60 (m, 10H), 7.70 (s, 1H), 7.95-8.07 (m, 1H), 8.49 (d, J=5.3 Hz, 1H), 11.80 (s, 1H), 12.51 (s, 1H)
Mass spectrometric value (ESI-MS, m/z): 586 (M+1)$^+$ Example 308

1-(3-Fluoro-4-{7-[3-(4-hydroxymethyl-piperidin-1-yl)-propoxy]-6-methoxy-quinolin-4-yloxy}-phenyl)-3-phenylacetyl-urea $^1$H-NMR (CDCl$_3$, 400 MHz): δ 1.22-2.43 (m, 9H), 2.50-2.65 (m, 2H), 2.98-3.12 (m, 2H), 3.39-3.49 (m, 2H), 3.70 (s, 2H), 3.95 (s, 3H), 4.13-4.26 (m, 2H), 6.31 (d, J=5.4 Hz, 1H), 7.04-7.41 (m, 7H), 7.35 (s, 1H), 7.48 (s, 1H), 7.57-7.63 (m, 1H), 8.21 (s, 1H), 8.40 (d, J=5.4 Hz, 1H), 10.69 (s, 1H)
Mass spectrometric value (ESI-MS, m/z): 617 (M$^+$+1)

Example 309

1-(3-Fluoro-4-{7-[3-(4-hydroxymethyl-piperidin-1-yl)-propoxy]-6-methoxy-quinolin-4-yloxy}-phenyl)-3-phenylacetyl-thiourea $^1$H-NMR (CDCl$_3$:CD$_3$OD=10:1, 400 MHz): δ 1.75-3.00 (m, 9H), 3.30-3.72 (m, 6H), 3.76 (s, 2H), 4.04 (s, 3H), 4.34 (t, J=5.4 Hz, 2H), 6.50 (d, J=5.4 Hz, 1H), 7.24-7.46 (m, 8H), 7.58 (s, 1H), 7.96 (dd, J=2.4, 11.7 Hz, 1H), 8.47 (d, J=5.4 Hz, 1H)
ESI-MS: m/z=633 (M+1)

Example 310

1-(3-Fluoro-4-{7-[3-(4-hydroxymethyl-piperidin-1-yl)-propoxy]-6-methoxy-quinolin-4-yloxy}-phenyl)-3-[2-(4-fluoro-phenyl)-acetyl]-thiourea $^1$H-NMR (CDCl$_3$:CD$_3$OD=20:1, 400 MHz): δ 1.00-3.20 (m, 15H), 3.73 (s, 2H), 4.02 (s, 3H), 4.27 (t, J=6.1 Hz, 2H), 6.45 (d, J=5.4 Hz, 1H), 7.08-7.17 (m, 2H), 2.22-7.44 (m, 5H), 7.54 (s, 1H), 7.94 (dd, J=2.4, 11.5 Hz, 1H), 8.49 (d, J=5.4 Hz, 1H)
ESI-MS: m/z=651 (M+1)

Example 311

1-(2-Fluoro-4-{7-[3-(4-hydroxymethyl-piperidin-1-yl)-propoxy]-6-methoxy-quinolin-4-yloxy}-phenyl)-3-phenyl-acetyl-urea $^1$H-NMR (CDCl$_3$, 400 MHz): δ 1.22-2.19 (m, 9H), 2.49-2.69 (m, 2H), 2.87-3.07 (m, 2H), 3.41-3.50 (m, 2H), 3.70 (s, 2H), 3.93 (s, 3H), 4.17-4.21 (m, 2H), 6.43 (d, J=5.3 Hz, 1H), 6.89-6.94 (m, 2H), 7.19-7.45 (m, 5H), 7.36 (s, 1H), 7.40 (s, 1H), 7.65 (s, 1H), 8.13 (t, J=8.8 Hz, 1H), 8.43 (d, J=5.3 Hz, 1H), 10.66 (s, 1H)
Mass spectrometric value (ESI-MS, m/z): 617 (M$^+$+1)

Example 312

1-{3-Fluoro-4-[7-(2-hydroxy-3-morpholin-4-yl-propoxy)-6-methoxy-quinolin-4-yloxy]-phenyl}-3-phenylacetyl-thiourea $^1$H-NMR (DMSO-d$_6$, 400 MHz): δ 3.17-3.40 (m, 6H), 3.50-3.65 (m, 4H), 3.83 (s, 2H), 3.94 (s, 3H), 4.00-4.13 (m, 2H), 4.13-4.26 (m, 1H), 4.90-5.00 (m, 1H), 6.48 (d, J=5.1 Hz, 1H), 7.17-7.57 (m, 9H), 7.93-8.10 (m, 1H), 8.49 (d, J=5.1 Hz, 1H), 11.81 (s, 1H), 12.50 (s, 1H)

Mass spectrometric value (ESI-MS, m/z): 621 (M+1)$^+$

Example 314

1-[2-(2-Chloro-phenyl)-acetyl]-3-{3-fluoro-4-[7-(2-hydroxy-3-morpholin-4-yl-propoxy)-6-methoxy-quinolin-4-yloxy]-phenyl}-thiourea $^1$H-NMR (CDCl$_3$, 400 MHz): δ 2.48-2.54 (m, 2H), 2.57-2.73 (m, 4H), 3.70-3.79 (m, 4H), 3.90 (s, 2H), 4.02 (s, 3H), 4.15-4.32 (m, 3H), 6.45 (d, J=5.4 Hz, 1H), 7.32-7.43 (m, 5H), 7.45 (s, 1H), 7.47-7.52 (m, 1H), 7.54 (s, 1H), 7.95 (dd, J=2.6, 11.6 Hz, 1H), 8.50 (d, J=5.4 Hz, 1H), 8.69 (s, 1H), 12.43 (s, 1H)

ESI-MS: m/z=655 (M+1)

Example 315

1-{3-Fluoro-4-[(7-(2-hydroxy-3-morpholin-4-yl-propoxy)-6-methoxy-quinolin-4-yloxy]-phenyl}-3-[2-(2-fluoro-phenyl)-acetyl]-thiourea $^1$H-NMR (CDCl$_3$, 400 MHz): δ 2.49-2.56 (m, 2H), 2.61-2.66 (m, 2H), 2.67-2.74 (m, 2H), 3.72-3.81 (m, 6H), 4.02 (s, 3H), 4.16-4.24 (m, 2H), 4.26-4.33 (m, 1H), 6.45 (d, J=5.4 Hz, 1H), 7.14-7.42 (m, 6H), 7.46 (s, 1H), 7.54 (s, 1H), 7.94 (dd, J=2.4, 11.5 Hz, 1H), 8.50 (d, J=5.4 Hz, 1H), 8.73 (s, 1H), 12.42 (s, 1H)

ESI-MS: m/z=639 (M+1)

Example 316

1-[2-(2-Chloro-phenyl)-acetyl]-3-{3-fluoro-4-[7-(2-hydroxy-3-piperidin-1-yl-propoxy)-6-methoxy-quinolin-4-yloxy]-phenyl}-thiourea $^1$H-NMR (DMSO, 400 MHz): δ 1.40-1.52 (m, 2H), 1.55-1.70 (m, 4H), 2.62-2.93 (m, 6H), 3.63 (s, 2H), 3.96 (s, 3H), 3.98-4.22 (m, 3H), 6.50 (d, J=5.1 Hz, 1H), 7.27-7.51 (m, 6H), 7.54 (s, 1H), 7.82 (dd, J=2.2, 11.9 Hz, 1H), 8.49 (d, J=5.1 Hz, 1H), 9.95 (s, 1H), 11.91 (br, 1H), 12.45 (br, 1H)

ESI-MS: m/z=653 (M+1)

Example 317

1-[2-(2-Chloro-phenyl)-acetyl]-3-{3-fluoro-4-[7-(2-hydroxy-3-pyrrolidin-1-yl-propoxy)-6-methoxy-quinolin-4-yloxy]-phenyl}-thiourea $^1$H-NMR (DMSO, 400 MHz): δ 1.84-1.92 (m, 4H), 3.01-3.36 (m, 6H), 3.63 (s, 2H), 3.97 (s, 3H), 4.10-4.26 (m, 3H), 6.51 (d, J=5.1 Hz, 1H), 7.27-7.51 (m, 6H), 7.55 (s, 1H), 7.84 (dd, J=2.4, 12.2 Hz, 1H), 8.51 (d, J=5.1 Hz, 1H), 9.96 (s, 1H), 11.91 (br, 1H), 12.45 (br, 1H)

ESI-MS: m/z=639 (M+1)

Example 318

1-(3-Fluoro-4-[7-(2-hydroxy-3-piperidin-1-yl-propoxy)-6-methoxy-quinolin-4-yloxy]-phenyl)-3-[2-(2-fluoro-phenyl)-acetyl]-thiourea $^1$H-NMR (DMSO, 400 MHz): δ 1.32-1.60 (m, 6H), 2.50-2.68 (m, 2H), 3.63 (s, 2H), 3.95 (s, 3H), 4.04-4.20 (m, 3H), 6.49 (d, J=5.1 Hz, 1H), 7.12-7.24 (m, 2H), 2.26-7.57 (m, 6H), 8.02 (dd, J=2.2, 12.2 Hz, 1H), 8.50 (d, J=5.1 Hz, 1H), 11.87 (br, 1H), 12.42 (br, 1H)

ESI-MS: m/z=637 (M+1)

Example 319

1-{3-Fluoro-4-[7-(2-hydroxy-3-pyrrolidin-1-yl-propoxy)-6-methoxy-quinolin-4-yloxy]-phenyl}-3-[2-(2-fluoro-phenyl)-acetyl]-thiourea $^1$H-NMR (DMSO, 400 MHz): δ 1.78-1.85 (m, 4H), 2.80-3.15 (m, 4H), 3.32-3.35 (m, 2H), 3.63 (s, 2H), 3.96 (s, 3H), 4.08-4.20 (m, 3H), 6.50 (d, J=5.4 Hz, 1H), 7.13-7.46 (m, 6H), 7.54 (s, 1H), 7.83 (dd, J=2.7, 12.9 Hz, 1H), 8.49 (d, J=5.4 Hz, 1H), 9.93 (s, 1H), 11.88 (br, 1H), 12.43 (br, 1H)

ESI-MS: m/z=623 (M+1)

Example 320

1-[2-(3-Chloro-phenyl)-acetyl]-3-{3-fluoro-4-[7-(2-hydroxy-3-morpholin-4-yl-propoxy)-6-methoxy-quinolin-4-yloxy]-phenyl}-thiourea $^1$H-NMR (DMSO, 400 MHz): δ 3.34-3,43 (m, 6H), 3.59-3.64 (m, 4H), 3.87 (s, 2H), 3.95 (s, 3H), 4.06-4.14 (m, 2H), 4.19 (d, J=6.6 Hz, 1H), 6.49 (d, J=5.4 Hz, 1H), 7.26-7.57 (m, 8H), 8.01 (dd, J=2.6, 12.4 Hz, 1H), 8.50 (d, J=5.4 Hz, 1H), 11.83 (s, 1H), 12.43 (s, 1H)

ESI-MS: m/z=655 (M+1)

Example 321

1-[2-(3-Chloro-phenyl)-acetyl]-3-{3-fluoro-4-[7-(2-hydroxy-3-piperidin-1-yl-propoxy)-6-methoxy-quinolin-4-yloxy]-phenyl}-thiourea $^1$H-NMR (DMSO, 400 MHz): δ 1.37-1.61 (m, 6H), 2.50-2.55 (m, 6H), 3.62 (s, 2H), 3.95 (s, 3H), 4.05-4.21 (m, 3H), 6.49 (d, J=5.1 Hz, 1H), 7.21-7.55 (m, 7H), 7.32 (dd, J=2.4, 12.4 Hz, 1H), 8.49 (d, J=5.1 Hz, 1H), 9.93 (s, 1H), 11.79 (br, 1H), 12.42 (br, 1H)

ESI-MS: m/z=655 (M+1)

Example 322

1-[2-(3-Chloro-phenyl)-acetyl]-3-{3-fluoro-4-[7-(2-hydroxy-3-pyrrolidin-1-yl-propoxy)-6-methoxy-quinolin-4-yloxy]-phenyl}-thiourea $^1$H-NMR (DMSO, 400 MHz): δ 1.82-1.90 (m, 4H), 2.90-3.50 (m, 6H), 3.62 (s, 2H), 3.97 (s, 3H), 4.09-4.25 (m, 3H), 6.51 (d, J=5.1 Hz, 1H), 7.22-7.57 (m, 7H), 7.82 (dd, J=2.2, 12.0 Hz, 1H), 8.50 (d, J=5.1 Hz, 1H), 9.94 (s, 1H), 11.83 (br, 1H), 12.44 (br, 1H)

Example 323

1-{3-Fluoro-4-[7-(2-hydroxy-3-morpholin-4-yl-propoxy)-6-methoxy-quinolin-4-yloxy]-phenyl}-3-[2-(3-fluoro-phenyl)-acetyl]-thiourea $^1$H-NMR (DMSO, 400 MHz): δ 3.33-3.41 (m, 6H), 3.57-3.63 (m, 4H), 3.87 (s, 2H), 3.95 (s, 3H), 4.04-4.22 (m, 3H), 6.48 (d, J=5.4 Hz, 1H), 7.05-7.23 (m, 3H), 7.36-7.56 (m, 5H), 8.01 (dd, J=2.1, 12.3 Hz, 1H), 8.50 (d, J=5.4 Hz, 1H), 11.83 (s, 1H), 12.45 (s, 1H)

ESI-MS: m/z=639 (M+1)

Example 324

1-{3-Fluoro-4-[7-(2-hydroxy-3-piperidin-1-yl-propoxy)-6-methoxy-quinolin-4-yloxy]-phenyl}-3-[2-(3-fluoro-phenyl)-acetyl]-thiourea $^1$H-NMR (DMSO, 400 MHz): δ 1.38-1.48 (m, 2H), 1.52-1.64 (m, 4H), 2.51-2.79 (m, 6H), 3.61 (s, 2H), 3.95 (s, 3H), 4.06-4.21 (m, 3H), 6.49 (d, J=5.1 Hz, 1H), 7.06-7.56 (m, 7H), 8.02 (dd, J=2.4, 12.4 Hz, 1H), 8.50 (d, J=5.1 Hz, 1H), 9.96 (s, 1H), 11.83 (br, 1H), 12.45 (br, 1H)
ESI-MS: m/z=637 (M+1)

Example 325

1-{3-Fluoro-4-[7-(2-hydroxy-3-pyrrolidin-1-yl-propoxy)-6-methoxy-quinolin-4-yloxy]-phenyl}-3-[2-(3-fluoro-phenyl)-acetyl]-thiourea $^1$H-NMR (DMSO, 400 MHz): δ 1.84-1.92 (m, 4H), 3.00-3.40 (m, 6H), 3.88 (s, 2H), 3.96 (s, 3H), 4.10-4.25 (m, 3H), 6.50 (d, J=5.1 Hz, 1H), 7.06-7.58 (m, 7H), 8.01 (dd, J=2.4, 12.2 Hz, 1H), 8.51 (d, J=5.1 Hz, 1H), 9.97 (s, 1H), 11.83 (br, 1H), 12.45 (br, 1H)
ESI-MS: m/z=623 (M+1)

Example 326

1-[2-(4-Chloro-phenyl)-acetyl]-3-{3-fluoro-4-[7-(2-hydroxy-3-morpholin-4-yl-propoxy)-6-methoxy-quinolin-4-yloxy]-phenyl}-thiourea $^1$H-NMR (CDCl$_3$:CD$_3$OD=20:1, 400 MHz): δ 2.53-2.73 (m, 6H), 3.72 (s, 2H), 3.73-3.78 (m, 4H), 4.03 (s, 3H), 4.14-4.34 (m, 3H), 6.47 (d, J=5.4 Hz, 1H), 7.20-7.34 (m, 4H), 7.37-7.42 (m, 2H), 7.44 (s, 1H), 7.56 (s, 1H), 7.94 (dd, J=2.6, 11.6 Hz, 1H), 8.48 (d, J=5.4 Hz, 1H)
ESI-MS: m/z=655 (M+1)

Example 327

1-[2-(4-Chloro-phenyl)-acetyl]-3-{3-fluoro-4-[7-(2-hydroxy-3-piperidin-1-yl-propoxy)-6-methoxy-quinolin-4-yloxy]-phenyl}-thiourea $^1$H-NMR (CDCl$_3$:CD$_3$OD=20:1, 400 MHz): δ 1.39-1.43 (m, 2H), 1.57-1.66 (m, 4H), 2.55-2.72 (m, 6H), 3.61 (s, 2H), 3.95 (s, 3H), 4.06-4.09 (m, 2H), 4.24-4.31 (m, 1H), 6.39 (d, J=5.4 Hz, 1H), 7.10-7.30 (m, 7H), 7.43-7.49 (m, 1H), 7.48 (s, 1H), 8.34 (d, J=5.4 Hz, 1H)
ESI-MS: m/z=653 (M+1)

Example 328

1-[2-(4-Chloro-phenyl)-acetyl]-3-{3-fluoro-4-[7-(2-hydroxy-3-pyrrolidin-1-yl-propoxy)-6-methoxy-quinolin-4-yloxy]-phenyl}-thiourea $^1$H-NMR (CDCl$_3$:CD$_3$OD=20:1, 400 MHz): δ 2.01-2.08 (m, 4H), 3.3.30-3.35 (m, 6H), 3.65 (s, 2H), 3.95 (s, 3H), 4.06-4.20 (m, 2H), 4.35-4.45 (m, 1H), 6.41 (d, J=5.4 Hz, 1H), 7.12-7.32 (m, 7H), 7.49 (s, 1H), 7.88 (dd, J=2.4, 11.7 Hz, 1H), 8.37 (d, J=5.4 Hz, 1H)
ESI-MS: m/z=639 (M+1)

Example 329

1-{3-Fluoro-4-[7-(2-hydroxy-3-piperidin-1-yl-propoxy)-6-methoxy-quinolin-4-yloxy]-phenyl}-3-[2-(4-fluoro-phenyl)-acetyl]-thiourea $^1$H-NMR (CDCl$_3$:CD$_3$OD=20:1, 400 MHz): δ 1.43-1.55 (m, 2H), 1.62-1.78 (m, 4H), 2.48-2.90 (m, 6H), 3.63 (s, 2H), 3.95 (s, 3H), 4.05-4.18 (m, 2H), 4.32-4.43 (m, 1H), 6.38 (d, J=5.4 Hz, 1H), 6.83-7.03 (m, 1H), 7.15-7.30 (m, 6H), 7.32 (s, 1H), 8.48 (s, 1H), 8.37 (d, J=5.4 Hz, 1H)
ESI-MS: m/z=637 (M-1-1)

Example 330

1-{3-Fluoro-4-[7-(2-hydroxy-3-pyrrolidin-1-yl-propoxy)-6-methoxy-quinolin-4-yloxy]-phenyl}-3-[2-(4-fluoro-phenyl)-acetyl]-thiourea $^1$H-NMR (CDCl$_3$:CD$_3$OD=20:1, 400 MHz): δ 2.09-2.15 (m, 4H), 3.33-3.43 (m, 6H), 3.70 (s, 2H), 4.04 (s, 3H), 4.14-4.27 (m, 2H), 4.46-4.53 (m, 1H), 6.49 (d, J=5.4 Hz, 1H), 6.96-7.13 (m, 2H), 7.22-7.40 (m, 5H), 7.58 (s, 1H), 7.96 (dd, J=2.4, 11.5 Hz, 1H), 8.44 (d, J=5.4 Hz, 1H)
ESI-MS: m/z=623 (M+1)

Example 331

1-{3-Fluoro-4-[(7-(2-hydroxy-3-piperidin-1-yl-propoxy)-6-methoxy-quinolin-4-yloxy]-phenyl}-3-(2-phenylacetyl)-thiourea $^1$H-NMR (CDCl$_3$:CD$_3$OD=20:1, 400 MHz): δ 1.50-1.60 (m, 2H), 1.76-1.84 (m, 4H), 2.93-3.07 (m, 6H), 3.70 (s, 2H), 3.97 (s, 3H), 4.08-4.19 (m, 2H), 4.43-4.51 (m, 1H), 6.42 (d, J=5.4 Hz, 1H), 7.18-7.40 (m, 8H), 7.51 (s, 1H), 7.90 (dd, J=2.3, 11.6 Hz, 1H) 8.40 (d, J=5.4 Hz, 1H)
ESI-MS: m/z=619 (M+1)

Example 332

1-{3-Fluoro-4-[7-(2-hydroxy-3-pyrrolidin-1-yl-propoxy)-6-methoxy-quinolin-4-yloxy]-phenyl}-3-(2-phenyl-acetyl)-thiourea $^1$H-NMR (CDCl$_3$:CD$_3$OD=20:1, 400 MHz): δ 2.03-2.11 (m, 4H), 3.20-3.40 (m, 6H), 3.70 (s, 2H), 3.98 (s, 3H), 4.09-4.22 (m, 2H), 4.43-4.51 (m, 1H), 6.43 (d, J=5.0 Hz, 1H), 7.19-7.40 (m, 8H), 7.52 (s, 1H), 7.90 (dd, J=2.6, 11.7 Hz, 1H), 8.41 (d, J=5.0 Hz, 1H)
ESI-MS: m/z=605 (M+1)

Example 333

1-{3-Fluoro-4-[7-(2-hydroxy-3-morpholin-1-yl-propoxy)-6-methoxy-quinolin-4-yloxy]-phenyl}-3-(2-o-toluoyl-acetyl)-thiourea $^1$H-NMR (CDCl$_3$, 400 MHz): δ 2.36 (s, 3H), 2.70-2.90 (m, 6H), 3.77-3.87 (m, 6H), 4.02 (s, 3H), 4.20-4.24 (m, 2H), 4.40-4.47 (m, 1H), 6.49 (d, J=5.4 Hz, 1H), 7.16-7.32 (m, 5H), 7.42 (d, J=9.0 Hz, 1H), 7.55 (s, 1H), 7.62 (s, 1H), 7.97 (dd, J=2.4, 11.7 Hz, 1H), 8.50 (d, J=5.4 Hz, 1H), 8.55 (s, 1H), 12.54 (s, 1H)
ESI-MS: m/z=635 (M+1)

Example 334

1-{3-Fluoro-4-[7-(2-hydroxy-3-morpholin-1-yl-propoxy)-6-methoxy-quinolin-4-yloxy]-phenyl}-3-(2-m-toluoyl-acetyl)-thiourea $^1$H-NMR (CDCl$_3$, 400 MHz): δ 2.39 (s, 3H), 2.60-2.85 (m, 6H), 3.72 (s, 2H), 3.77-3.83 (m, 4H), 4.02 (s, 3H), 4.22 (d, J=5.1 Hz, 2H), 4.34-4.42 (m, 1H), 6.49 (d, J=5.4 Hz, 1H), 7.09-7.35 (m, 5H), 7.41 (d, J=9.0 Hz, 1H), 7.54 (s, 1H), 7.55 (s, 1H), 7.95 (dd, J=2.6, 11.6 Hz, 1H), 8.51 (d, J=5.4 Hz, 1H), 8.57 (s, 1H), 12.52 (s, 1H)
ESI-MS: m/z=635 (M+1)

Example 335

1-{3-Fluoro-4-[7-(2-hydroxy-3-morpholin-1-yl-propoxy)-6-methoxy-quinolin-4-yloxy]-phenyl}-3-(2-p-toluoyl-acetyl)-thiourea $^1$H-NMR (CDCl$_3$, 400 MHz): δ 2.37 (s, 3H), 2.55-2.79 (m, 6H), 3.70-3.80 (m, 6H), 4.01 (s, 3H), 4.19-4.23 (m, 2H), 4.31-4.38 (m, 1H), 6.46 (d, J=5.4 Hz, 1H), 7.10-7.28 (m, 5H), 7.40 (d, J=9.0 Hz, 1H), 7.51 (s, 1H), 7.56 (s, 1H), 7.93 (dd, J=2.4, 11.7 Hz, 1H), 8.51 (d, J=5.4 Hz, 1H), 8.84 (s, 1H), 12.54 (s, 1H)
ESI-MS: m/z=635 (M+1)

Example 336

1-{3-Fluoro-4-[7-(2-hydroxy-3-morpholin-1-yl-propoxy)-6-methoxy-quinolin-4-yloxy]-phenyl}-3-[2-(4-fluoro-phenyl)-acetyl]-urea $^1$H-NMR (CDCl$_3$, 400 MHz): δ 2.43-2.65 (m, 6H), 3.62-3.72 (m, 4H), 3.67 (s, 2H), 3.94 (s, 3H), 4.09-4.25 (m, 3H), 6.33 (d, J=5.4 Hz, 1H), 6.91-7.24 (m, 6H), 7.38 (s, 1H), 7.48 (s, 1H), 7.60-7.64 (m, 1H), 8.41 (d, J=5.4 Hz, 1H), 8.88 (s, 1H), 10.62 (s, 1H)
Mass spectrometric value (ESI-MS, m/z): 623 (M$^+$+1)

Example 337

1-{3-Fluoro-4-[7-(2-hydroxy-3-morpholin-1-yl-propoxy)-6-methoxy-quinolin-4-yloxy]-phenyl}-3-(2-phenyl-acetyl)-urea $^1$H-NMR (CDCl$_3$, 400 MHz): δ 2.44-2.65 (m, 6H), 3.68-3.76 (m, 4H), 3.69 (s, 2H), 3.94 (s, 3H), 4.08-4.23 (m, 3H), 6.32 (d, J=5.1 Hz, 1H), 7.11-7.35 (m, 7H), 7.39 (s, 1H), 7.49 (s, 1H), 7.60-7.63 (m, 1H), 8.41 (m, d, J=5.1 Hz, 1H), 8.60 (s, 1H), 10.64 (s, 1H)
Mass spectrometric value (ESI-MS, m/z): 605 (M$^+$+1)

Pharmacological Test Example 1

Measurement (1) of Inhibitory Activity Against Met-Autophosphorylation Using ELISA Method Human epidermal cancer cells A431 were cultured in an RPMI 1640 medium containing 10% fetal calf serum (purchased from GIBCO BRL) within a 5% carbon dioxide incubator until 50 to 90% confluent. Cells were cultured with RPMI medium containing 0.1% fetal calf serum in 96-well flat-bottom plate in an amount of 3×10$^4$ per well, and were incubated at 37° C. overnight. The medium was then replaced by a fresh RPMI medium containing 0.1% fetal calf serum. A solution of the test compound in dimethyl sulfoxide was added to each well, and the cells were incubated at 37° C. for additional one hr. A human recombinant hepatocyte growth factor (hereinafter abbreviated to "HGF") was added to a final concentration of 50 ng/ml, and the stimulation of cells was carried out at 37° C. for 5 min. The medium was removed, the cells were washed with phosphate buffered saline (pH 7.4), and 50 µl of lysis buffer (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM Na$_4$P$_2$O$_7$) was then added thereto. The mixture was shaken at 4° C. for 2 hr to prepare a cell extract.

Separately, phosphate buffered saline (50 µl, pH 7.4) containing 5 µg/ml of anti-phospho-tyrosine antibody (PY20; purchased from Transduction Laboratories) was added to a microplate for ELISA (Maxisorp; purchased from NUNC), followed by gentle agitation at 4° C. overnight to coat the surface of the wells with the antibody. After washing of the plate, 300 µl of a blocking solution was added, followed by gentle agitation at room temperature for 2 hr to perform blocking. After washing, the whole quantity of the cell extract was transferred to the wells, and the plate was then allowed to incubate at 4° C. overnight. After washing, an anti-HGF receptor antibody (h-Met (C-12), purchased from Santa Cruz Biotechnology) was allowed to react at room temperature for one hr, and, after washing, a peroxidase-labeled anti-rabbit Ig antibody (purchased from Amersham) was allowed to react at room temperature for one hr. After washing, a chromophoric substrate for peroxidase (purchased from Sumitomo Bakelite Co., Ltd.) was added thereto to initiate a reaction. After a suitable level of color development, a reaction termination solution was added to stop the reaction, and the absorbance at 450 nm was measured with a microplate reader. The met-phosphorylation inhibitory activity for each well was determined by presuming the absorbance with the addition of HGF and the vehicle to compounds to be 0% met-phosphorylation inhibitory activity and the absorbance with the addition of the vehicle to compounds and without HGF to be 100% met phosphorylation inhibitory activity. The concentration of the test compound was varied on several levels, the inhibition (%) of met-phosphorylation was determined for each case, and the concentration of the test compound necessary for inhibiting 50% of met phosphorylation (IC$_{50}$) was calculated. The results are shown in Table 1.

TABLE 1

| Example No. | IC$_{50}$, µM |
|---|---|
| 1 | 0.0087 |
| 2 | 0.0118 |
| 3 | 0.0197 |
| 11 | 0.0581 |

Pharmacological Test Example 2

Measurement (2) of Inhibitory Activity Against Met-Autophosphorylation Using ELISA Method Human gastric cancer cells MKN45 were maintained in RPMI 1640 medium containing 10% fetal calf serum (purchased from GIBCO BRL) in 5% carbon dioxide incubator until 50 to 90% confluent. Cells were cultured with RPMI medium containing 0.1% fetal calf serum in 96-well flat-bottom plate in an amount of 3×10$^4$ per well, and were incubated at 37° C. overnight. The medium was then replaced by a fresh RPMI medium containing 0.1% fetal calf serum. A solution of the test compound in dimethyl sulfoxide was added to each well, and the incuvation was continued at 37° C. for additional one hr. The medium was removed, the cells were washed with phosphate buffered saline (pH 7.4), and 50 µl of a lysis buffer (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM $Na_4P_2O_7$) was then added thereto. The mixture was shaken at 4° C. for 2 hr to prepare a cell extract.

Separately, phosphate buffered saline (50 µl, pH 7.4) containing 5 µg/ml of anti-phospho-tyrosine antibody (PY20; purchased from Transduction Laboratories) was added to a microplate for ELISA (Maxisorp; purchased from NUNC), followed by gentle agitation at 4° C. overnight to coat the surface of the wells with the antibody. After washing of the plate, 300 µl of a blocking solution was added, followed by gentle agitation at room temperature for 2 hr to perform blocking. After washing, the whole quantity of the cell extract was transferred to the wells, and the plate was then allowed to stand at 4° C. overnight. After washing, an anti-HGF receptor antibody (h-Met (C-12), purchased from Santa Cruz Biotechnology) was allowed to react at room temperature for one hr, and, after washing, a peroxidase-labeled anti-rabbit Ig antibody (purchased from Amersham) was allowed to react at room temperature for one hr. After washing, a chromophoric substrate for peroxidase (purchased from Sumitomo Bakelite Co., Ltd.) was added thereto to initiate a reaction. After a suitable level of color development, a reaction termination solution was added to stop the reaction, and the absorbance at 450 nm was measured with a microplate reader. The met phosphorylation activity for each well was determined by presuming the absorbance with the addition of the vehicle to be 100% met phosphorylation activity and the absorbance with the addition of a largely excessive amount of positive control (compound 1, 1000 nM) to be 0% met phosphorylation activity. The concentration of the test compound was varied on several levels, the inhibition (%) of met-phosphorylation was determined for each case, and the concentration of the test compound necessary for inhibiting 50% of met phosphorylation ($IC_{50}$) was calculated. The results are shown in Table 2.

TABLE 2

| Ex. No. | $IC_{50}$, µM |
|---|---|
| 1 | 0.0112 |
| 2 | 0.0181 |
| 3 | 0.0304 |
| 4 | 0.0750 |
| 5 | 0.0189 |
| 6 | 0.0316 |
| 7 | 0.2922 |
| 8 | 0.2976 |
| 9 | 0.0364 |
| 10 | 0.1459 |
| 11 | 0.0202 |
| 12 | 0.1990 |
| 13 | 0.1411 |
| 14 | 0.2909 |
| 15 | 0.3017 |
| 16 | 0.0328 |
| 17 | 0.0307 |
| 18 | 0.1496 |
| 19 | 0.1040 |
| 20 | 0.0318 |
| 21 | 0.1876 |
| 22 | 0.0246 |
| 23 | 0.0263 |
| 24 | 0.0277 |
| 25 | 0.1401 |

TABLE 2-continued

| Ex. No. | $IC_{50}$, µM |
|---|---|
| 26 | 0.1256 |
| 27 | 0.0800 |
| 28 | 0.1624 |
| 29 | 0.0371 |
| 30 | 0.0351 |
| 31 | 0.0341 |
| 32 | 0.1709 |
| 33 | 0.0618 |
| 34 | 0.0463 |
| 35 | 0.0414 |
| 36 | 0.1982 |
| 37 | 0.0584 |
| 38 | 0.0291 |
| 39 | 0.1145 |
| 40 | 0.2421 |
| 41 | 0.2807 |
| 42 | 0.1899 |
| 43 | 0.1674 |
| 44 | 0.2915 |
| 45 | 0.2071 |
| 46 | 0.2290 |
| 47 | 0.2153 |
| 48 | 0.2240 |
| 49 | 0.0514 |
| 50 | 0.2355 |
| 51 | 0.2035 |
| 52 | 0.1706 |
| 53 | 0.0374 |
| 54 | 0.0261 |
| 55 | 0.2449 |
| 56 | 0.1400 |
| 57 | 0.1320 |
| 58 | 0.0270 |
| 59 | 0.1930 |
| 60 | 0.0370 |
| 61 | 0.1130 |
| 62 | 0.0920 |
| 63 | 0.0244 |
| 64 | 0.1405 |
| 65 | 0.0663 |
| 66 | 0.0792 |
| 67 | 0.0197 |
| 68 | 0.1944 |
| 69 | 0.0044 |
| 70 | 0.0153 |
| 71 | 0.0299 |
| 72 | 0.0279 |
| 73 | 0.0281 |
| 74 | 0.1825 |
| 75 | 0.0336 |
| 76 | 0.0517 |
| 77 | 0.1776 |
| 78 | 0.0663 |
| 79 | 0.1454 |
| 80 | 0.0302 |
| 81 | 0.0277 |
| 82 | 0.0743 |
| 83 | 0.0391 |
| 84 | 0.0400 |
| 85 | 0.0488 |
| 86 | 0.0235 |
| 87 | 0.1983 |
| 88 | 0.0492 |
| 89 | 0.0526 |
| 90 | 0.0281 |
| 91 | 0.0401 |
| 92 | 0.1480 |
| 93 | 0.1215 |
| 94 | 0.0307 |
| 95 | 0.0413 |
| 96 | 0.1706 |
| 97 | 0.0376 |
| 98 | 0.0278 |
| 99 | 0.0256 |
| 100 | 0.0308 |
| 101 | 0.0444 |
| 102 | 0.0918 |
| 103 | 2.7714 |

TABLE 2-continued

| Ex. No. | IC$_{50}$, μM |
|---|---|
| 104 | 0.3442 |
| 105 | 0.1037 |
| 106 | 0.0427 |
| 107 | 0.3450 |
| 108 | 2.0800 |
| 109 | 1.4756 |
| 110 | 2.3751 |
| 111 | 1.8118 |
| 112 | 1.7334 |
| 113 | 0.6535 |
| 114 | 0.4850 |
| 115 | 0.3592 |
| 116 | 0.3440 |
| 117 | 1.3037 |
| 118 | 0.2114 |
| 119 | 0.4420 |
| 120 | 1.5748 |
| 121 | 0.3380 |
| 122 | 0.3026 |
| 123 | 2.0088 |
| 124 | 0.2643 |
| 125 | 0.2933 |
| 126 | 0.3295 |
| 127 | 0.3189 |
| 128 | 0.2847 |
| 129 | 1.0060 |
| 130 | 2.1555 |
| 131 | 2.3731 |
| 132 | 0.2683 |
| 133 | 0.2610 |
| 134 | 0.2319 |
| 135 | 0.2260 |
| 136 | 0.3417 |
| 137 | 0.2707 |
| 138 | 0.2843 |
| 139 | 0.2432 |
| 140 | 0.2288 |
| 141 | 0.3361 |
| 142 | 0.2847 |
| 143 | 3.5910 |
| 144 | 0.6990 |
| 145 | 0.3640 |
| 146 | 1.2100 |
| 147 | 1.1660 |
| 148 | 2.4790 |
| 149 | 0.2360 |
| 150 | 1.2780 |
| 151 | 0.2561 |
| 152 | 0.2475 |
| 153 | 0.2320 |
| 154 | 0.8760 |
| 155 | 0.9820 |
| 156 | 0.3730 |
| 157 | 0.4820 |
| 158 | 0.4650 |
| 159 | 0.5850 |
| 160 | 1.6327 |
| 161 | 0.2460 |
| 162 | 0.2096 |
| 163 | 0.2018 |
| 164 | 0.2417 |
| 165 | 0.4950 |
| 166 | 0.3183 |
| 167 | 0.2586 |
| 168 | 0.3056 |
| 169 | 0.2759 |
| 170 | 0.2736 |
| 171 | 0.2817 |
| 172 | 0.4228 |
| 173 | 0.2217 |
| 174 | 0.2522 |
| 175 | 0.9552 |
| 176 | 0.2211 |
| 177 | 0.2672 |
| 178 | 0.2680 |
| 179 | 0.2613 |
| 180 | 2.5610 |
| 181 | 0.2431 |

TABLE 2-continued

| Ex. No. | IC$_{50}$, μM |
|---|---|
| 182 | 0.2559 |
| 183 | 0.2238 |
| 184 | 0.2677 |
| 185 | 0.2477 |
| 186 | 0.2340 |
| 187 | 0.2575 |
| 188 | 0.2525 |
| 189 | 0.2323 |
| 190 | 0.2237 |
| 191 | 0.9767 |
| 192 | 0.6874 |
| 193 | 0.4442 |
| 194 | 0.3188 |
| 195 | 0.2914 |
| 196 | 0.3219 |
| 197 | 0.2842 |
| 198 | 0.2938 |
| 199 | 0.2415 |
| 200 | 0.3052 |
| 201 | 0.2255 |
| 202 | 0.6416 |
| 203 | 0.2813 |
| 204 | 0.3209 |
| 205 | 0.2651 |
| 206 | 0.4436 |
| 207 | 0.2998 |
| 208 | 0.2580 |
| 209 | 0.9285 |
| 210 | 0.2277 |
| 211 | 0.2521 |
| 212 | 0.3787 |
| 213 | 2.4266 |
| 214 | 2.5273 |
| 215 | 1.9770 |
| 216 | 0.2278 |
| 217 | 0.3331 |
| 218 | 0.4793 |
| 219 | 0.7359 |
| 220 | 0.2967 |
| 221 | 0.2212 |
| 222 | 0.2014 |
| 223 | 0.2680 |
| 224 | 0.3160 |
| 225 | 0.2814 |
| 226 | 3.2308 |
| 227 | 4.3638 |
| 228 | 0.3936 |
| 229 | 0.2730 |
| 230 | 0.3403 |
| 231 | 0.3288 |
| 232 | 0.2557 |
| 233 | 0.3217 |
| 234 | 0.4568 |
| 235 | 0.2146 |
| 236 | 0.2351 |
| 237 | 1.4669 |
| 238 | 4.0204 |
| 239 | 1.5818 |
| 240 | 2.7412 |
| 241 | 3.3169 |
| 242 | 0.8512 |
| 243 | 3.0098 |
| 244 | 0.3419 |
| 245 | 0.3082 |
| 246 | 2.9114 |
| 247 | 0.6502 |
| 248 | 0.9569 |
| 249 | 0.5256 |
| 250 | 0.4474 |
| 251 | 0.3862 |
| 252 | 0.3005 |
| 253 | 1.3400 |
| 254 | 0.3655 |
| 255 | 0.2601 |
| 256 | 0.2808 |
| 257 | 0.2859 |
| 258 | 0.3574 |
| 259 | 0.6143 |

TABLE 2-continued

| Ex. No. | IC$_{50}$, μM |
|---|---|
| 260 | 2.2325 |
| 261 | 0.3426 |
| 262 | 0.2689 |
| 263 | 0.4835 |
| 264 | 0.3472 |
| 265 | 0.2589 |
| 266 | 0.1806 |
| 267 | 0.1091 |
| 268 | 0.0228 |
| 269 | 0.0125 |
| 270 | 0.0267 |
| 271 | 0.0391 |
| 272 | 0.0336 |
| 273 | 0.0240 |
| 275 | 0.0230 |
| 276 | 0.0190 |
| 277 | 0.0204 |
| 278 | 0.0251 |
| 279 | 0.0204 |
| 282 | 0.0166 |
| 283 | 0.0146 |
| 284 | 0.0150 |
| 285 | 0.0753 |
| 286 | 0.0293 |
| 287 | 0.0225 |
| 288 | 0.0226 |
| 289 | 0.0238 |
| 291 | 0.0195 |
| 292 | 0.0203 |
| 293 | 0.0211 |
| 294 | 0.0230 |
| 295 | 0.0241 |
| 296 | 0.0197 |
| 297 | 0.0532 |
| 298 | 0.0890 |
| 299 | 0.0435 |
| 300 | 0.0224 |
| 301 | 0.0611 |
| 302 | 0.0231 |
| 303 | 0.0267 |
| 304 | 0.0659 |
| 305 | 0.0214 |
| 306 | 0.0339 |
| 307 | 0.0574 |
| 308 | 0.0214 |
| 309 | 0.0201 |
| 310 | 0.0211 |
| 311 | 0.0185 |
| 312 | 0.0191 |
| 313 | 0.0211 |
| 314 | 0.0232 |
| 315 | 0.0210 |
| 316 | 0.1882 |
| 317 | 0.0422 |
| 318 | 0.0283 |
| 319 | 0.1267 |
| 320 | 0.0140 |
| 321 | 0.1248 |
| 322 | 0.0426 |
| 323 | <0.0100 |
| 324 | 0.0234 |
| 325 | 0.0185 |
| 326 | 0.0131 |
| 327 | 0.7978 |
| 328 | 0.0432 |
| 329 | 0.0518 |
| 330 | 0.0206 |
| 331 | 0.0220 |
| 332 | 0.0142 |
| 333 | 0.0211 |
| 334 | 0.0227 |
| 335 | 0.0236 |
| 336 | 0.0328 |
| 337 | 0.0220 |

Pharmacological Test Example 3

Tumor Growth Inhibitory Activity Against Human Gastric Cancer Cells (MKN 45)

Human gastric cancer cells (MKN 45) were transplanted into nude mice. When the tumor volume became about 100 to 200 mm$^3$, the mice were grouped so that the groups each consisted of five mice and had an even average tumor volume. The test compound suspended in 0.5% methylcellulose was orally administered twice a day for 5 days.

Only 0.5% methylcellulose was administered to the control group in the manner as in the test groups. The tumor growth inhibition rate (TGIR) was calculated as follows: The tumor growth inhibition rate (TGIR)=(1−TX/CX)×100 wherein CX represents the relative tumor volume at day X for the control group when the tumor volume at the day of the start of the administration was presumed to be 1; and TX represents the relative tumor volume for test compound administration groups.

The tumor growth inhibition rate for representative examples of a group of compounds according to the present invention is shown in Table 3.

TABLE 3

|  | Dose, mg/kg/time | TGIR, % |
|---|---|---|
| Example 1 | 10 | 21 |
|  | 30 | 47 |
|  | 100 | 54 |
| Example 2 | 10 | 31 |
|  | 30 | 65 |
| Example 3 | 10 | 24 |
|  | 30 | 52 |
| Example 11 | 10 | 23 |
|  | 30 | 52 |
| Example 268 | 30 | 81 |

Pharmacological Test Example 4

Tumor Growth Inhibitory Activity Against Human Brain Tumor Cells (U87MG)

Human brain tumor cells (U87MG) were transplanted into nude mice. When the tumor volume became about 100 to 200 mm$^3$, the mice were grouped so that the groups each consisted of five mice and had an even average tumor volume. The test compound suspended in 0.5% methylcellulose was orally administered twice a day for 5 days.

Only 0.5% methylcellulose was administered to the control group in the manner as in the test groups. The tumor growth inhibition rate (TGIR) was calculated as follows: The tumor growth inhibition rate (TGIR)=(1−TX/CX)×100 wherein CX represents the relative tumor volume at day X for the control group when the tumor volume at the day of the start of the administration was presumed to be 1; and TX represents the relative tumor volume for test compound administration groups.

The tumor growth inhibition rate for representative examples of a group of compounds according to the present invention is shown in Table 4.

TABLE 4

| | Dose, mg/kg/time | TGIR, % |
|---|---|---|
| Example 1 | 30 | 42 |
| | 100 | 70 |
| Example 2 | 10 | 38 |
| | 30 | 61 |
| Example 3 | 30 | 51 |
| | 100 | 60 |

Pharmacological Test Example 5

Tumor Growth Inhibitory Activity Against Various Human Tumor Cells

Human gastric cancer cells (MKN 45) (obtained from RIKEN), human brain tumor cells (U87MG) (obtained from ATCC), human pancreatic cancer cells (KP4) (obtained from RIKEN), human pancreatic cancer cells (SUIT-2) (obtained from National Kyushu Cancer Center), and human signet-ring type gastric cancer cells (NUGC-4) (obtained from RIKEN), or human lung cancer cells (LC6) (obtained from Central Laboratories for Experimental Animals) were transplanted into nude mice. When the tumor volume became about 100 mm³, the mice were grouped so that the groups each consisted of four or five mice and had an even average tumor volume. The test compound suspended in 0.5% methylcellulose was orally administered once or twice a day for 5 days. Only 0.5% methylcellulose was administered to the control group in the manner as in the test groups. Alternatively, the test compound dissolved in physiological saline (with a 1 N aqueous hydrochloric acid solution added thereto) was intraveneously injected once a day for 5 days, and only physiological saline (with a 1 N aqueous hydrochloric acid solution added thereto) was administered to the control group in the same manner as in the test groups. The tumor growth inhibition rate (TGIR) was calculated as follows: The tumor growth inhibition rate (TGIR)=(1−TX/CX)×100 wherein CX represents the relative tumor volume at the 5$^{th}$ day for the control group when the tumor volume at the day of the start of the administration was presumed to be 1; and TX represents the relative tumor volume for test compound administration groups.

The tumor growth inhibition rate for representative examples of a group of compounds according to the present invention is shown in Table 5.

TABLE 5

| Ex. No. | Tumor | Administration method | Dose, mg/kg × number of times | TGIR, % |
|---|---|---|---|---|
| 1 | LC6 | Oral | 30 × 2 | 26 |
| 2 | NUGC-4 | Oral | 30 × 2 | 75 |
| 2 | LC6 | Oral | 30 × 2 | 27 |
| 2 | KP-4 | Oral | 30 × 2 | 54 |
| 3 | NUGC-4 | Oral | 30 × 2 | 71 |
| 3 | LC6 | Oral | 30 × 2 | 18 |
| 3 | KP-4 | Oral | 30 × 2 | 31 |
| 11 | MKN45 | Oral | 30 × 2 | 63 |
| 11 | U87MG | Oral | 30 × 2 | 62 |
| 11 | LC6 | Oral | 30 × 2 | 26 |
| 46 | MKN45 | Oral | 25 × 1 | 38 |
| 268 | MKN45 | i.v. injection | 10 × 1 | 52 |
| 268 | LC6 | Oral | 30 × 2 | 35 |
| 268 | U87MG | Oral | 30 × 2 | 74 |
| 277 | MKN45 | Oral | 30 × 2 | 17 |
| 282 | MKN45 | Oral | 30 × 2 | 13 |
| 282 | MKN45 | i.v. injection | 10 × 1 | 31 |
| 285 | MKN45 | Oral | 30 × 2 | 66 |
| 285 | LC6 | Oral | 30 × 2 | 48 |
| 286 | MKN45 | Oral | 30 × 2 | 64 |
| 286 | LC6 | Oral | 30 × 2 | 37 |
| 286 | U87MG | Oral | 30 × 2 | 66 |
| 288 | MKN45 | Oral | 30 × 2 | 64 |
| 299 | MKN45 | Oral | 25 × 1 | 14 |
| 312 | MKN45 | Oral | 30 × 2 | 75 |
| 313 | MKN45 | Oral | 12.5 × 1 | 37 |
| 313 | MKN45 | Oral | 25 × 1 | 73 |
| 313 | MKN45 | Oral | 50 × 1 | 78 |
| 313 | MKN45 | i.v. injection | 10 × 1 | 68 |
| 313 | SUIT-2 | Oral | 25 × 1 | 28 |
| 313 | KP-4 | Oral | 12.5 × 1 | 34 |
| 313 | KP-4 | Oral | 25 × 1 | 45 |
| 313 | KP-4 | Oral | 50 × 1 | 48 |
| 314 | MKN45 | Oral | 30 × 2 | 38 |
| 315 | MKN45 | Oral | 30 × 2 | 36 |
| 320 | MKN45 | Oral | 30 × 2 | 20 |
| 323 | MKN45 | Oral | 30 × 2 | 34 |
| 326 | MKN45 | Oral | 30 × 2 | 17 |
| 331 | MKN45 | Oral | 30 × 2 | 40 |
| 332 | MKN45 | Oral | 30 × 2 | 14 |
| 333 | MKN45 | Oral | 30 × 2 | 75 |
| 334 | MKN45 | Oral | 30 × 2 | 65 |

The invention claimed is:

1. A compound represented by formula (I) or a pharmaceutically acceptable salt thereof:

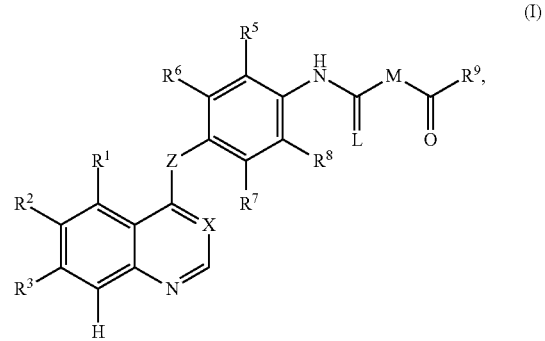

wherein
X represents CH or N;
Z represents O or S;
L represents O;
M represents
 (1-1) —$CR^{10}R^{11}$— wherein $R^{10}$ and $R^{11}$ may be the same or different, and each represents a hydrogen atom, $C_{1-4}$ alkyl, or $C_{1-4}$ alkoxy, or
 (1-2) —$NR^{12}$—, wherein $R^{12}$ represents a hydrogen atom or $C_{1-4}$ alkyl;
$R^1$, $R^2$, and $R^3$ may be the same or different, and each represents (2-1) a hydrogen atom, (2-2) hydroxyl, (2-3) a halogen atom, (2-4) nitro, (2-5) —$NR^{20}R^{21}$, wherein $R^{20}$ and $R^{21}$ may be the same or different, and each represents a hydrogen atom or $C_{1-6}$ alkyl optionally substituted by hydroxyl or $C_{1-6}$ alkoxy, (2-6) $C_{1-6}$ alkyl, (2-7) $C_{2-6}$ alkenyl, (2-8) $C_{2-6}$ alkynyl, or (2-9) $C_{1-6}$ alkoxy; wherein the (2-6) $C_{1-6}$ alkyl, the (2-7) $C_{2-6}$ alkenyl, the (2-8) $C_{2-6}$ alkynyl, and the (2-9) $C_{1-6}$ alkoxy are optionally substituted by (3-1) hydroxyl, (3-2) a halogen atom, (3-3) $C_{1-6}$ alkoxy, (3-4) $C_{1-6}$ alkylcarbonyl, (3-5)

$C_{1-6}$ alkoxy carbonyl, (3-6) —$NR^{22}R^{23}$ wherein $R^{22}$ and $R^{23}$ may be the same or different, and each represents a hydrogen atom or $C_{1-6}$ alkyl optionally substituted by hydroxyl or $C_{1-6}$ alkoxy, or (3-7) a saturated or unsaturated three- to eight-membered carbocyclic or heterocyclic group, wherein the saturated or unsaturated three- to eight-membered carbocyclic or heterocyclic group is optionally substituted by $C_{1-6}$ alkyl, wherein the $C_{1-6}$ alkyl is optionally substituted by hydroxyl or $C_{1-6}$ alkoxy;

$R^5$, $R^6$, $R^7$, and $R^8$ may be the same or different, and each represents (4-1) a hydrogen atom, (4-2) a halogen atom, (4-3) $C_{1-4}$ alkyl, or (4-4) $C_{1-4}$ alkoxy; and $R^9$ represents (5-1) $C_{1-6}$ alkyl wherein one or more hydrogen atoms on the $C_{1-6}$ alkyl are optionally substituted by (6-1) a saturated or unsaturated three- to eight-membered carbocyclic or heterocyclic group, wherein the saturated or unsaturated three- to eight-membered carbocyclic or heterocyclic group may be a bicyclic group condensed with another saturated or unsaturated three- to eight-membered carbocyclic or heterocyclic group, and the saturated or unsaturated three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated three- to eight-membered carbocyclic or heterocyclic group is substituted by two $C_{1-6}$ alkyl groups, the two alkyl groups may combine together to form an alkylene chain, (6-2) -T-$R^{15}$, wherein T represents O, S, or NH, and $R^{15}$ represents $C_{1-6}$ alkyl or a saturated or unsaturated three- to eight-membered carbocyclic or heterocyclic group wherein the saturated or unsaturated three- to eight-membered carbocyclic or heterocyclic group may be a bicyclic group condensed with another saturated or unsaturated three- to eight-membered carbocyclic or heterocyclic group, and the saturated or unsaturated three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated three- to eight-membered carbocyclic or heterocyclic group is substituted by two $C_{1-6}$ alkyl groups, the two alkyl groups may combine together to form an alkylene chain, or (6-3) —$NR^{16}R^{17}$ wherein $R^{16}$ and $R^{17}$ may be the same or different, and each represents $C_{1-6}$ alkyl or a saturated or unsaturated three- to eight-membered carbocyclic or heterocyclic group wherein the saturated or unsaturated three- to eight-membered carbocyclic or heterocyclic group may be a bicyclic group condensed with another saturated or unsaturated three- to eight-membered carbocyclic or heterocyclic group, and the saturated or unsaturated three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated three- to eight-membered carbocyclic or heterocyclic group is substituted by two $C_{1-6}$ alkyl groups, the two alkyl groups may combine together to form an alkylene chain; (5-2) a saturated or unsaturated three- to eight-membered carbocyclic or heterocyclic group, wherein the saturated or unsaturated three- to eight-membered carbocyclic or heterocyclic group may be a bicyclic group condensed with another saturated or unsaturated three- to eight-membered carbocyclic or heterocyclic group, and the saturated or unsaturated three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated three- to eight-membered carbocyclic or heterocyclic group is substituted by two $C_{1-6}$ alkyl groups, the two alkyl groups may combine together to form an alkylene chain; or (5-3) —$NR^{18}R^{19}$, wherein $R^{18}$ and $R^{19}$ may be the same or different, and each represents (7-1) a hydrogen atom, (7-2) a saturated or unsaturated three- to eight-membered carbocyclic or heterocyclic group, wherein the saturated or unsaturated three- to eight-membered carbocyclic or heterocyclic group may be a bicyclic group condensed with another saturated or unsaturated three- to eight-membered carbocyclic or heterocyclic group, and the saturated or unsaturated three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated three- to eight-membered carbocyclic or heterocyclic group is substituted by two $C_{1-6}$ alkyl groups, the two alkyl groups may combine together to form an alkylene chain, or (7-3) $C_{1-6}$ alkyl optionally substituted by $C_{1-6}$ alkoxy, $C_{1-6}$ alkylthio, or a saturated or unsaturated three- to eight-membered carbocyclic or heterocyclic group, wherein the saturated or unsaturated three- to eight-membered carbocyclic or heterocyclic group may be a bicyclic group condensed with another saturated or unsaturated three- to eight-membered carbocyclic or heterocyclic group, and the saturated or unsaturated three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated three- to eight-membered carbocyclic or heterocyclic group is substituted by two $C_{1-6}$ alkyl groups, the two alkyl groups may combine together to form an alkylene chain, provided that, when X represents CH; Z represents O; L represents O; M represents —NH—; $R^1$, $R^5$, $R^6$, $R^7$, and $R^8$ represent a hydrogen atom; and $R^2$ and $R^3$ represent methoxy, $R^9$ represents neither phenyl, ethoxy, nor pyridin-2-yl.

2. The compound or a pharmaceutically acceptable salt thereof according to claim 1 wherein Z is O.

3. The compound or a pharmaceutically acceptable salt thereof according to claim 1 wherein $R^1$ is a hydrogen atom.

4. The compound or a pharmaceutically acceptable salt thereof according to claim 1, wherein $R^2$ is $C_{1-6}$ alkoxy.

5. The compound or a pharmaceutically acceptable salt thereof according to claim 1, wherein $R^2$ is methoxy.

6. The compound or a pharmaceutically acceptable salt thereof according to claim 1 wherein $R^3$ is (8-1) hydroxyl, or (8-2) $C_{1-6}$ alkoxy wherein the $C_{1-6}$ alkoxy is optionally substituted by (9-1) hydroxyl, (9-2) a halogen atom, (9-3) —$NR^{22}R^{23}$ wherein $R^{22}$ and $R^{23}$ have the same meanings as defined above, or (9-4) a saturated or unsaturated five- to seven-membered carbocyclic or heterocyclic group wherein the saturated or unsaturated five- to seven-membered carbocyclic or heterocyclic group is optionally substituted by $C_{1-6}$ alkyl wherein the $C_{1-6}$ alkyl is optionally substituted by hydroxyl or $C_{1-6}$ alkoxy.

7. The compound or a pharmaceutically acceptable salt thereof according to claim 1 wherein $R^3$ is (10-1) hydroxyl, or (10-2) $C_{1-4}$ alkoxy, wherein the $C_{1-4}$ alkoxy is optionally substituted by (11-1) hydroxyl, (11-2) a halogen atom, (11-3) —$NR^{22}R^{23}$ wherein $R^{22}$ and $R^{23}$ have the same meanings as defined above, or (11-4) a saturated or unsaturated five- to seven-membered carbocyclic or heterocyclic group wherein the saturated or unsaturated five- to seven-membered carbocyclic or heterocyclic group is optionally substituted by $C_{1-6}$ alkyl wherein the $C_{1-6}$ alkyl is optionally substituted by hydroxyl or $C_{1-6}$ alkoxy.

8. The compound or a pharmaceutically acceptable salt thereof according to claim 1 wherein $R^3$ is methoxy.

9. The compound or a pharmaceutically acceptable salt thereof according to claim 1, wherein M is —$NR^{12}$— wherein $R^{12}$ has the same meaning as defined above.

10. The compound or a pharmaceutically acceptable salt thereof according to claim 1, wherein M is —$CR^{10}R^{11}$— and wherein $R^{10}$ and $R^{11}$ have the same meanings as defined above.

11. The compound or a pharmaceutically acceptable salt thereof according to claim 1,
wherein $R^9$ is $C_{1-6}$ alkyl wherein one or more hydrogen atoms on the $C_{1-6}$ alkyl are optionally substituted by (12-1) a saturated or unsaturated three- to eight-membered carbocyclic or heterocyclic group, wherein the saturated or unsaturated three- to eight-membered carbocyclic or heterocyclic group may be a bicyclic group condensed with another saturated or unsaturated three- to eight-membered carbocyclic or heterocyclic group, and the saturated or unsaturated three- to eight-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated three- to eight-membered carbocyclic or heterocyclic group is substituted by two $C_{1-6}$ alkyl groups, the two alkyl groups may combine together to form an alkylene chain, (12-2) -T-$R^{15}$, wherein T and $R^{15}$ have the same meanings as defined above, or (12-3) —$NR^{16}R^{17}$, wherein $R^{16}$ and $R^{17}$ have the same meanings as defined above.

12. The compound or a pharmaceutically acceptable salt thereof according to claim 1, wherein $R^9$ is —$CH_2$—$R^{24}$ wherein $R^{24}$ represents a saturated or unsaturated five- or six-membered carbocyclic or heterocyclic group wherein the saturated or unsaturated five- or six-membered carbocyclic or heterocyclic group is optionally substituted by $C_{1-6}$ alkyl, $C_{1-6}$ alkoxy, or a halogen atom.

13. The compound or a pharmaceutically acceptable salt thereof according to claim 1 wherein $R^9$ is:
(13-1) —$NR^{25}R^{26}$, wherein $R^{25}$ represents a hydrogen atom or $C_{1-4}$ alkyl, and $R^{26}$ represents
(14-1) $C_{1-4}$ alkyl optionally substituted by a saturated or unsaturated six-membered carbocyclic group, wherein the saturated or unsaturated six-membered carbocyclic group may be a bicyclic group condensed with another saturated or unsaturated three- to eight-membered carbocyclic or heterocyclic group, and the saturated or unsaturated six-membered carbocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated six-membered carbocyclic group is substituted by two $C_{1-6}$ alkyl groups, the two alkyl groups may combine together to form an alkylene chain, or (14-2) a saturated or unsaturated four- to seven-membered carbocyclic or heterocyclic group, wherein the saturated or unsaturated four- to seven-membered carbocyclic or heterocyclic group may be a bicyclic group condensed with another saturated or unsaturated three- to eight-membered carbocyclic or heterocyclic group, and the saturated or unsaturated four- to seven-membered carbocyclic or heterocyclic group is optionally substituted by $C_{1-6}$ alkyl, $C_{1-6}$ alkoxy, a halogen atom, nitro, trifluoromethyl, $C_{1-6}$ alkoxy carbonyl, cyano, cyano $C_{1-6}$ alkyl, $C_{1-6}$ alkylthio, phenoxy, acetyl, or a saturated or unsaturated five- or six-membered heterocyclic ring, and when the saturated or unsaturated four- to seven-membered carbocyclic or heterocyclic group is substituted by two $C_{1-6}$ alkyl groups, the two alkyl groups may combine together to form an alkylene chain.

14. A pharmaceutical composition comprising the compound or a pharmaceutically acceptable salt thereof according to claim 1.

15. A method for inhibiting met autophosphorylation comprising administering the compound of claim 1 to a subject in need thereof.

16. The method of claim 15, wherein said subject has a tumor or cancer whose proliferation, invasion or metastasis is mediated by an HGF-met signal.

* * * * *